US009868705B2

(12) United States Patent
Katzenellenbogen et al.

(10) Patent No.: US 9,868,705 B2
(45) Date of Patent: Jan. 16, 2018

(54) TETRA-ARYL CYCLOBUTANE INHIBITORS OF ANDROGEN RECEPTOR ACTION FOR THE TREATMENT OF HORMONE REFRACTORY CANCER

(71) Applicants: The Board of Trustees of the University of Illinois, Urbana, IL (US); Duke University, Durham, NC (US)

(72) Inventors: John Katzenellenbogen, Urbana, IL (US); Donald McDonnell, Chapel Hill, NC (US); John D. Norris, Raleigh, NC (US); Alexander Parent, Medford, MA (US); Julie Pollock, Henrick, VA (US); Jillian Gunther, Houston, TX (US); Kathryn E. Carlson, Champaign, IL (US); Teresa Martin, Champaign, IL (US)

(73) Assignees: THE BOARD OF TRUSTEES OF THE UNIVERSITY OF ILLINOIS, Urbana, IL (US); DUKE UNIVERSITY, Durham, NC (US)

( * ) Notice: Subject to any disclaimer, the term of this patent is extended or adjusted under 35 U.S.C. 154(b) by 0 days.

(21) Appl. No.: 15/023,159

(22) PCT Filed: Sep. 25, 2014

(86) PCT No.: PCT/US2014/057391
§ 371 (c)(1),
(2) Date: Mar. 18, 2016

(87) PCT Pub. No.: WO2015/048246
PCT Pub. Date: Apr. 2, 2015

(65) Prior Publication Data
US 2016/0229811 A1 Aug. 11, 2016

Related U.S. Application Data

(60) Provisional application No. 61/925,603, filed on Jan. 9, 2014, provisional application No. 61/883,231, filed on Sep. 27, 2013.

(51) Int. Cl.
| C07D 239/48 | (2006.01) |
| F23K 3/00 | (2006.01) |
| F23K 1/04 | (2006.01) |
| F23G 5/04 | (2006.01) |
| F01K 5/02 | (2006.01) |
| C07D 213/24 | (2006.01) |
| C07D 213/74 | (2006.01) |
| C07D 239/26 | (2006.01) |
| C07D 239/30 | (2006.01) |
| C07D 239/34 | (2006.01) |
| C07D 239/47 | (2006.01) |
| C07D 239/52 | (2006.01) |
| C07D 239/54 | (2006.01) |
| C07D 239/58 | (2006.01) |
| C07D 241/12 | (2006.01) |
| C07D 241/16 | (2006.01) |
| C07D 241/18 | (2006.01) |
| C07D 401/14 | (2006.01) |
| C07D 403/08 | (2006.01) |
| C07D 403/14 | (2006.01) |
| C07D 407/08 | (2006.01) |
| C07D 409/14 | (2006.01) |

(52) U.S. Cl.
CPC ......... *C07D 239/48* (2013.01); *C07D 213/24* (2013.01); *C07D 213/74* (2013.01); *C07D 239/26* (2013.01); *C07D 239/30* (2013.01); *C07D 239/34* (2013.01); *C07D 239/47* (2013.01); *C07D 239/52* (2013.01); *C07D 239/54* (2013.01); *C07D 239/58* (2013.01); *C07D 241/12* (2013.01); *C07D 241/16* (2013.01); *C07D 241/18* (2013.01); *C07D 401/14* (2013.01); *C07D 403/08* (2013.01); *C07D 403/14* (2013.01); *C07D 407/08* (2013.01); *C07D 409/14* (2013.01); *F01K 5/02* (2013.01); *F23G 5/04* (2013.01); *F23K 1/04* (2013.01); *F23K 3/00* (2013.01); *F23K 2201/20* (2013.01); *F23K 2203/103* (2013.01)

(58) Field of Classification Search
CPC .. C07D 213/24; C07D 213/74; C07D 239/26; C07D 239/30; C07D 239/34; C07D 239/47; C07D 239/48; C07D 239/52; C07D 239/54; C07D 239/58; C07D 241/12; C07D 241/16; C07D 241/18; C07D 401/14; C07D 403/08; C07D 403/14; C07D 407/08; C07D 407/14; A61K 31/505; A61K 31/506
USPC ............. 544/296, 357; 546/255; 514/252.11, 514/256, 269, 274, 332
See application file for complete search history.

(56) References Cited

U.S. PATENT DOCUMENTS
2007/0049629 A1    3/2007   Scanlan et al.

FOREIGN PATENT DOCUMENTS
WO    2005120477 A2    12/2005

OTHER PUBLICATIONS

Bundgaard, Design of Prodrugs, p. 1, 1985.*
Silverman, Prodrugs and Drug Delivery Systems, The Organic Chemistry of Drug Design and Drug Action, pp. 352-399, 1992.*
Banker et al., eds., "Modem Pharmaceutics 3rd Ed", Marcel Dekker, New York, 1996, pp. 451 and 596, 3 pages.*
Wolff, ed., "Burger's Medicinal Chemistry, Fourth Edition, Part 1, The Basis of Medicinal Chemistry," John Wiley & Sons, New York, 1979, pp. 336-337, 4 pages.*

(Continued)

*Primary Examiner* — Deepak R Rao
(74) *Attorney, Agent, or Firm* — Dilworth IP LLC

(57) ABSTRACT

The present disclosure provides tetra-substituted cyclobutane inhibitors of Androgen Receptor Action, and methods of using such inhibitors, for the treatment of hormone-refractory cancers.

31 Claims, 60 Drawing Sheets

(56) References Cited

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-101 O, 1995.*
Nakata, CAPLUS Abstract 55:70658 (1961).*
Williams et al., CAPLUS Abstract 56:73413 (1962).*
Greene et al., CAPLUS Abstract 58:73201 (1963).*
Williams et al., CAPLUS Abstract 58:73202 (1963).*
Quina et al., CAPLUS Abstract 86:120416 (1977).*
Vansant et al., CAPLUS Abstract 92:214546 (1980).*
Horner et al., CAPLUS Abstract 97:91358 (1982).*
Kaupp et al., CAPLUS Abstract 110:22964 (1989).*
Takagi et al., CAPLUS Abstract 120:269327 (1994).*
Baret et al., CAPLUS Abstract 127:72899 (1997).*
Kim et al., CAPLUS Abstract 131:215647 (1999).*
Zhang et al., CAPLUS Abstract 133:142503 (2000).*
Pattabhiraman et al., CAPLUS Abstract 143:440227 (2005).*
Usami, Hisanao. et al., "Controlled Photocycloaddition of Stilbazolium Ions Intercalated in Saponite Clay Laers", J. Chem. Soc. Perkin Trans2, 1990, pp. 1723-1728. See p. 1723, p. 1727.
Williams, J. et al., "Photodimers of 4'-Substitute 2-Styrylpyridines", Journal of Organic Chemistry, vol. 28, 1963, pp. 1317-1320. See table 1 and Experimental.
Hasegawa, Masaki et al., "Topochemical Photopolymerization and Photo-Copolymerization of the Crystals of Unsymmetrically Substituted Diolefin Compounds Having Pyrimidine Ring", Bull. Chem. Soc. Jpn, vol. 62, 1989, pp. 1556-1560. See scheme2.
Chen, Yu et al., "Anti-adrogens and adrogen-depleting therapies in prostate cancer: new agents for an established target", Lancet Oncol. Vo. 10, 2009, pp. 981-991.
PCT International Search Report and Written Opinion dated Jan. 16, 2015 from corresponding Application No. PCT/US2014/057391, 14 pages.
PCT International Preliminary Report on Patentability dated Apr. 7, 2016 from corresponding Application No. PCT/US2014/057391, 9 pages.
Parent A. et al., J. A., J. Med Chem. 2008, 51, 6512-6530.
Williams A. et al., J. A. Org. Lett. 2009, 11, 5370-5373.
Lafrate, A. et al., J. A. Bioorg. Med. Chem. 2008, 16, 10075-10084.
Becerril, J. et al., Angew. Chem. Int. Ed. 2007, 46, 4471-4473.
Gunther, J. et al., J. A. Acs Chem. Bio. 2008, 3, 282-286.
Gunther, J. et al., J. A. ACS Chem. Bio. 2009, 4, 435-440.
Joseph, J. et al., (2009) Inhibition of prostate cancer cell growth by second-site androgen receptor antagonists, Proc. Natl. Acad. Sci. U. S. A. 106, 12178-12183, S12178/12171-S12178/12113.
Anderson, R. et al. Cancer Cell 2010, 17, 535-546.
Estebanez-Perpina, E. et al. PNAS 2007, 104, 16074-16079.
Jones, J. O. et al. PNAS 2009, 106, 7233-7238.
Siegel, R. et.al., Cancer Statistics, 2012, CA Cancer J. Clin. 2012, 62, 10-29.
Korpal, M. et al., (2013) An F876L mutation in androgen receptor confers genetic and phenotypic resistance to MDV3100 (enzalutamide), Cancer Discov 3, 1030-1043.
Taplin, M. et al., (1999) Selection for Androgen Receptor Mutations in Prostate Cancers Treated with Androgen Antagonist, Cancer Research 59, 2511-2515.
Chatterjee, B., (2003) The role of the androgen receptor in the development of prostatic hyperplasia and prostate cancer, Molecular and Cellular Biochemistry 253, 89-101.
Taplin, M. et al., (2007) Drug Insight: role of the androgen receptor in the development and progression of prostate cancer, Nature Clinical Practice Oncology 4, 236-244.
Liebermann, C. et al., Berichte der Deutschen Chemischen Gesellschaft 1889, 22, 782.
Marckwald, W., Zeitschrift fuer Physikalische Chemie, Stoechiometrie und Verwandtschaftslehre 1899, 30, 140.
Ciamician, G. et al., Ber. Dtsch. chem. Ges. 1901, 34, 2040.
Senier, A. et al., Journal of the Chemical Society, Transactions 1909, 95, 1943.
Kohlschutter, V. et al., Zeitschrift fuer Anorganische und Allgemeine Chemie 1919, 105, 121.
Stobbe, H. et al., Berichte der Deutschen Chemischen Gesellschaft [Abteilung] B: Abhandlungen 1922, 55B, 2225.
Bernstein, H. et al., Journal of the American Chemical Society 1943, 65, 1845.
Schmidt, G., Pure and Applied Chemistry 1971, 27, 647.
Cohen, M. et al., Journal of the Chemical Society 1964, 1996.
Cohen, M. et al., Journal of the Chemical Society 1964, 2000.
Schmidt, G., Journal of the Chemical Society 1964, 2014.
Cohen, M., Angewandte Chemie 1975, 87, 439.
Gnanaguru, K. et al., Journal of Organic Chemistry 1985, 50, 2337.
Bhadbhade, M. et al., Chemical Physics Letters 1984, 109, 259.
Murthy, G. et al., Tetrahedron 1987, 43, 1225.
Ramdas, S. et al., Chemical Physics Letters 1978, 57, 468.
Natarajan, A. et al., Chemistry of Cyclobutanes 2005, 2, 807.
Natarajan, A. et al., Supramolecular Photochemistry 2011, 175.
Ito, Y. et al., Journal of Organic Chemistry 1989, 54, 587.
Syamala, M. et al., Journal of Organic Chemistry 1986, 51, 3712.
Papagni, A. et al., New Journal of Chemistry 2010, 34, 2612.
Coates, G. et al., Journal of the American Chemical Society 1998, 120, 3641.
Stegemeyer, H., Chimia 1965, 19, 536.
Ulrich, H. et al., Journal of Organic Chemistry 1970, 35, 1121.
Williams, J., Journal of Organic Chemistry 1961, 26, 4893.
Williams, J., Journal of Organic Chemistry 1960, 25, 1839.
Horner, M. et al., Liebigs Annalen der Chemie 1982, 1183.
Yamada, S. et al., Journal of the American Chemical Society 2007, 129, 12100.
Vansant, J. et al., Journal of Organic Chemistry 1980, 45, 1565.
Mondal, B., et al., V. Photochemical & Photobiological Sciences 2011, 10, 891.
Chung, C. et al., Chemistry Letters 1991, 779.
Kaupp, G. et al., Chemische Berichte 1988, 121, 2135.
Kato, T. et al., Journal of Heterocyclic Chemistry 1979, 16, 1575.
Pure and Applied Chemistry 1976, 45, 11.
Whitten, D. et al., Amer. Chem. Soc. 1972, 94, 9142.
Dudek, R. et al., Chemical Educator 2011, 16, 76.
Vaske, Y. et al., Journal of the American Chemical Society 2010, 132, 11379.
Wheeler, S. et al., Journal of the American Chemical Society 2008, 130, 10854.
Wheeler, S. et al., Journal of the Chemical Theory and Computation 2009, 5, 2301.
Frisch, M. et al., Gaussian, Inc., Wallingford CT 2009.
Zhao, Y. et al., Accounts of Chemical Research 2008, 41, 157.
Grimme, S., Journal of Chemical Physics 2003, 118, 9095.
Loader, C. et al., Journal of the Chemical Society [Section] C: Organic 1967, 1343.
Hazai, L. et al., ACH—Models in Chemistry 1998, 135, 493.
Perkampus, H. et al., Tetrahedron 1972, 28, 2099.
Fehn, H. et al., Tetrahedron 1978, 34, 1971.
Leiserowitz, L. et al., Acta Crystallographica 1965, 18, 1058.
Steiner, T., NATO Science Series, Series E: Applied Sciences 1999, 360, 185.
Desiraju, G., Accounts of Chemical Research 2002, 35, 565.
Desiraju, G., Journal of the American Chemical Society 2013, 135, 9952.
Nagarathinam, M. et al., Chemical Communications (Cambridge, United Kingdom) 2008, 5277.
Biradha, K. et al., Chemical Society Reviews 2013, 42, 950.
Elacqua, E., et al., Supramolecular Chemistry: From Molecules to Nanomaterials 2012, 6, 3153.
Feldman, K. et al., Journal of Organic Chemistry 1995, 60, 1924.
Marras, G. et al., New Journal of Chemistry 2006, 30, 1397.
Liu, J. et al., Organic Letters 2005, 7, 1007.

(56) References Cited

OTHER PUBLICATIONS

Bhogala, B. et al., Journal of the American Chemical Society 2010, 132, 13434.
Song, Q. et al., Journal of Photochemistry and Photobiology, A: Chemistry 2006, 183, 198.
Pangborn, A., Organometallics 1996, 15, 1518.
Still, W. et al., Journal of Organic Chemistry 1978, 43, 2923.
Tan, J. et al., Synthetic Communications 2004, 34, 3773.
Anderson, J. (2003) The role of antiandrogen monotherapy in the treatment of prostate cancer, BJU International 91, 455-461.
Chodak, G. et al., (2007) Combined Androgen Blockade in Advanced Prostate Cancer. Looking Back to Move Forward, Clinical Genitourinary Cancer 5, 371-378.
Gillatt, D. (2006) Antiandrogen treatments in locally advanced prostate cancer: are they all the same?, Journal of Cancer Research and Clinical Oncology 132, 17-26.
Tran, C. et al. (2009) Development of a Second-Generation Antiandrogen for Treatment of Advanced Prostate Cancer, Science 324, 787-790.
Scher, H. et al., (2010) Antitumour activity of MDV3100 in castration-resistant prostate cancer: a phase 1?2 study, The Lancet 375, 1437-1446.
Scher, H. et al., (2012) Increased Survival with Enzalutamide in Prostate Cancer after Chemotherapy, New England Journal of Medicine 367, 1187-1197.
Li, Y. et al., (2013) Androgen Receptor Splice Variants Mediate Enzalutamide Resistance in Castration-Resistant Prostate Cancer Cell Lines, Cancer Research 73, 483-489.
He, B. et al., (2000) FXXLF and WXXLF sequences mediate the NH2-terminal interaction with the ligand binding domain of the androgen receptor, Journal of Biological Chemistry 275, 22986-22994.
He, B. et al. (2002) Dependence of selective gene activation on the androgen receptor NH2- and COOH-terminal Interaction, Journal of Biological Chemistry 277, 25631-25639.
Callewaert, L. et al., (2006) Interplay between Two Hormone-Independent Activation Domains in the Androgen Receptor, Cancer Research 66, 543-553.
He, B. et al., (2004) Structural basis for androgen receptor interdomain and coactivator interactions suggests a transition in nuclear receptor activation function dominance, Molecular Cell 16, 425-438.
McEwan, I. et al. (2004) Molecular mechanisms of androgen receptor-mediated gene regulation: structure-function analysis of the AF-1 domain, Endocrine-Related Cancer 11, 281-293.
Gelmann, E. et al., (2002) Molecular biology of the androgen receptor, Journal of Clinical Oncology 20, 3001-3015.
Hanstein, B. et al., (2004) Insights into the molecular biology of the estrogen receptor define novel therapeutic targets for breast cancer, European Journal of Endocrinology 150, 243-255.
Hall, J. et al., (2005) Coregulators in nuclear estrogen receptor action: from concept to therapeutic targeting, Molecular Interventions 5, 343-357.
Fuerstner, A. et al., (2002) Iron-catalyzed cross-coupling reactions of alkyl-Grignard reagents with aryl chlorides, tosylates, and triflates, Angew. Chem., Int. Ed. 41, 609-612.
Korenchuk, S. et al., (2001) VCaP, a cell-based model system of human prostate cancer, In Vivo. 15, 163-168.
Norris, J. et al., (2009) Differential Presentation of Protein Interaction Surfaces on the Androgen Receptor Defines the Pharmacological Actions of Bound Ligands, Chem. Biol. (Cambridge, MA, U. S.) 16, 452-460.
Hara, T. et al., (2003) Novel Mutations of Androgen Receptor: A Possible Mechanism of Bicalutamide Withdrawal Syndrome, Cancer Research 63, 149-153.
Wakabayashi, K. et al., (2008) 4-(Anilino)pyrrole-2-carboxamides: Novel non-steroidal/non-anilide type androgen antagonists effective upon human prostate tumor LNCaP cells with mutated nuclear androgen receptor, Bioorg Med Chem 16, 6799-6812.
Oh, S. et al., (2010) Development of a benzopyran-containing androgen receptor antagonist to treat antiandrogen-resistant prostate cancer, ChemMedChem 5, 529-533.
Yamamoto, S. et al., (2013) Design, synthesis, and biological evaluation of 3-aryl-3-hydroxy-1-phenylpyrrolidine derivatives as novel androgen receptor antagonists, Bioorg Med Chem 21, 70-83.
Bollag, G. et al., (2010) Clinical efficacy of a RAF inhibitor needs broad target blockade in BRAF-mutant melanoma, Nature 467, 596-599.
Flaherty, K. et al., (2009) Phase I study of PLX4032: Proof of concept for V600E BRAF mutation as a therapeutic target in human cancer, Journal of Clinical Oncology 27.
Flaherty, K. et al., (2010) Inhibition of mutated, activated BRAF in metastatic melanoma, N Engl J Med 363, 809-819.
Parent, A. et al., (2013) π-π Interaction Energies as Determinants of the Photodimerization of Mono-, Di- and Triazastilbenes Photochemistry Photobiology.
Pearce, A. et al., (2008) Orthidines A-E, tubastrine, 3,4-dimethoxyphenethyl-β-guanidine, and 1,14-sperminedihomovanillamide: potential anti-inflammatory alkaloids isolated from the New Zealand ascidian Aplidium orthium that act as inhibitors of neutrophil respiratory burst, Tetrahedron 64, 5748-5755.
Watanabe, K. et al., (2007) Sarusubine A, a new dimeric Lythraceae alkaloid from Lagerstroemia subcostata, Tetrahedron Lett. 48, 7502-7504.
Davis, R. et al., (2007) Endiandrin A, a Potent Glucocorticoid Receptor Binder Isolated from the Australian Plant *Endiandra anthropophagorum*, J. Nat. Prod. 70, 1118-1121.
Lu, Y. et al., (1999) Rosmarinic acid derivatives from Salvia officinalis, Phytochemistry 51, 91-94.
Dembitsky, V., (2008) Bioactive cyclobutane-containing alkaloids, J. Nat. Med. 62, 1-33.
Sagawa, T. et al., (2005) Cyclobutane dimers from the Colombian medicinal plant *Achyrocline bogotensis*, J. Nat. Prod. 68, 502-505.
Hockemeyer, J. et al., (2004) Multigram-Scale Syntheses, Stability, and Photoreactions of A2A Adenosine Receptor Antagonists with 8-Styrylxanthine Structure: Potential Drugs for Parkinson's Disease, J. Org. Chem. 69, 3308-3318.
Chen, D. et al., (2007) A nonpeptidic agonist of glucagon-like peptide 1 receptors with efficacy in diabetic db/db mice, Proc. Natl. Acad. Sci. U. S. A. 104, 943-948.
Liu, Q. et al., (2012) Cyclobutane derivatives as novel nonpeptidic small molecule agonists of glucagon-like peptide-1 receptor, J Med Chem 55, 250-267.
Siegel, R. et al., (2014) Cancer statistics, 2014, CA Cancer J Clin 64, 9-29.
Chen, C. et al., (2004) Molecular determinants of resistance to antiandrogen therapy, Nat Med 10, 33-39.
Beltran, H. et al., (2013) Targeted next-generation sequencing of advanced prostate cancer identifies potential therapeutic targets and disease heterogeneity, Eur Urol 63, 920-926.
Veldscholte, J. et al., (1990) A mutation in the ligand binding domain of the androgen receptor of human LNCaP cells affects steroid binding characteristics and response to anti-androgens, Biochem Biophys Res Commun 173, 534-540.
Clegg, N. et al., (2012) ARN-509: a novel antiandrogen for prostate cancer treatment, Cancer Res 72, 1494-1503.
Joseph, J. et al., (2013) A clinically relevant androgen receptor mutation confers resistance to second-generation antiandrogens enzalutamide and ARN-509, Cancer Discov 3, 1020-1029.
Parent, A. et al., (2013) pi-pi Interaction energies as determinants of the photodimerization of mono-, di- and triazastilbenes, J Org Chem.
Tan et al., "Androgen receptor: structure, role in prostate cancer and drug discovery", Acta Pharmacologica Sinica (2015) 36:3-23.

\* cited by examiner

ER Coactivator Binding:
- The coactivator binding groove of the ER Ligand Binding Domain (LBD) interacts with Steroid Receptor Coactivator (SRC) LXXLL motifs.
- Binding is facilitated by three or four hydrophobic contacts as well as positive interaction between E542 and K362 (charge clamp) of the LBD and the backbone of the coactivator peptide.

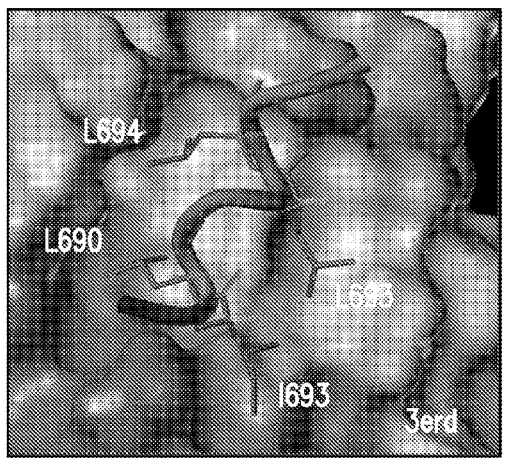

ERα-LBD bound to SRC-2 Box III

Surface-binding ER inhibitors

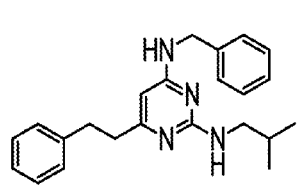

$K_i$ = 1.7 μM[1]

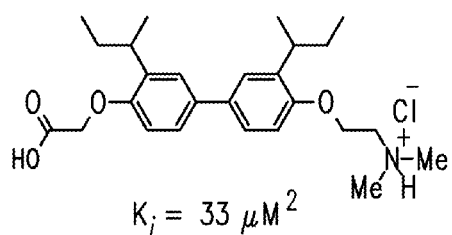

$K_i$ = 33 μM[2]

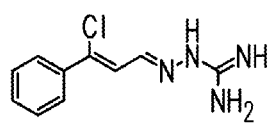

$IC_{50}$ = 0.9 μM[3]

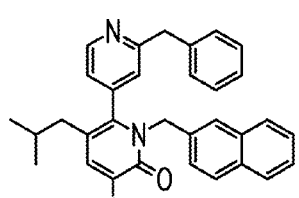

$K_i$ = 4.0 μM[4]

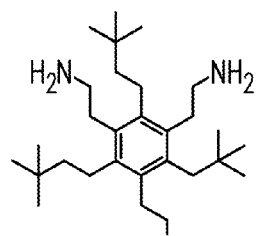

AR Coactivator Binding:
- AR-LBD AF-2/Coactivator interaction is similar to ER-LBD except it interacts with LXXLL, FXXLF, and WXXLF peptide motifs.
- AR CBI selectivity based on probing affinity for larger hydrophobic groups that mimic phenylalanine and tryptophan.

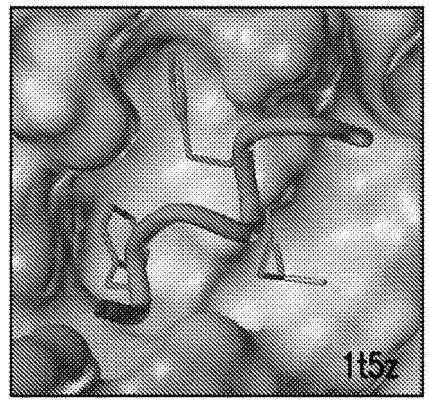

AR-LBD bound to ARA70 FXXLF peptide

Surface-binding AR inhibitors

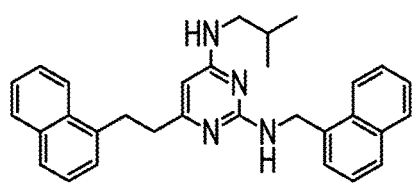

$IC_{50} = 1.5\ \mu M^6$

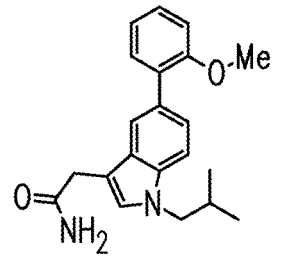

$K_i = 9.0\ \mu M^7$

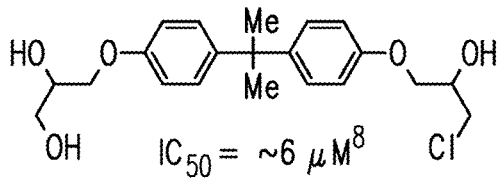

$IC_{50} = \sim 6\ \mu M^8$

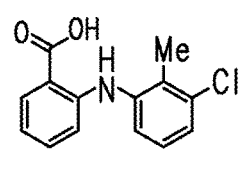

$IC_{50} = 47\ \mu M^9$

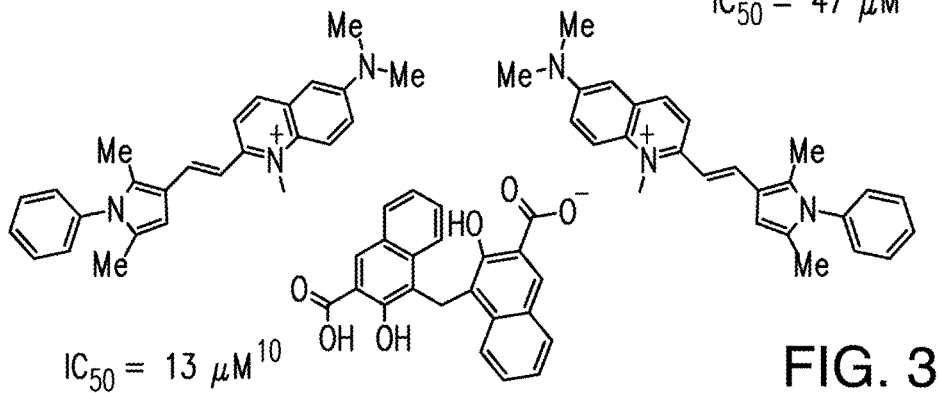

Table 1: Symmetrically-substituted cyclobutanes in ER and AR reporter gene assays

| Cmpd # | R | ER IC$_{50}$ (μM) | AR IC$_{50}$ (μM) |
|---|---|---|---|
| 1 | -CH$_3$ | 3.2 | 2.6 |
| 2 | ⊢⁄ | 0.75 | 1.3 |
| 3 | ⊢∼ | 0.73 | -- |
| 4 | ⊢∼∼ | 1.9 | -- |
| 5 | ⊢∼∼∼ | NB | NB |
| 6 | ⊢∼∼∼∼ | NB | -- |
| 7 | ⊢⋋ | 1.4 | 1.8 |
| 8 | ⊢⋋⋌ | 1.2 | -- |
| 9 | ⊢∼⋋ | NB | NB |
| 10 | ⊢Ph | NB | -- |
| 11 | ⊢Ph-OMe | NB | -- |
| 12 | ⊢naphthyl | NB | NB |

Table 2: Unsymmetric cyclobutanes in ER and AR reporter gene assays

| Cmpd # | R | R' | ER IC$_{50}$ (μM) | AR IC$_{50}$ (μM) |
|---|---|---|---|---|
| 13 | isopropyl | benzyl | NB | NB |
| 14 | isopropyl | 1-naphthylmethyl | NB | NB |
| 15 | benzyl | isopropyl | 5 | 1.8 |
| 16 | 1-naphthylmethyl | isopropyl | NB | NB |

Table 3: Solubilized CBIs in ER TR-FRET assay

| Cmpd # | R | ER $K_i$ (μM) |
|---|---|---|
| 21 | –CH₃ | 9.4 |
| 22 | ethyl | 3.3 |
| 23 | propyl | 1.45 |
| 24 | butyl | 0.74 |
| 25 | pentyl | 25 |
| 26 | hexyl | 31 |
| 27 | isopropyl | 27.5 |
| 28 | isobutyl | 0.78 |
| 29 | isopentyl | 0.55 |
| 30 | benzyl | 1.6 |

Table 4: Miscellaneous cyclobutane CBIs in ER TR-FRET assay
| Cmpd # | Structure | ER $K_i$ (µM) |
|---|---|---|
| 31 | 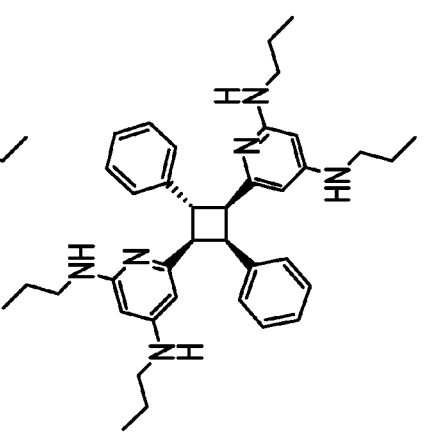 | 0.92 |
| 32 | 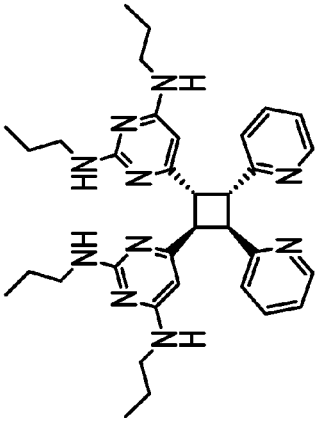 | 4.0 |
| 33 | 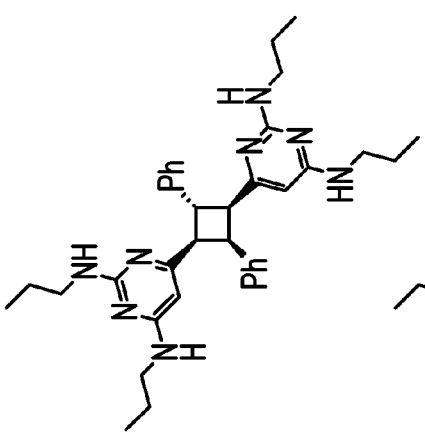 | 17 |
| 34 | 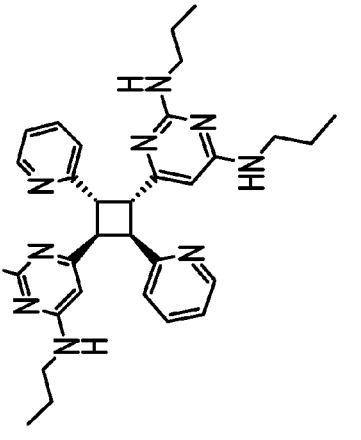 | 4.0 |
FIG. 12

ER and AR TR-FRET Assay
 —ERα LBD selectively biotinylated
 —AR-LBD with glutathione-S-transferase (GST) tag
 —Streptavidin-Tb (ER) or anti-GST-Tb antibody (AR) as FRET donor
 —Fluorescein-labeled SRC3, with 3 LXXLL motifs as FRET acceptor
 —SRC1-Box II as control (LXXLL motif)
 —Performed in presence of 17β-estradiol or DHT agonist Prostate Cancer
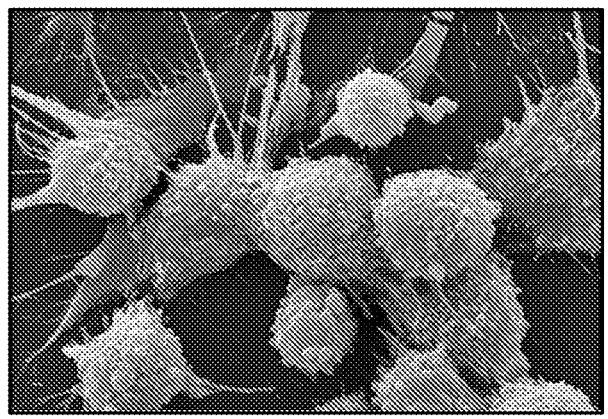
Most common tumor among men
In United States, in 2012
240,000+ diagnoses
~28,000 deaths
Current therapies
Androgen deprivation
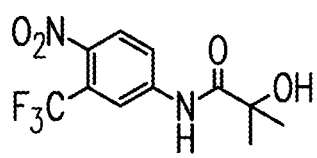
Hydroxy-flutamide
(OHF)
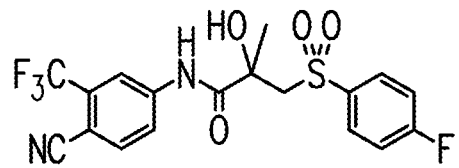
Bicalutamide
(CSX)
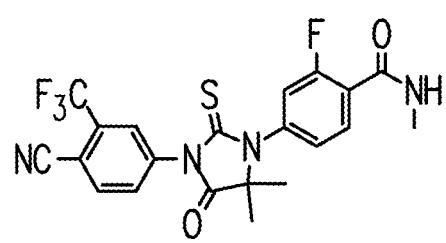
Enzalutamide
(MDV3100)
FIG. 22

AR Ligand binding domain (orange)
bound to testosterone (blue)
Image made in VMD using PMBID 2AM9

▒ orange    ■ blue

<u>Castration-Resistant Prostate Cancer (CRPC)</u>

—Reactivation of the wild type (wt) AR
—Mutations in AR that result in therapy resistance
        OHF        T877A
        CSX        W741C
        MDV3100  F876L CB-7 increases survival of mice in LNCaP (AR-T877A) xenograft model of prostate cancer at comparable concentrations to MDV3100.

CB-7 decreases tumor size in an LNCaP (AR-T877A) xenograft model of prostate cancer.

| Compound | IC$_{50}$ ($\mu$M) | | | |
|---|---|---|---|---|
| | WT | T877A | W741C | F876L |
| CB-1 | >20 | 0.81 | 2.36 | 1.64 |
| CB-2 | >20 | 2.83 | 8.69 | 1.04 |
| CB-3 | >20 | 1.02 | 6.33 | 1.95 |
| CB-4 | >20 | 4.38 | >20 | 0.86 |

FIG. 25A

| Compound | | IC$_{50}$ ($\mu$M) | | | |
|---|---|---|---|---|---|
| | | WT | T877A | W741C | F876L |
| CB-5 | 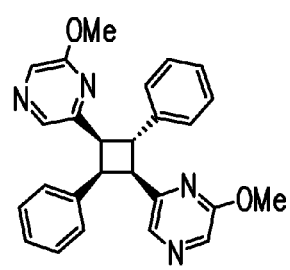 | >20 | 0.89 | 3.43 | 0.91 |
| CB-6 | 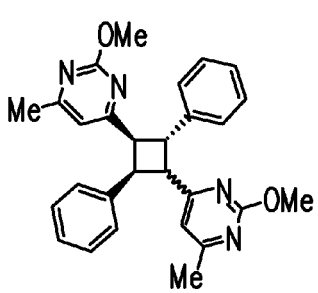 | >20 | 0.36 | 2.25 | 0.46 |
| CB-7 | 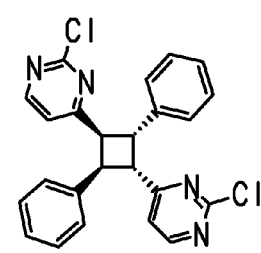 | >20 | 0.20 | 1.15 | 0.36 |
| CB-8 | 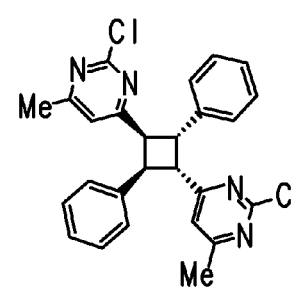 | >20 | 0.90 | 3.56 | 0.96 |
| MDV3100 | | 0.16 | 0.21 | 3.15 | Agonist |
| CSX | | 0.14 | 0.34 | >20 | 0.26 |
| OHF | | 0.05 | >20 | 0.06 | 0.07 |
FIG. 25B CBs compete with 3H-R1881 for binding to AR in whole cell binding assays in transfected HEK293 cells.

| Cmpd | IC$_{50}$ ($\mu$M) | | | |
| --- | --- | --- | --- | --- |
| | WT | F 876L | T 877A | W741C |
| 1 | 97.0 | 7.34 | 1.24 | 2.21 |
| 10 | 8.30 | 0.65 | 0.81 | 3.53 |
| 15 | 16.6 | 1.11 | 1.19 | 0.91 |
| MDV | 0.16 | 0.04 | 0.37 | 5.57 |
| CSX | 0.69 | 1.27 | 1.78 | 0.49 |
| OHF | 0.06 | 0.46 | 0.08 | 0.35 |

FIG. 48E

TETRA-ARYL CYCLOBUTANE INHIBITORS OF ANDROGEN RECEPTOR ACTION FOR THE TREATMENT OF HORMONE REFRACTORY CANCER

RELATED APPLICATIONS

This application claims priority to U.S. Provisional Patent Application No. 61/883,231 filed on Sep. 27, 2013 and U.S. Provisional Patent Application No. 61/925,603 filed on Jan. 9, 2014, the disclosures of each of which are incorporated by reference herein in their entirety.

FEDERAL FUNDING LEGEND

This invention was made with government support under NIH NIDDK Grant No. 1 F30 DK083899 A awarded by the National Institutes of Health, NIH NIDDK Grant No. F30 ES 016484 awarded by the National Institutes of Health, and DOD Grant No. A2360 Army W81XWH-10-1-0180 awarded by the United States Army. The government has certain rights in the invention.

FIELD OF THE INVENTION

The present invention relates to novel, substituted cyclobutane-core (CB) inhibitors of Androgen Receptor Action, and methods of using such inhibitors, for the treatment of cancers. These inhibitors are tetra-substituted cyclobutane derivatives and are useful for treating, for example, hormone-refractory cancers such as prostate cancer. Also provided are pharmaceutical compositions containing these inhibitors.

BACKGROUND

The androgen receptor (AR) plays an integral role in primary and secondary male sexual development. While abnormalities resulting in an attenuation of the AR response to endogenous hormones (testosterone and its reduced form, 5α-dihydrotestosterone or DHT) produce male infertility and feminization, excessive stimulation of AR can also result in pathologies. The most commonly presented diseases of this type are prostate cancer and the related, but benign, prostatic hyperplasia. Both of these diseases are responsive to endocrine-based treatments that attempt to suppress tumor/prostate growth either by direct administration of an AR antagonist or by 'chemical castration' techniques that result in decreased gonadal production of the endogenous agonist, testosterone.

Prostate tumors treated with current clinically-applied antiandrogens generally develop resistance to these drugs over the course of months to a few years; at this point the cancer will continue to progress despite administration of the compound. The major benefit of the cyclobutane-core AR inhibitors (CB) is their ability to inhibit activation of AR under cellular conditions that are resistant to treatment using current clinically-available antiandrogens (i.e., flutamide, bicalutamide, nilutamide, enzalutamide, and cyproterone acetate). Consequently, the CB antiandrogens could either be used as a first line hormone therapy for prostate cancer (usually post radiation and/or surgery), or as a second line therapy after an initial course of antiandrogen therapy fails.

Initial cell-based results suggest that the CB antiandrogens may prove especially efficacious in those patients with certain AR point mutations, arising after initial treatment with an antiandrogen. Most notable among these is the mutation known as the LNCaP mutation, T877A, which is estimated to appear in as many as 30% of prostate cancer patients previously treated with flutamide. As such, this drug may prove to be a viable selective, targeted therapy for patients having this specific mutation, allowing for successful treatment of the cancer with minimal disruption of the natural hormonal actions of the wild type androgen receptors present in non-cancerous tissues. This drug may provide similar selective, targeted therapy for patients having other point mutations in AR that confer resistance to other AR antagonists. As far as we are aware, this form of selective, targeted hormonal therapy has not been considered before: it has novelty and the potential of significantly reducing the side effects (impaired sexual activity, muscle wasting, etc.) associated with current prostate cancer hormone therapy in this select subset of patients.

SUMMARY OF THE INVENTION

The present disclosure describes herein the design, synthesis and analysis of a group of novel inhibitors of the androgen receptor: cyclobutane-core (CB) antiandrogens. These compounds bind to the hormone binding site of the receptor, displacing endogenous ligand and causing the protein to adopt a unique antagonist conformation. In this conformation, AR does not recruit the coactivator machinery necessary for DNA transcription and consequently, AR-dependent cells (i.e., prostate cancer cells) cease their growth and eventually regress. The CB antiandrogens have shown efficacy in a number of different cell-based assays that approximate the prostate cancer tumor response, including hormone-refractory models in which the androgen receptor contains a common point mutation associated with the accommodation of current clinical AR antagonists (i.e., hydroxyflutamide, bicalutamide, and enzalutamide) such that they become AR agonists, as well as in models in which the wild type and/or mutant receptor is overexpressed, an important clinical hallmark of hormone refractory prostate cancer. These compounds are noteworthy in their ability to suppress androgen receptor activity below the levels observed with unliganded AR as measured by proliferation, luciferase transfection, and endogenous gene expression assays.

The present invention relates to a compound having the formula:

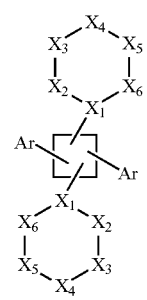

wherein in each ring system,

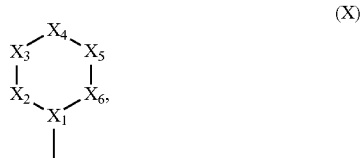

each $X_1$ is —C≡;
each of $X_2$, $X_3$, $X_4$, $X_5$, and $X_6$ is independently selected from —CH≡, —CR≡, —CR$^2$≡, —NH—, —NR$^1$—, —NR$^2$—, —N≡, and —CO—;
such that each ring system (X) contains 1 to 3 nitrogen atoms, each ring system (X) contains no more than 2-CO—, and each ring system (X) contains no more than one of each $R^1$ and each $R^2$;
each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocycle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —OR$^3$, (o) —NR$^3$R$^3$, (p) —CN, (q) —N$_3$, (r) —SR$^3$, (s) —SOR$^3$, (t) —SO$_2$R$^3$, (u) —COOR$^3$, (v) —COR$^3$, (w) —CONR$^3$R$^3$, (x) —NR$^3$COR$^3$—, (y) —NR$^3$CONR$^3$R$^3$, (z) —($C_1$-$C_8$ alkyl)OR$^3$, (aa) —($C_1$-$C_8$ alkyl)NR$^3$R$^3$, (bb) —($C_1$-$C_8$ alkyl)SR$^3$, (cc) —($C_1$-$C_8$ alkyl)SOR$^3$, (dd) —($C_1$-$C_8$ alkyl)SO$_2$R$^3$, (ee) —($C_1$-$C_8$ alkyl)COOR$^3$, (ff) —($C_1$-$C_8$ alkyl)COR$^3$, (gg) —($C_1$-$C_8$ alkyl)CONR$^3$R$^3$, (hh) —($C_1$-$C_8$ alkyl)NR$^3$COR$^3$, and (ii) —($C_1$-$C_8$ alkyl)NR$^3$CONR$^3$R$^3$,
wherein each of (e) through (j) immediately recited above is optionally substituted with one or more F, Cl, Br, I, —OH, —SH, —NH$_2$, —NH($C_1$-$C_8$ alkyl), or —N($C_1$-$C_8$ alkyl)$_2$ and wherein each of (k) through (l) immediately recited above is optionally substituted with one or more $R^4$ or $R^5$;
each $R^3$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (k) immediately recited above is optionally substituted with one or more $R^5$;
each $R^4$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, and (j) —$C_8$ cycloalkynyl, wherein each of (e) through (j) immediately recited above is optionally substituted with one or more $R^5$;
each $R^5$ is independently selected from (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$,
each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof,
wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —OR$^6$, (m) —NR$^6$R$^6$, (n) —CN, (o) —N$_3$, -(p) —SR$^6$, (q) —SOR$^6$, (r) —SO$_2$R$^6$, (s) —COOR$^6$, (t) —COR$^6$, (u) —CONR$^6$R$^6$, (v) —NR$^6$COR$^6$—, and (w) —NR$^6$CONR$^6$R$^6$,
wherein each of (e) through (k) immediately recited above is optionally substituted with one or more F, Cl, Br, I, —OH, —SH, —NH$_2$, —NH($C_1$-$C_8$ alkyl), and —N($C_1$-$C_8$ alkyl)$_2$;
each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (i) immediately recited above is optionally substituted with one or more $R^7$; and
each $R^7$ is independently selected from one or more (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$; and
or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

The present invention also relates to pharmaceutical compositions containing these compounds. The present invention also relates to methods of using these compounds and pharmaceutical compositions for the treatment of hormone-refractory cancers.

DESCRIPTION OF THE FIGURES

FIG. 2 depicts the estrogen receptor (ER) coactivator binding, showing the coactivator binding groove of the ER ligand binding domain (LBD) interacting with the steroid receptor coactivator (SRC) LXXLL motifs.

FIG. 3 depicts the androgen receptor (AR) coactivator binding.

FIG. 12 depicts data for various cyclobutane compounds in an ER TR-FRET (estrogen receptor time-resolved fluorescence energy transfer) assay for compounds 31 to 34, as shown in Table 4 of the figure.

FIG. 22 is an image of prostate cancer cells.

FIGS. 25A and B depict data on androgen receptor mutant selectivity for various cyclobutane inhibitor compounds.

FIG. 31A shows t½ vs. interaction energy.

DETAILED DESCRIPTION OF THE INVENTION

Figure 1:
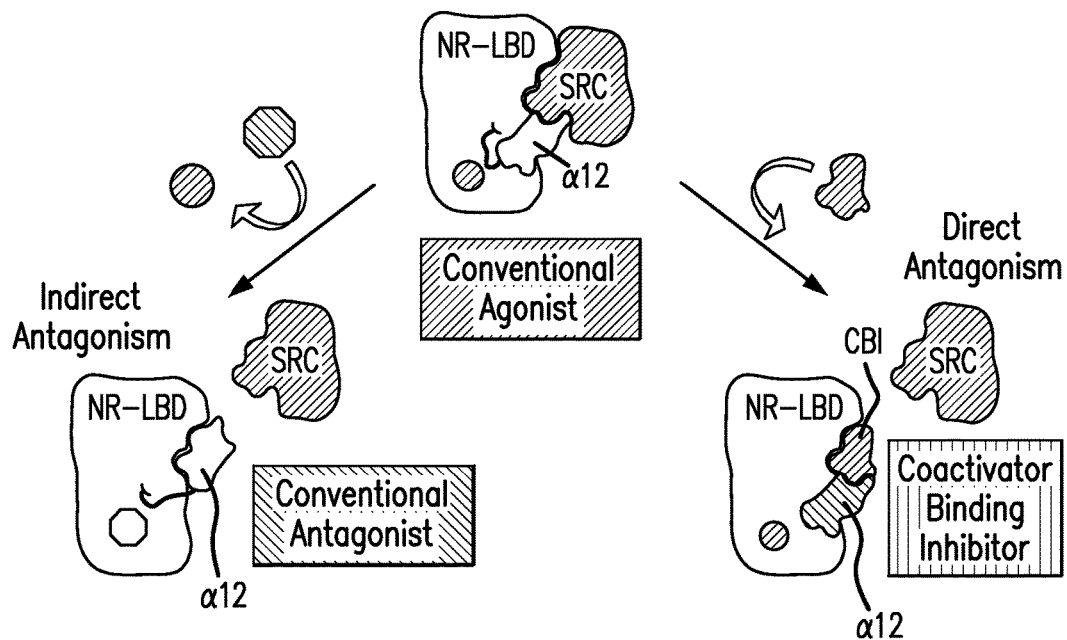
FIG. 1 depicts the nuclear receptor ligand binding domain (NROLBD) and the cyclobutane inhibitors (CBIs) in the presence of an agonist.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

The approach disclosed here is innovative because it presents novel compounds for treating hormone refractory prostate cancer, especially under cellular conditions that are resistant to treatment using current clinically-available anti-androgens (i.e., flutamide, bicalutamide, nilutamide, enzalutamide, and cyproterone acetate).

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

Chemical Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. In this application, the use of "or" means "and/or" unless stated otherwise. Furthermore, use of the term "including" as well as other forms, such as "include", "includes," and "included," is not limiting.

An "alkoxy" group refers to a (alkyl)O— group, where alkyl is as defined herein.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The "alkyl" moiety may have 1 to 8 carbon atoms (whenever it appears herein, a numerical range such as "1 to 8" refers to each integer in the given range; e.g., "1 to 8 carbon atoms" means that the alkyl group may consist of 1 carbon atom, 2 carbon atoms, 3 carbon atoms, etc., up to and including 8 carbon atoms, although the present definition also covers the occurrence of the term "alkyl" where no numerical range is designated). It is also intended that a numerical range, as described in the foregoing sentence, is used in conjunction with other chemical groups such as "alkenyl", etc. The alkyl group could also be a "lower alkyl" having 1 to 5 carbon atoms. The alkyl group of the compounds described herein may be designated as "$C_1$-$C_8$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkylamine" refers to the —N(alkyl)$_x$H$_y$ group, where x and y are selected from the group x=1, y=1 and x=2, y=0. When x=2, the alkyl groups, taken together, can optionally form a cyclic ring system.

The term "alkenyl" refers to a type of alkyl group in which the first two atoms of the alkyl group form a double bond that is not part of an aromatic group. That is, an alkenyl group begins with the atoms C(R)=C—R, wherein R refers to the remaining portions of the alkenyl group, which may be the same or different. Non-limiting examples of an alkenyl group include —CH=CH—, —C(CH$_3$)=CH—, —CH=CCH$_3$— and —C(CH$_3$)=CCH$_3$—. The alkenyl moiety may be branched, straight chain, or cyclic (in which case, it would also be known as a "cycloalkenyl" group).

The term "alkynyl" refers to a type of alkyl group in which the first two atoms of the alkyl group form a triple bond. That is, an alkynyl group begins with the atoms —C≡CR, wherein R refers to the remaining portions of the alkynyl group, which may be the same or different. Non-limiting examples of an alkynyl group include —C≡CH, —C≡CCH$_3$, and —C≡CH$_2$CH$_3$. The "R" portion of the alkynyl moiety may be branched, straight chain, or cyclic.

An "amide" is a chemical moiety with formula —C(O)NHR or —NHC(O)R, where R is selected from the group consisting of alkyl, cycloalkyl, aryl, heteroaryl (bonded through a ring carbon) and heteroalicyclic (bonded through a ring carbon). An amide may be an amino acid or a peptide molecule attached to any compound of the present invention, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

The term "aromatic" or "aryl" refers to an aromatic group which has at least one ring having a conjugated pi electron system and includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms.

The term thus distinguishes carbocyclic from heterocyclic rings in which the ring backbone contains at least one atom which is different from carbon.

The term "Boc" refers to the tert-butyloxycarbonyl group which is a common protecting group in synthetic chemistry for amino groups The term "bond" or "single bond" refers to a chemical bond between two atoms, or two moieties when the atoms joined by the bond are considered to be part of larger substructure.

A "cyano" group refers to a —CN group.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

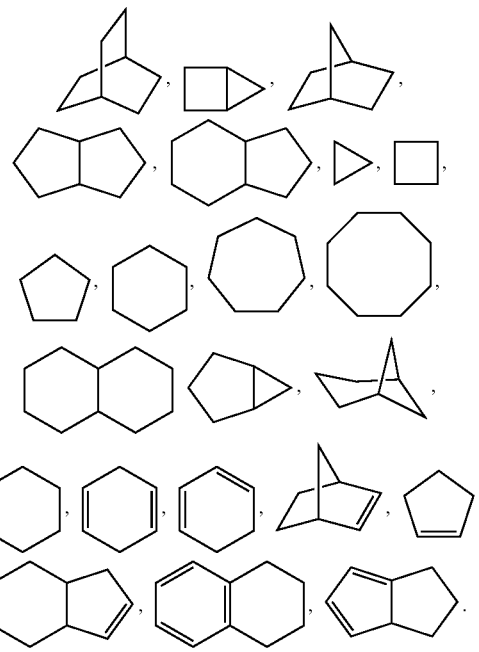

and the like.

The term "ester" refers to a chemical moiety with forumula COOR, where R is selected from the group consisting of alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety. The term "halo" or, alternatively, "halogen" means fluoro, chloro, bromo or iodo.

The terms "haloalkyl," "haloalkenyl," "haloalkynyl" and "haloalkoxy" include alkyl, alkenyl, alkynyl and alkoxy structures that are substituted with one or more halo groups or with combinations thereof. The terms "fluoroalkyl" and "fluoroalkoxy" include haloalkyl and haloalkoxy groups, respectively, in which the halo is fluorine.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group may be fused or non-fused. Illustrative examples of heteroaryl groups include the following moieties:

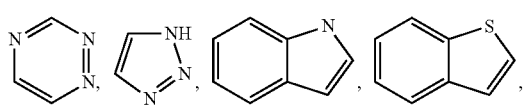

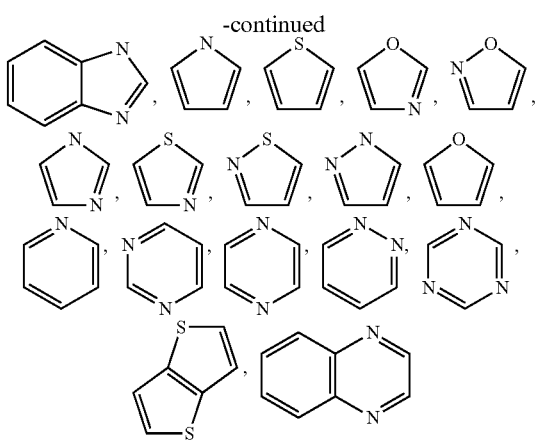

and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one.

A "heteroalicyclic" group refers to a cycloalkyl group that includes at least one heteroatom selected from nitrogen, oxygen and sulfur, i.e., non-aromatic heterocycle groups.

The radicals may be fused with an aryl or heteroaryl. Illustrative examples of heterocycloalkyl groups, also referred to as heteroalicyclic groups, include:

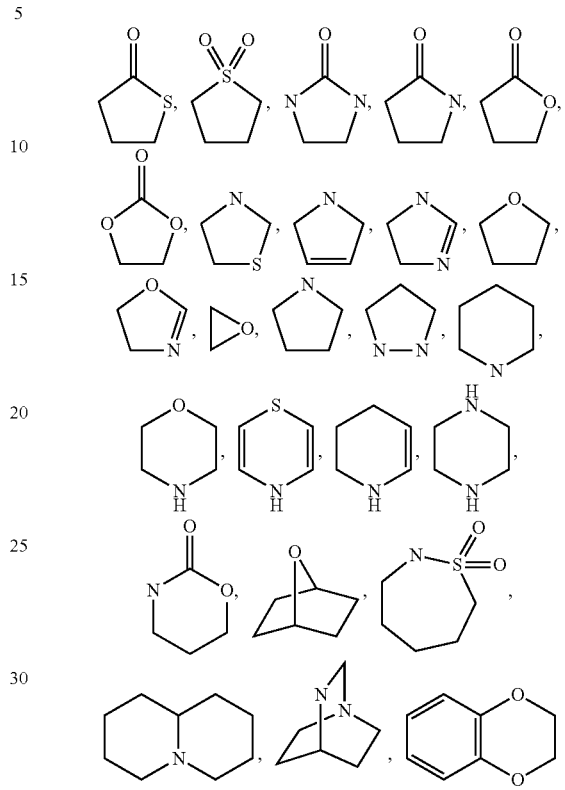

and the like. The term heteroalicyclic also includes all ring forms of the carbohydrates, including but not limited to the monosaccharides, the disaccharides and the oligosaccharides.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

An "isocyanato" group refers to a —NCO group.

An "isothiocyanato" group refers to a —NCS group.

A "mercaptyl" group refers to a (alkyl)S— group.

The term "moiety" refers to a specific segment or functional group of a molecule. Chemical moieties are often recognized chemical entities embedded in or appended to a molecule.

A "sulfinyl" group refers to a —S(=O)—R, where R is selected from the group consisting of alkyl, cycloalkyl, aryl, heteroaryl (bonded through a ring carbon) and heteroalicyclic (bonded through a ring carbon)

A "sulfonyl" group refers to a —S(=O)₂—R, where R is selected from the group consisting of alkyl, cycloalkyl, aryl, heteroaryl (bonded through a ring carbon) and heteroalicyclic (bonded through a ring carbon)

The term "tautomer" refers to one or more organic compounds that are interconvertible by a chemical reaction called tautomeriazation. Usually, the reaction involves the migration of a hydrogen atom or proton, accompanied by a switch of a single bond and adjacent double bond or a double bond and adjacent single bond. A non limiting example of a tautomerization between a pair of tautomers is the carbonyl-enol tautomerization.

A "thiocyanato" group refers to a —CNS group.

The term "optionally substituted" or "substituted" means that the referenced group may be substituted with one or more additional group(s) individually and independently selected as described herein. Nonlimiting examples of such substituents are selected from, for example, alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, carbonyl, thiocarbonyl, isocyanato, thiocyanato, isothiocyanato, nitro, perhaloalkyl, perfluoroalkyl, silyl, and amino, including mono- and di-substituted amino groups, and the protected derivatives thereof. By way of example an optional substituents may be $L_sR_s$, wherein each $L_s$ is independently selected from a bond, —O—, —C(=O)—, —S—, —S(=O)—, —S(=O)$_2$—, —NH—, —NHC(O)—, —C(O)NH—, —S(=O)$_2$NH—, —NHS(=O)$_2$—, —OC(O)NH—, —NHC(O)O—, -(substituted or unsubstituted $C_1$-$C_6$ alkyl), or -(substituted or unsubstituted $C_2$-$C_6$ alkenyl); and each $R_s$ is independently selected from H, (substituted or unsubstituted lower alkyl), (substituted or unsubstituted lower cycloalkyl), heteroaryl, or heteroalkyl. The protecting groups that may form the protective derivatives of the above substituents are known to those of skill in the art and may be found in references such as Greene and Wuts, above.

The compounds presented herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

In the formulas for the compounds of the present invention, variable or undefined substitution positions and stereochemistry are indicated using common chemical structure drawing conventions such as "line through a ring system", "squiggly bonds", or a "straight line bond" in place of a "bold wedge bond" or "dashed wedge bond", which by convention indicate a substituent coming out from the indicated plane ("bold wedge bond") or going away from the indicated plane ("dashed wedge bond").

The methods and formulations described herein may also include the use of N-oxides, crystalline forms (also known as polymorphs), or pharmaceutically acceptable salts of compounds described herein, as well as active metabolites of these compounds having the same type of activity. In some situations, compounds may exist as tautomers. In such instances, all tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Certain Pharmaceutical Terminology

The term "acceptable" or "pharmaceutically acceptable" with respect to a compound, formulation, composition, ingredient, salt, or the like, as used herein, means having no persistent detrimental effect on the general health of the subject being treated.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "cancer,' as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "enzymatically cleavable linker," as used herein refers to unstable or degradable linkages which may be degraded by one or more enzymes.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of any of the compounds of the present invention, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description. All references cited herein, including patents, patent applications, and publications, are hereby incorporated by reference in their entirety.

The compounds described herein may have asymmetric centers or non-superimposable mirror image or enatiomeric forms, and such compounds may be isolated in optically active or racemic forms. It is well known in the art how to prepare optically active forms, such as by resolution of racemic forms or by synthesis from optically active starting materials. Many geometric isomers of olefins, carbon-nitrogen double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, enantiomeric, diastereomeric, racemic, and geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The methods of treatment using the compounds or pharmaceutical compositions of the present invention, in various embodiments also include the compounds of the present invention in the manufacture of a medicament for the desired treatment.

The invention can be embodied in other specific forms without departing from the spirit or essential characteristics thereof. The foregoing embodiments are to be considered in all respects illustrative rather than limiting on the invention described herein. In the various embodiments where the term comprises is used, it is also contemplated to include consists or consisting essentially of, and also consists of or consisting of. Further, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

One aspect of the present invention disclosure provides a compound having the formula:

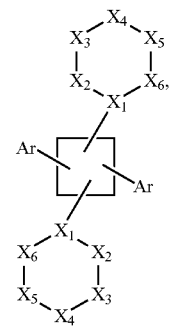

wherein in each ring system,

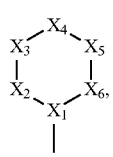
(X)

each $X_1$ is —C═;
each of $X_2$, $X_3$, $X_4$, $X_5$, and $X_6$ is independently selected from —CH═, —CR$^1$═, —CR$^2$═, —NH—, —NR$^1$—, —NR$^2$—, —N═, and —CO—;
such that each ring system (X) contains 1 to 3 nitrogen atoms, each ring system (X) contains no more than 2-CO—, and each ring system (X) contains no more than one of each $R^1$ and each $R^2$;
each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —OR$^3$, (o) —NR$^3$R$^3$, (p) —CN, (q) —N$_3$, (r) —SR$^3$, (s) —SOR$^3$, (t) —SO$_2$R$^3$, (u) —COOR$^3$, (v) —COR$^3$, (w) —CONR$^3$R$^3$, (x) —NR$^3$COR$^3$—, (y) —NR$^3$CONR$^3$R$^3$, (z) —($C_1$-$C_8$ alkyl)OR$^3$, (aa) —($C_1$-$C_8$ alkyl)NR$^3$R$^3$, (bb) —($C_1$-$C_8$ alkyl)SR$^3$, (cc) —($C_1$-$C_8$ alkyl)SOR$^3$, (dd) —($C_1$-$C_8$ alkyl)SO$_2$R$^3$, (ee) —($C_1$-$C_8$ alkyl)COOR$^3$, (ff) —($C_1$-$C_8$ alkyl)COR$^3$, (gg) —($C_1$-$C_8$ alkyl)CONR$^3$R$^3$, (hh) —($C_1$-$C_8$ alkyl)NR$^3$COR$^3$, and (ii) —($C_1$-$C_8$ alkyl)NR$^3$CONR$^3$R$^3$,
wherein each of (e) through (j) immediately recited above is optionally substituted with one or more F, Cl, Br, I, —OH, —SH, —NH$_2$, —NH($C_1$-$C_8$ alkyl), or —N($C_1$-$C_8$ alkyl)$_2$ and
wherein each of (k) through (l) immediately recited above is optionally substituted with one or more $R^4$ or $R^5$;
each $R^3$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (k) immediately recited above is optionally substituted with one or more $R^5$;
each $R^4$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, and (j) —$C_8$ cycloalkynyl, wherein each of (e) through (j) immediately recited above is optionally substituted with one or more $R^5$;
each $R^5$ is independently selected from (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$,
each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof,
wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —OR$^6$, (m) —NR$^6$R$^6$, (n) —CN, (o) —N$_3$, -(p) —SR$^6$, (q) —SOR$^6$, (r) —SO$_2$R$^6$, (s) —COOR$^6$, (t) —COR$^6$, (u) —CONR$^6$R$^6$, (v) —NR$^6$COR$^6$—, and (w) —NR$^6$CONR$^6$R$^6$,
wherein each of (e) through (k) immediately recited above is optionally substituted with one or more F, Cl, Br, I, —OH, —SH, —NH$_2$, —NH($C_1$-$C_8$ alkyl), and —N($C_1$-$C_8$ alkyl)$_2$;
each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (i) immediately recited above is optionally substituted with one or more $R^7$; and
each $R^7$ is independently selected from one or more (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$; and
or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound having the formula:

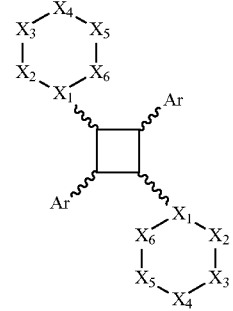

wherein in each ring system,

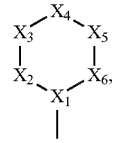
(X)

each $X_1$ is —C═;
each of $X_2$, $X_3$, $X_4$, $X_5$, and $X_6$ is independently selected from —CH═, —CR═, —CR$^2$═, —NH—, —NR$^1$-, —NR$^2$-, —N═, and —CO—;
such that each ring system (X) contains 1 to 3 nitrogen atoms, each ring system (X) contains no more than 2-CO—, and each ring system (X) contains no more than one of each $R^1$ and each $R^2$;

each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocycle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —$OR^3$, (o) —$NR^3R^3$, (p) —CN, (q) —$N_3$, (r) —$SR^3$, (s) —$SOR^3$, (t) —$SO_2R^3$, (u) —$COOR^3$, (v) —$COR^3$, (w) —$CONR^3R^3$, (x) —$NR^3COR^3$—, (y) —$NR^3CONR^3R^3$, (z) —($C_1$-$C_8$ alkyl)$OR^3$, (aa) —($C_1$-$C_8$ alkyl)$NR^3R^3$, (bb) —($C_1$-$C_8$ alkyl)$SR^3$, (cc) —($C_1$-$C_8$ alkyl)$SOR^3$, (dd) —($C_1$-$C_8$ alkyl)$SO_2R^3$, (ee) —($C_1$-$C_8$ alkyl)$COOR^3$, (ff) —($C_1$-$C_8$ alkyl)$COR^3$, (gg) —($C_1$-$C_8$ alkyl)$CONR^3R^3$, (hh) —($C_1$-$C_8$ alkyl)$NR^3COR^3$, and (ii) —($C_1$-$C_8$ alkyl)$NR^3CONR^3R^3$, wherein each of (e) through (j) immediately recited above is optionally substituted with one or more F, Cl, Br, I, —OH, —SH, —$NH_2$, —NH($C_1$-$C_8$ alkyl), or —N($C_1$-$C_8$ alkyl)$_2$ and wherein each of (k) through (l) immediately recited above is optionally substituted with one or more $R^4$ or $R^5$;

each $R^3$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (k) immediately recited above is optionally substituted with one or more $R^5$;

each $R^4$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, and (j) —$C_8$ cycloalkynyl, wherein each of (e) through (j) immediately recited above is optionally substituted with one or more $R^5$;

each $R^5$ is independently selected from (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^6$, (r) —$SO_2R^6$, (s) —$COOR^6$, (t) —$COR^6$, (u) —$CONR^6R^6$, (v) —$NR^6COR^6$—, and (w) —$NR^6CONR^6R^6$, wherein each of (e) through (k) immediately recited above is optionally substituted with one or more F, Cl, Br, I, —OH, —SH, —$NH_2$, —NH($C_1$-$C_8$ alkyl), and —N($C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (i) immediately recited above is optionally substituted with one or more $R^7$; and each $R^7$ is independently selected from one or more (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$; and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound having the formula:

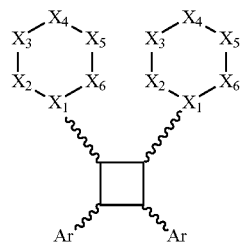

wherein in each ring system,

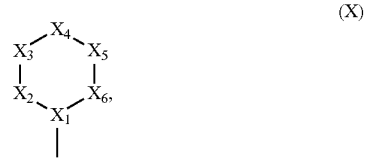

(X)

each $X_1$ is —C=;
each of $X_2$, $X_3$, $X_4$, $X_5$, and $X_6$ is independently selected from —CH=, —$CR^1$=, —$CR^2$=, —NH—, —$NR^1$—, —$NR^2$—, —N=, and —CO—;
such that each ring system (X) contains 1 to 3 nitrogen atoms, each ring system (X) contains no more than 2-CO—, and each ring system (X) contains no more than one of each $R^1$ and each $R^2$;

each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocycle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —$OR^3$, (o) —$NR^3R^3$, (p) —CN, (q) —$N_3$, (r) —$SR^3$, (s) —$SOR^3$, (t) —$SO_2R^3$, (u) —$COOR^3$, (v) —$COR^3$, (w) —$CONR^3R^3$, (x) —$NR^3COR^3$—, (y) —$NR^3CONR^3R^3$, (z) —($C_1$-$C_8$ alkyl)$OR^3$, (aa) —($C_1$-$C_8$ alkyl)$NR^3R^3$, (bb) —($C_1$-$C_8$ alkyl)$SR^3$, (cc) —($C_1$-$C_8$ alkyl)$SOR^3$, (dd) —($C_1$-$C_8$ alkyl)$SO_2R^3$, (ee) —($C_1$-$C_8$ alkyl)$COOR^3$, (ff) —($C_1$-$C_8$ alkyl)$COR^3$, (gg) —($C_1$-$C_8$ alkyl)$CONR^3R^3$, (hh) —($C_1$-$C_8$ alkyl)$NR^3COR^3$, and (ii) —($C_1$-$C_8$ alkyl)$NR^3CONR^3R^3$, wherein each of (e) through (j) immediately recited above is optionally substituted with one or more F, Cl, Br, I, —OH, —SH, —NH$_2$, —NH(C$_1$-C$_8$ alkyl), or —N(C$_1$-C$_8$ alkyl)$_2$ and wherein each of (k) through (l) immediately recited above is optionally substituted with one or more R$^4$ or R;

each R$^3$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (k) immediately recited above is optionally substituted with one or more R$^5$;

each R$^4$ is independently selected from (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, and (j) —C$_8$ cycloalkynyl, wherein each of (e) through (j) immediately recited above is optionally substituted with one or more R$^5$;

each R$^5$ is independently selected from (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, (j) —C$_8$ cycloalkynyl, (k) phenyl, (l) —OR$^6$, (m) —NR$^6$R$^6$, (n) —CN, (o) —N$_3$, -(p) —SR$^6$, (q) —SOR$^6$, (r) —SO$_2$R$^6$, (s) —COOR$^6$, (t) —COR$^6$, (u) —CONR$^6$R$^6$, (v) —NR$^6$COR$^6$—, and (w) —NR$^6$CONR$^6$R$^6$, wherein each of (e) through (k) immediately recited above is optionally substituted with one or more F, Cl, Br, I, —OH, —SH, —NH$_2$, —NH(C$_1$-C$_8$ alkyl), and —N(C$_1$-C$_8$ alkyl)$_2$;

each R$^6$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (i) immediately recited above is optionally substituted with one or more R$^7$; and each R$^7$ is independently selected from one or more (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$; and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound having the formula:

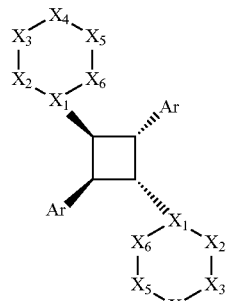

wherein in each ring system,

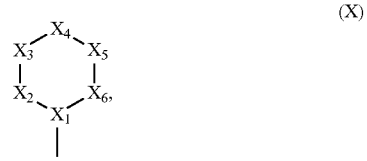

(X)

each X$_1$ is —C=;
each of X$_2$, X$_3$, X$_4$, X$_5$, and X$_6$ is independently selected from —CH=, —CR$^1$=, —CR$^2$=, —NH—, —NR$^1$—, —NR$^2$—, —N=, and —CO—;
such that each ring system (X) contains 1 to 3 nitrogen atoms, each ring system (X) contains no more than 2-CO—, and each ring system (X) contains no more than one of each R$^1$ and each R$^2$;

each R$^1$ and R$^2$ is independently selected from (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, (j) —C$_8$ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —OR$^3$, (o) —NR$^3$R$^3$, (p) —CN, (q) —N$_3$, (r) —SR$^3$, (s) —SOR$^3$, (t) —SO$_2$R$^3$, (u) —COOR$^3$, (v) —COR$^3$, (w) —CONR$^3$R$^3$, (x) —NR$^3$COR$^3$—, (y) —NR$^3$CONR$^3$R$^3$, (z) —(C$_1$-C$_8$ alkyl)OR$^3$, (aa) —(C$_1$-C$_8$ alkyl)NR$^3$R$^3$, (bb) —(C$_1$-C$_8$ alkyl)SR$^3$, (cc) —(C$_1$-C$_8$ alkyl)SOR$^3$, (dd) —(C$_1$-C$_8$ alkyl)SO$_2$R$^3$, (ee) —(C$_1$-C$_8$ alkyl)COOR$^3$, (ff) —(C$_1$-C$_8$ alkyl)COR$^3$, (gg) —(C$_1$-C$_8$ alkyl)CONR$^3$R$^3$, (hh) —(C$_1$-C$_8$ alkyl)NR$^3$COR$^3$, and (ii) —(C$_1$-C$_8$ alkyl)NR$^3$CONR$^3$R$^3$, wherein each of (e) through (j) immediately recited above is optionally substituted with one or more F, Cl, Br, I, —OH, —SH, —NH$_2$, —NH(C$_1$-C$_8$ alkyl), or —N(C$_1$-C$_8$ alkyl)$_2$ and wherein each of (k) through (l) immediately recited above is optionally substituted with one or more R$^4$ or R$^5$;

each R$^3$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (k) immediately recited above is optionally substituted with one or more R$^5$;

each R$^4$ is independently selected from (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, and (j) —C$_8$ cycloalkynyl, wherein each of (e) through (j) immediately recited above is optionally substituted with one or more R$^5$;

each R$^5$ is independently selected from (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, (j) —C$_8$ cycloalkynyl, (k) phenyl, (l) —OR$^6$, (m) —NR$^6$R$^6$, (n) —CN, (o) —N$_3$, -(p) —SR$^6$, (q) —SOR$^6$, (r) —SO$_2$R$^6$, (s) —COOR$^6$, (t) —COR$^6$, (u) —CONR$^6$R$^6$, (v) —NR$^6$COR$^6$—, and (w) —NR$^6$CONR$^6$R$^6$, wherein each of (e) through (k) immediately recited above is optionally substituted with one or more F, Cl, Br, I, —OH, —SH, —NH$_2$, —NH(C$_1$-C$_8$ alkyl), and —N(C$_1$-C$_8$ alkyl)$_2$;

each R$^6$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (i) immediately recited above is optionally substituted with one or more R$^7$; and each R$^7$ is independently selected from one or more (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$; and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound having the formula:

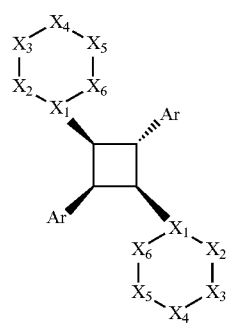

wherein in each ring system,

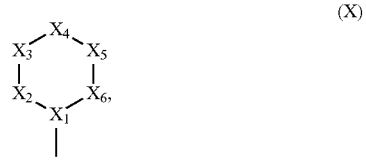

each X$_1$ is —C=;
each of X$_2$, X$_3$, X$_4$, X$_5$, and X$_6$ is independently selected from —CH=, —CR$^1$=, —CR$^2$=, —NH—, —NR$^1$—, —NR$^2$—, —N=, and —CO—;

such that each ring system (X) contains 1 to 3 nitrogen atoms, each ring system (X) contains no more than 2-CO—, and each ring system (X) contains no more than one of each R$^1$ and each R$^2$;

each R$^1$ and R$^2$ is independently selected from (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, (j) —C$_8$ cycloalkynyl, (k) phenyl, (l) a 7 to 10-membered saturated, unsaturated, or aromatic fused bicyclic carbocycle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —OR$^3$, (o) —NR$^3$R$^3$, (p) —CN, (q) —N$_3$, (r) —SR$^3$, (s) —SOR$^3$, (t) —SO$_2$R$^3$, (u) —COOR$^3$, (v) —COR$^3$, (w) —CONR$^3$R$^3$, (x) —NR$^3$COR$^3$—, (y) —NR$^3$CONR$^3$R$^3$, (z) —(C$_1$-C$_8$ alkyl)OR$^3$, (aa) —(C$_1$-C$_8$ alkyl)NR$^3$R$^3$, (bb) —(C$_1$-C$_8$ alkyl)SR$^3$, (cc) —(C$_1$-C$_8$ alkyl)SOR$^3$, (dd) —(C$_1$-C$_8$ alkyl)SO$_2$R$^3$, (ee) —(C$_1$-C$_8$ alkyl)COOR$^3$, (ff) —(C$_1$-C$_8$ alkyl)COR$^3$, (gg) —(C$_1$-C$_8$ alkyl)CONR$^3$R$^3$, (hh) —(C$_1$-C$_8$ alkyl)NR$^3$COR$^3$, and (ii) —(C$_1$-C$_8$ alkyl)NR$^3$CONR$^3$R$^3$, wherein each of (e) through (j) immediately recited above is optionally substituted with one or more F, Cl, Br, I, —OH, —SH, —NH$_2$, —NH(C$_1$-C$_8$ alkyl), or —N(C$_1$-C$_8$ alkyl)$_2$ and wherein each of (k) through (l) immediately recited above is optionally substituted with one or more R$^4$ or R;

each R$^3$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (k) immediately recited above is optionally substituted with one or more R$^5$;

each R$^4$ is independently selected from (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, and (j) —C$_8$ cycloalkynyl, wherein each of (e) through (j) immediately recited above is optionally substituted with one or more R$^5$;

each R$^5$ is independently selected from (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^6$, (r) —$SO_2R^6$, (s) —$COOR^6$, (t) —$COR^6$, (u) —$CONR^6R^6$, (v) —$NR^6COR^6$—, and (w) —$NR^6CONR^6R^6$, wherein each of (e) through (k) immediately recited above is optionally substituted with one or more F, Cl, Br, I, —OH, —SH, —$NH_2$, —NH($C_1$-$C_8$ alkyl), and —N($C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (i) immediately recited above is optionally substituted with one or more $R^7$; and each $R^7$ is independently selected from one or more (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$; and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound having the formula:

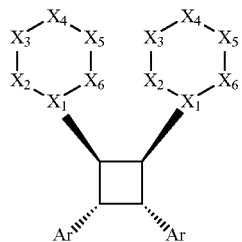

wherein in each ring system,

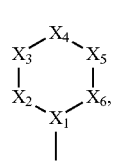

(X)

each $X_1$ is —C≡;
each of $X_2$, $X_3$, $X_4$, $X_5$, and $X_6$ is independently selected from —CH═, —$CR^1$═, —$CR^2$═, —NH—, —$NR^1$—, —$NR^2$—, —N═, and —CO—;
such that each ring system (X) contains 1 to 3 nitrogen atoms, each ring system (X) contains no more than 2-CO—, and each ring system (X) contains no more than one of each $R^1$ and each $R^2$;

each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —$OR^3$, (o) —$NR^3R^3$, (p) —CN, (q) —$N_3$, (r) —$SR^3$, (s) —$SOR^3$, (t) —$SO_2R^3$, (u) —$COOR^3$, (v) —$COR^3$, (w) —$CONR^3R^3$, (x) —$NR^3COR^3$—, (y) —$NR^3CONR^3R^3$, (z) —($C_1$-$C_8$ alkyl)$OR^3$, (aa) —($C_1$-$C_8$ alkyl)$NR^3R^3$, (bb) —($C_1$-$C_8$ alkyl)$SR^3$, (cc) —($C_1$-$C_8$ alkyl)$SOR^3$, (dd) —($C_1$-$C_8$ alkyl)$SO_2R^3$, (ee) —($C_1$-$C_8$ alkyl)$COOR^3$, (ff) —($C_1$-$C_8$ alkyl)$COR^3$, (gg) —($C_1$-$C_8$ alkyl)$CONR^3R^3$, (hh) —($C_1$-$C_8$ alkyl)$NR^3COR^3$, and (ii) —($C_1$-$C_8$ alkyl)$NR^3CONR^3R^3$, wherein each of (e) through (j) immediately recited above is optionally substituted with one or more F, Cl, Br, I, —OH, —SH, —$NH_2$, —NH($C_1$-$C_8$ alkyl), or —N($C_1$-$C_8$ alkyl)$_2$ and wherein each of (k) through (l) immediately recited above is optionally substituted with one or more $R^4$ or $R^5$;

each $R^3$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (k) immediately recited above is optionally substituted with one or more $R^5$;

each $R^4$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, and (j) —$C_8$ cycloalkynyl, wherein each of (e) through (j) immediately recited above is optionally substituted with one or more $R^5$;

each $R^5$ is independently selected from (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^6$, (r) —$SO_2R^6$, (s) —$COOR^6$, (t) —$COR^6$, (u) —$CONR^6R^6$, (v) —$NR^6COR^6$—, and (w) —$NR^6CONR^6R^6$, wherein each of (e) through (k) immediately recited above is optionally substituted with one or more F, Cl, Br, I, —OH, —SH, —$NH_2$, —NH($C_1$-$C_8$ alkyl), and —N($C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k)

—C₁-C₈ alkyl(naphthyl), wherein each of (b) through (i) immediately recited above is optionally substituted with one or more R⁷; and each R⁷ is independently selected from one or more (a) F, (b) Cl, (c) Br, (d) I, (e) —OH, (f) —NH₂, (g) —CN, (h) —SH, (i) —COOH, (j) —CHO, (k) —CONH₂, (l) —O(—C₁-C₈ alkyl), (m) —NH(—C₁-C₈ alkyl), (n) —N(—C₁-C₈ alkyl)₂, (o) —S(—C₁-C₈ alkyl), (p) —COO(—C₁-C₈ alkyl), (q) —CO(—C₁-C₈ alkyl), (r) —CONH(—C₁-C₈ alkyl), and (s) —CON(—C₁-C₈ alkyl)₂; and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound having the formula:

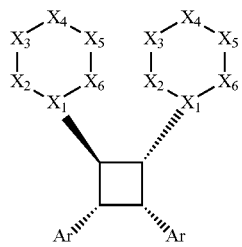

wherein in each ring system,

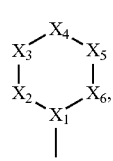

(X)

each X₁ is —C═;

each of X₂, X₃, X₄, X₅, and X₆ is independently selected from —CH═, —CR═, —CR²═, —NH—, —NR¹—, —NR²—, —N═, and —CO—;

such that each ring system (X) contains 1 to 3 nitrogen atoms, each ring system (X) contains no more than 2 —CO—, and each ring system (X) contains no more than one of each R¹ and each R²;

each R¹ and R² is independently selected from (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, (j) —C₈ cycloalkynyl, (k) phenyl, (l) a 7 to 10-membered saturated, unsaturated, or aromatic fused bicyclic carbocycle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —OR³, (o) —NR³R³, (p) —CN, (q) —N₃, (r) —SR³, (s) —SOR³, (t) —SO₂R³, (u) —COOR³, (v) —COR³, (w) —CONR³R³, (x) —NR³COR³—, (y) —NR³CONR³R³, (z) —(C₁-C₈ alkyl)OR³, (aa) —(C₁-C₈ alkyl)NR³R³, (bb) —(C₁-C₈ alkyl)SR³, (cc) —(C₁-C₈ alkyl)SOR³, (dd) —(C₁-C₈ alkyl)SO₂R³, (ee) —(C₁-C₈ alkyl)COOR³, (ff) —(C₁-C₈ alkyl)COR³, (gg) —(C₁-C₈ alkyl)CONR³R³, (hh) —(C₁-C₈ alkyl)NR³COR³, and (ii) —(C₁-C₈ alkyl)NR³CONR³R³, wherein each of (e) through (j) immediately recited above is optionally substituted with one or more F, Cl, Br, I, —OH, —SH, —NH₂, —NH(C₁-C₈ alkyl), or —N(C₁-C₈ alkyl)₂ and wherein each of (k) through (l) immediately recited above is optionally substituted with one or more R⁴ or R⁵;

each R³ is independently selected from (a) H, (b) —C₁-C₈ alkyl, (c) —C₂-C₈ alkenyl, (d) —C₂-C₈ alkynyl, (e) —C₃-C₈ cycloalkyl, (f) —C₃-C₈ cycloalkenyl, (g) —C₈ cycloalkynyl, (h) phenyl, (i) naphthyl, (j) —C₁-C₈ alkyl(phenyl), and (k) —C₁-C₈ alkyl(naphthyl), wherein each of (b) through (k) immediately recited above is optionally substituted with one or more R⁵;

each R⁴ is independently selected from (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, and (j) —C₈ cycloalkynyl, wherein each of (e) through (j) immediately recited above is optionally substituted with one or more R⁵;

each R⁵ is independently selected from (a) F, (b) Cl, (c) Br, (d) I, (e) —OH, (f) —NH₂, (g) —CN, (h) —SH, (i) —COOH, (j) —CHO, (k) —CONH₂, (l) —O(—C₁-C₈ alkyl), (m) —NH(—C₁-C₈ alkyl), (n) —N(—C₁-C₈ alkyl)₂, (o) —S(—C₁-C₈ alkyl), (p) —COO(—C₁-C₈ alkyl), (q) —CO(—C₁-C₈ alkyl), (r) —CONH(—C₁-C₈ alkyl), and (s) —CON(—C₁-C₈ alkyl)₂, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, (j) —C₈ cycloalkynyl, (k) phenyl, (l) —OR⁶, (m) —NR⁶R⁶, (n) —CN, (o) —N₃, -(p) —SR⁶, (q) —SOR⁶, (r) —SO₂R⁶, (s) —COOR⁶, (t) —COR⁶, (u) —CONR⁶R⁶, (v) —NR⁶COR⁶—, and (w) —NR⁶CONR⁶R⁶, wherein each of (e) through (k) immediately recited above is optionally substituted with one or more F, Cl, Br, I, —OH, —SH, —NH₂, —NH(C₁-C₈ alkyl), and —N(C₁-C₈ alkyl)₂;

each R⁶ is independently selected from (a) H, (b) —C₁-C₈ alkyl, (c) —C₂-C₈ alkenyl, (d) —C₂-C₈ alkynyl, (e) —C₃-C₈ cycloalkyl, (f) —C₃-C₈ cycloalkenyl, (g) —C₈ cycloalkynyl, (h) phenyl, (i) naphthyl, (j) —C₁-C₈ alkyl(phenyl), and (k) —C₁-C₈ alkyl(naphthyl), wherein each of (b) through (i) immediately recited above is optionally substituted with one or more R⁷; and each R⁷ is independently selected from one or more (a) F, (b) Cl, (c) Br, (d) I, (e) —OH, (f) —NH₂, (g) —CN, (h) —SH, (i) —COOH, (j) —CHO, (k) —CONH₂, (l) —O(—C₁-C₈ alkyl), (m) —NH(—C₁-C₈ alkyl), (n) —N(—C₁-C₈ alkyl)₂, (o) —S(—C₁-C₈ alkyl), (p) —COO(—C₁-C₈ alkyl), (q) —CO(—C₁-C₈ alkyl), (r) —CONH(—C₁-C₈ alkyl), and (s) —CON(—C₁-C₈ alkyl)₂; and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein in each ring system,

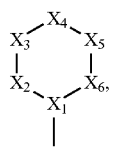

(X)

each $X_1$ is —C≡;

each of $X_2$, $X_3$, $X_4$, $X_5$, and $X_6$ is independently selected from —CH, —CR≡, —CR$^2$≡, and —N≡;

such that each ring system (X) contains 1 to 3 nitrogen atoms and each ring system (X) contains no more than one of each $R^1$ and each $R^2$;

or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each ring system,

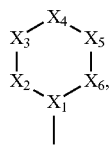

(X)

is independently selected from

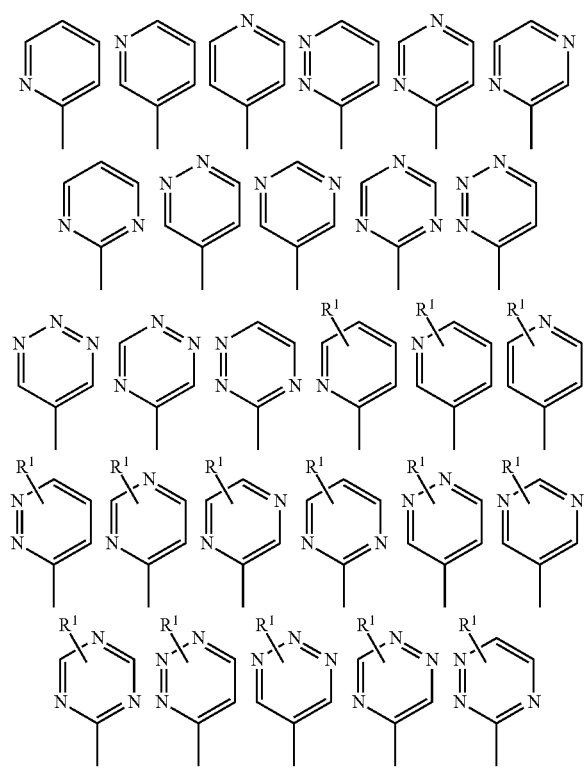

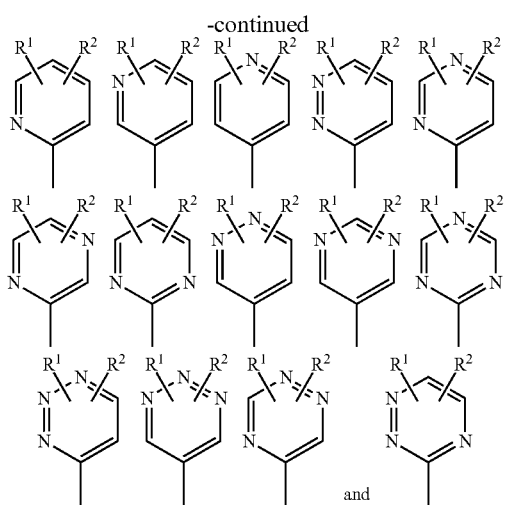

and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each ring system,

(X)

is independently selected from

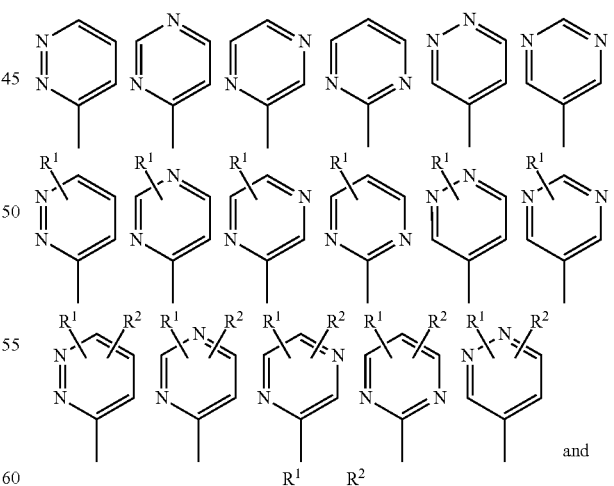

and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each ring system,

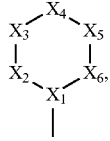 (X)

is independently selected from

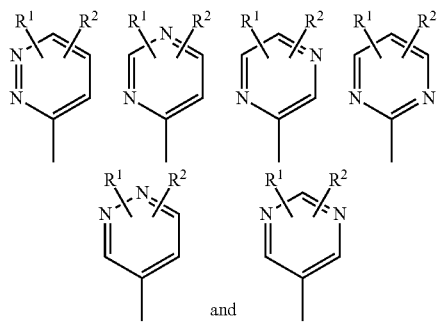

and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each ring system,

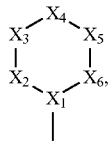 (X)

is independently selected from

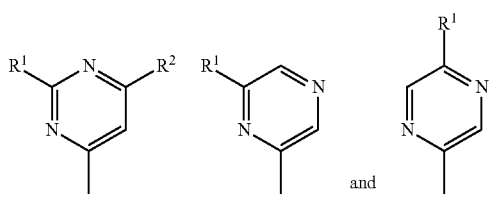

or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each ring system,

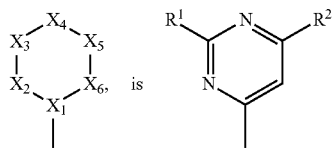 (X)

is or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound having the formula:

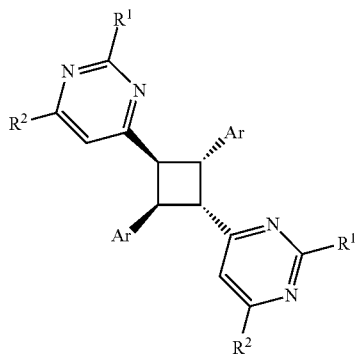

wherein
each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —$OR^3$, (o) —$NR^3R^3$, (p) —CN, (q) —$N_3$, (r) —$SR^3$, (s) —$SOR^3$, (t) —$SO_2R^3$, (u) —$COOR^3$, (v) —$COR^3$, (w) —$CONR^3R^3$, (x) —$NR^3COR^3$—, (y) —$NR^3CONR^3R^3$, (z) —($C_1$-$C_8$ alkyl)$OR^3$, (aa) —($C_1$-$C_8$ alkyl)$NR^3R^3$, (bb) —($C_1$-$C_8$ alkyl)$SR^3$, (cc) —($C_1$-$C_8$ alkyl)$SOR^3$, (dd) —($C_1$-$C_8$ alkyl)$SO_2R^3$, (ee) —($C_1$-$C_8$ alkyl)$COOR^3$, (ff) —($C_1$-$C_8$ alkyl)$COR^3$, (gg) —($C_1$-$C_8$ alkyl)$CONR^3R^3$, (hh) —($C_1$-$C_8$ alkyl)$NR^3COR^3$, and (ii) —($C_1$-$C_8$ alkyl)$NR^3CONR^3R^3$,
wherein each of (e) through (j) immediately recited above is optionally substituted with one or more F, Cl, Br, I, —OH, —SH, —$NH_2$, —NH($C_1$-$C_8$ alkyl), or —N($C_1$-$C_8$ alkyl)$_2$ and
wherein each of (k) through (l) immediately recited above is optionally substituted with one or more $R^4$ or $R^5$;

each R³ is independently selected from (a) H, (b) —C₁-C₈ alkyl, (c) —C₂-C₈ alkenyl, (d) —C₂-C₈ alkynyl, (e) —C₃-C₈ cycloalkyl, (f) —C₃-C₈ cycloalkenyl, (g) —C₈ cycloalkynyl, (h) phenyl, (i) naphthyl, (j) —C₁-C₈ alkyl(phenyl), and (k) —C₁-C₈ alkyl(naphthyl), wherein each of (b) through (k) immediately recited above is optionally substituted with one or more R⁵;

each R⁴ is independently selected from (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, and (j) —C₈ cycloalkynyl, wherein each of (e) through (j) immediately recited above is optionally substituted with one or more R⁵;

each R⁵ is independently selected from (a) F, (b) Cl, (c) Br, (d) I, (e) —OH, (f) —NH₂, (g) —CN, (h) —SH, (i) —COOH, (j) —CHO, (k) —CONH₂, (l) —O(—C₁-C₈ alkyl), (m) —NH(—C₁-C₈ alkyl), (n) —N(—C₁-C₈ alkyl)₂, (o) —S(—C₁-C₈ alkyl), (p) —COO(—C₁-C₈ alkyl), (q) —CO(—C₁-C₈ alkyl), (r) —CONH(—C₁-C₈ alkyl), and (s) —CON(—C₁-C₈ alkyl)₂, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, (j) —C₈ cycloalkynyl, (k) phenyl, (l) —OR⁶, (m) —NR⁶R⁶, (n) —CN, (o) —N₃, -(p) —SR⁶, (q) —SOR⁶, (r) —SO₂R⁶, (s) —COOR⁶, (t) —COR⁶, (u) —CONR⁶R⁶, (v) —NR⁶COR⁶—, and (w) —NR⁶CONR⁶R⁶, wherein each of (e) through (k) immediately recited above is optionally substituted with one or more F, Cl, Br, I, —OH, —SH, —NH₂, —NH(C₁-C₈ alkyl), and —N(C₁-C₈ alkyl)₂;

each R⁶ is independently selected from (a) H, (b) —C₁-C₈ alkyl, (c) —C₂-C₈ alkenyl, (d) —C₂-C₈ alkynyl, (e) —C₃-C₈ cycloalkyl, (f) —C₃-C₈ cycloalkenyl, (g) —C₈ cycloalkynyl, (h) phenyl, (i) naphthyl, (j) —C₁-C₈ alkyl(phenyl), and (k) —C₁-C₈ alkyl(naphthyl), wherein each of (b) through (i) immediately recited above is optionally substituted with one or more R⁷; and each R⁷ is independently selected from one or more (a) F, (b) Cl, (c) Br, (d) I, (e) —OH, (f) —NH₂, (g) —CN, (h) —SH, (i) —COOH, (j) —CHO, (k) —CONH₂, (l) —O(—C₁-C₈ alkyl), (m) —NH(—C₁-C₈ alkyl), (n) —N(—C₁-C₈ alkyl)₂, (o) —S(—C₁-C₈ alkyl), (p) —COO(—C₁-C₈ alkyl), (q) —CO(—C₁-C₈ alkyl), (r) —CONH(—C₁-C₈ alkyl), and (s) —CON(—C₁-C₈ alkyl)₂; and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound having the formula:

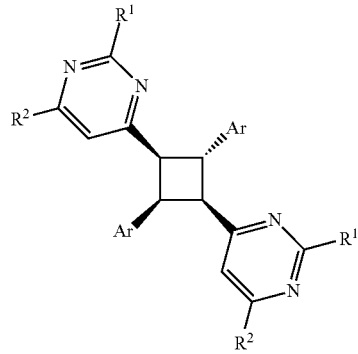

wherein each R¹ and R² is independently selected from (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, (j) —C₈ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —OR³, (o) —NR³R³, (p) —CN, (q) —N₃, (r) —SR³, (s) —SOR³, (t) —SO₂R³, (u) —COOR³, (v) —COR³, (w) —CONR³R³, (x) —NR³COR³—, (y) —NR³CONR³R³, (z) —(C₁-C₈ alkyl)OR³, (aa) —(C₁-C₈ alkyl)NR³R³, (bb) —(C₁-C₈ alkyl)SR³, (cc) —(C₁-C₈ alkyl)SOR³, (dd) —(C₁-C₈ alkyl)SO₂R³, (ee) —(C₁-C₈ alkyl)COOR³, (ff) —(C₁-C₈ alkyl)COR³, (gg) —(C₁-C₈ alkyl)CONR³R³, (hh) —(C₁-C₈ alkyl)NR³COR³, and (ii) —(C₁-C₈ alkyl)NR³CONR³R³, wherein each of (e) through (j) immediately recited above is optionally substituted with one or more F, Cl, Br, I, —OH, —SH, —NH₂, —NH(C₁-C₈ alkyl), or —N(C₁-C₈ alkyl)₂ and wherein each of (k) through (l) immediately recited above is optionally substituted with one or more R⁴ or R⁵;

each R³ is independently selected from (a) H, (b) —C₁-C₈ alkyl, (c) —C₂-C₈ alkenyl, (d) —C₂-C₈ alkynyl, (e) —C₃-C₈ cycloalkyl, (f) —C₃-C₈ cycloalkenyl, (g) —C₈ cycloalkynyl, (h) phenyl, (i) naphthyl, (j) —C₁-C₈ alkyl(phenyl), and (k) —C₁-C₈ alkyl(naphthyl), wherein each of (b) through (k) immediately recited above is optionally substituted with one or more R⁵;

each R⁴ is independently selected from (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, and (j) —C₈ cycloalkynyl, wherein each of (e) through (j) immediately recited above is optionally substituted with one or more R⁵;

each R⁵ is independently selected from (a) F, (b) Cl, (c) Br, (d) I, (e) —OH, (f) —NH₂, (g) —CN, (h) —SH, (i) —COOH, (j) —CHO, (k) —CONH₂, (l) —O(—C₁-C₈ alkyl), (m) —NH(—C₁-C₈ alkyl), (n) —N(—C₁-C₈ alkyl)₂, (o) —S(—C₁-C₈ alkyl), (p) —COO(—C₁-C₈ alkyl), (q) —CO(—C₁-C₈ alkyl), (r) —CONH(—C₁-C₈ alkyl), and (s) —CON(—C₁-C₈ alkyl)₂, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^6$, (r) —$SO_2R^6$, (s) —$COOR^6$, (t) —$COR^6$, (u) —$CONR^6R^6$, (v) —$NR^6COR^6$—, and (w) —$NR^6CONR^6R^6$, wherein each of (e) through (k) immediately recited above is optionally substituted with one or more F, Cl, Br, I, —OH, —SH, —$NH_2$, —$NH(C_1$-$C_8$ alkyl), and —$N(C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (i) immediately recited above is optionally substituted with one or more $R^7$; and each $R^7$ is independently selected from one or more (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$; and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound having the formula:

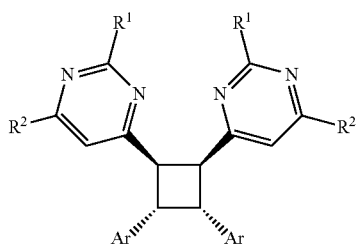

wherein
each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —$OR^3$, (o) —$NR^3R^3$, (p) —CN, (q) —$N_3$, (r) —$SR^3$, (s) —$SOR^3$, (t) —$SO_2R^3$, (u) —$COOR^3$, (v) —$COR^3$, (w) —$CONR^3R^3$, (x) —$NR^3COR^3$—, (y) —$NR^3CONR^3R^3$, (z) —($C_1$-$C_8$ alkyl)$OR^3$, (aa) —($C_1$-$C_8$ alkyl)$NR^3R^3$, (bb) —($C_1$-$C_8$ alkyl)$SR^3$, (cc) —($C_1$-$C_8$ alkyl)$SOR^3$, (dd) —($C_1$-$C_8$ alkyl)$SO_2R^3$, (ee) —($C_1$-$C_8$ alkyl)$COOR^3$, (ff) —($C_1$-$C_8$ alkyl)$COR^3$, (gg) —($C_1$-$C_8$ alkyl)$CONR^3R^3$, (hh) —($C_1$-$C_8$ alkyl)$NR^3COR^3$, and (ii) —($C_1$-$C_8$ alkyl)$NR^3CONR^3R^3$, wherein each of (e) through (j) immediately recited above is optionally substituted with one or more F, Cl, Br, I, —OH, —SH, —$NH_2$, —$NH(C_1$-$C_8$ alkyl), or —$N(C_1$-$C_8$ alkyl)$_2$ and wherein each of (k) through (l) immediately recited above is optionally substituted with one or more $R^4$ or $R^5$;

each $R^3$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (k) immediately recited above is optionally substituted with one or more $R^5$;

each $R^4$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, and (j) —$C_8$ cycloalkynyl, wherein each of (e) through (j) immediately recited above is optionally substituted with one or more $R^5$;

each $R^5$ is independently selected from (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^6$, (r) —$SO_2R^6$, (s) —$COOR^6$, (t) —$COR^6$, (u) —$CONR^6R^6$, (v) —$NR^6COR^6$—, and (w) —$NR^6CONR^6R^6$, wherein each of (e) through (k) immediately recited above is optionally substituted with one or more F, Cl, Br, I, —OH, —SH, —$NH_2$, —$NH(C_1$-$C_8$ alkyl), and —$N(C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (i) immediately recited above is optionally substituted with one or more $R^7$; and each $R^7$ is independently selected from one or more (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$; and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound having the formula:

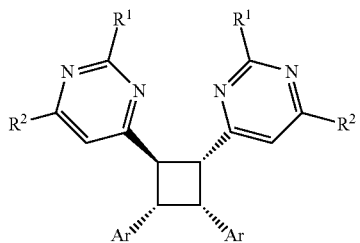

wherein each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocycle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —$OR^3$, (o) —$NR^3R^3$, (p) —CN, (q) —$N_3$, (r) —$SR^3$, (s) —$SOR^3$, (t) —$SO_2R^3$, (u) —$COOR^3$, (v) —$COR^3$, (w) —$CONR^3R^3$, (x) —$NR^3COR^3$—, (y) —$NR^3CONR^3R^3$, (z) —($C_1$-$C_8$ alkyl)$OR^3$, (aa) —($C_1$-$C_8$ alkyl)$NR^3R^3$, (bb) —($C_1$-$C_8$ alkyl)$SR^3$, (cc) —($C_1$-$C_8$ alkyl)$SOR^3$, (dd) —($C_1$-$C_8$ alkyl)$SO_2R^3$, (ee) —($C_1$-$C_8$ alkyl)$COOR^3$, (ff) —($C_1$-$C_8$ alkyl)$COR^3$, (gg) —($C_1$-$C_8$ alkyl)$CONR^3R^3$, (hh) —($C_1$-$C_8$ alkyl)$NR^3COR^3$, and (ii) —($C_1$-$C_8$ alkyl)$NR^3CONR^3R^3$, wherein each of (e) through (j) immediately recited above is optionally substituted with one or more F, Cl, Br, I, —OH, —SH, —$NH_2$, —NH($C_1$-$C_8$ alkyl), or —N($C_1$-$C_8$ alkyl)$_2$ and wherein each of (k) through (l) immediately recited above is optionally substituted with one or more $R^4$ or $R^5$;

each $R^3$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (k) immediately recited above is optionally substituted with one or more $R^5$;

each $R^4$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, and (j) —$C_8$ cycloalkynyl, wherein each of (e) through (j) immediately recited above is optionally substituted with one or more $R^5$;

each $R^5$ is independently selected from (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^6$, (r) —$SO_2R^6$, (s) —$COOR^6$, (t) —$COR^6$, (u) —$CONR^6R^6$, (v) —$NR^6COR^6$—, and (w) —$NR^6CONR^6R^6$, wherein each of (e) through (k) immediately recited above is optionally substituted with one or more F, Cl, Br, I, —OH, —SH, —$NH_2$, —NH($C_1$-$C_8$ alkyl), and —N($C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (i) immediately recited above is optionally substituted with one or more $R^7$; and each $R^7$ is independently selected from one or more (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$; and or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each of $R^1$ and $R^2$ are independently selected from (a) F, (b) Cl, (c) —$C_1$-$C_8$ alkyl, (d) —$C_3$-$C_8$ cycloalkyl, (e) phenyl, (f) a 7 to 10-membered saturated, unsaturated, or aromatic fused bicyclic carbocycle, (g) a 3 to 10-membered saturated, unsaturated, or aromatic heterocycle or fused bicyclic heterocycle containing one or more heteroatoms selected from nitrogen, oxygen, sulfur, and combinations thereof, (h) —$OR^3$, (i) —$NR^3R^3$, (j) —CN, (k) —$SR^3$, (l) —$SOR^3$, (m) —$SO_2R^3$, (n) —$COOR^3$, (o) —$COR^3$, (p) —$CONR^3R^3$, (q) —$NR^3COR^3$—, (r) —$NR^3CONR^3R^3$, (s) —($C_1$-$C_8$ alkyl)$OR^3$, (t) —($C_1$-$C_8$ alkyl)$NR^3R^3$, (u) —($C_1$-$C_8$ alkyl)$SR^3$, (v) —($C_1$-$C_8$ alkyl)$SOR^3$, (w) —($C_1$-$C_8$ alkyl)$SO_2R^3$, (x) —($C_1$-$C_8$ alkyl)$COOR^3$, (y) —($C_1$-$C_8$ alkyl)$COR^3$, (z) —($C_1$-$C_8$ alkyl)$CONR^3R^3$, (aa) —($C_1$-$C_8$ alkyl)$NR^3COR^3$, and (bb) —($C_1$-$C_8$ alkyl)$NR^3CONR^3R^3$, wherein each of (c) or (d) immediately recited above is optionally substituted with one or more F, Cl, —OH, —SH, —$NH_2$, —NH($C_1$-$C_8$ alkyl), or —N($C_1$-$C_8$ alkyl)$_2$ and wherein each of (e) through (g) immediately recited above is optionally substituted with one more $R^4$ or $R^5$;

each $R^3$ is independently selected from (a) H, (b) —$C_1$-$C_8$ alkyl, (c) —$C_3$-$C_8$ cycloalkyl, (d) phenyl, (e) naphthyl, (f) —$C_1$-$C_8$ alkyl(phenyl), and (g) —$C_1$-$C_8$ alkyl(naphthyl), wherein each of (b) through (g) immediately recited above is optionally substituted with one or more $R^5$;

each $R^4$ is independently selected from one or more (a) F, (b) Cl, (c) —$C_1$-$C_8$ alkyl, and (d) —$C_3$-$C_8$ cycloalkyl, wherein each of (c) or (d) immediately recited above is optionally substituted with one or more $R^5$;

each $R^5$ is independently selected from one or more (a) F, (b) Cl, (c) —OH, (d) —$NH_2$, (e) —CN, (f) —SH, (g) —COOH, (h) —CHO, (i) —$CONH_2$, (j) —O(—$C_1$-$C_8$ alkyl), (k) —NH(—$C_1$-$C_8$ alkyl), (l) —N(—$C_1$-$C_8$ alkyl)$_2$, (m) —S(—$C_1$-$C_8$ alkyl), (n) —COO(—$C_1$-$C_8$ alkyl), (o) —CO(—$C_1$-$C_8$ alkyl), (p) —CONH(—$C_1$-$C_8$ alkyl), and (q) —CON(—$C_1$-$C_8$ alkyl)$_2$, or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each of $R^1$ and $R^2$ are independently selected from (a) F, (b) Cl, (c) —$C_1$-$C_8$ alkyl, (d) phenyl, (e) a 7 to 10-membered saturated, unsaturated, or aromatic fused bicyclic carbocyle, (f) a 3 to 10-membered saturated, unsaturated, or aromatic heterocycle or fused bicyclic heterocycle containing one or more heteroatoms selected from nitrogen, oxygen, sulfur, and combinations thereof, (g) —$OR^3$, (h) —$NR^3R^3$, (i) —$SR^3$, (j) —$COOR^3$, (k) —$COR^3$, and (l) —$CONR^3R^3$, wherein each (c) immediately recited above is optionally substituted with one or more F, Cl, —OH, —SH, —$NH_2$, —NH($C_1$-$C_8$ alkyl), or —N($C_1$-$C_8$ alkyl)$_2$ and wherein each (d) through (f) immediately recited above is optionally substituted with one more more $R^4$ or $R^5$;

each $R^3$ is independently selected from (a) H, (b) —$C_1$-$C_8$ alkyl, (c) phenyl, and (d) naphthyl, wherein each of (b) through (d) immediately recited above is optionally substituted with one or more R;

each $R^4$ is independently selected from one or more (a) F, (b) Cl, (c) —$C_1$-$C_8$ alkyl, (d) —$C_3$-$C_8$ cycloalkyl, wherein each of (c) or (d) immediately recited above is optionally substituted with one or more $R^5$;

each $R^5$ is independently selected from one or more (a) F, (b) Cl, (c) —OH, (d) —$NH_2$, (e) —SH, (f) —COOH, (g) —$COCH_3$, (h) —CHO, or (i) —$CONH_2$, or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof nitrogen, wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^6$, (r) —$SO_2R^6$, (s) —$COOR^6$, (t) —$COR^6$, (u) —$CONR^6R^6$, (v) —$NR^6COR^6$—, and (w) —$NR^6CONR^6R^6$, wherein each of (e) through (k) immediately recited above is optionally substituted with one or more F, Cl, Br, I, —OH, —SH, —$NH_2$, —NH($C_1$-$C_8$ alkyl), and —N($C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (k) immediately recited above is optionally substituted with one or more $R^7$;

each $R^7$ is independently selected from one or more (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$, wherein each of (a) through (d) immediately recited above is optionally substituted with one or more (a) F, (b) Cl, (c) —$C_1$-$C_8$ alkyl, (d) —$C_3$-$C_8$ cycloalkyl, (e) phenyl, (f) —$OR^6$, (g) —$NR^6R^6$, (h) —CN, (i) —$N_3$, -(j) —$SR^6$, (k) —$SOR^6$, (l) —$SO_2^{63}$, (m) —$COOR^6$, (n) —$COR^6$, (o) —$CONR^6R^6$, (p) —$NR^6COR^6$—, and (q) —$NR^6CONR^6R^6$, wherein each of (c) through (e) immediately recited above is optionally substituted with one or more F, Cl, —OH, —SH, —$NH_2$, —NH($C_1$-$C_8$ alkyl), and —N($C_1$-$C_8$ alkyl)$_2$;

each $R^6$ is independently selected from (a) H, (b) —$C_1$-$C_8$ alkyl, (c) —$C_3$-$C_8$ cycloalkyl, (d) phenyl, (e) naphthyl, (f) —$C_1$-$C_8$ alkyl(phenyl), and (g) —$C_1$-$C_8$ alkyl(naphthyl), wherein each of (b) through (g) immediately recited above is optionally substituted with one or more $R^7$;

each $R^7$ is independently selected from one or more (a) F, (b) Cl, (c) —OH, (d) —$NH_2$, (e) —CN, (f) —SH, (g) —COOH, (h) —CHO, (i) —$CONH_2$, (j) —O(—$C_1$-$C_8$ alkyl), (k) —NH(—$C_1$-$C_8$ alkyl), (l) —N(—$C_1$-$C_8$ alkyl)$_2$, (m) —S(—$C_1$-$C_8$ alkyl), (n) —COO(—$C_1$-$C_8$ alkyl), (o) —CO(—$C_1$-$C_8$ alkyl), (p) —CONH(—$C_1$-$C_8$ alkyl), and (q) —CON(—$C_1$-$C_8$ alkyl)$_2$, or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each Ar is independently selected from (a) phenyl, (b) naphthyl, (c) pyridyl, (d) pyrimidyl (e) furanyl, (f) thienyl (g) pyrazolyl, (h) pyrazinyl (i) quinolyl, (j) oxazolyl, (k) isoxazolyl, (l) imidazolyl, (m) isothiazolyl, (n) thiazolyl, (o) triazolyl, (p) tetrazolyl, (q) indolyl, (r) benzofuranyl, (s) benzoxazolyl, (t) benzisoxazolyl, and (u) isoquinolinyl, wherein each of (a) through (u) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^6$, (r) —$SO_2R^6$, (s) —$COOR^6$, (t) —$COR^6$, (u) —$CONR^6R^6$, (v) —$NR^6COR^6$—, and (w) —$NR^6CONR^6R^6$, wherein each of (e) through (k) immediately recited above is optionally substituted with one or more F, Cl, Br, I, —OH, —SH, —$NH_2$, —NH($C_1$-$C_8$ alkyl), and —N($C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (k) immediately recited above is optionally substituted with one or more $R^7$;

each $R^7$ is independently selected from one or more (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$, or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each Ar is independently selected from (a) phenyl, (b) naphthyl, (c) pyridyl, (d) pyrimidyl (e) furanyl, (f) thienyl (g) pyrazolyl, (h) pyrazinyl (i) quinolyl, (j) oxazolyl, (k) isoxazolyl, (l) imidazolyl, (m) isothiazolyl, (n) thiazolyl, (o) triazolyl, (p) tetrazolyl, (q) indolyl, (r) benzofuranyl, (s) benzoxazolyl, (t) benzisoxazolyl, and (u) isoquinolinyl, wherein each of (a) through (d) immediately recited above is optionally substituted with one or more (a) F, (b) Cl, (c) —$C_1$-$C_8$ alkyl, (d) —$C_3$-$C_8$ cycloalkyl, (e) phenyl, (f) —$OR^6$, (g) —$NR^6R^6$, (h) —CN, (i) —$N_3$, -(j) —$SR^6$, (k) —$SOR^6$, (l) —$SO_2 6^3$, (m) —$COOR^6$, (n) —$COR^6$, (o) —$CONR^6R^6$, (p) —$NR^6COR^6$—, and (q) —$NR^6CONR^6R^6$, wherein each of (c) through (e) immediately recited above is optionally substituted with one or more F, Cl, —OH, —SH, —$NH_2$, —NH($C_1$-$C_8$ alkyl), and —N($C_1$-$C_8$ alkyl)$_2$;
each $R^6$ is independently selected from (a) H, (b) —$C_1$-$C_8$ alkyl, (c) —$C_3$-$C_8$ cycloalkyl, (d) phenyl, (e) naphthyl, (f) —$C_1$-$C_8$ alkyl(phenyl), and (g) —$C_1$-$C_8$ alkyl(naphthyl), wherein each of (b) through (g) immediately recited above is optionally substituted with one or more $R^7$;
each $R^7$ is independently selected from one or more (a) F, (b) Cl, (c) —OH, (d) —$NH_2$, (e) —CN, (f) —SH, (g) —COOH, (h) —CHO, (i) —$CONH_2$, (j) —O(—$C_1$-$C_8$ alkyl), (k) —NH(—$C_1$-$C_8$ alkyl), (l) —N(—$C_1$-$C_8$ alkyl)$_2$, (m) —S(—$C_1$-$C_8$ alkyl), (n) —COO(—$C_1$-$C_8$ alkyl), (o) —CO(—$C_1$-$C_8$ alkyl), (p) —CONH(—$C_1$-$C_8$ alkyl), and (q) —CON(—$C_1$-$C_8$ alkyl)$_2$,
or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound according to any of the foregoing aspects wherein each Ar is independently selected from (a) phenyl, (b) naphthyl, (c) 2-thienyl, (d) 3-thienyl (e) 2-furanyl, and (f) 3-furanyl
wherein
each of (a) through (f) immediately recited above is optionally substituted with one or more (a) F, (b) Cl, (c) —$C_1$-$C_8$ alkyl, (d) —$C_3$-$C_8$ cycloalkyl, (e) phenyl, (f) —$OR^6$, (g) —$NR^6R^6$, (h) —CN, -(i) —$SR^6$, (j) —$SOR^6$, (k) —$SO_2 6^3$, (l) —$COOR^6$, (m) —$COR^6$, (n) —$CONR^6R^6$, (o) —$NR^6COR^6$—, and (p) —$NR^6CONR^6R^6$,
wherein each of (c) through (e) immediately recited above is optionally substituted with one or more F, Cl, —OH, —SH, —$NH_2$, —NH($C_1$-$C_8$ alkyl), and —N($C_1$-$C_8$ alkyl)$_2$;
each $R^6$ is independently selected from (a) H, (b) —$C_1$-$C_8$ alkyl, (c) —$C_3$-$C_8$ cycloalkyl, (d) phenyl, (e) naphthyl, (f) —$C_1$-$C_8$ alkyl(phenyl), and (g) —$C_1$-$C_8$ alkyl(naphthyl), wherein each of (b) through (g) immediately recited above is optionally substituted with one or more $R^7$;
each $R^7$ is independently selected from one or more (a) F, (b) Cl, (c) —OH, (d) —$NH_2$, (e) —CN, (f) —SH, (g) —COOH, (h) —CHO, (i) —$CONH_2$, (j) —O(—$C_1$-$C_8$ alkyl), (k) —NH(—$C_1$-$C_8$ alkyl), (l) —N(—$C_1$-$C_8$ alkyl)$_2$, (m) —S(—$C_1$-$C_8$ alkyl), (n) —COO(—$C_1$-$C_8$ alkyl), (o) —CO(—$C_1$-$C_8$ alkyl), (p) —CONH(—$C_1$-$C_8$ alkyl), and (q) —CON(—$C_1$-$C_8$ alkyl)$_2$,
or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a compound comprising, consisting of, or consisting essentially of the following structure:

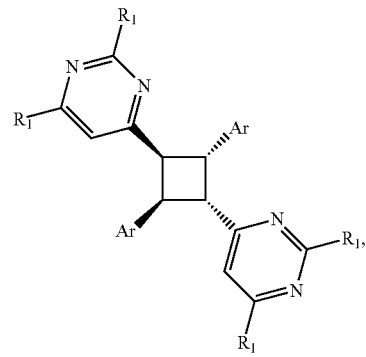

wherein $R_1$=Cl, N($R_2$), OR, OH, SR, $SO_2R$ or $CH_3$ and Ar=Ph, 2-thienyl, 3-thienyl, 2-furanyl, substituted Ph, or other heterocycles.

Another aspect of the present disclosure provides a compound comprising, consisting of, or consisting essentially of the following structure:

I

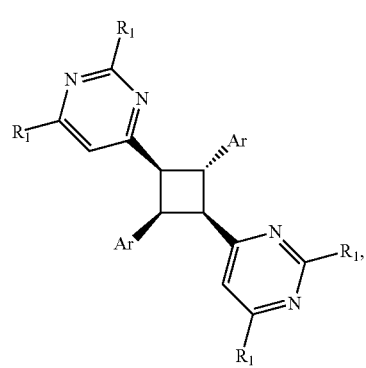

wherein $R_1$=Cl, N($R_2$), OR, OH, SR, $SO_2R$ or $CH_3$ and Ar=Ph, 2-thienyl, 3-thienyl, 2-furanyl, substituted Ph, or other heterocycles.

Another aspect of the present disclosure provides a compound comprising, consisting of, or consisting essentially of the following structure:

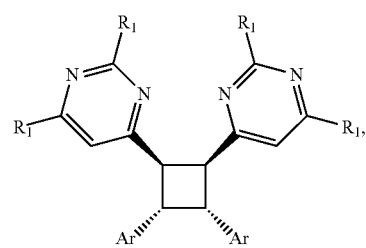

wherein $R_1$=Cl, N($R_2$), OR, OH, SR, $SO_2R$ or $CH_3$ and Ar=Ph, 2-thienyl, 3-thienyl, 2-furanyl, substituted Ph, or other heterocycles.

Another aspect of the present disclosure provides a compound comprising, consisting of, or consisting essentially of the following structure:

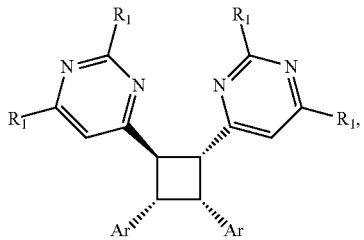

wherein $R_1$=Cl, $N(R_2)$, OR, OH, SR, $SO_2R$ or $CH_3$ and Ar=Ph, 2-thienyl, 3-thienyl, 2-furanyl, substituted Ph, or other heterocycles.

Another aspect of the present disclosure provides a compound comprising, consisting of, or consisting essentially of the following structure:

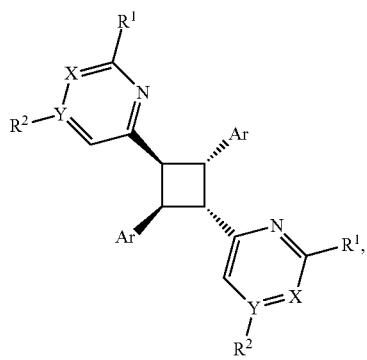

wherein $R_1$=Cl, or H; $R_2$=Cl, H, $OCH_3$ or $CH_3$; X=CH, or N; and Y=C or N.

Another aspect of the present disclosure provides a compound comprising, consisting of, or consisting essentially of the following structure:

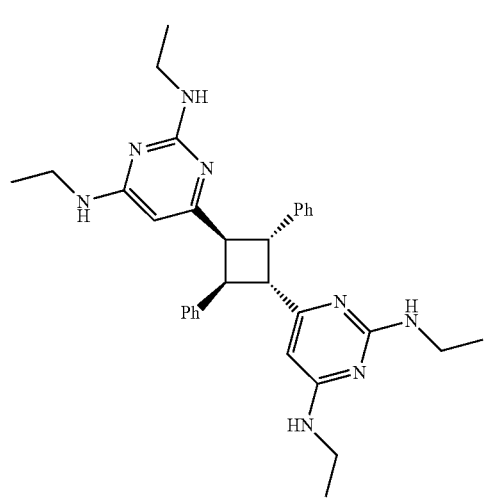

wherein $R_1$=Cl, or H; $R_2$=Cl, H, $OCH_3$ or $CH_3$; X=CH, or N; and Y=C or N.

Another aspect of the present invention is that the following provisos (I) and (II) apply to the foregoing compounds:

(I) the compound is not selected from any of the following compounds (a) through (qq):

(a)

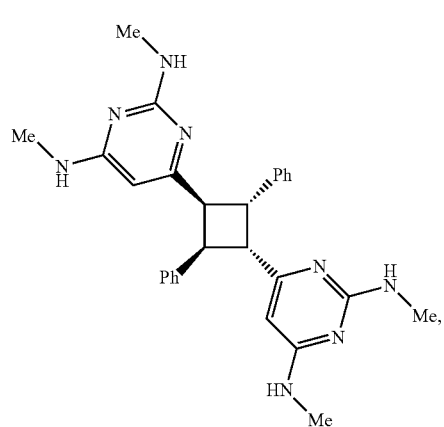

(b)

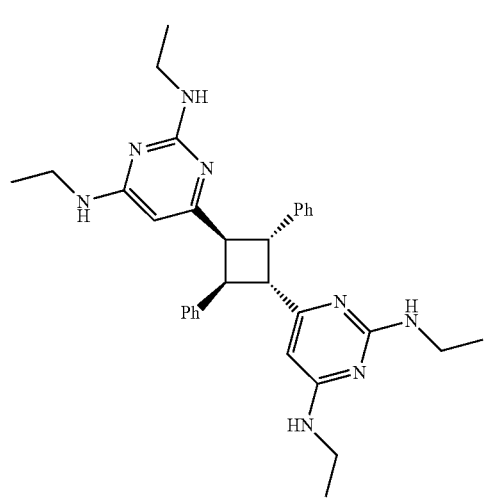

-continued
(c)
45
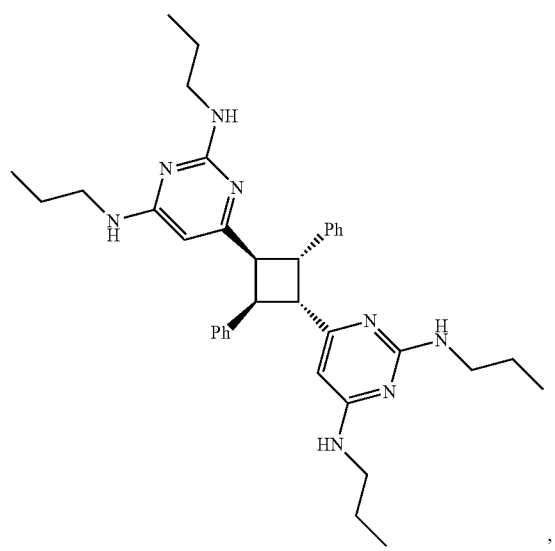
(d)
46
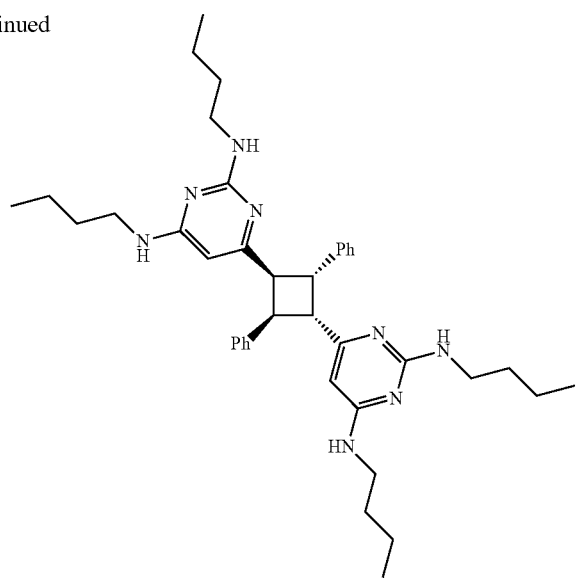
(e)
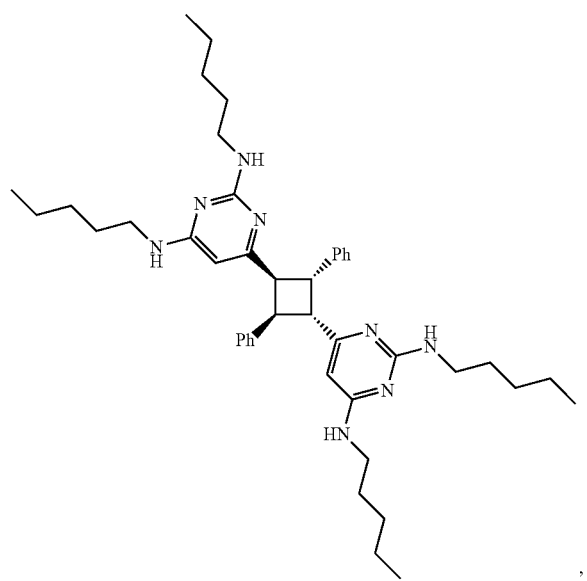
(f)
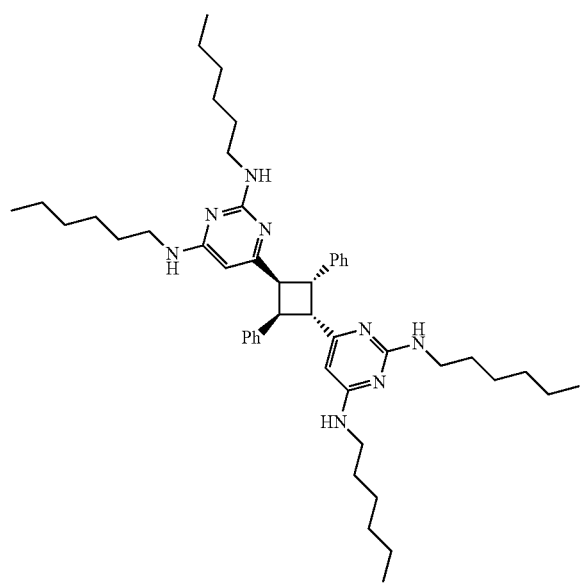
(g)
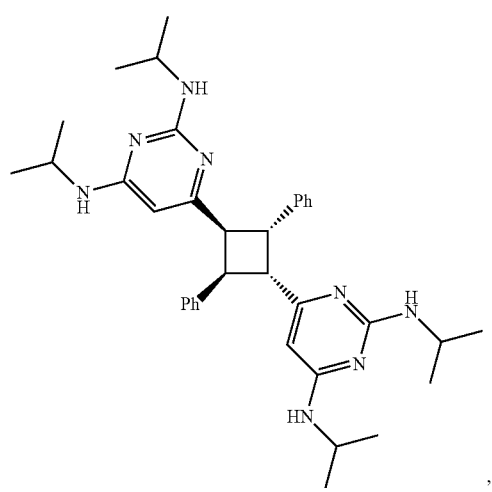
(h)
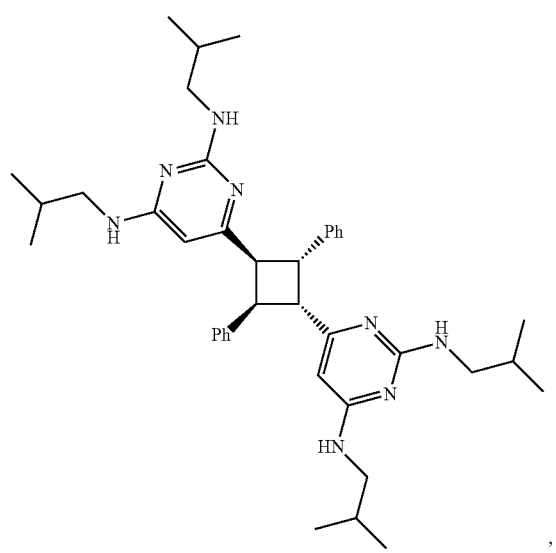

(i)
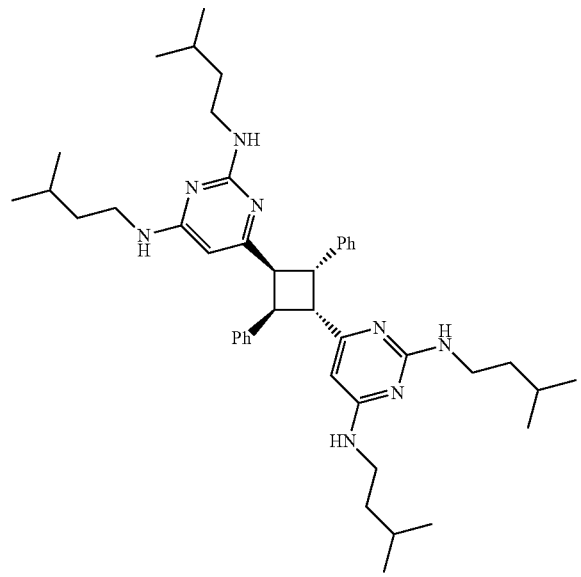
(j)
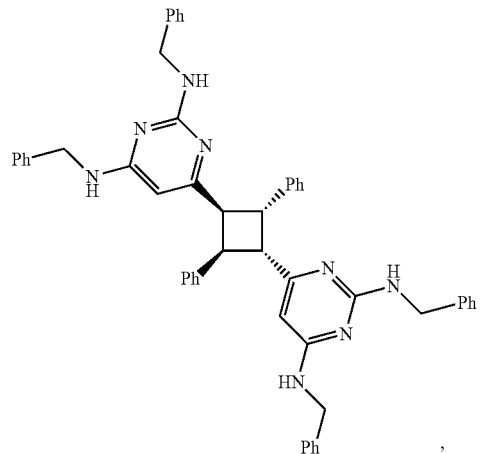
(k)
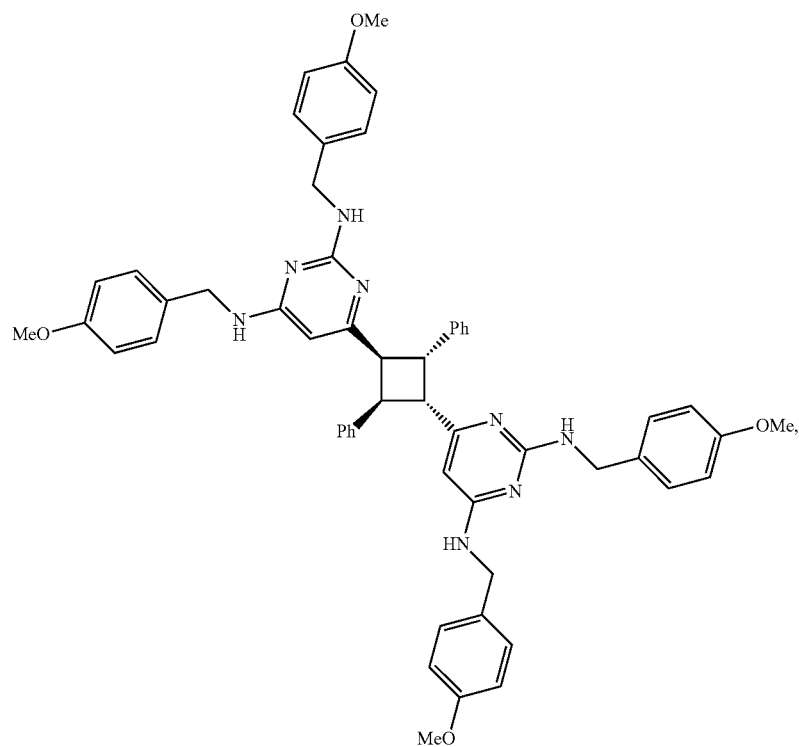

(l)
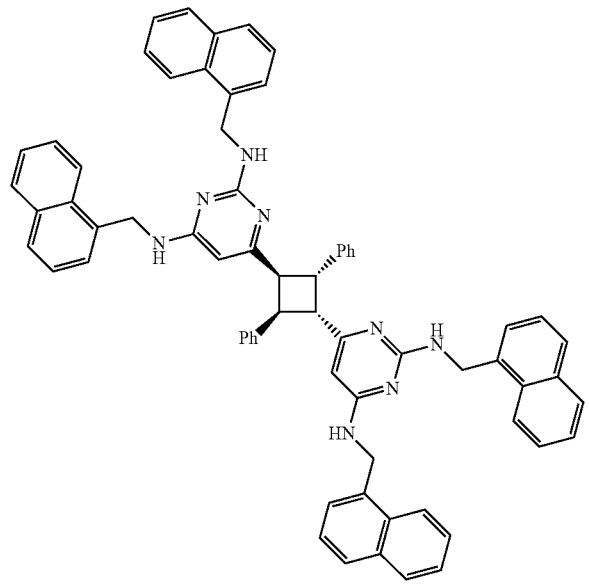
(m)
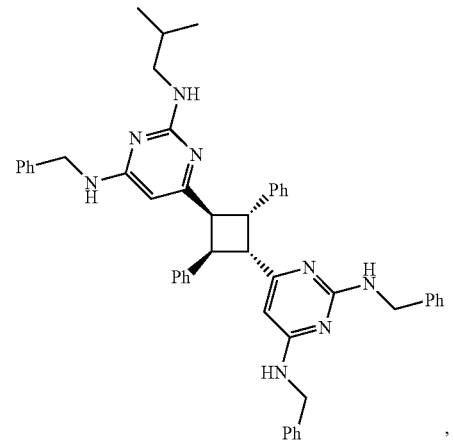
(n)
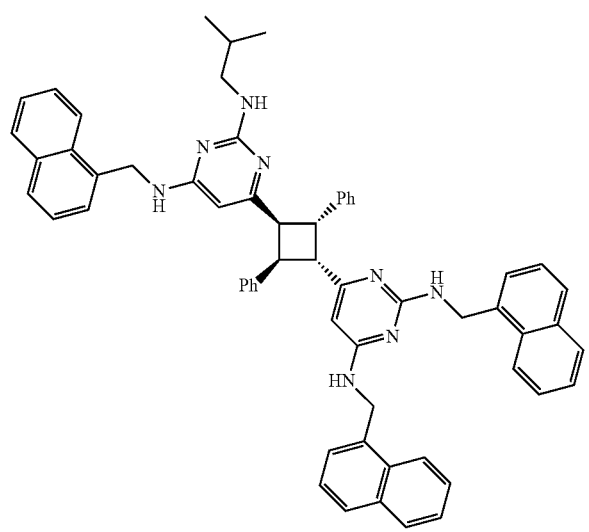
(o)
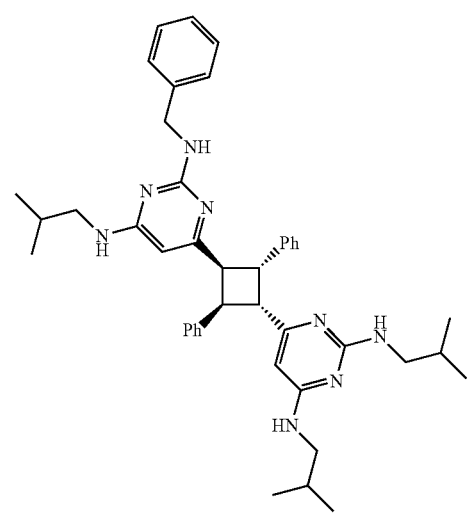
(p)
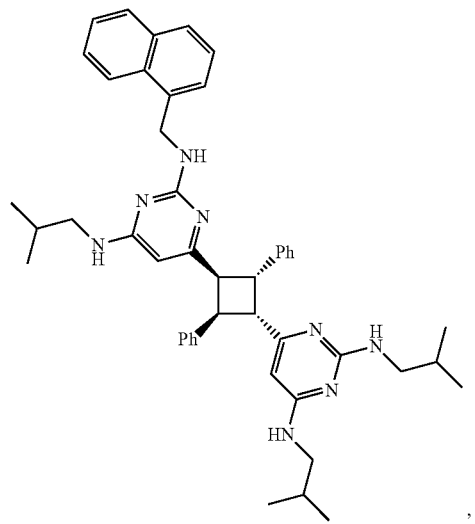
(q)
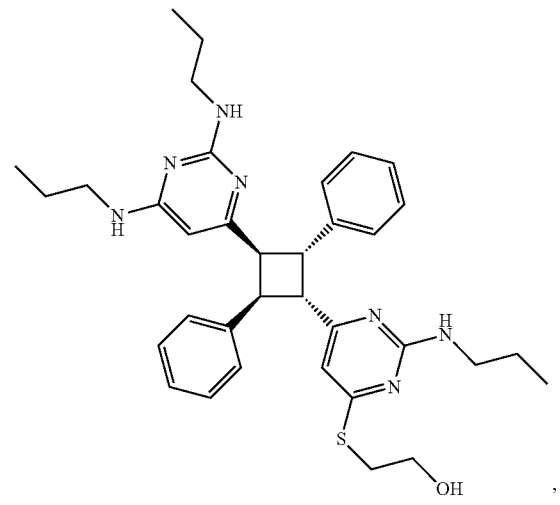

-continued
(r)
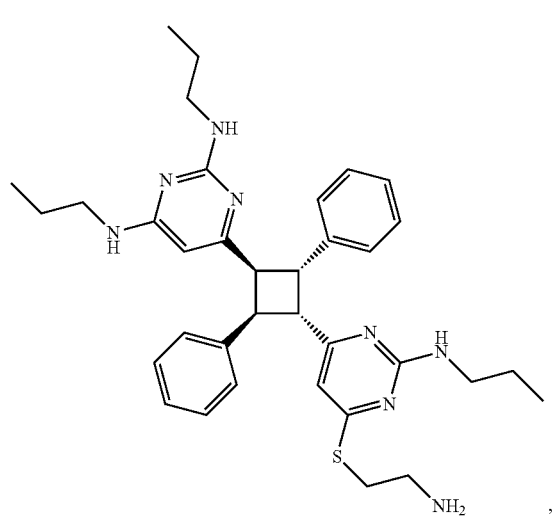
(s)
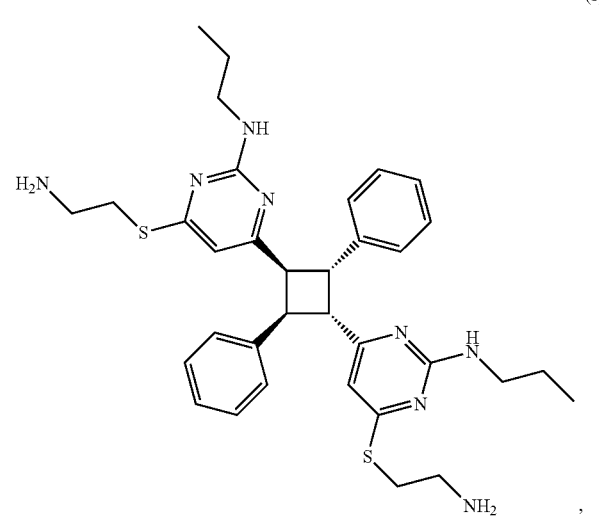
(t)
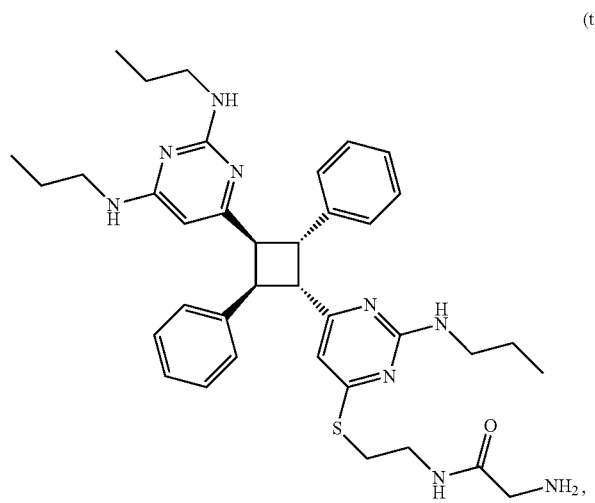
(u)
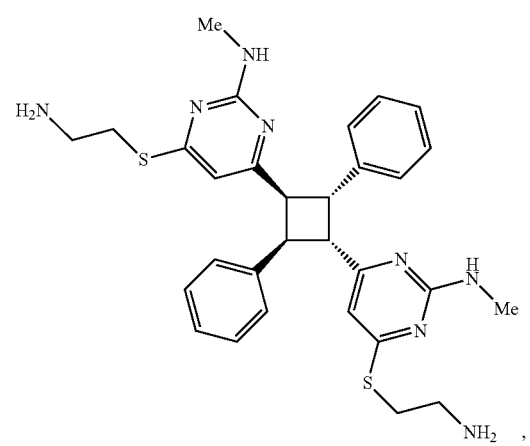
(v)
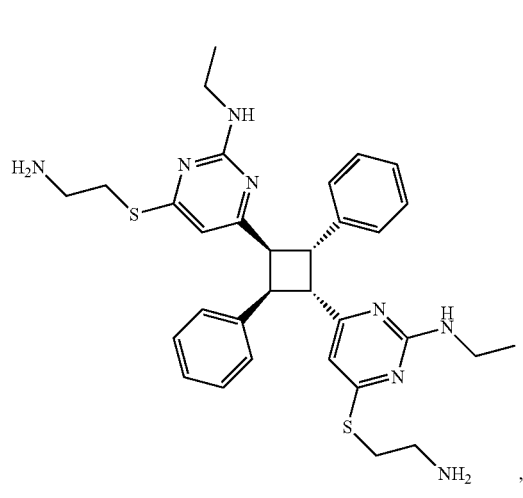
(w)
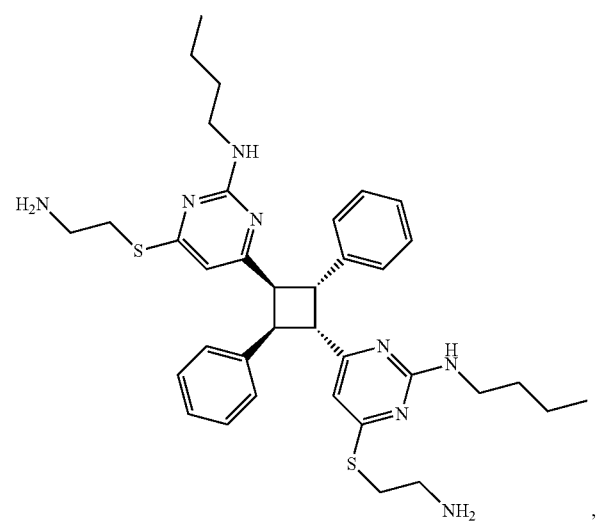

-continued
(x)
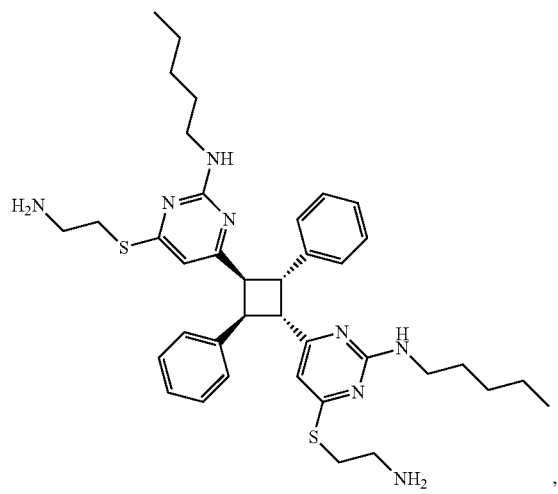
(y)
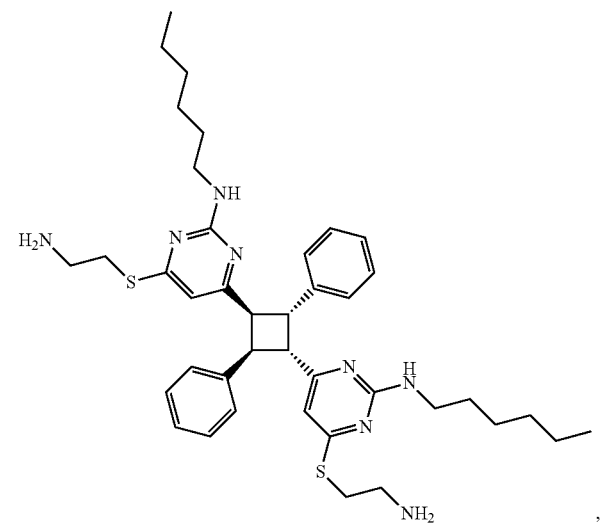
(z)
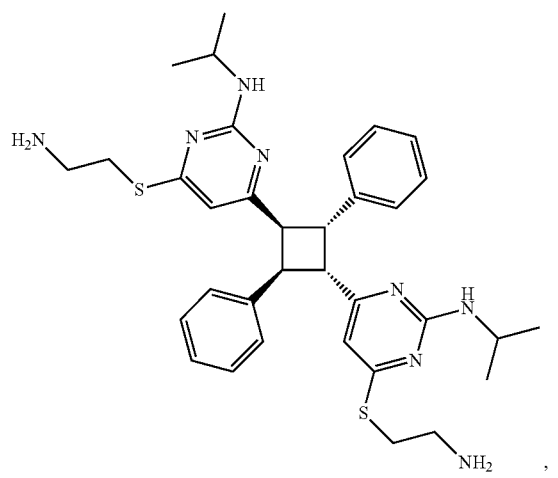
(aa)
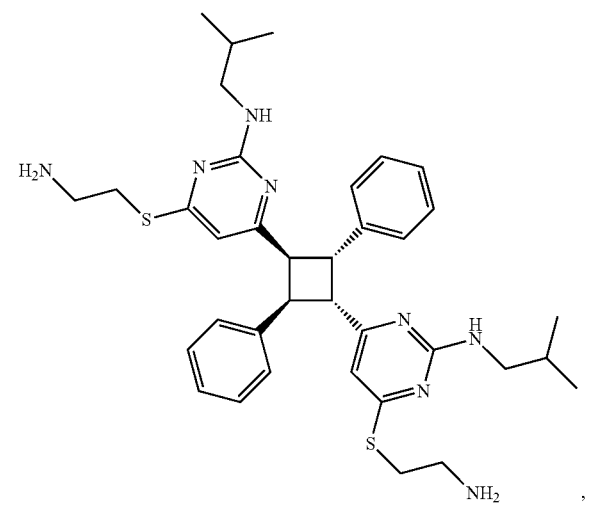
(bb)
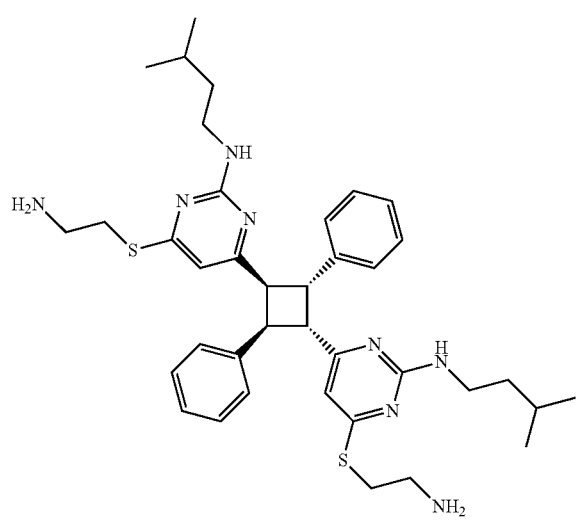
(cc)
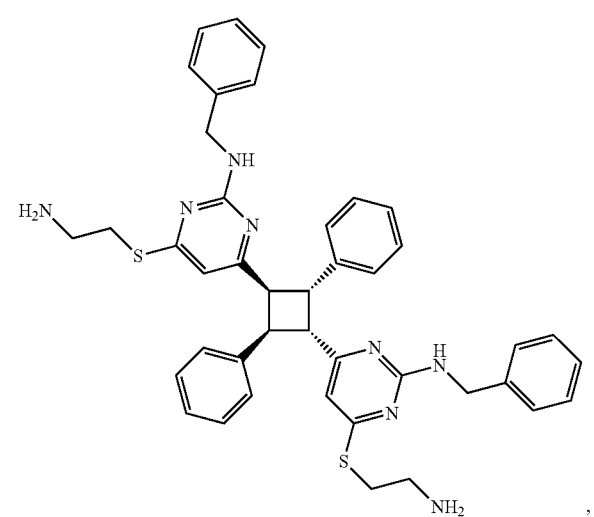

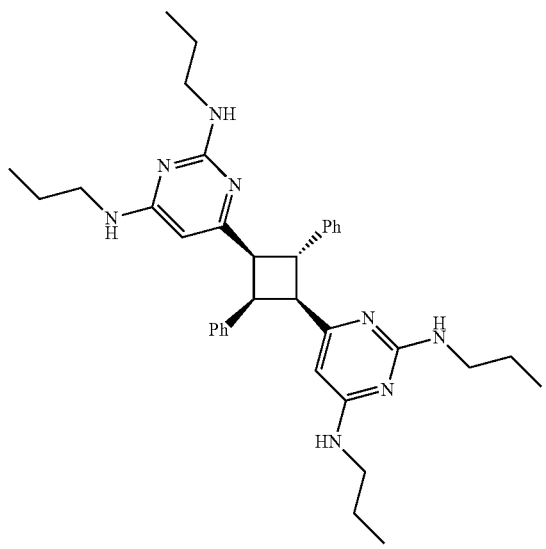
(dd)
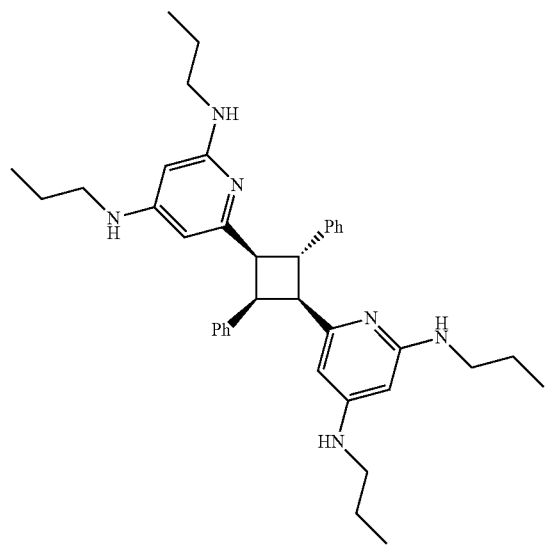
(ee)
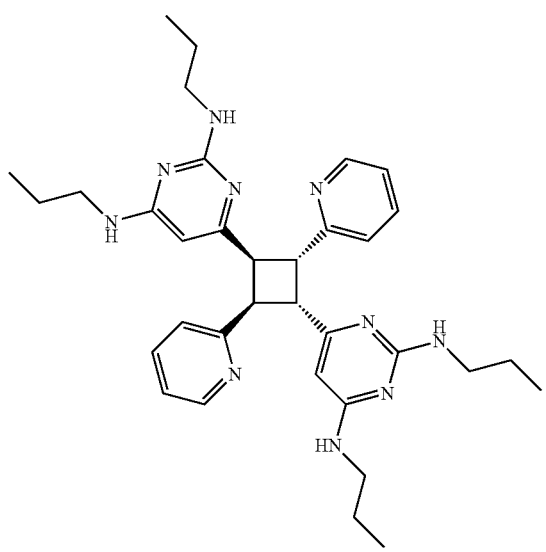
(ff)
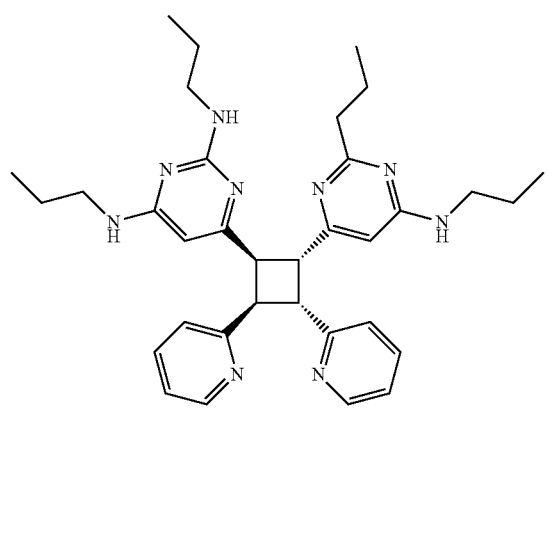
(gg)
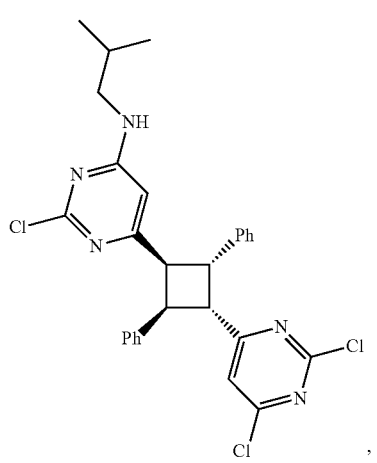
(hh)
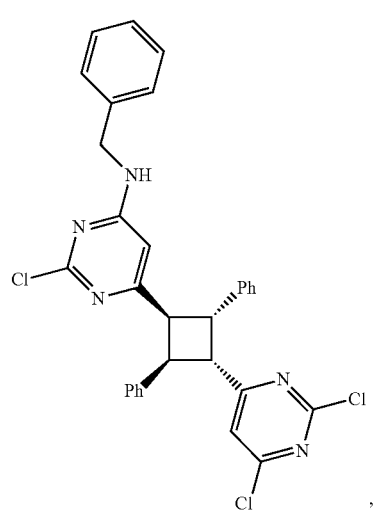
(ii)

-continued
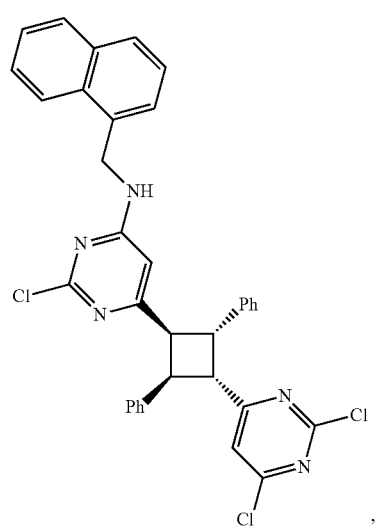
(jj)
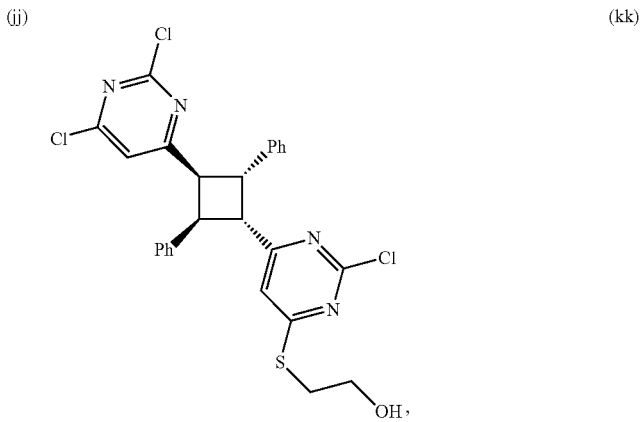
(kk)
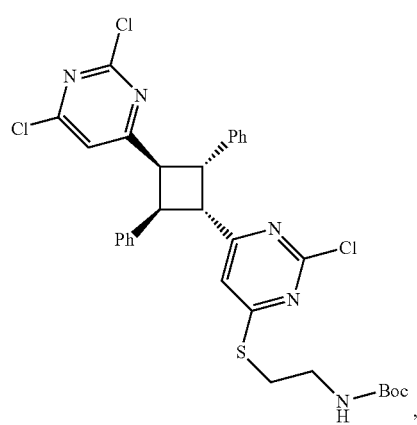
(ll)
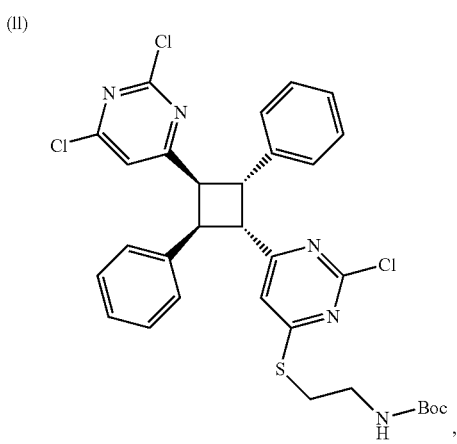
(mm)
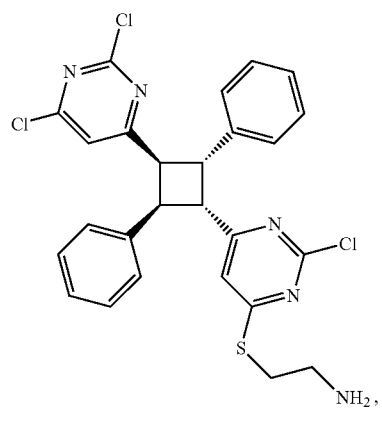
(nn)
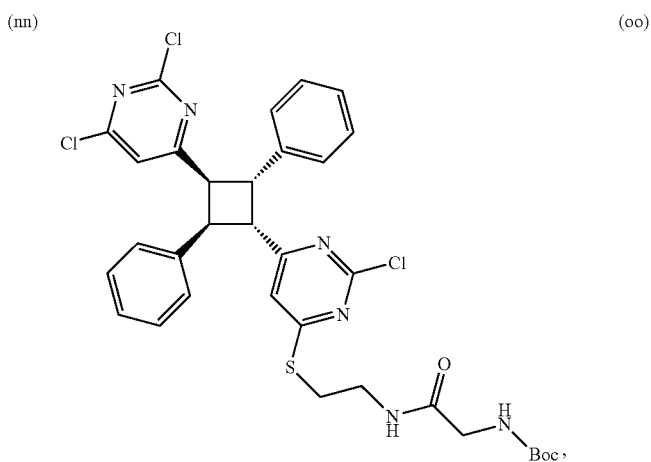
(oo)

(pp)
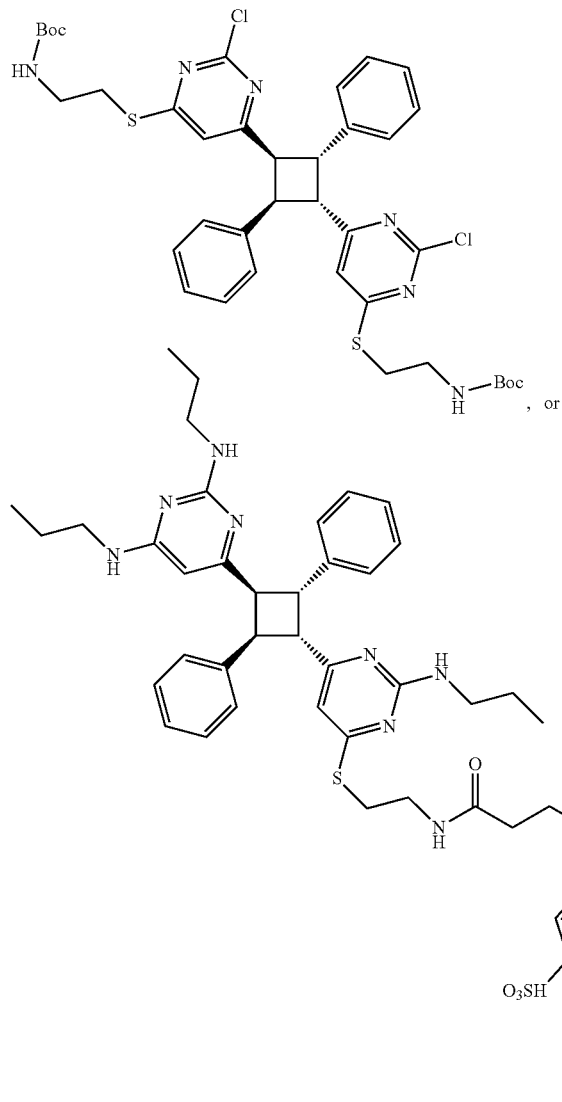
, or
(qq)
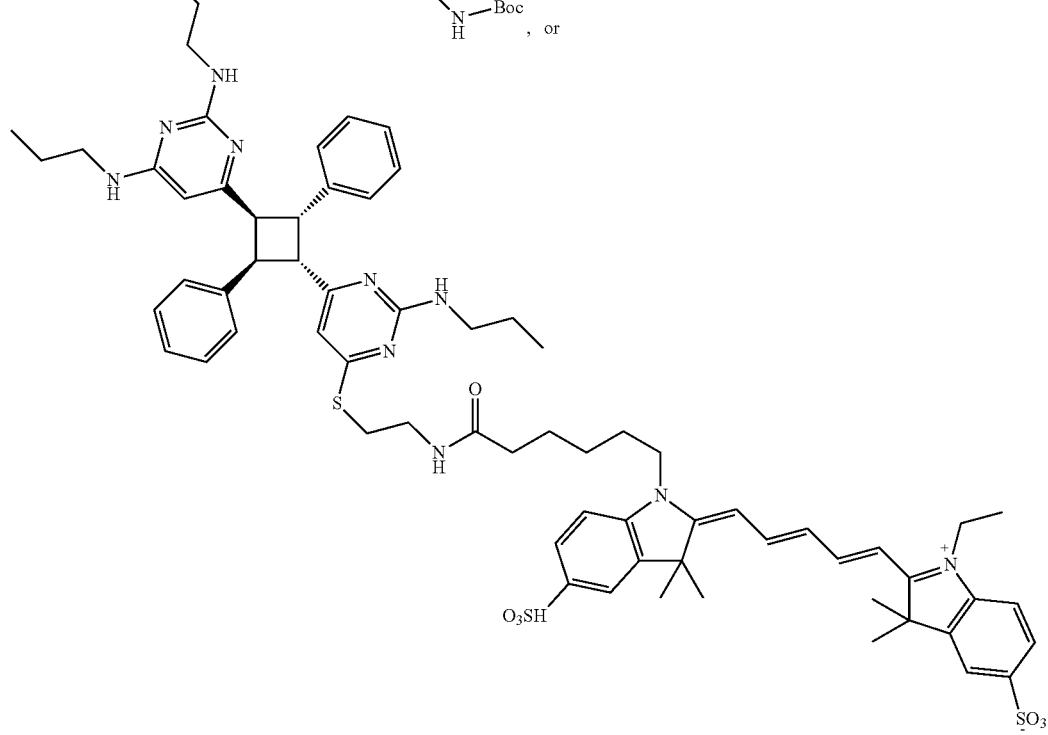
or an enantiomer or diastereomer of any of the immediately foregoing compounds;
and
(II) the compound is not selected from a compound represented by the following formula
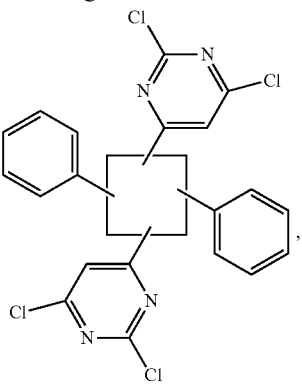
or stereoisomers, enantiomers or diastereoisomers of compounds represented by the foregoing formula.
Another aspect of the present disclosure provides a compound selected from
(a)
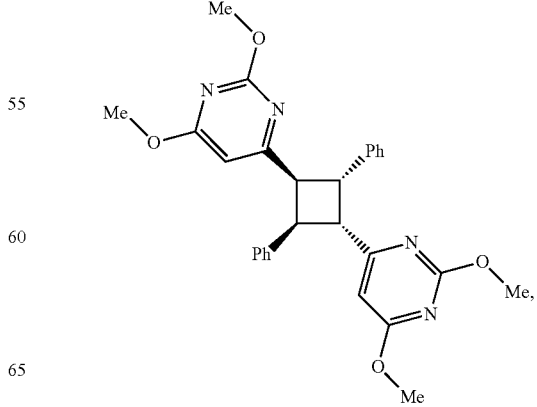

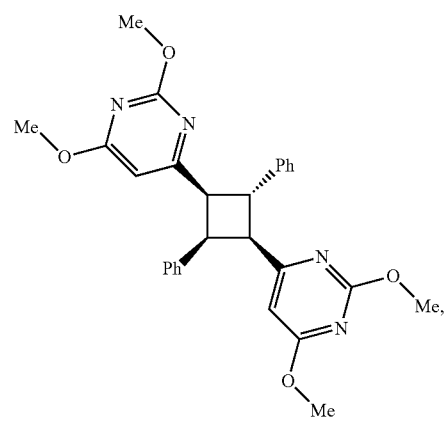
(b)
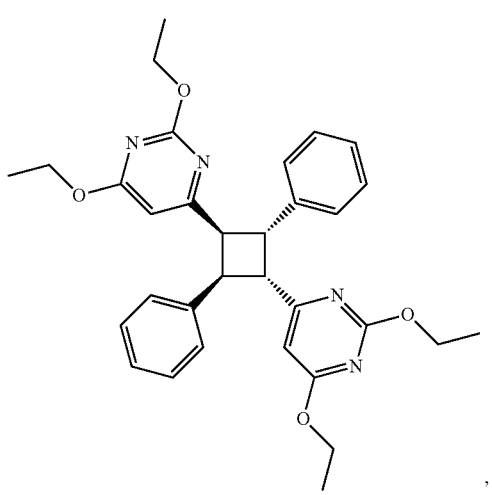
(c)
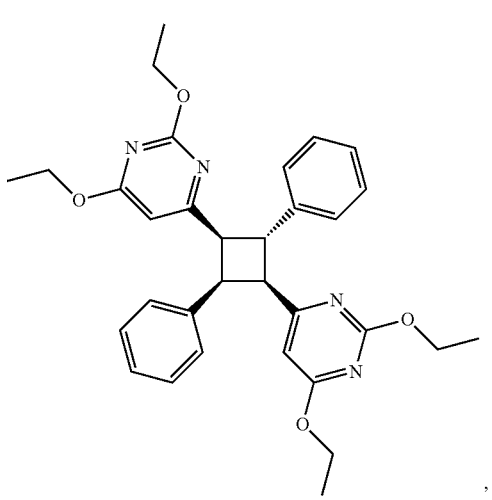
(d)
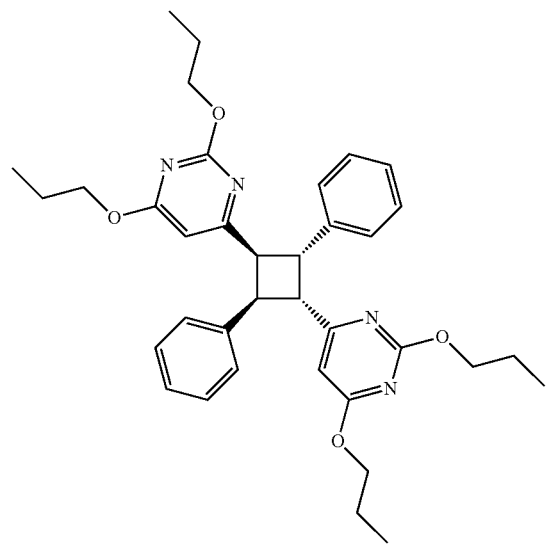
(e)
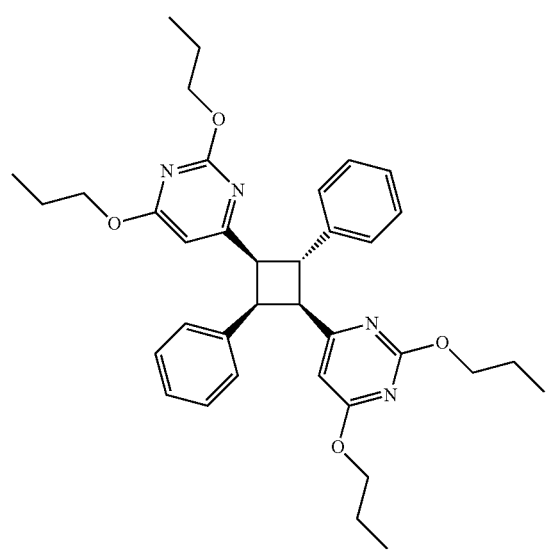
(f)
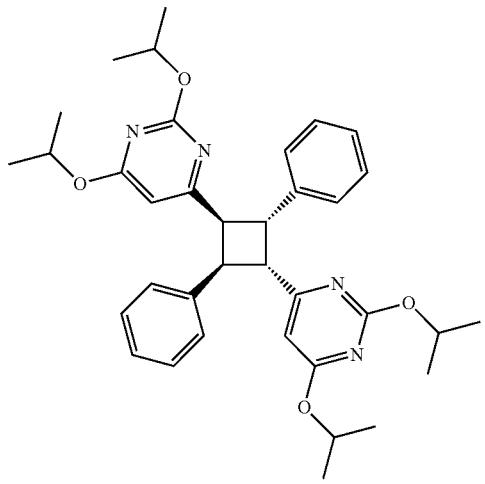
(g)

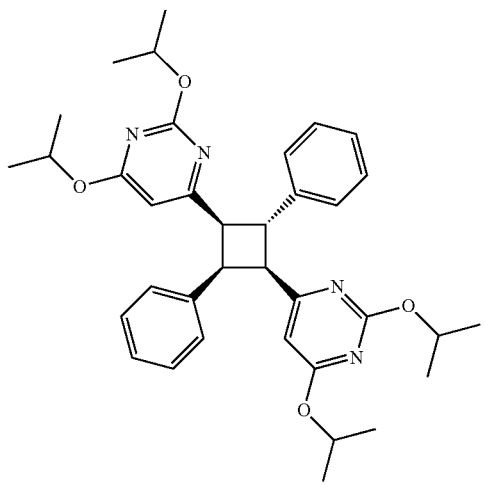
(h)
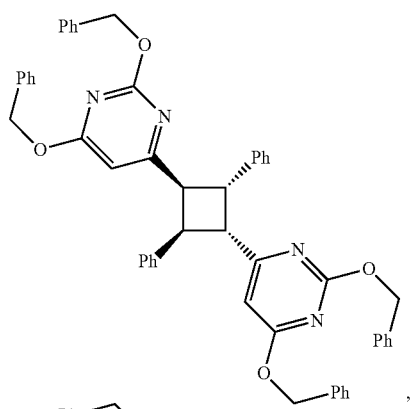
(i)
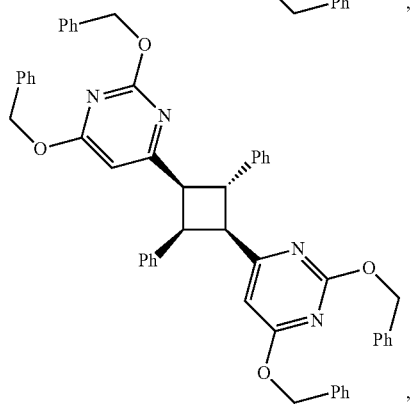
(j)
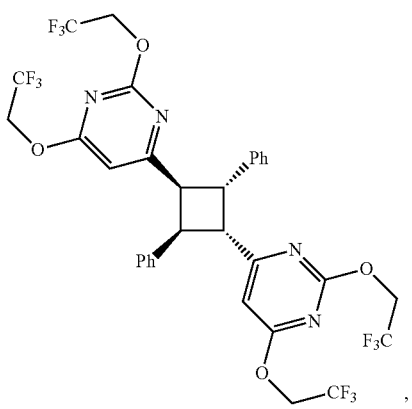
(k)
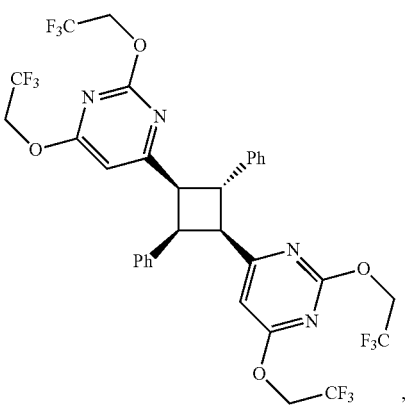
(l)
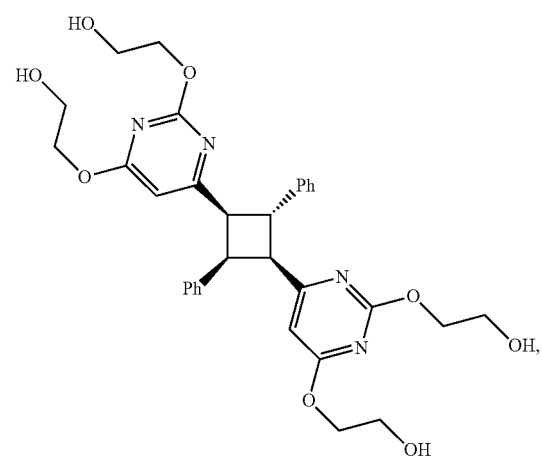
(m)
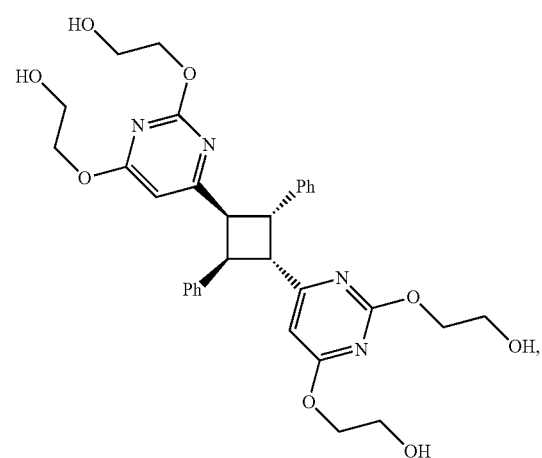
(n)
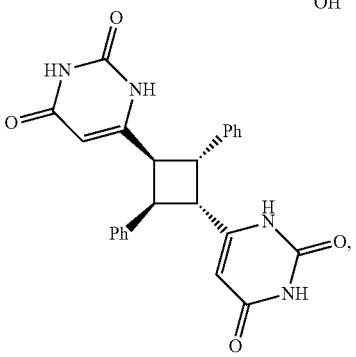
(o)

(p) 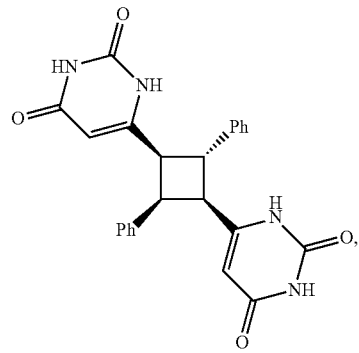
(q) 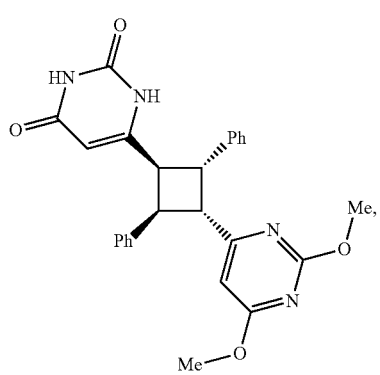
(r) 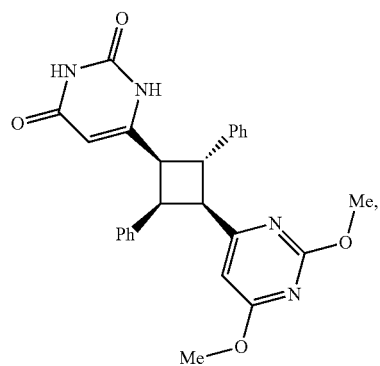
(s) 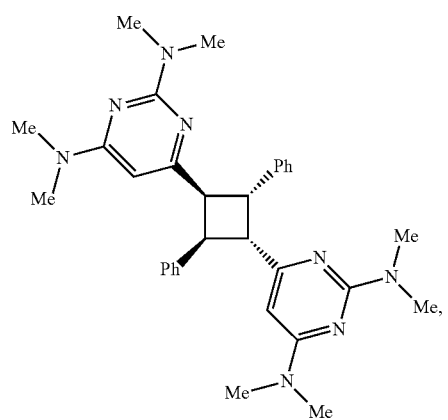
(t) 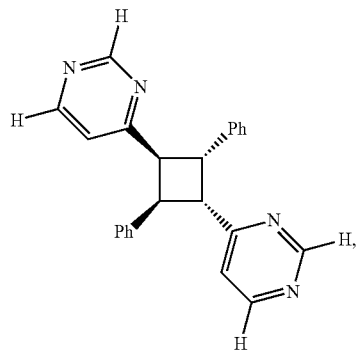
(u) 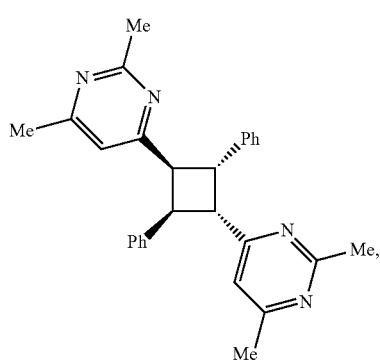
(v) 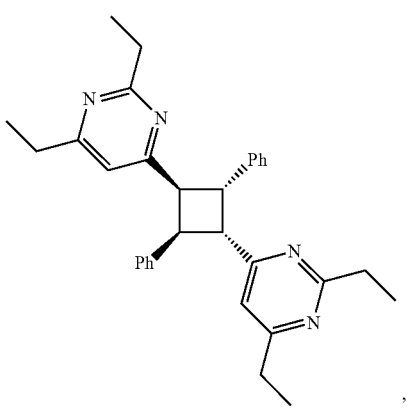
(w) 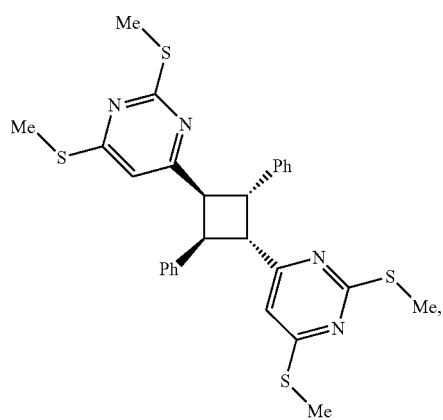

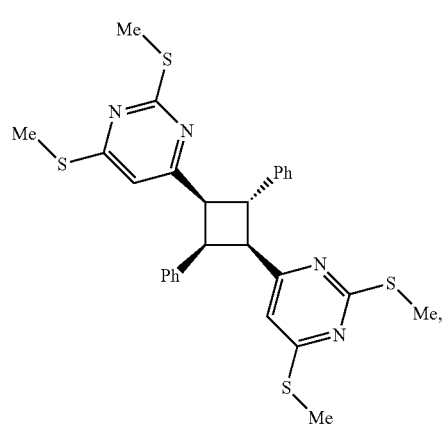
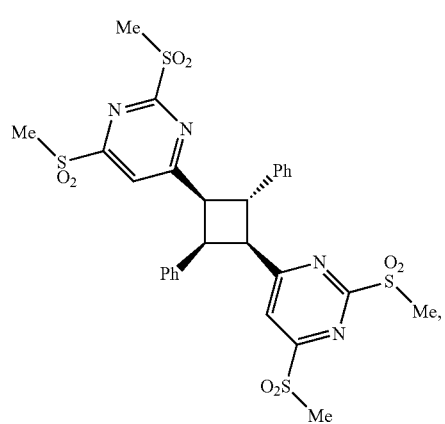

-continued
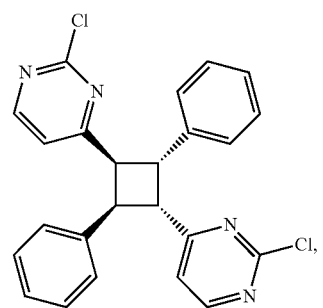 (dd)
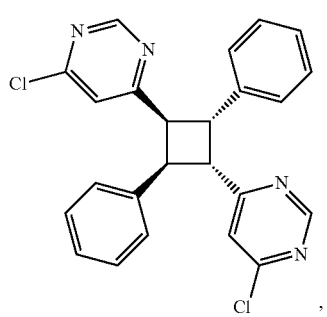 (ee)
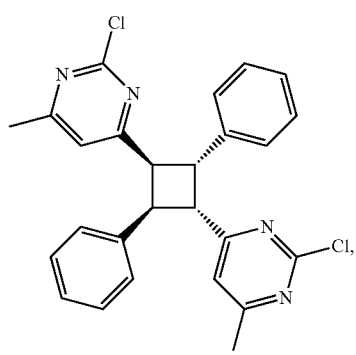 (ff)
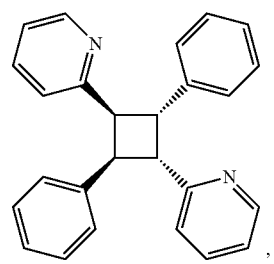 (gg)
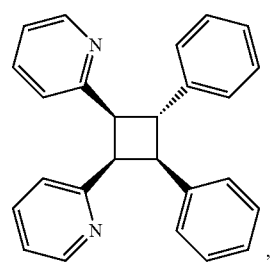 (hh)
-continued
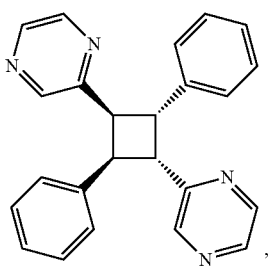 (ii)
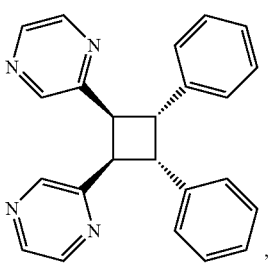 (jj)
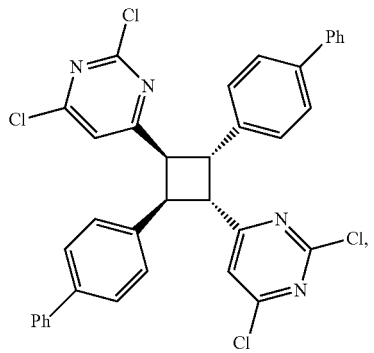 (kk)
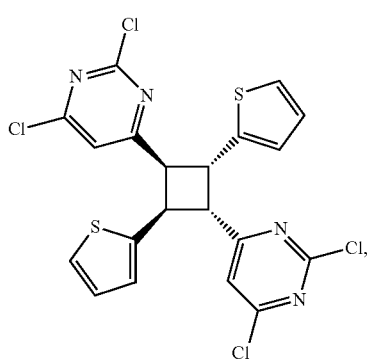 (ll)
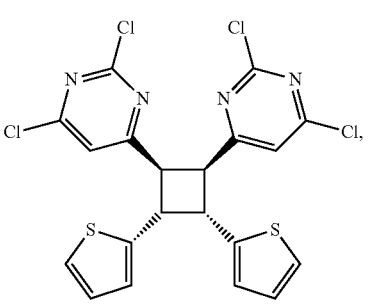 (mm)

-continued
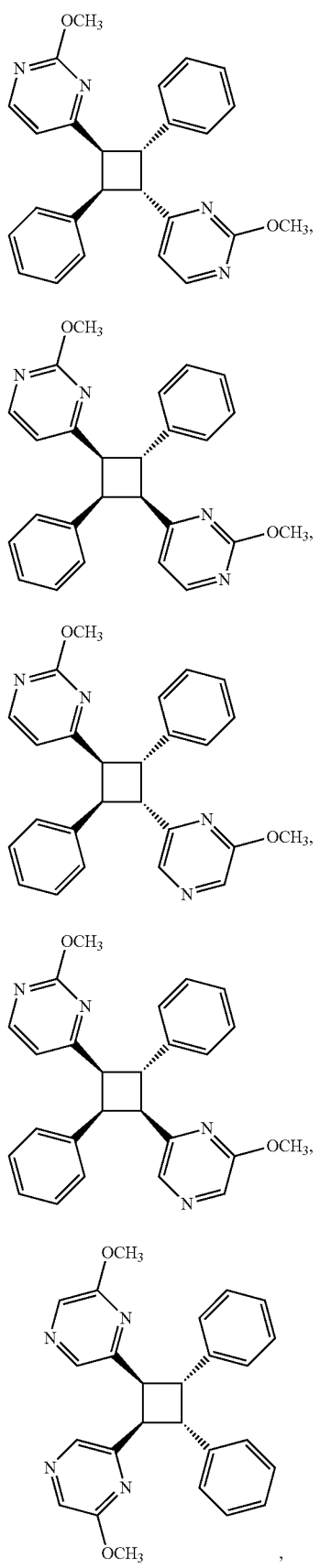
(nn)
(oo)
(pp)
(qq)
(rr)
-continued
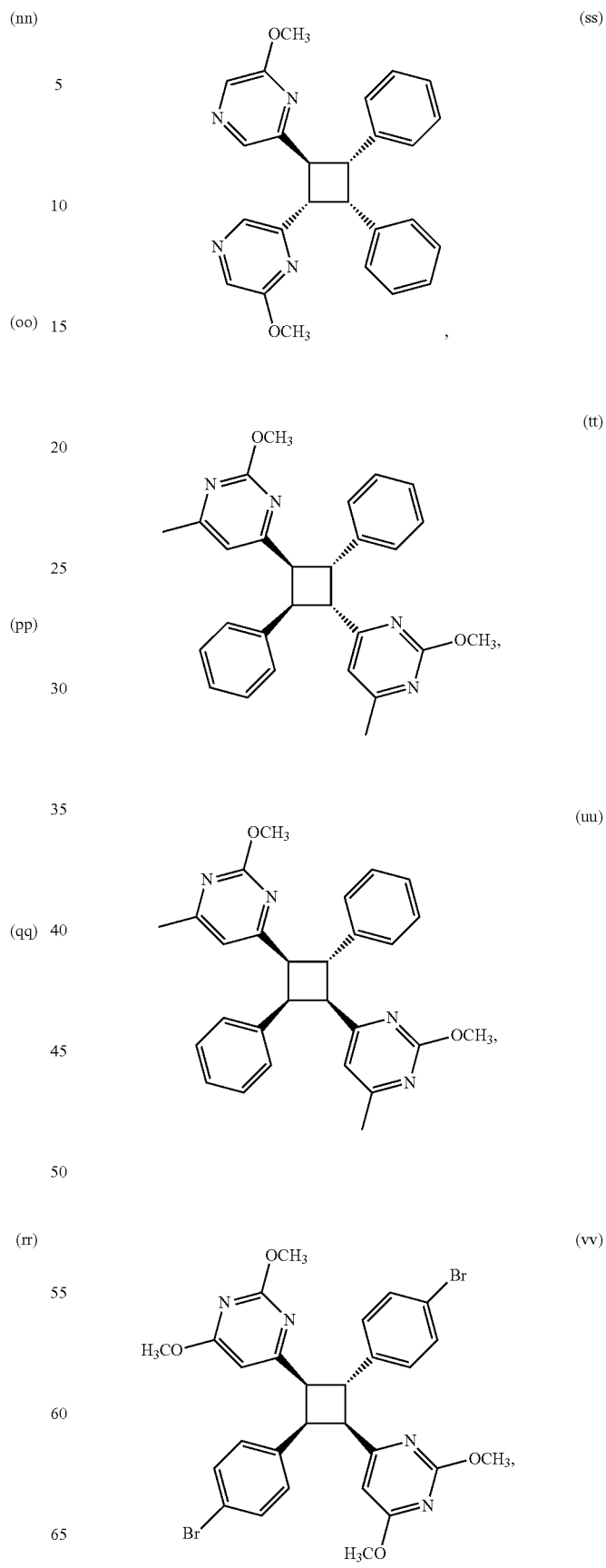
(ss)
(tt)
(uu)
(vv)

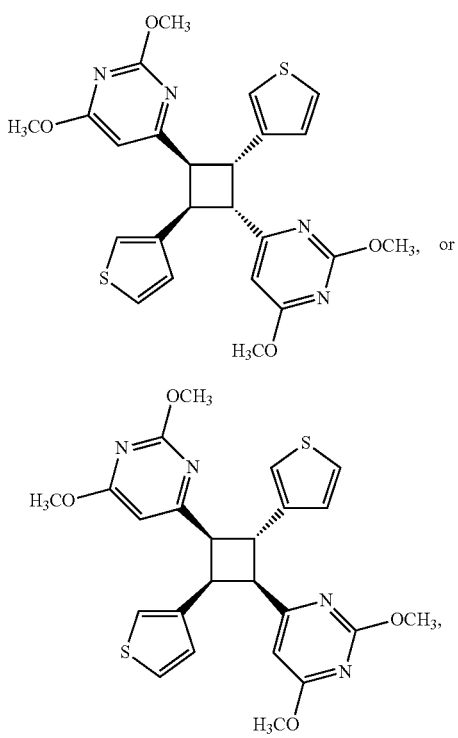

(ww)

(xx)

or combinations thereof,
or an enantiomer, diastereomer, or tautomer of said compound, or a pharmaceutically acceptable, salt, ester, or prodrug of said compound, of said enantiomer of said compound, of said diastereomer of said compound, or of said tautomer of said compound.

Another aspect of the present disclosure provides a pharmaceutical composition comprising, consisting essentially of, or consisting of a compound described herein and a pharmaceutically acceptable carrier.

Another aspect of the present disclosure provides a method of treating a hormone responsive cancer in a subject comprising administering to the subject a therapeutically effective amount of a compound or pharmaceutical composition described herein such that the cancer is treated.

Another aspect of the present disclosure provides a method of treating a hormone refractory cancer in a subject comprising administering to the subject a therapeutically effective amount of a compound or pharmaceutical composition described herein such that the cancer is treated.

Another aspect of the present disclosure provides a method of treating a hormone refractory cancer in a subject comprising administering to the subject a therapeutically effective amount of a compound or pharmaceutical composition described herein to inhibit the androgen receptor of the tumor cells of the cancer such that the cancer is treated.

Another aspect of the present invention provides a method of treating a hormone refractory cancer in a subject wherein the cancer is characterized by having one or more mutations in the androgen receptors of the cancer cells comprising administering to the subject a therapeutically effective amount of a compound or pharmaceutical composition according to any of the foregoing aspects such that the cancer is treated.

Another aspect of the present invention provides a method of treating a hormone refractory cancer in a subject wherein the cancer is characterized by having one or more mutations in the ligand-binding domain of the androgen receptors of the cancer cells comprising administering to the subject a therapeutically effective amount of a compound or pharmaceutical composition according to any one of the foregoing aspects such that the cancer is treated.

Another aspect of the present invention provides a method according to any of the foregoing aspects wherein the one or more mutations of the androgen receptor are selected from T877A, W741C, W741L, L701H, H874Y, and F876L.

Another aspect of the present invention provides a method according to any of the foregoing aspects wherein the androgen receptor in the tumor cells is selectively inhibited compared to the androgen receptor in non-tumor cells.

Another aspect of the present invention provides a method for inhibiting the subcellular relocalization of an androgen receptor of a cancer cell in a subject comprising administering to the subject a therapeutically effective amount of a compound or pharmaceutical composition as described herein such that the cancer is treated.

Another aspect of the present invention provides a method wherein the subcellular relocalization of the androgen receptor is subcellular relocation from the cytoplasm to the nucleus.

Another aspect of the present invention provides a method for trapping an androgen receptor in the cytoplasm of a cancer cell in a subject comprising administering to the subject a therapeutically effective amount of a compound or pharmaceutical composition as described herein such that the cancer is treated.

Another aspect of the present invention provides a method wherein the cancer cell is a hormone responsive cancer cell.

Another aspect of the present invention provides a method wherein the cancer cell is a hormone refractory cancer cell.

Another aspect of the present invention provides a method wherein the androgen receptor is characterized as having one or more mutations.

Another aspect of the present invention provides a method wherein the one or more mutations of the androgen receptor is in the ligand-binding domain of the androgen receptor.

Another aspect of the present invention provides a method wherein the one or more mutations of the androgen receptor are selected from T877A, W741C, W741L, L701H, H874Y, and F876, and combinations thereof.

Another aspect of the present invention provides a method according to any of the foregoing aspects wherein the subject is further administered with additional anticancer therapy.

Another aspect of the present invention provides a method according to any of the foregoing aspects wherein the additional anticancer therapy is selected from radiation therapy, chemotherapy, and combinations thereof.

Another aspect of the present invention provides a method according to any of the foregoing aspects wherein the additional anticancer therapy is radiation therapy.

Another aspect of the present invention provides a method according to any of the foregoing aspects wherein the additional anticancer therapy is chemotherapy.

Another aspect of the present invention provides a method according to any of the foregoing aspects wherein the subject is further administered with other androgen deprivation therapy agents.

Another aspect of the present invention provides a method according to any of the foregoing aspects wherein the subject is further administered with other antagonists of the androgen receptor.

Another aspect of the present invention provides a method according to any of the foregoing aspects wherein the subject is further administered with inhibitors of androgen biosynthesis.

Another aspect of the present invention provides a method according to any of the foregoing aspects wherein the cancer is prostate cancer.

Another aspect of the present invention provides a compound as described herein for the manufacture of a medicament for treating a hormone refractory cancer, or any of the other foregoing treatment aspects, in a subject comprising administering to the subject a therapeutically effective amount of the medicament such that the cancer is treated.

Another aspect of the present disclosure provides all that is disclosed and illustrated herein.

Pharmaceutical Salts and Compositions

The said compounds according to the present disclosure can be used in their final non-salt form. On the other hand, the present disclosure also encompasses the use of these compounds in the form of their pharmaceutically acceptable salts, which can be derived from various organic and inorganic acids and bases by procedures known in the art. By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained Pharmaceutically acceptable salts may be obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts may also be obtained by reacting a compound described herein, with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods known in the art.

With regard to that stated above, it can be seen that the expression "pharmaceutically acceptable salt" in the present connection is taken to mean an active compound which comprises a compound described herein in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The present disclosure furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active compounds. The term "pharmaceutical composition" refers to a mixture of a compound described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The present disclosure furthermore relates to medicaments comprising at least one compound described herein and/or pharmaceutically usable derivatives, solvates and stereoisomers thereof, including mixtures thereof in all ratios, and optionally excipients and/or adjuvants. The term "pharmaceutical combination" or "pharmaceutical formulation" are used interchangeably herein and refer to a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

Pharmaceutical formulations can be administered in the form of dosage units which comprise a predetermined amount of active compound per dosage unit. Such a unit can comprise, for example, 0.1 mg to 3 g, preferably 1 mg to 700 mg, particularly preferably 5 mg to 100 mg, of a compound according to the present disclosure, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavor, preservative, dispersant and dye may likewise be present.

Capsules are produced by preparing a powder mixture as described above and filling shaped gelatin shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubilizer, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatin, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatin or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting molds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavor, while elixirs are prepared using a non-toxic alcoholic vehicle. Suspensions can be formulated by dispersion of the compound in a non-toxic vehicle. Solubilizers and emulsifiers, such as, for example, ethoxylated isostearyl alcohols and polyoxyethylene sorbitol ethers, preservatives, flavor additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds provided herein and their salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds provided herein and their salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurized dispensers with aerosols, nebulizers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

A therapeutically effective amount of a compound provided herein depends on a number of factors, including, for example, the age and weight of the human or animal, the precise condition that requires treatment, and its severity, the nature of the formulation and the method of administration, and is ultimately determined by the treating doctor or vet. However, an effective amount of a compound according to the invention for the treatment is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se. It can be assumed that similar doses are suitable for the treatment of the other conditions mentioned above.

The present disclosure further relates to medicaments comprising at least one compound provided herein and/or pharmaceutically usable derivatives, solvates and stereoisomers thereof, including mixtures thereof in all ratios, and optionally excipients and/or adjuvants and at least one further medicament active compound.

The present disclosure furthermore relates to the use of compounds provided herein and pharmaceutically usable derivatives, salts, solvates, tautomers and stereoisomers thereof, including mixtures thereof in all ratios, for the preparation of a medicament for the treatment and/or combating of cancer, tumor growth, metastatic growth, where the tumor is selected from the group of tumors of the squamous epithelium, of the bladder, of the stomach, of the kidneys, of head and neck, of the esophagus, of the cervix, of the thyroid, of the intestine, of the liver, of the brain, of the prostate, of the urogenital tract, of the lymphatic system, of the stomach, of the larynx, of the lung, lung adenocarcinoma, small-cell lung carcinoma, pancreatic cancer, glioblastoma, colon carcinoma, breast carcinoma, tumor of the blood and immune system, acute myeloid leukemia, chronic myeloid leukemia, acute lymphatic leukemia, chronic lymphatic leukemia.

Further medicament active compounds are preferably chemotherapeutic agents, in particular those which inhibit angiogenesis and thus inhibit the growth and spread of tumor cells; preference is given here to VEGF receptor inhibitors, including ribozymes and antisense which are directed to VEGF receptors, and angiostatin and endostatin.

Examples of antineoplastic agents which can be used in combination with the compounds according to the present disclosure generally include alkylating agents, antimetabolites; epidophyllotoxin; an antineoplastic enzyme; a topoisomerase inhibitor; procarbazin; mitoxantron or platinum coordination complexes.

Antineoplastic agents are preferably selected from the following classes: anthracyclins, vinca medicaments, mitomycins, bleomycins, cytotoxic nucleosides, epothilones, discodermolides, pteridines, diynenes and podophyllotoxins.

In some embodiments, preference is given in the said classes to, for example, caminomycin, daunorubicin, aminopterin, methotrexate, methopterin, dichloromethotrexate, mitomycin C, porfiromycin, 5-fluorouracil, 5-fluorodeoxyuridine monophosphate, cytarabines, 5-azacytidine, thioguanine, azathioprines, adenosine, pentostatin, erythrohydroxynonyladenine, cladribines, 6-mercaptopurine, gemcitabine, cytosinarabinoside, podophyllotoxin or podophyllotoxin derivatives, such as, for example, etoposide, etoposide phosphate or teniposide, melphalan, vinblastine, vincristine, leurosidine, vindesine, leurosine and paclitaxel. Other preferred antineoplastic agents are selected from the group estramustine, carboplatin, cyclophosphamide, bleomycin, gemcitabine, ifosamide, melphalan, hexamethylmelamine, thiotepa, cytarabin, idatrexate, trimetrexate, dacarbazine, L-asparaginase, camptothecin, CPT-11, topotecan, arabinosylcytosine, bicalutamide, flutamide, leuprolide, pyridobenzoindole derivatives, interferons and interleukins.

Further medicament active compounds include antibiotics, including but not limited to dactinomycin, daunorubicin, idarubicin, epirubicin, mitoxantrone, bleomycin, plicamycin, mitomycin and combinations thereof.

Further medicament active compounds may include enzyme inhibitors. Examples of suitable enzyme inhibitors include, but are not limited to, histone deacetylation inhibitors (for example suberoyl anilide hydroxamic acid [SAHA]) and the tyrosine kinase inhibitors (for example ZD 1839 [Iressa]).

Further medicament active compounds include nuclear export inhibitors. Nuclear export inhibitors prevent the expression of biopolymers (for example RNA) from the cell nucleus. Examples include those selected from the group callystatin, leptomycin B, ratjadone.

Further medicament active compounds include nuclear export inhibitors. Nuclear export inhibitors prevent the expression of biopolymers (for example RNA) from the cell nucleus. Examples include those selected from the group callystatin, leptomycin B, ratjadone.

Further medicament active compounds include immunosuppressants, such as those selected from the group rapamycin, CC1-779 (Wyeth), RAD001 (Novartis), AP23573 (Ariad Pharmaceuticals).

The present disclosure also relates to a set (kit) consisting of separate packs of (a) an effective amount of a compound provided herein and/or pharmaceutically usable derivatives, solvates and stereoisomers thereof, including mixtures thereof in all ratios, and (b) an effective amount of a further medicament active compound.

The set/kit may further comprise suitable containers, such as boxes, individual bottles, bags or ampoules. The set may, for example, comprise separate ampoules, each containing an effective amount of a compound provided herein and/or pharmaceutically usable derivatives, solvates and stereoisomers thereof, including mixtures thereof in all ratios, and an effective amount of a further medicament active compound in dissolved or lyophilized form.

The compounds according to the present disclosure and pharmaceutically usable derivatives, salts, solvates, tautomers and stereoisomers thereof, including mixtures thereof in all ratios, are suitable as pharmaceutical active compounds for mammals, in particular for humans, for the preparation of a medicament for the treatment and/or combating of cancer, tumor growth, metastatic growth, fibrosis and the like.

The present disclosure therefore relates to the use of compounds provided herein and pharmaceutically usable derivatives, salts, solvates, tautomers and stereoisomers thereof, including mixtures thereof in all ratios, for the preparation of a medicament for the treatment and/or combating of cancer, tumor growth, metastatic growth, fibrosis, and the like.

Particular preference is given to the use for the treatment of a disease, where the disease is a solid tumor.

The solid tumor is preferably selected from the group of tumors of the squamous epithelium, the bladder, the stomach, the kidneys, of head and neck, the esophagus, the cervix, the thyroid, the intestine, the liver, the brain, the prostate, the urogenital tract, the lymphatic system, the stomach, the larynx and/or the lung. In certain embodiments, the tumor is in the prostate.

The present disclosure also relates to the use of compounds provided herein and/or physiologically acceptable salts and solvates thereof for the preparation of a medicament for the treatment of solid tumors, where a therapeutically effective amount of a compound such as an androgen receptor modulator and/or further angiogenesis inhibitors.

The present compounds are also suitable for combination with known anticancer agents. These known anticancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy.

The present disclosure therefore also relates to the use of compounds provided herein and/or physiologically acceptable salts and solvates thereof for the preparation of a medicament for the treatment of solid tumors, where a therapeutically effective amount of a compound of the formula I is administered in combination with (1) radiotherapy, and/or an (2) androgen receptor modulator, and/or (3) cytotoxic agents, and/or (4) further angiogenesis inhibitors.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamineplatinum(II)]bis[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, and elinafide.

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS 184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butyla-mide, TDX258 and BMS 188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamin-e, 1-amino-9-ethyl-5-fluoro-2,3-dihydro-9-hydroxy-4-methyl-1H,12H-benzo[de-]pyrano[3',4':b,7]indolizino[1,2b]quinoline-10,13(9H, 15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazo-le-1-carboxamide, asulacrine, (5a,5aB,8aa,9b)-9-[2-[N-[2-(dimethylamino)ethyl]-N-methylamino]ethyl]-5-[-4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium-, 6,9-bis[[(2-aminoethyl)amino]benzo[g]isoquinoline-5,10-dione, 5-(3-aminopropylamino)-7, 10-dihydroxy-2-(2-hydroxyethylaminomethyl)-6H-pyrazolo[4,5,1-de]-acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-on-e and dimesna.

"Antiproliferative agents" include antisense RNA and DNA oligonucleotides such as G3139, ODN698, RVASKRAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetr-acyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumor suppressor genes, such as p53, which can be delivered, for example, via recombinant virus-mediated gene transfer.

The following examples are offered by way of illustration and not by way of limitation. The compound numbers cited in the Examples are cited for convenience and consistency within the examples. Further numbers for the compounds are found at other places herein including, for example, Example VI.

EXAMPLES

Figure 4:
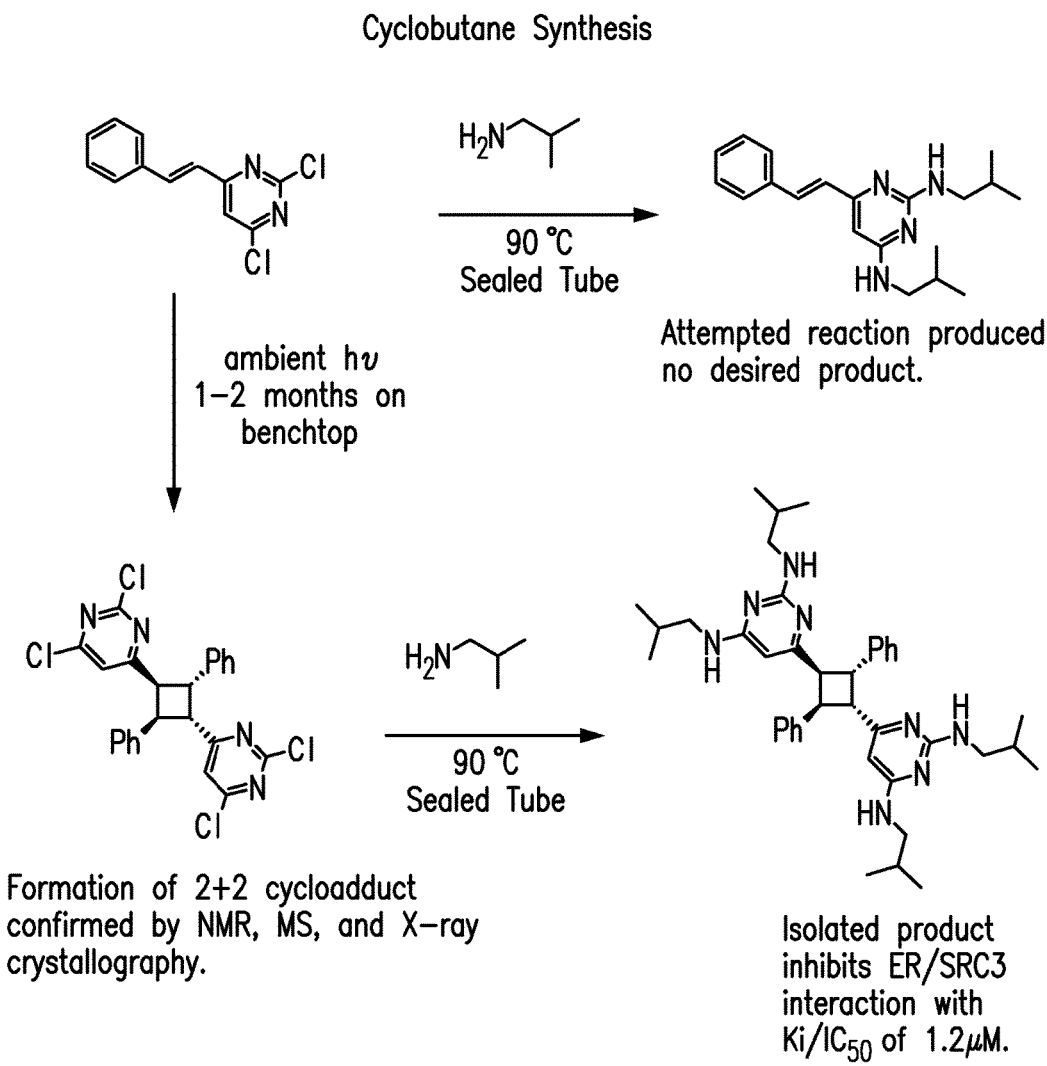
FIG. 4 depicts the cyclobutane synthesis from the photo cycloaddition of 2,4-dichloro-6-styrylpyrimidine versus a thermal reaction.
Figure 5:
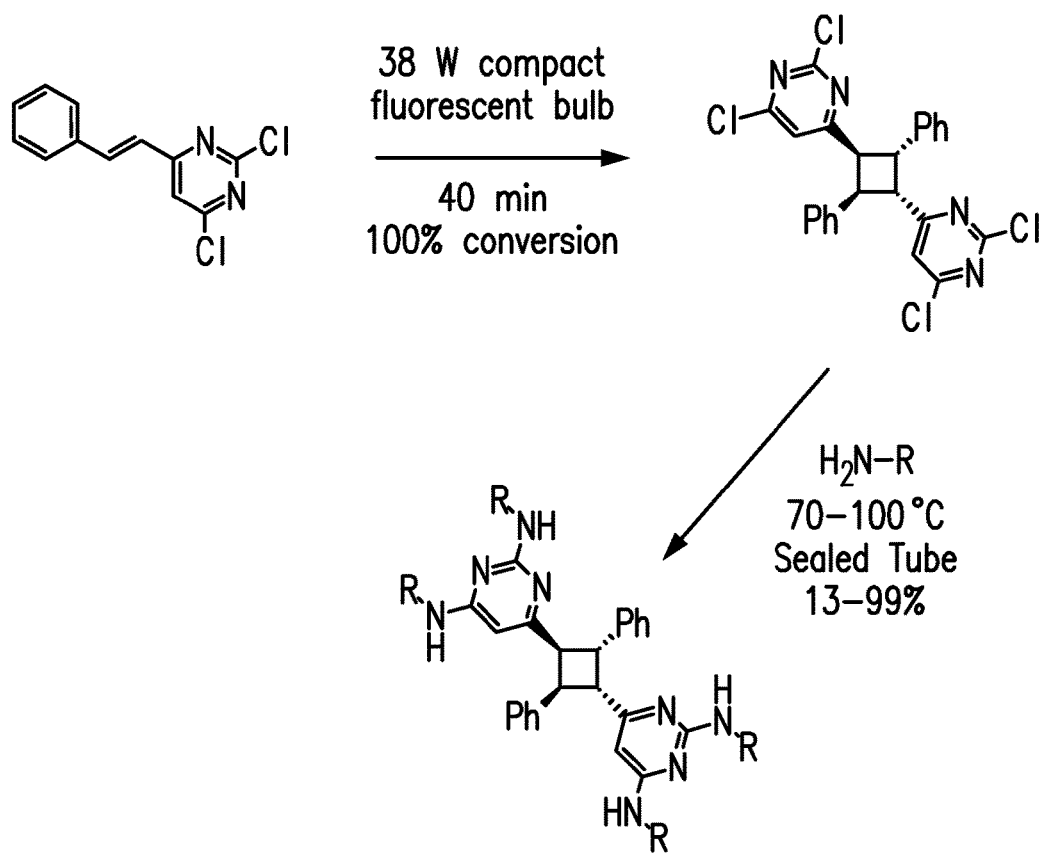
FIG. 5 depicts the synthesis of symmetrically-substituted tetraamino cyclobutanes.
Figure 6:
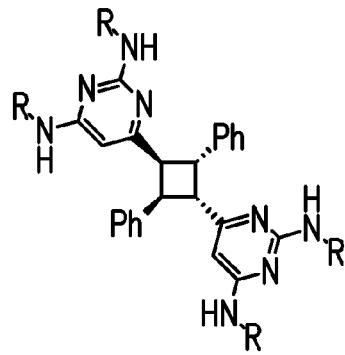
FIG. 6 depicts symmetrically-substituted cyclobutanes in estrogen receptor (ER) and androgen receptor (AR) reporter gene assays with IC50 values, as shown in Table 1 of the figure. IC50 is the concentration of an inhibitor where the response (or binding) is reduced by half.
Figure 7:
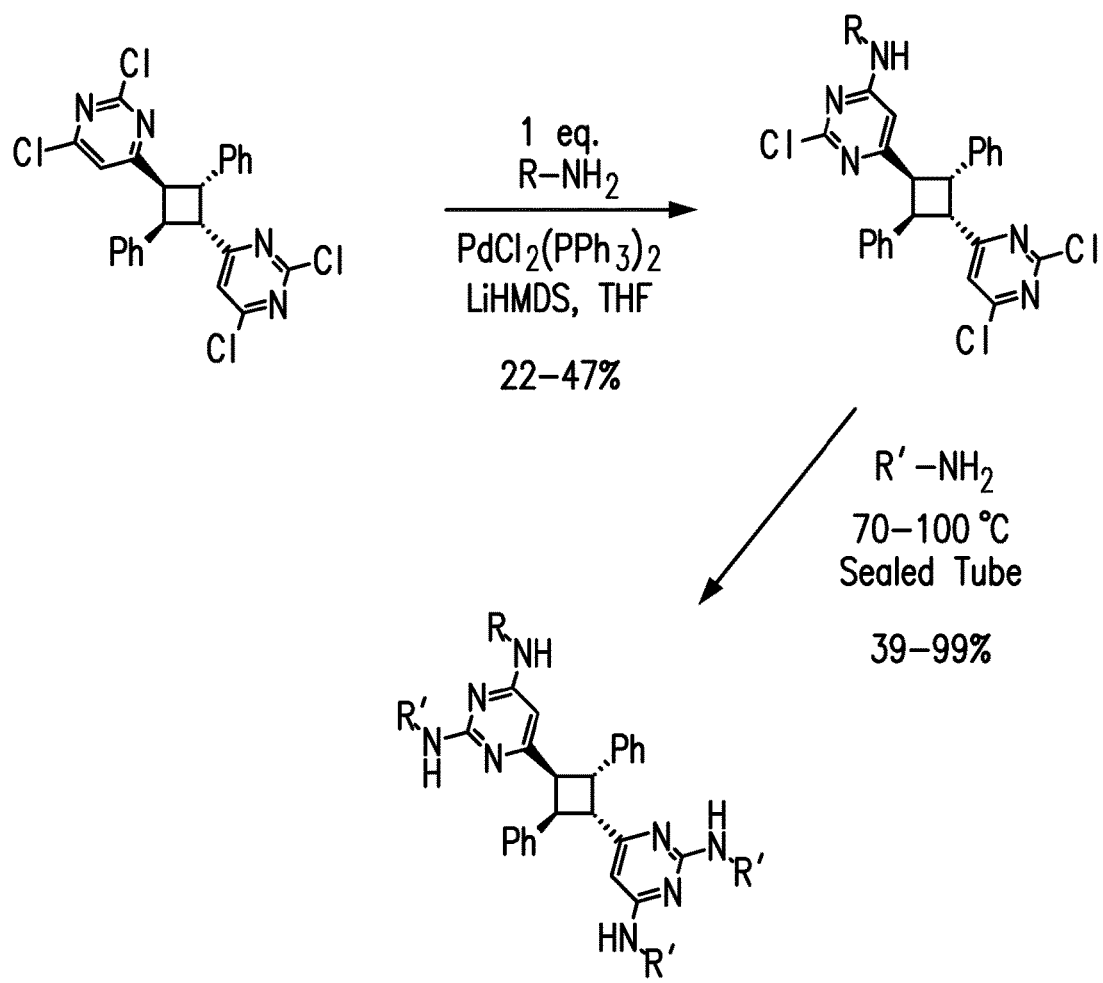
FIG. 7 depicts the synthesis of unsymmetrical tetraamino cyclobutanes.
Figure 8:
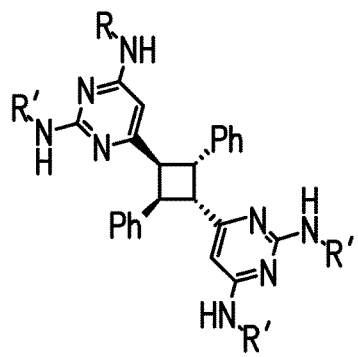
FIG. 8 depicts unsymmetrical cyclobutanes in estrogen receptor (ER) and androgen receptor (AR) reporter gene assays with IC50 values, as shown in Table 2 of the figure.
Figure 9A:
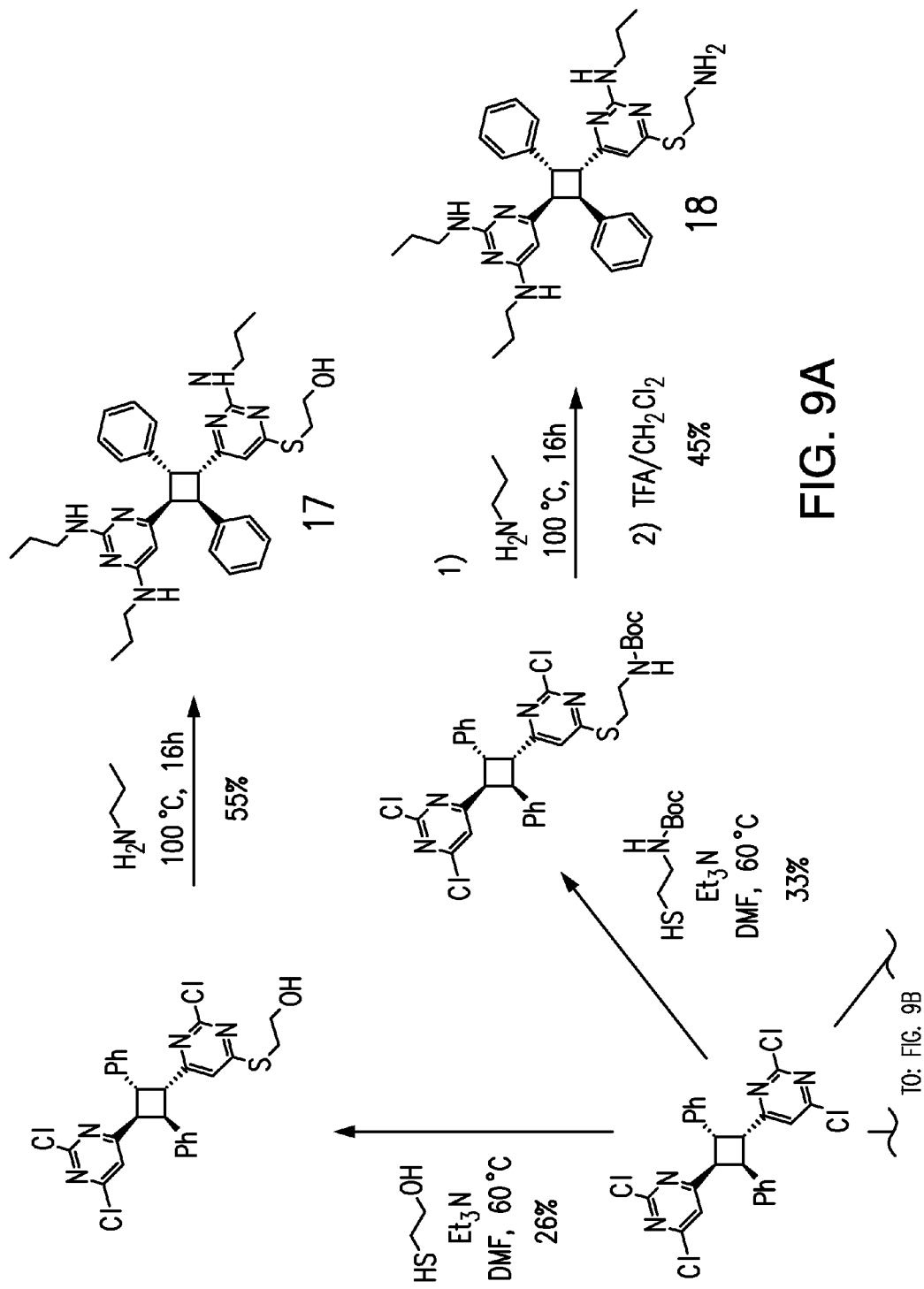
FIGS. 9A and 9B depict a synthetic reaction scheme for the synthesis of compounds 17, 18, 19, and 20 of Example I.
Figure 9B:
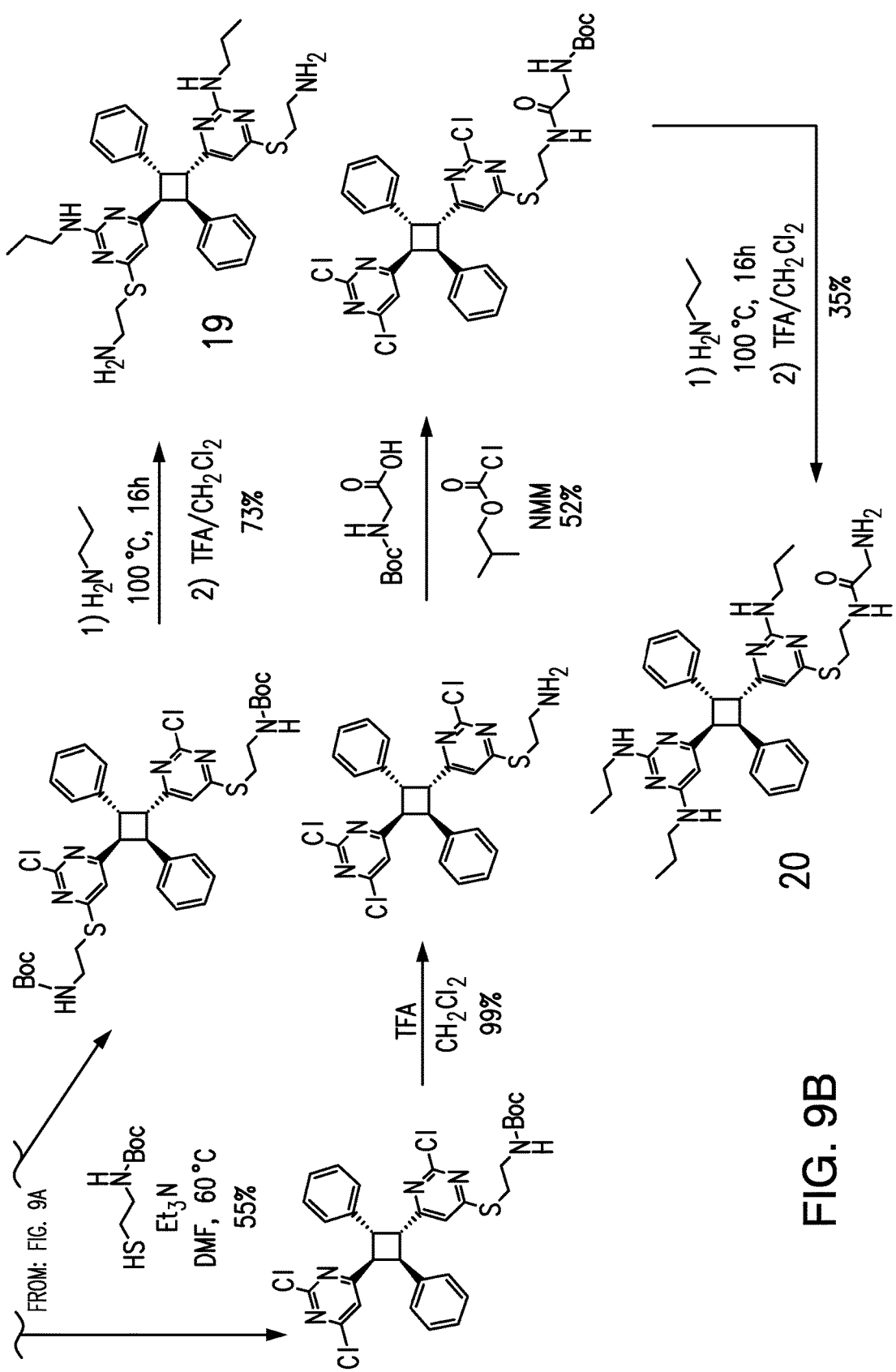
Figure 10:
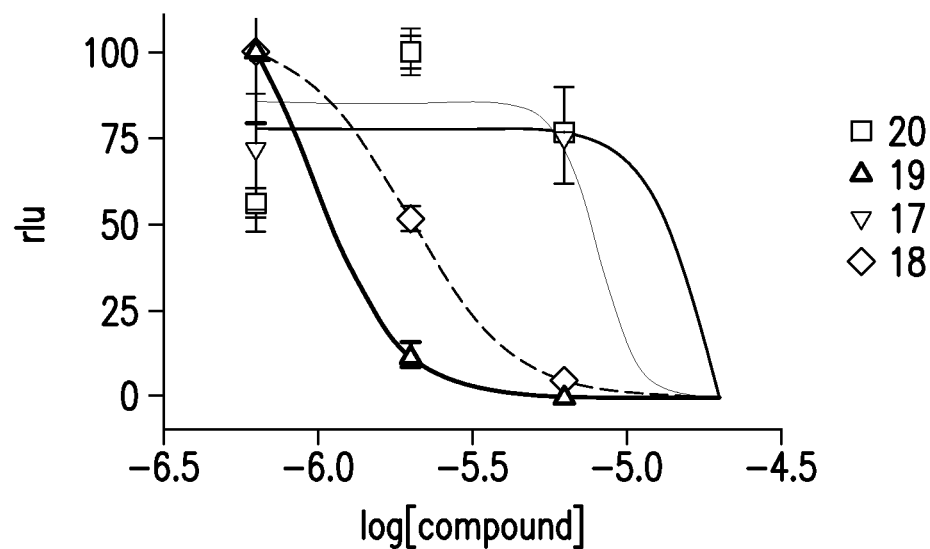
FIG. 10 depicts estrogen receptor (ER) reporter gene assay data for compounds 17, 18, 19, and 20 of Example I.
Figure 11:
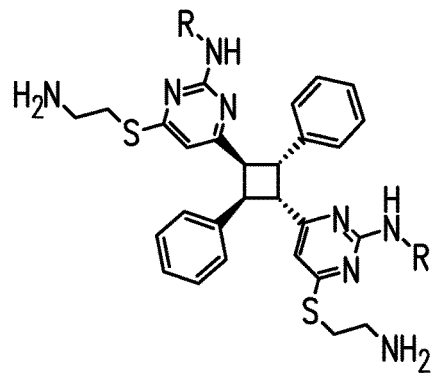
FIG. 11 depicts data for various cyclobutane compounds in an ER TR-FRET (estrogen receptor time-resolved fluorescence energy transfer) assay for compounds 21 to 30 of Example I, as shown in Table 3 of the figure.
Figure 13:
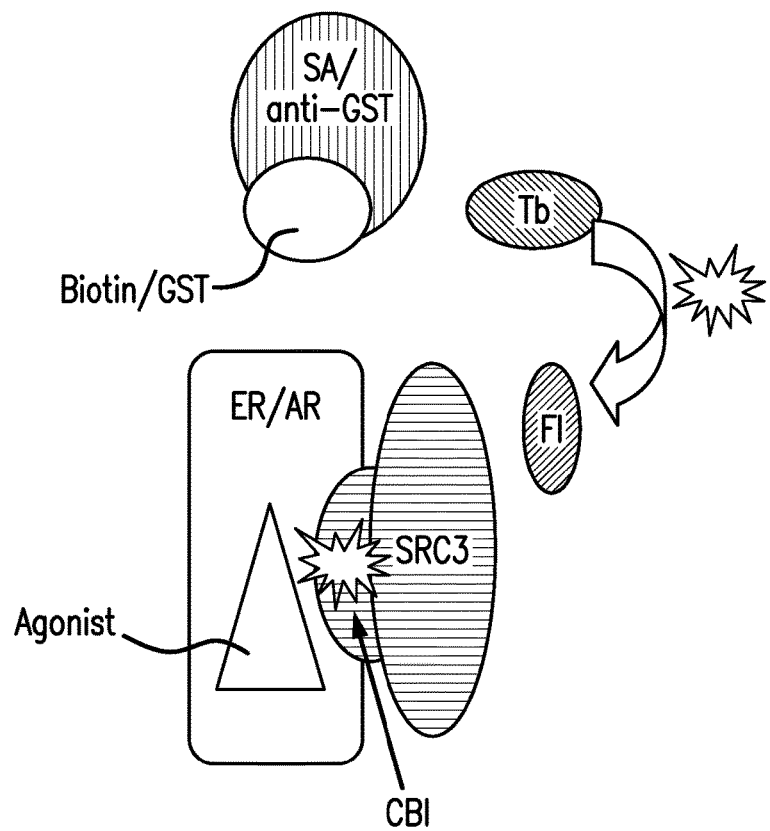
FIG. 13 depicts an estrogen receptor (ER) and androgen receptor (AR) TR-FRET (androgen receptor time-resolved fluorescence energy transfer) assay with: ERα LBD selectively biotinylated; AR-LBD with glutathione-S-transferase (GST) tag; Streptavidin-Tb (ER) or anti-GST-Tb antibody (AR) as FRET donor; Fluorescein-labeled SRC3, with 3 LXXLL motifs as FRET acceptor; and SRC1-Box II as control (LXXLL motif), performed in the presence of 17β-estradiol or DHT agonist.
Figure 14:
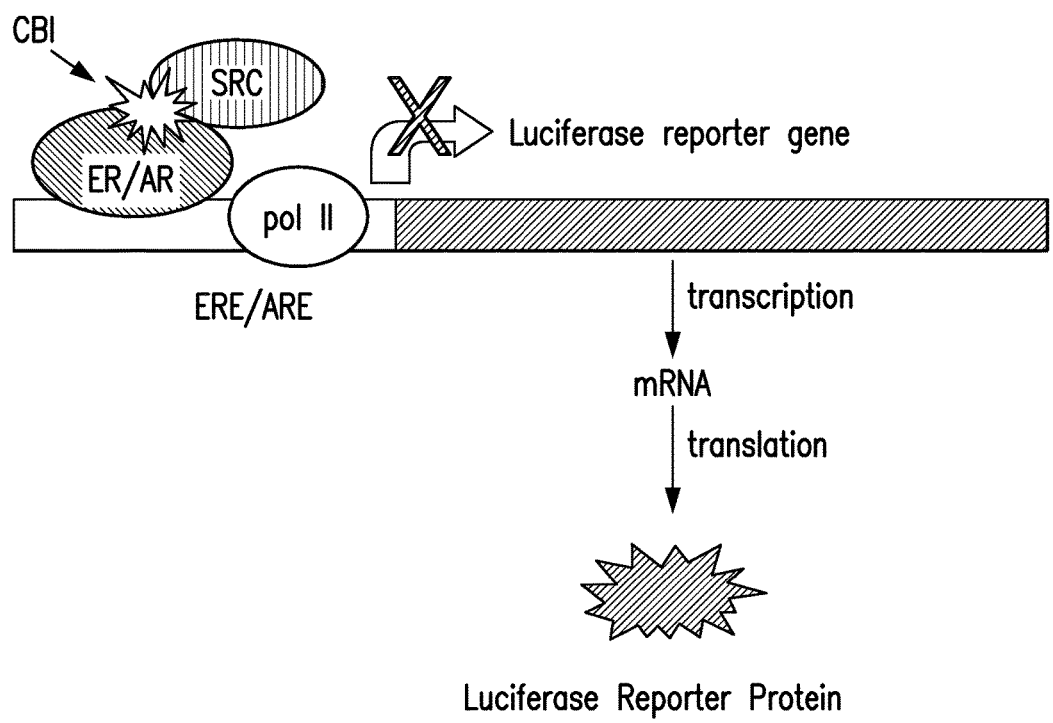
FIG. 14 depicts an estrogen receptor (ER) and androgen receptor (AR) luciferase reporter gene assay with full-length ER or AR expression vector; ERE-Luc or ARE-Luc plasmid expressed in HEC-1 cells; and B-gal plasmid used for transfection control, performed in presence of 17β-estradiol or DHT agonist.
Figure 15A:
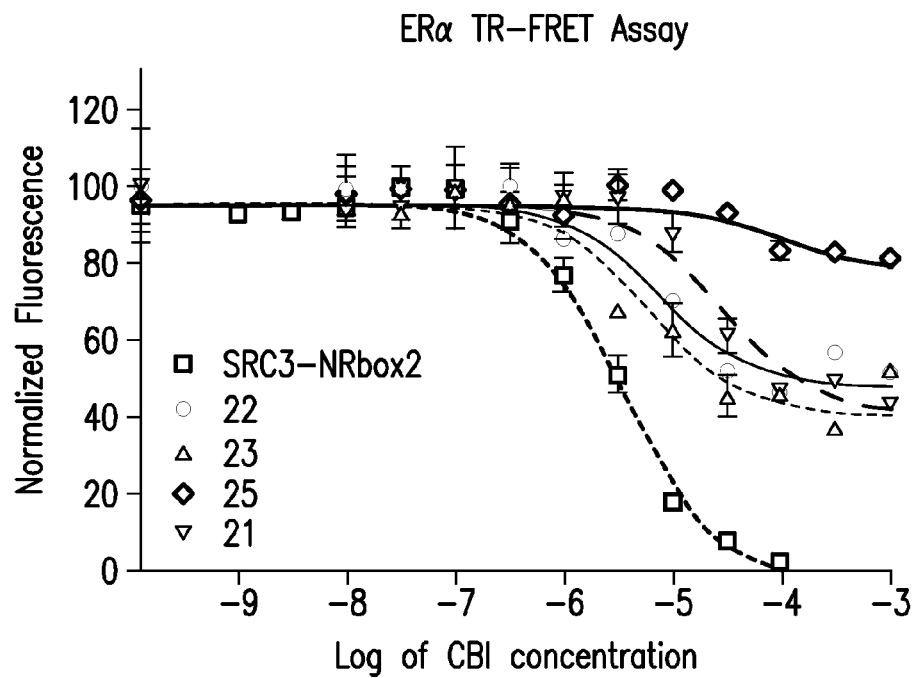
FIG. 15A depicts data as a plot of normalized fluorescence versus log of CBI concentration from an ERα TR-FRET assay for compounds 21, 22, 23, and 25 of Example I.
Figure 15B:
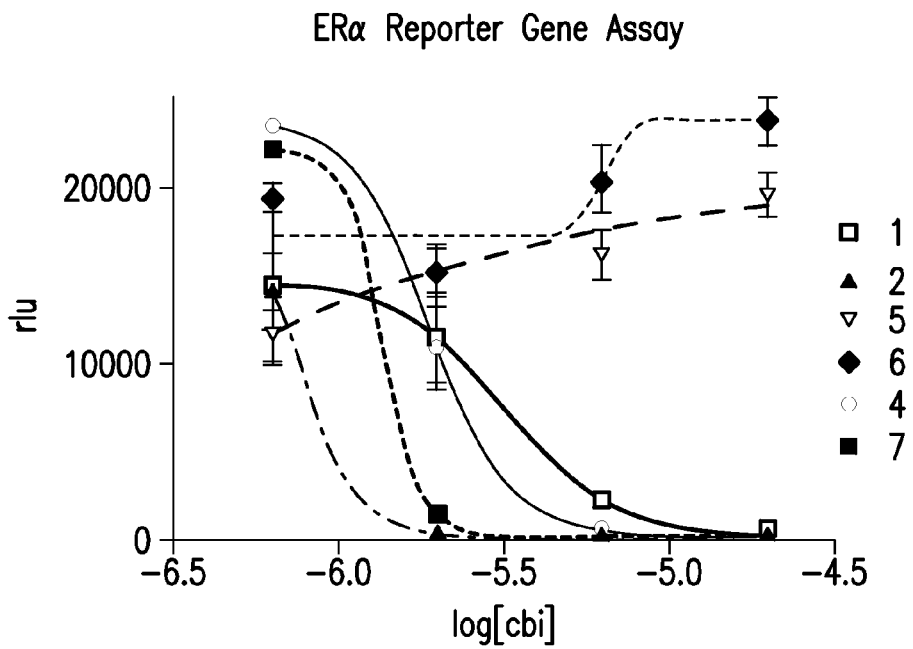
FIG. 15B depicts data as a plot of relative light units (rlu) versus log [cyclobutane inhibitor] from an ERα Reporter Gene luminescent assay for compounds 1, 2, 4, 5, 6, and 7 of Example I.
Figure 16:
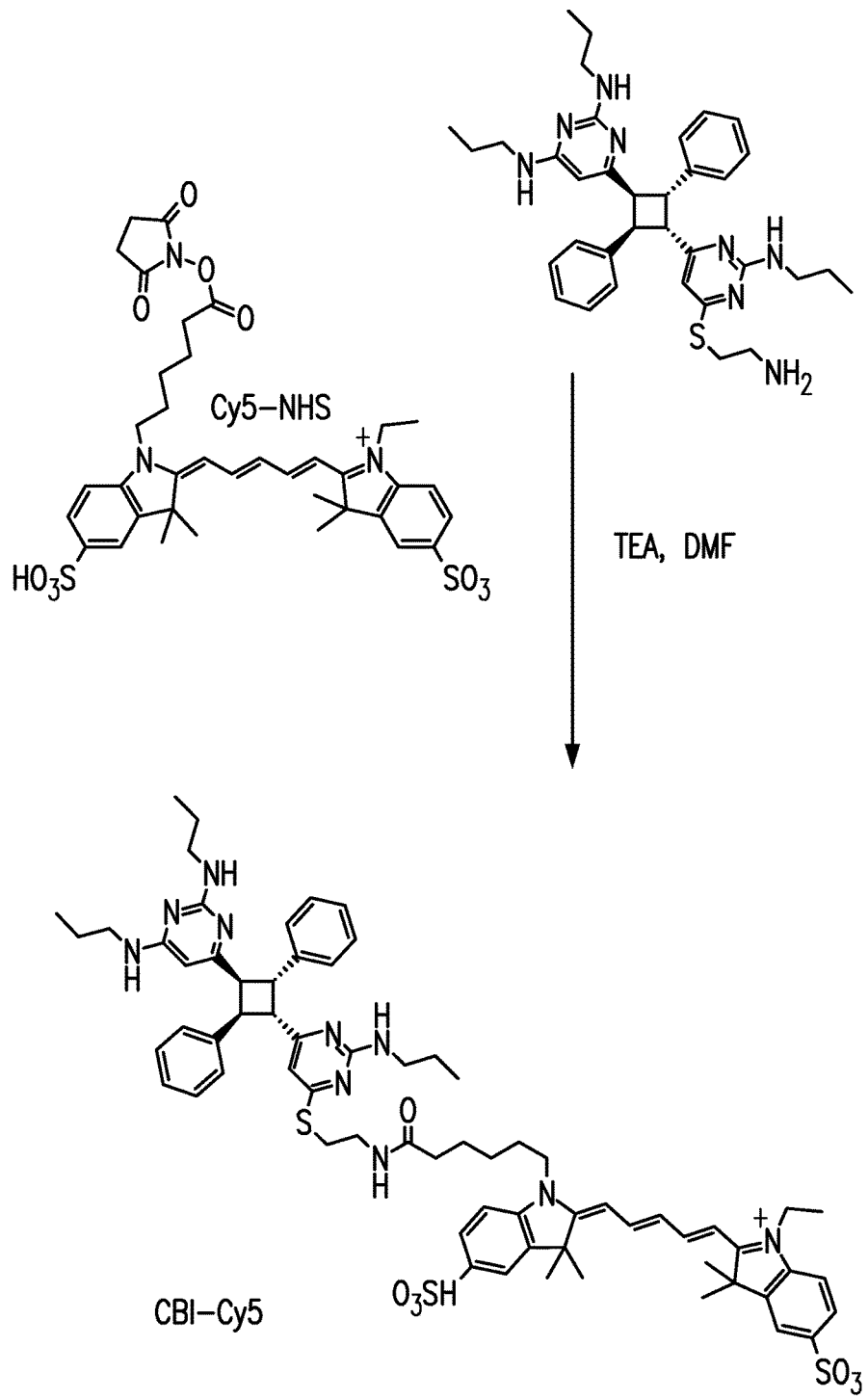
FIG. 16 depicts a synthetic reaction scheme for making a cyclobutane inhibitor (CBI)-Cy5 fluorophore conjugate.
Figure 17:
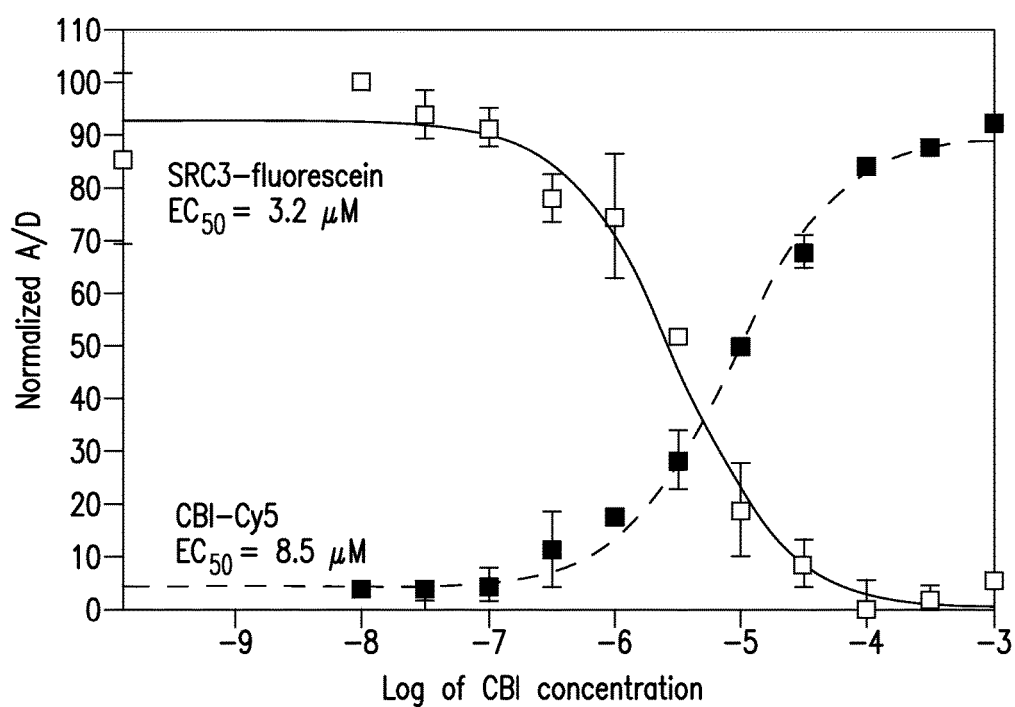
FIG. 17 depicts a dual ER TR-FRET analysis of cyclobutane inhibitor (CBI)-Cy5 conjugate and SRC3-fluorescein showing direct binding of CBI to ER with concomitant inhibition of the ER/SRC3 interaction. Data is plotted as normalized A/D versus log of CBI concentration.

Example I. Tetra-Aryl Cyclobutanes as Direct Inhibitors of the Nuclear Receptor/Coactivator Interaction In a continued effort to develop novel therapeutics for the management of hormone receptor-driven cancers, we have developed a set of 1,3-biphenyl-2,4-bipyrimidynyl-cyclobutanes that directly disrupt the interaction between the estrogen and androgen receptors and their coactivators. These compounds differ from traditional nuclear hormone receptor antagonists in that they bind to the surface of the receptors, as opposed to an internal hydrophobic pocket, and are active even in the presence of an agonist ligand. The cyclobutanes (CBs) are active in both in vitro (time-resolved FRET) and cell-based (luciferase reporter gene) assays, and bind with affinities ranging from submicromolar to low micromolar. These preliminary results suggest that compounds with this mechanism of action may prove efficacious in the treatment of hormone-refractory breast and prostate cancers. As illustrated in FIG. 1, the cyclobutatne inhbititors (CBIs) act in the presence of an agonist by binding to surface of the NR and disrupting protein/coactivator interaction. FIG. 2 illustrates the estrogen receptor (ER) coactivator binding, showing the coactivator binding groove of the ER ligand binding domain (LBD) interacting with the steroid receptor coactive (SRC) LXXLL motifs. Binding is facilitated by three or four hydrophobic contacts as well as positive interaction between E542 and K362 (charge clamp) of the LBD and the backbone of the coactivator peptide. FIG. 3 illustrates the androgen receptor (AR) coactivator binding, showing the AR-LBD AF-2/coactivator interaction is similar to the ER-LBD, except it interacts with LXXLL, FXXLF, and WXXLF peptide motifs and AR CBI selectivity based on probing affinity for larger hydrophobic groups that mimic phenylalanine tryptophan. FIG. 4 illustrates a cyclobutane synthesis from the photo cycloaddition of 2,4-dichloro-6-styrylpyrimidine versus a thermal reaction. FIG. 5 illustrates the synthesis of symmetrically-substituted tetraamino cyclobutanes. FIG. 6 illustrates symmetrically-substituted cyclobutanes in ER and AR reporter gene assays with IC50 values, as shown in Table 1 of the figure. FIG. 7 illustrates the synthesis of unsymmetrical tetraamino cyclobutanes. FIG. 8 illustrates unsymmetrical cyclobutanes in ER and AR reporter gene assays with IC50 values, as shown in Table 2 of the figure. FIGS. 9A and 9B illustrate a synthetic reaction scheme showing the synthesis of compounds 17, 18, 19, and 20. ER reporter gene assay data for these compounds 17, 18, 19, and 20 are presented in FIG. 10. FIG. 11 (and its Table 3) provides data for various cyclobutane compounds in an ER TR-FRET assay for compounds 21 to 30 of Example 1. FIG. 12 (and its Table 4) provide data for various cyclobutane compounds in an ER TR-FRET assay for compounds 31 to 34. FIG. 13 depicts an estrogen receptor (ER) and androgen receptor (AR) TR-FRET (androgen receptor time-resolved fluorescence energy transfer) assay with: ERa LBD selectively biotinylated; AR-LBD with glutathione-S-transferase (GST) tag; Streptavidin-Tb (ER) or anti-GST-Tb antibody (AR) as FRET donor; Fluorescein-labeled SRC3, with 3 LXXLL motifs as FRET acceptor; and SRC1-Box II as control (LXXLL motif), performed in the presence of 17β-estradiol or DHT agonist. FIG. 14 depicts an estrogen receptor (ER) and androgen receptor (AR) luciferase reporter gene assay with: full-length ER or AR expression vector; ERE-Luc or ARE-Luc plasmid expressed in HEC-1 cells; and B-gal plasmid used for transfection control, performed in presence of 17β-estradiol or DHT agonist. FIG. 15A shows data from an ERa TR-FRET assay for compounds 21, 22, 23, and 25 and FIG. 15B shows data from an ERa Reporter Gene luminescent assay for compounds 1, 2, 4, 5, 6, and 7. FIG. 16 illustrates a synthetic reaction scheme for making a CBI-Cy5 fluorophore conjugate. FIG. 17 illustrates a Dual ER TR-FRET analysis of CBI-Cy5 conjugate and SRC3-fluorescein showing direct binding of cyclobutane CBI to ER with concomitant inhibition of the ER/SRC3 interaction.

REFERENCES FOR EXAMPLE I (1) Parent, A. A.; Gunther, J. R.; Katzenellenbogen, J. A. *J. Med Chem.* 2008, 51, 6512-6530.
(2) Williams, A. B.; Weiser, P. T.; Hanson, R. N.; Gunther, J. R.; Katzenellenbogen, J. A. *Org. Lett.* 2009, 11, 5370-5373.
(3) LaFrate, A. L.; Gunther, J. R.; Carlson, K. E.; Katzenellenbogen, J. A. *Bioorg. Med. Chem.* 2008, 16, 10075-10084.
(4) Becerril, J.; Hamilton, A. D. *Angew. Chem. Int. Ed.* 2007, 46, 4471-4473.
(5) Gunther, J. R.; Moore, T. W.; Collins, M. L.; Katzenellenbogen, J. A. *ACS Chem. Bio.* 2008, 3, 282-286.
(6) Gunther, J. R.; Parent, A. A.; Katzenellenbogen, J. A. *ACS Chem. Bio.* 2009, 4, 435-440.
(7) Joseph, J. D.; et al. *PNAS* 2009, 106, 12178-12183.
(8) Anderson, R. J.; et al. *Cancer Cell* 2010, 17, 535-546.
(9) Estebanez-Perina, E.; et al. *PNAS* 2007, 104, 16074-16079.
(10) Jones, J. O.; et al. *PNAS* 2009, 106, 7233-7238.

Example II. Antagonists with Selectivity for Mutant Androgen Receptors: Synthesis and Evaluation of Tetra-Aryl Substituted Cyclobutanes Chemical structures for the compounds CB-1 to CB-8 of Example II are shown in FIGS. 25 A and B.

Figure 18:
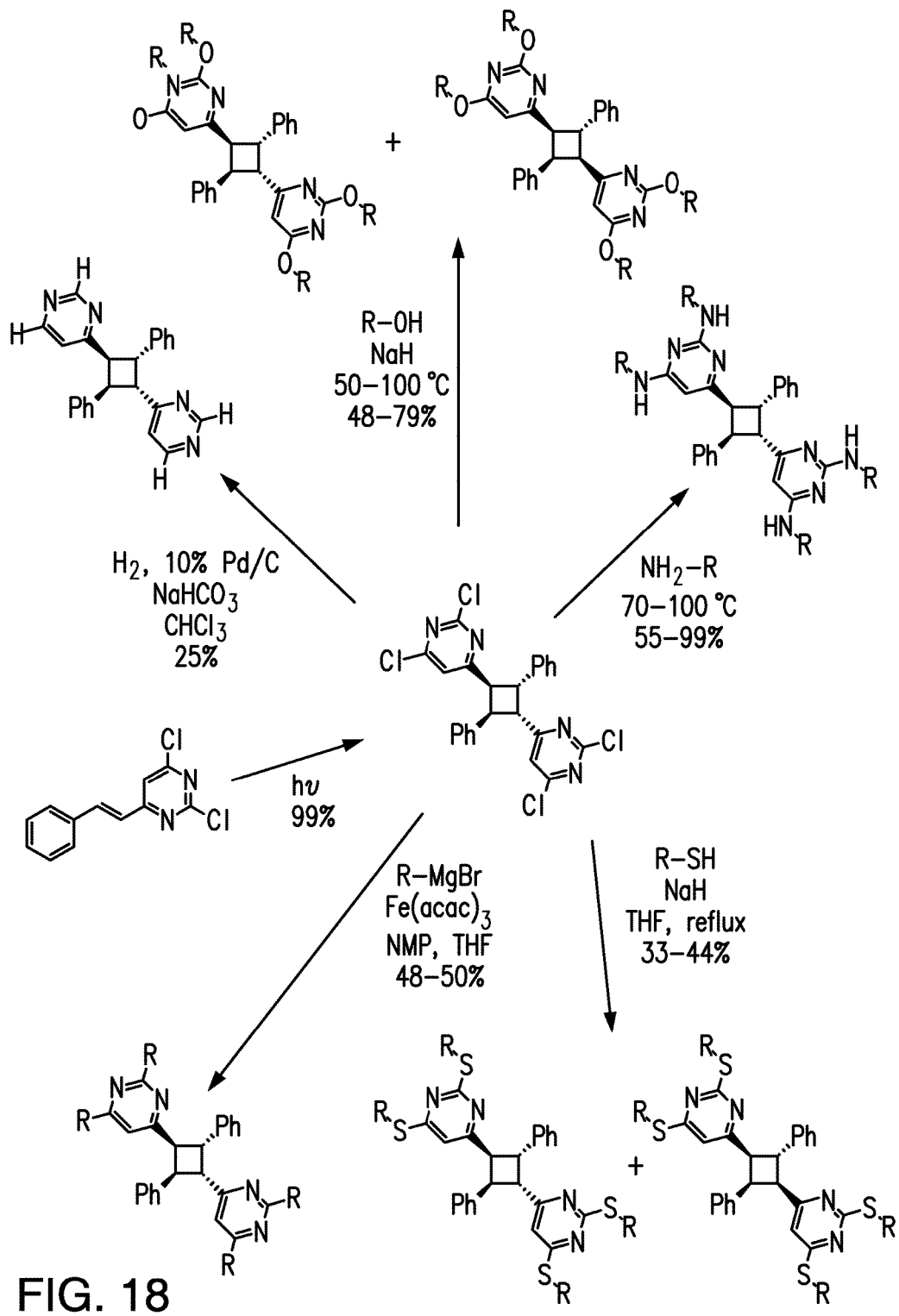
FIG. 18 depicts a reaction scheme for the synthesis of compounds from the photo cycloaddition of 2,4-dichloro-6-styrylpyrimidine.
Figure 19:
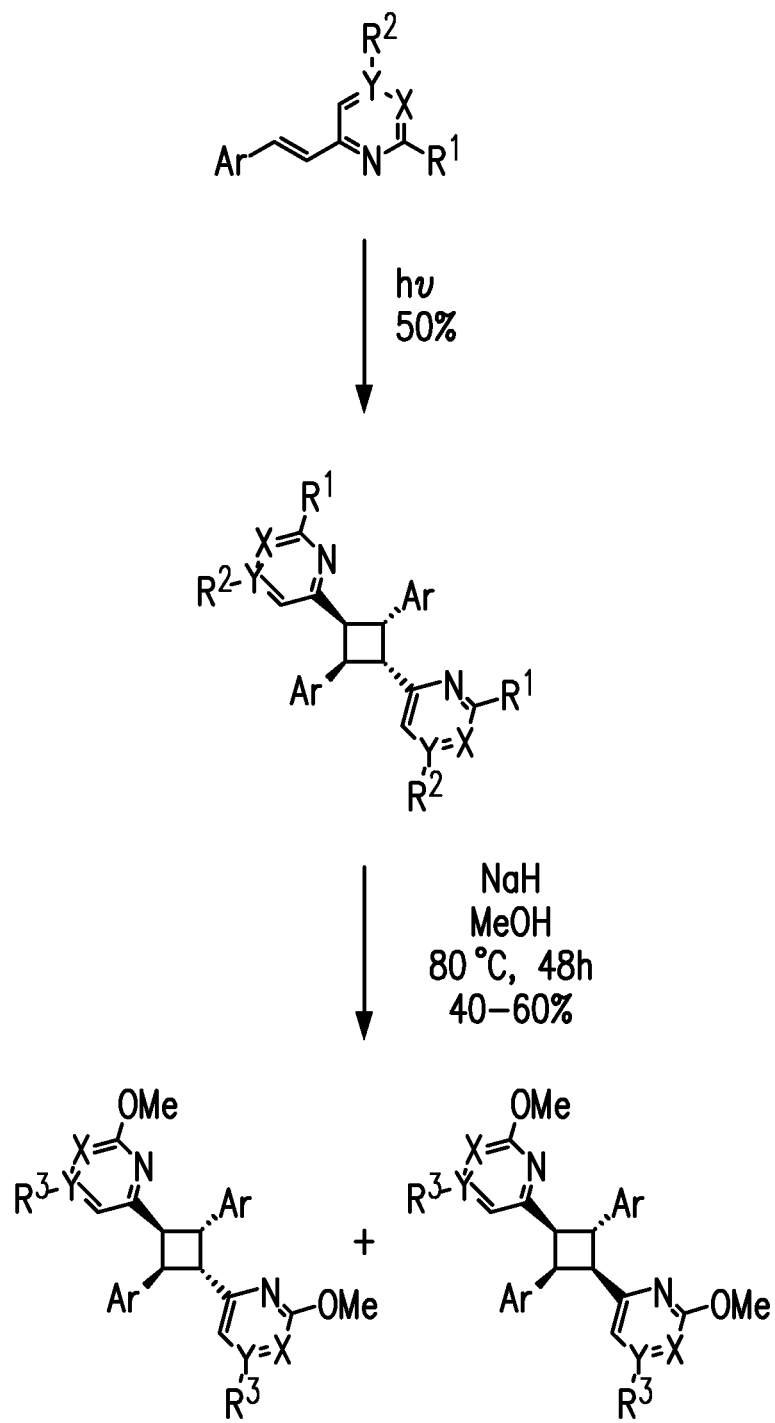
FIG. 19 depicts a reaction scheme for the synthesis of compounds from the photo cycloaddition of 2,4-disubstituted 6-styrylpyrimidines.
Figure 20A:
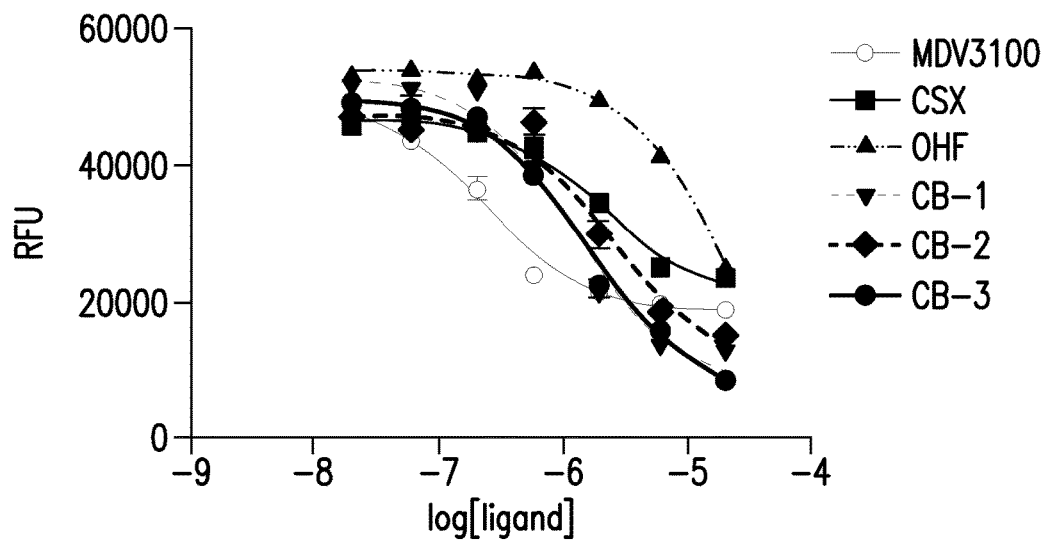
FIGS. 20A and B depict inhibition plots of selected cyclobutane inhibitor compounds versus controls for inhibition of proliferation of mutant androgen receptors versus wild type androgen receptor-containing cancer cells.
Figure 20B:
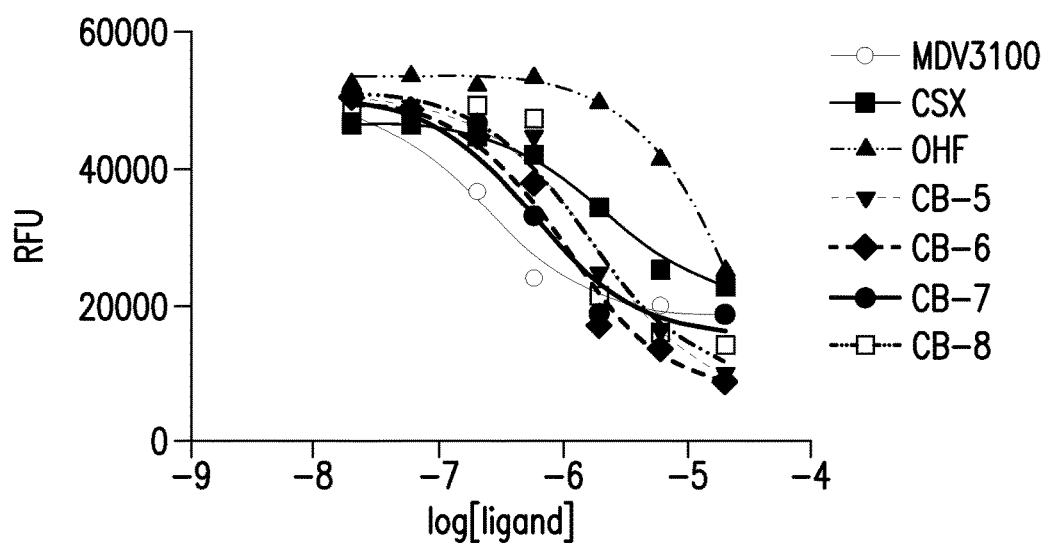
Figure 21A:
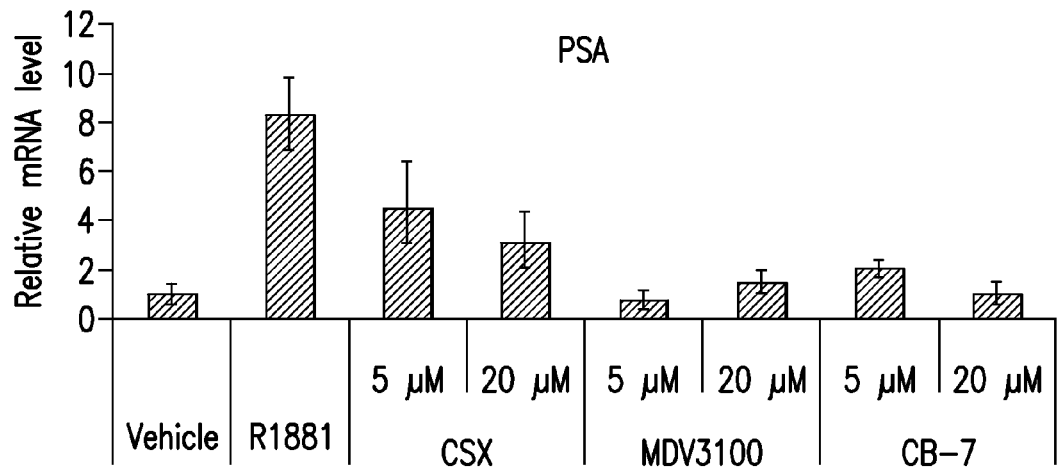
FIGS. 21A, B, C, and D depict plots of data for compound CB-7 showing inhibition of R1881 activation of androgen receptor target genes.
Figure 21B:
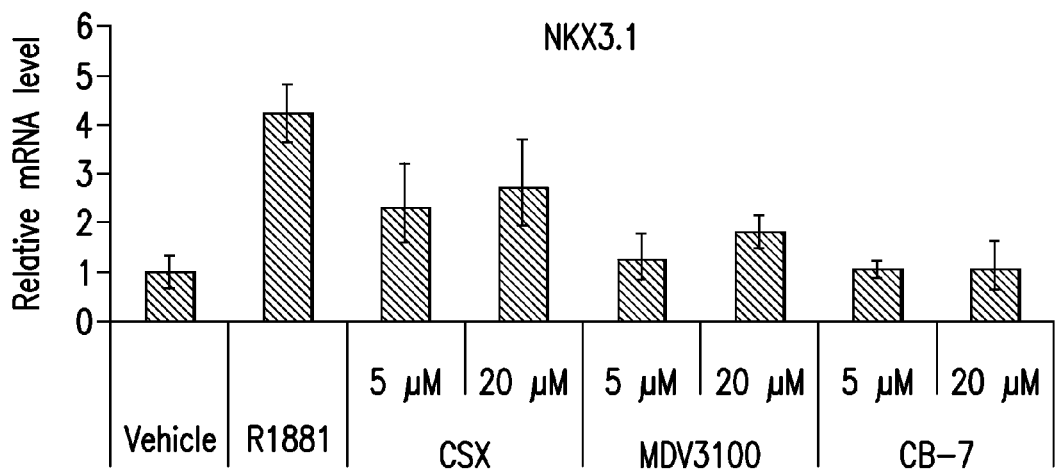
Figure 21C:
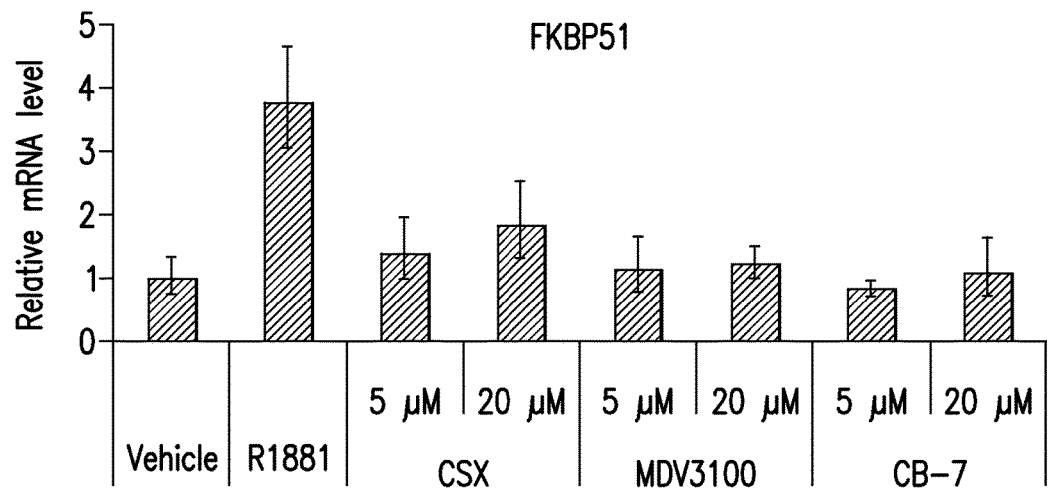
Figure 21D:
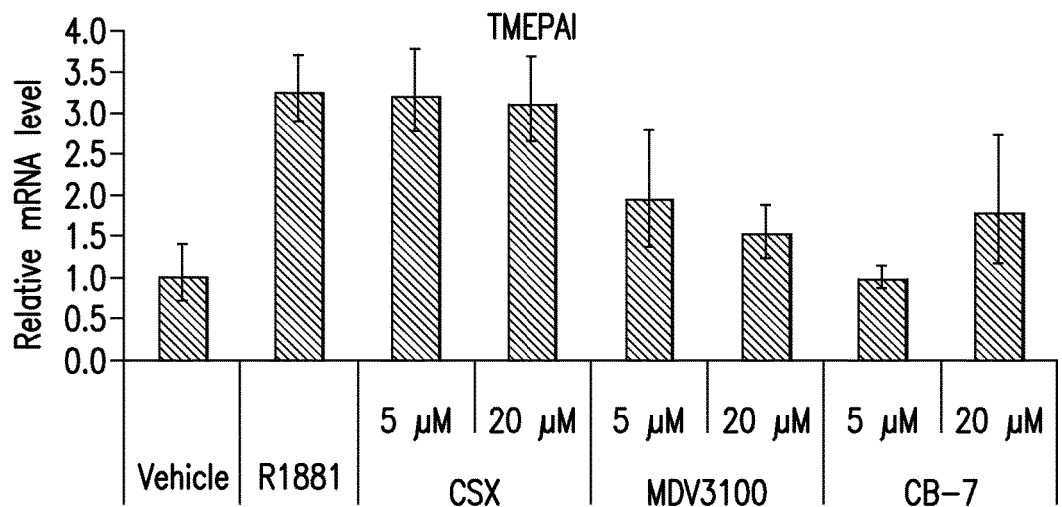
Figure 23:
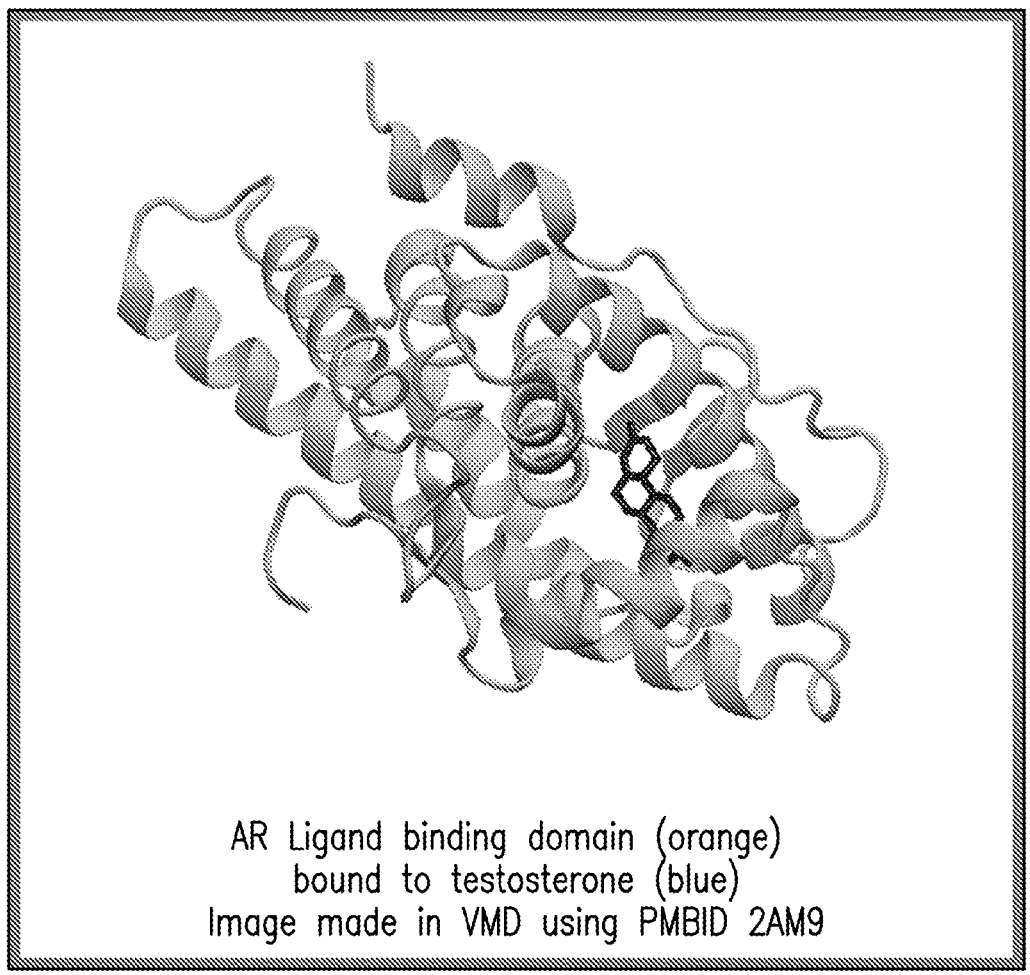
FIG. 23 depicts the androgen receptor ligand binding domain bound to testosterone.
Figure 24:
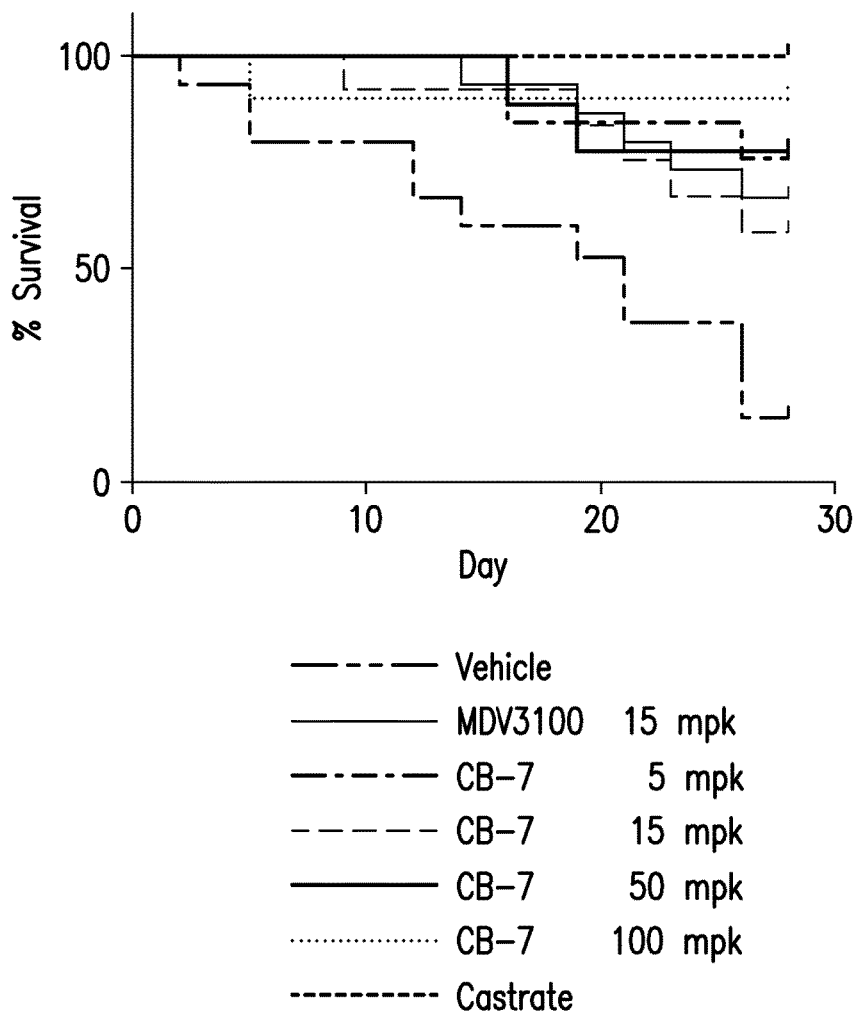
FIG. 24 depicts mouse survival data from a mutant androgen receptor-T877A xenograft experiment for compound CB-7 at various concentrations.
Figure 26:
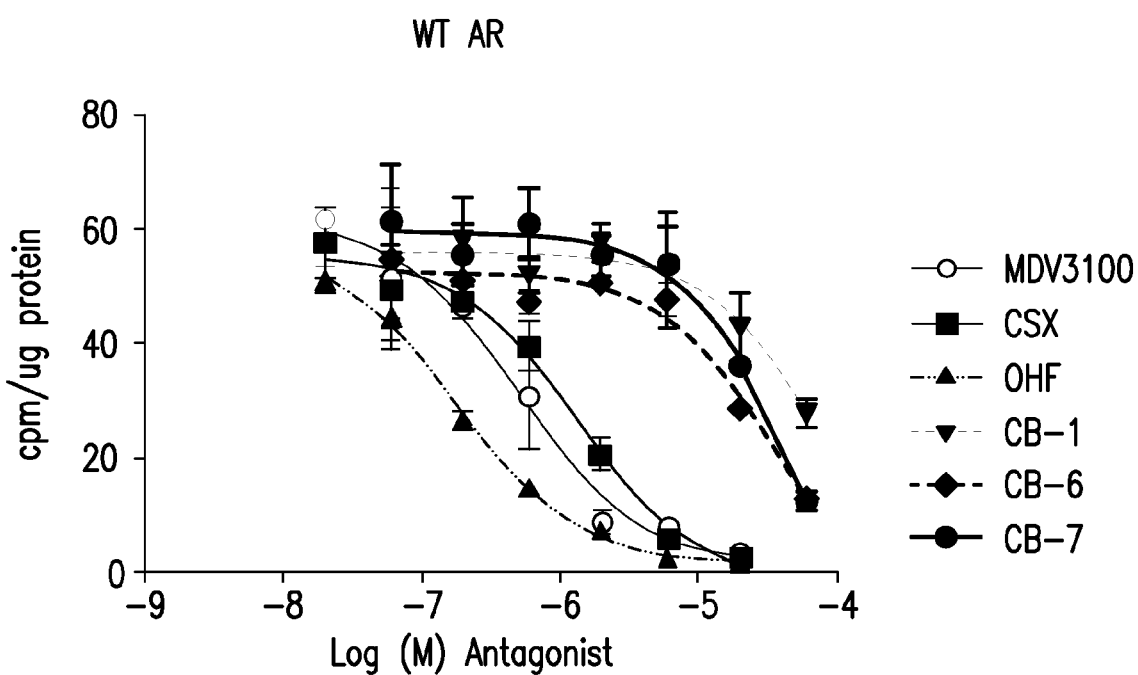
FIG. 26 depicts data from a ligand competition assay for various cyclobutane inhibitor compounds.
Figure 27A:
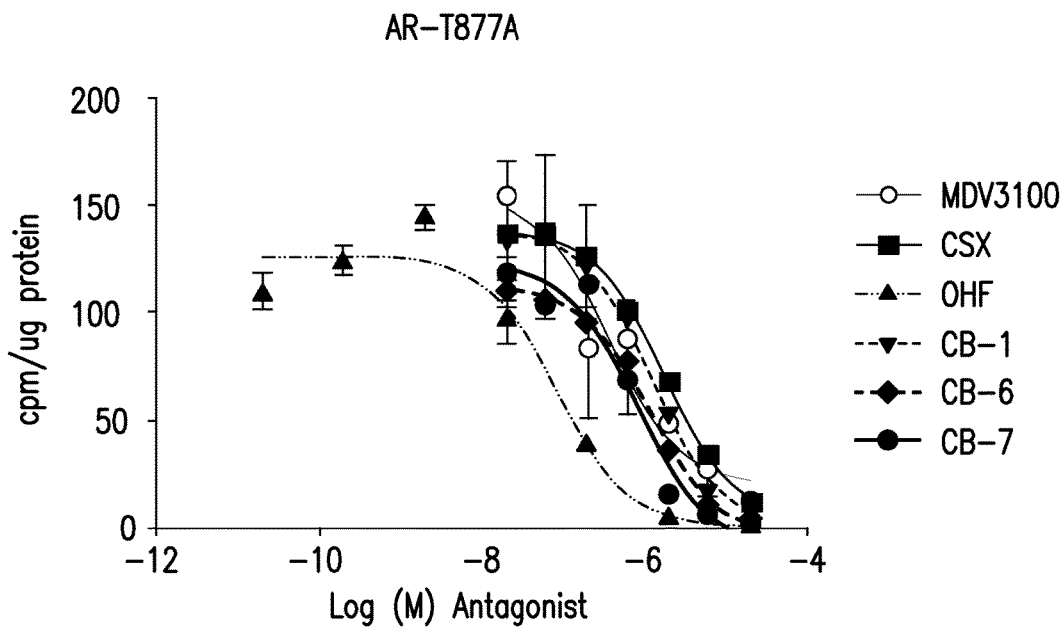
FIGS. 27A and B depict data from a ligand competition assay for various cyclobutane inhibitor compounds.
Figure 27B:
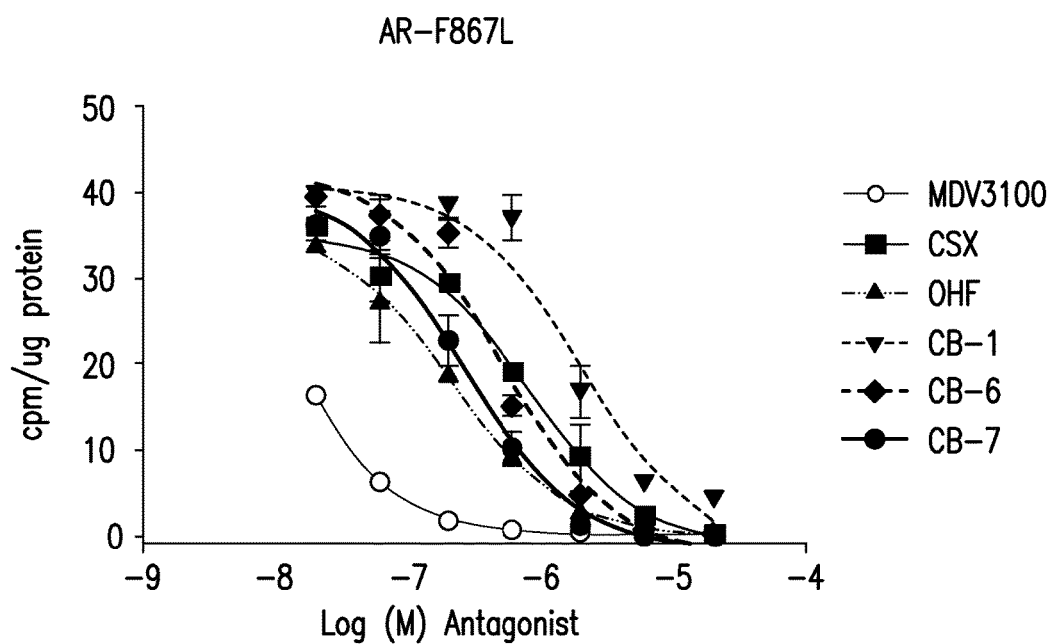

Our goal in this example is to identify small molecules that block activity of mutant androgen receptors (ARs) but not wild type AR, by synthesizing a library of compounds, to explore possible mechanisms of action, and to evaluate therapeutic potential. A total of 75 tetra-aryl substituted cyclobutanes (CBs) were synthesized. FIG. 18 illustrates a general reaction scheme for the synthesis of some of these compounds from the photo cycloaddition of 2,4-dichloro- 6-styrylpyrimidine. FIG. 19 illustrates a general reaction scheme for the synthesis from the photo cycloaddition of 2,4-disubstituted 6-styrylpyrimidines. LNCaP cell proliferation was evaluated. LNCaP cells are a cell line of human cells commonly used in the field of oncology. LNCaP cells are androgen-sensitive human prostate adenocarcinoma cells derived from the left supraclavicular lymph node metastasis from a 50-year-old Caucasian male in 1977. They are adherent epithelial cells growing in aggregates and as single cells. The CBs selectively inhibit proliferation of mutant AR vs. wild type (WT) AR-containing cancer cells. The inhibition plots are presented in FIG. 20A and FIG. 20B where MDV3100 is the androgen receptor antagonist enzalutamide, CSX is bicaluamide, OHF is hydroxyflutamide, and CB-1 through CB-8, indicate eight of the cyclobutane compounds disclosed herein. The CBs also inhibit R1881 activation of AR target genes in LNCaP prostate cancer cells comparable to MDV3100. FIGS. 21A, B, C, and D are graphic summaries of the results for cyclobutane compound CB-7. FIG. 22 shows an image of prostate cancer cells. Prostate cancer was the most common tumor among men in the United States in 2012, with over 240,000 diagnoses and approximately 28,000 deaths. Structures for the current androgen therapies, OHF, CSX, and MDV3100, are shown. FIG. 23 illustrates the androgen receptor ligand binding domain bound to testosterone. FIG. 24 illustrates mouse survival data from a mutant androgen receptor-T877A xenograft experiment for CB-7 at various concentrations. It is seen that CB-7 increases survival of mice and decreases tumor size in a LNCaP (AR-T877A) xenograft model of prostate cancer at comparable concentrations to MDV3100. FIGS. 25A and B provide data on AR mutant selectivity for compounds CB-1 to CB-8. Data is presented as IC50 values against the wild type (WT) and mutant androgen receptors T877A, W741C, and F876L. It is seen that the cyclobutanes show selectivity of mutant androgen receptor activation in the luciferase transcriptional assay in CV-1 cells (a commercially available cell line derived from the kidney of an African green monkey). FIGS. 26 and 27A and B illustrate data from a ligand competition assay for compounds CB-1, CB-6, and CB-7. It is seen that the CBs compete with 3H-R1881 for bind to the androgen receptor in whole cell binding assays in transfected HEK293 cells.

REFERENCES FOR EXAMPLE II (1) Siegel, R. et. al. *CA Cancer J. Clin.* 2012, 62, 10.
(2) Korpal, M. et. al. *Cancer Discov.* 2013, 3(9), 1030.
(3) Taplin, M. E. et. al. *Cancer Research* 1999, 59, 2511.
(4) Chatterjee, B. *Mol. Cell. Biochem.* 2003, 253, 89.
(5) Taplin, M. E. et. al. *Nature Clin. Prac. Oncol.* 2007, 4, 236.

Example III: π-π Interaction Energies as Determinants of the Photodimerization of Mono-, Di- and Triazastilbenes The references numbers cited in Example III correspond to the references listed at the end of this Example III. The Scheme, Table, and Compound Numbers recited in this Example III are with respect to this Example III.

We describe the quantitative [2+2] photocycloaddition of crystalline trans-2,4-dichloro-6-styrylpyrimidine to produce the corresponding htt r-ctt cyclobutane dimer, and we present $^1$H NMR analysis of the photolysis of this and six other mono, di, and triazastilbenes in solid and solution states. Density functional (M06-2X) and correlated ab initio (MP2) calculations were used to obtain interaction energies between two monomers of each azastilbene. These energies mirror the relative polarization of the stilbene moieties, and can be quantitatively correlated with the rate of reaction and selective formation of the htt r-ctt dimers. In the solid-state, poor correlation is observed between interaction energy and reactivity/selectivity. This lack of correlation is explained through X-ray analysis of the azastilbene monomers, and is shown to be in accordance with the principles of Schmidt's topochemical postulate. Conversely, in solution there is a strong positive correlation ($R^2$=0.96) between interaction energies and formation of the htt r-ctt dimer. These results are the first to show this correlation and to demonstrate the utility of calculated interaction energies as a tool for the prediction of stereo- and regioselectivity in solution-state stilbene-type photocycloadditions.

Although alkene photodimerization in the solid state, which holds the allure of controlling both regio- and stereochemistry based on the crystal orientation of the reactants, has been known since the beginning of organic chemistry,[1] it has recently undergone a resurgence of interest due to applications in organic materials chemistry. While isolated reports from more than a century ago describe the regio- and stereoselectivity of this transformation,[2-7] it was not until the 1960s that Schmidt articulated the 'topochemical postulate',[8] which attempts to predict which alkenes readily undergo [2+2] photocycloaddition based on the crystal packing of the starting alkenes.[9-11] Schmidt noted two essential criteria for dimerization to occur: the double bonds of crystalline reactants must be parallel to each other, and the center-to-center distance of the reacting alkenes must be less than 4.2 Å apart. When these criteria are satisfied, photocycloaddition was predicted to proceed under 'topochemical' control, producing selectively the regio- and stereoisomer dictated by the molecular packing of the alkenes in the crystal.

While Schmidt's principles successfully rationalized topochemical control in the solid-state photodimerization of cinnamic acids and many other disubstituted olefins, a range of exceptions to these rules developed, including crystalline olefins that failed to react as expected and crystals that underwent dimerization despite a lack of double bond planarity or greatly increased separation of the reacting atoms. The 'reaction cavity' concept, in which the inter- and intramolecular motion of the reactive pair is constrained by its crystal lattice, was proposed by Cohen,[12] and this concept, together with crystal lattice energy calculations, effectively explained both positive and negative exceptions: for close-stacking, parallel-oriented disubstituted olefins with <4.2 Å center-to-center distance that failed to react in the solid state, the lattice perturbation needed to accommodate the photodimerization product would have required an enormous input of energy (i.e., thousands of kcal/mol).[13] Conversely, for alkenes that undergo dimerization yet had crystal packing predicted to be unreactive, calculations showed surprisingly little disturbance in their molecular environment despite the movement required for cyclobutane formation with minimal increase lattice energy.[14-16] Thus, while Schmidt's original topochemical postulate continues to be a good 'rule-of-thumb', additional exceptions that will doubtless arise will require a more in-depth analysis than a cursory examination of the X-ray crystal structure of the starting material. For a review, see Natarajan and Ramamurthy.[17,18]

While the photochemistry of stilbenes and its derivatives has been well studied,[17,19-24] there are relatively few reports on the photolysis of stilbene derivatives with nitrogen-bearing rings. Nonetheless, the [2+2] photocycloaddition of 2- and 4-azastilbene derivatives has been studied extensively in both the solid and solution state. In solution, styrylpyridines, both as free bases as well as various pyridinium salts, produce low yields of dimers upon irradiation, with the ionic compounds generally giving higher cyclobutane yields and increased stereo- and regioselectivity.[25-28] With 4-styrylpyridines, salt formation accelerated solution-state [2+2]-photocycloaddition,[29] with increasing addition of acid giving more rapid and more selective dimer formation. In addition, when the highly polarized 4-(4'-methoxystyryl) pyridine was irradiated, an overall yield of 95% was obtained, with 64% being a single cyclobutane isomer, whereas irradiation of the analogous trifluoromethyl azastilbene, 4-(4'-trifluoromethylstyryl)pyridine, produced the major cyclobutane isomer in only 24% yield. Based upon the effect of alkene polarization, it was argued that cation-π interactions are responsible for the increased yield and selectivity observed with solution-state irradiations of styrylpyridinium salts vs. their uncharged counterparts.

Photolysis reactions in the solid state produce markedly different results than those in solution, with the styrylpyridine free bases forming only very low yields of cyclobutanes (<5%) and percent conversion to the dimer from the pyridinium salt varying greatly depending on the alkyl group and counter ion used.[27,28] The effect of counter anion on dimerization yield suggests that changes in molecular packing might be at play and thus might be explained by the topochemical postulate. This presumption was reinforced by results with 1,2-bis(4-pyridyl)ethylenes and 1,2-bis(2-pyrazinyl)ethylenes, which demonstrated an inverse correlation between the distance separating the double bonds and the rate of dimerization,[30] and more recently by the solid-state photolysis of a wide array of 4-stilbazole HCl salts.[31]

While there are other examples of azastilbene solid-state photochemical reactions, a thorough literature search of the photodimerization of styrylpyrimidines revealed only three examples,[32-35] one of which appears to be an accidental dimerization that occurred during a recrystallization.[34] The most pertinent of these reports compares the irradiation products from three different styrylpyrimidines, with the pyrimidine rings in various oxidation states, as well as that of various other heteroaromatic stilbenes.[33] Only in systems highly polarized by electron-withdrawing heteroaromatics were cyclobutanes produced in good yields and high selectivity, leading the authors to conclude that the polarity of the stilbene-type systems governs photoreactivity by directly influencing crystal packing.

In this study, we determine the yield and regio- and stereoselectivity of the photodimerization of a variety of mono, di, and triazastilbenes in both solid state and solution. Density functional theory and ab initio correlated calculations are performed on each of the azastilbenes in order to determine dimer interaction energies, and these energies are correlated to the photochemical outcomes. While strong correlation exists between interaction energies and solution reaction rate and selectivity, photodimerization in the solid state is rationalized by consideration of the topochemical postulate and the concept of reaction cavity as supported by X-ray crystal structure analysis of the photoreactive monomers.

Our interest in topochemically-controlled reactions was triggered by the accidental discovery of the light-initiated dimerization of trans-2,4-dichloro-6-styrylpyrimidine 1 to form cyclobutane 2, which occurred in the solid-state over the course of approximately one month in a round-bottom flask on the benchtop under ambient lighting and temperature (Scheme 1). Intrigued by the facile nature and complete stereo-control exhibited by this reaction, we attempted to replicate the photocycloaddition under more controlled conditions. Irradiation of 1 g of styrylpyrimidine 1 layered between two sheets of borosilicate glass with a water-cooled 450 W Hanovia medium-pressure mercury arc-lamp gave complete conversion of the starting material at approximately 1.5 h, with similar retention of stereo and regioselectivity. Less intense light sources—a Rayonet reactor equipped with either 8 W ultraviolet bulbs and a 250 W infrared sun lamp used in a light-reflective box—also efficiently converted 1 to 2, with the sun lamp providing quantitative conversion of 50 mg of 1 to the cyclobutane in less than 40 minutes.

Scheme 1. Unanticipated synthesis of tetra-aryl cyclobutane 1.

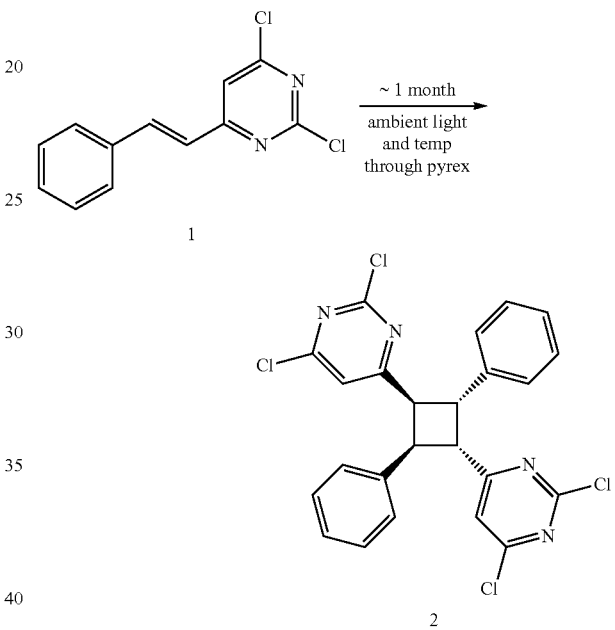

Solution-state photolysis was also performed on 1 with varying degrees of success. A 5 mg/mL solution of 1 in three different solvents, benzene, acetonitrile, and methanol, was irradiated in a photochemical reaction vessel with a water-cooled 450 W Hanovia medium-pressure mercury arc-lamp for 4 to 5 hours. The results of these trials, as measured by $^1$H NMR of the crude reaction mixture, are shown in Table 1. This analysis is based on the integration and comparison of the vinyl and cyclobutyl protons of the various isomers formed during photolysis, each of which generally produces at least one unique signal that is adequately separated from those of the other isomers.

Scheme A shows the five possible head-to-tail (htt) stereoisomers and eight possible head-to-head (hth) stereoisomers (including three pairs of enantiomers) that can be formed from the irradiation of 1. Labeling of the isomers in both Table 1 and Scheme A is according to IUPAC convention,[36] where r refers to the reference carbon (labeled with a small '1' in Scheme A) and c or t refers to the stereochemistry (cis or trans, respectively) of the group on subsequently numbered carbon atoms in relation to the substituent on the reference carbon. The analysis of the spectrum of each cyclobutane isomer, which is necessary for this type of examination, is described below.

TABLE 1

Solid and solution-state irradiation products of 2,4-dichloro-6-styrylpyrimidine, 1, presented in mass % of the crude product mixture as determined by analysis of the alkene/cyclobutane proton peaks in $^1$H NMR.

| solvent | diazastilbene | | head-to-tail cyclobutane isomers | | | | | head-to-head cyclobutane isomers | | | | | red./add. |
|---|---|---|---|---|---|---|---|---|---|---|---|---|---|
| | trans | cis | r-ctt | r-cct | r-ctc | r-tct | r-ccc | r-ctt | r-tcc | r-ctc | r-tct | r-ccc | |
| solid-state | 0% | 0% | 100% | 0% | 0% | 0% | 0% | 0% | 0% | 0% | 0% | 0% | 0% |
| Ph-H | 36% | 52% | 7% | 1% | 0% | 1% | 0% | 1% | 0% | 0% | 1% | 0% | 0% |
| ACN | 38% | 45% | 8% | 3% | 0% | 3% | 0% | 2% | 0% | 0% | 2% | 0% | 0% |
| MeOH | 24% | 48% | 3% | 2% | 0% | 2% | 0% | 2% | 0% | 0% | 2% | 0% | 23% |

Scheme A. The 13 regio and stereoisomers that can hypothetically arise from the irradiation of 1. The reference (r) carbon is denoted by the small '1'.

Head-to-Tail Dimers

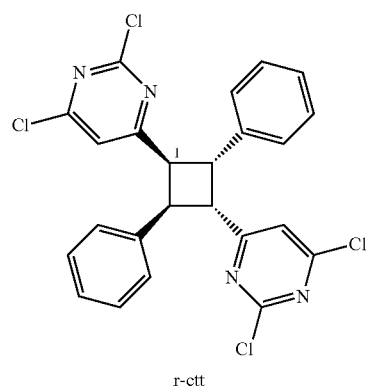

r-ctt

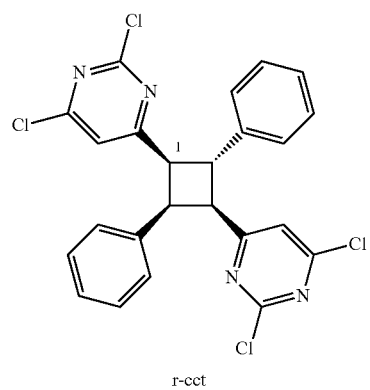

r-cct

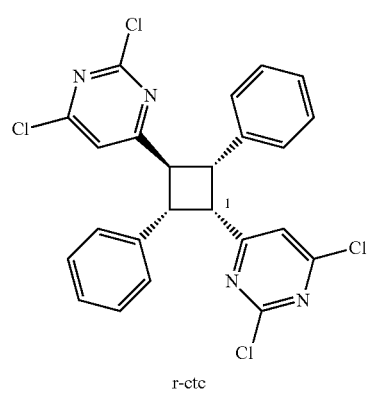

r-ctc

-continued

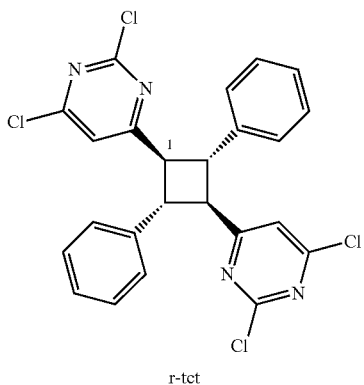

r-tct

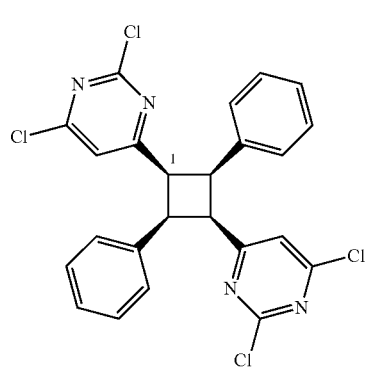

r-ccc

Head-to-Head Dimers

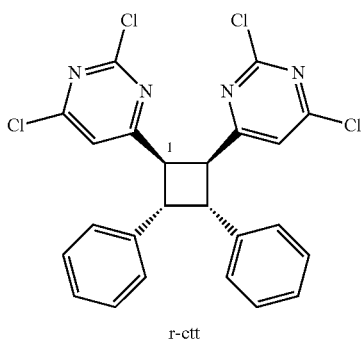

r-ctt

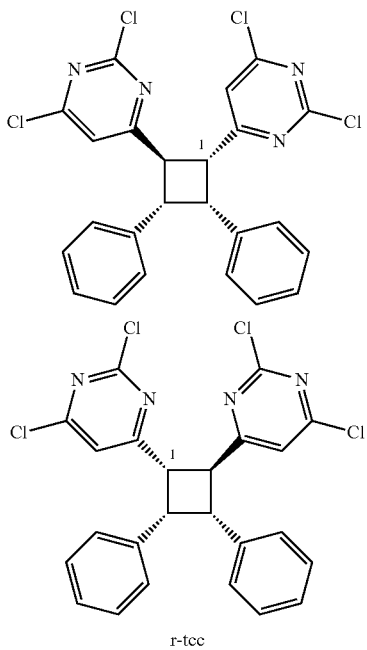

r-tcc

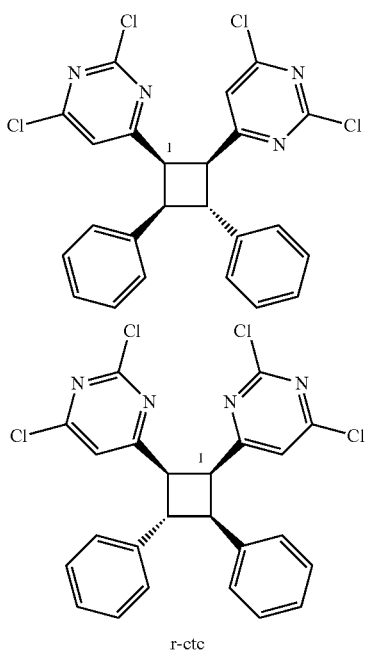

r-ctc

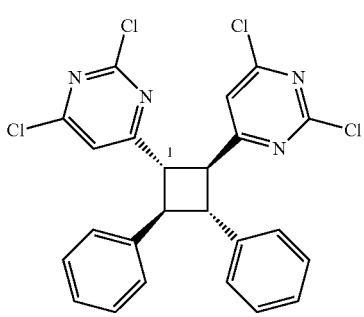

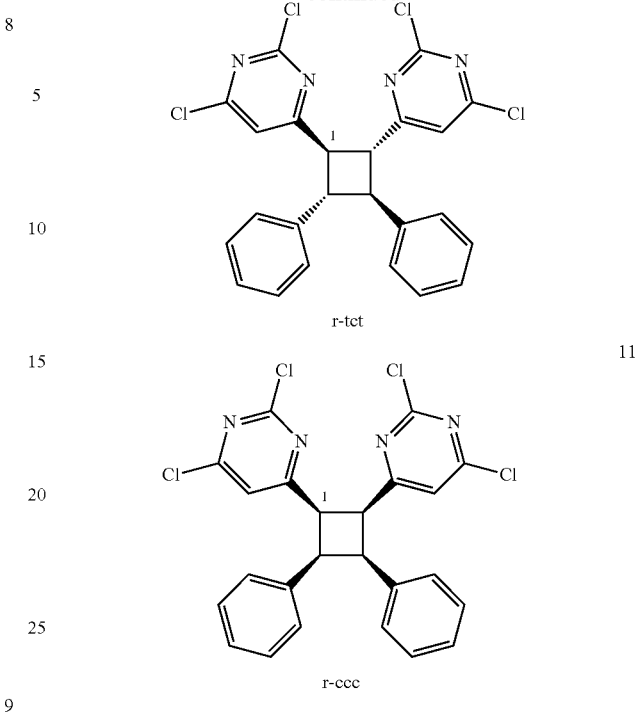

r-tct r-ccc

The results of the solution-state irradiations differ markedly from those obtained from the solid-state examples above. Despite prolonged irradiation times, photolysis in benzene or acetonitrile gives mostly trans/cis isomerization, with cis-2,4-dichloro-6-styrylpyrimidine, cis-1, as the major product (in 52 and 45%, respectively). In both solvents, cyclobutane dimers are minor products (12% in benzene and 17% in acetonitrile), and while there is some selectivity for the htt r-ctt isomer 2 relative to the other cyclobutanes formed (65% and 45% for benzene and acetonitrile, respectively), this fails to approach the essentially exclusive formation of 2 obtained from the lower-power solid state irradiations. Irradiation in methanol provides similar results, with the additional appearance of large amounts of alkene reduction and solvent addition products, a conversion known from irradiation of other azastilbenes in protic solvents.[37] Nevertheless, dimer formation remains comparable at 15%, and while the htt r-ctt isomer 2 is still the dominant cyclobutane, it represents only 28% of the total cyclobutanes.

Isolation and Elucidation of the Photoproducts of Trans-2, 4-Dichloro-6-Styrylpyrimidine To isolate adequate quantities of the minor cyclobutane isomers for full characterization, we combined chromatographic fractions from the above solution-state irradiations. Solid-state irradiation (4 h, medium-pressure mercury lamp) of the cis-2,4-dichloro-6-styrylpyrimidine isolated from the solution-state irradiations also helped provide additional cyclobutane products containing appreciable quantities of the minor cyclobutane dimers. Extensive chromatographic separations of these products eventually produced pure or nearly-pure samples of 8 of the 10 theoretical diastereomers and enantiomeric pairs (compounds 2-5 and 7-10).

Figure 28:
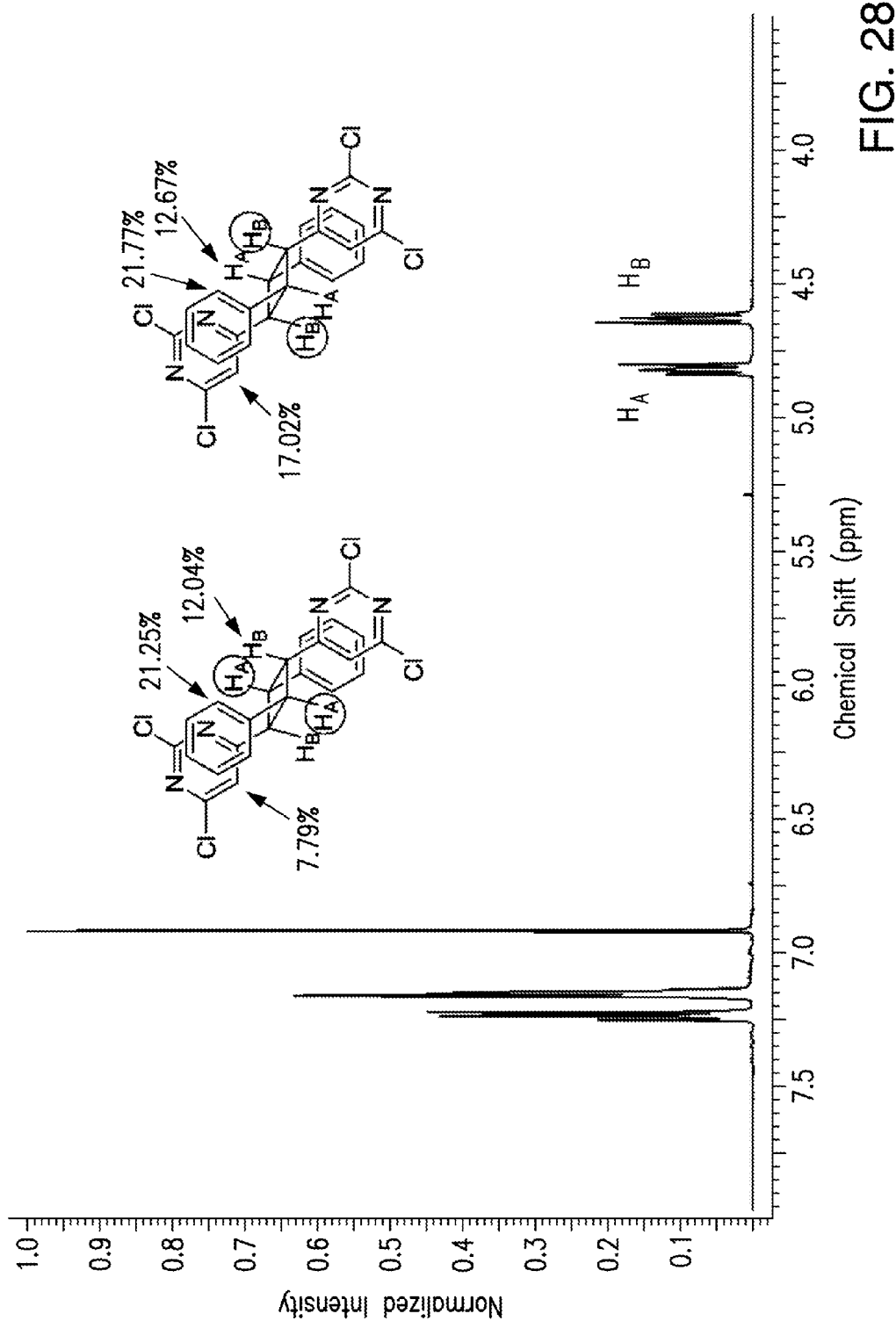
FIG. 28 is a $^1$H NMR (500 MHz, CDCl$_3$) spectrum and percent NOEs for the htt r-ctt dimer 2 of Example III. The irradiated protons for each structure are circled and the percent NOEs based on this proton are indicated

To confirm its regio and stereochemistry, a crystal structure of the initial htt r-ctt cyclobutane, 2, was obtained. Nuclear Overhauser Effect (NOE) spectra of 2 allowed us to make $^1$H NMR assignment of the cyclobutyl protons. The percent NOEs for each cyclobutyl proton of 2 along with the corresponding parent $^1$H NMR spectrum are shown in FIG. 28. With the regio and stereochemistry of dimer 2 firmly established, NOE analysis became the basis for structural determination and $^1$H NMR peak assignment of the other cyclobutanes. This approach permitted confident identification of five of the seven remaining isolated isomers, with some ambiguity associated with differentiation between the two remaining cyclobutanes (compounds 8 and 9). The rationale behind the assignment of each $^1$H NMR spectral/compound pair is described. These assignments are used throughout the remainder of this Example III.

Synthesis and Solid-State Irradiation of Azastilbene Derivatives of Styrylpyrimidine 1

We next explored how varying the electron withdrawing and donating nature of the two aromatic rings affected the rate of solid-state photocycloaddition of these compounds. Based on earlier precedent for styrylpyridines and styrylpyrimidines,[29,33] we hypothesized that more polarized compounds would interact with increasing strength through head-to-tail π-stacking, producing tightly packed crystals that are readily photoreactive. Conversely, we expected that less polarized compounds would either fail to undergo photocycloaddion or react only slowly, with an accompanying loss of stereo and regioselectivity. To test this hypothesis, we prepared a set of five additional azastilbenes bearing electron-withdrawing (chlorine), electron-donating (methoxy), or electron-neutral (hydrogen) substituents on the pyrimidine or pyridine rings. The phenyl substituent was also replaced in two of the derivatives by a methoxyphenyl or pyridine moiety.

The synthesis of the azastilbenes was straightforward and in each case proceeded in only a single step from readily available starting materials (Scheme 2). The trans-2,4-dimethoxy-6-styrylpyrimidine 12 is formed by the $S_NAr$ reaction of 1 in a 25% solution of NaOMe in methanol, heated at reflux overnight. trans-6-Styrylpyrimidine 13 and trans-2,4-dichloro-6-styrylpyridine 14 are synthesized by simple Suzuki-Miyaura cross-couplings from trans-styrylboronic acid and the corresponding heteroaryl chlorides. Finally, the triazastilbene 15 and 4-methoxystyrylpyrimidine 16 are produced from the base-catalyzed condensation of 2,4-dichloro-6-methylpyrimidine with the appropriate aryl aldehydes.

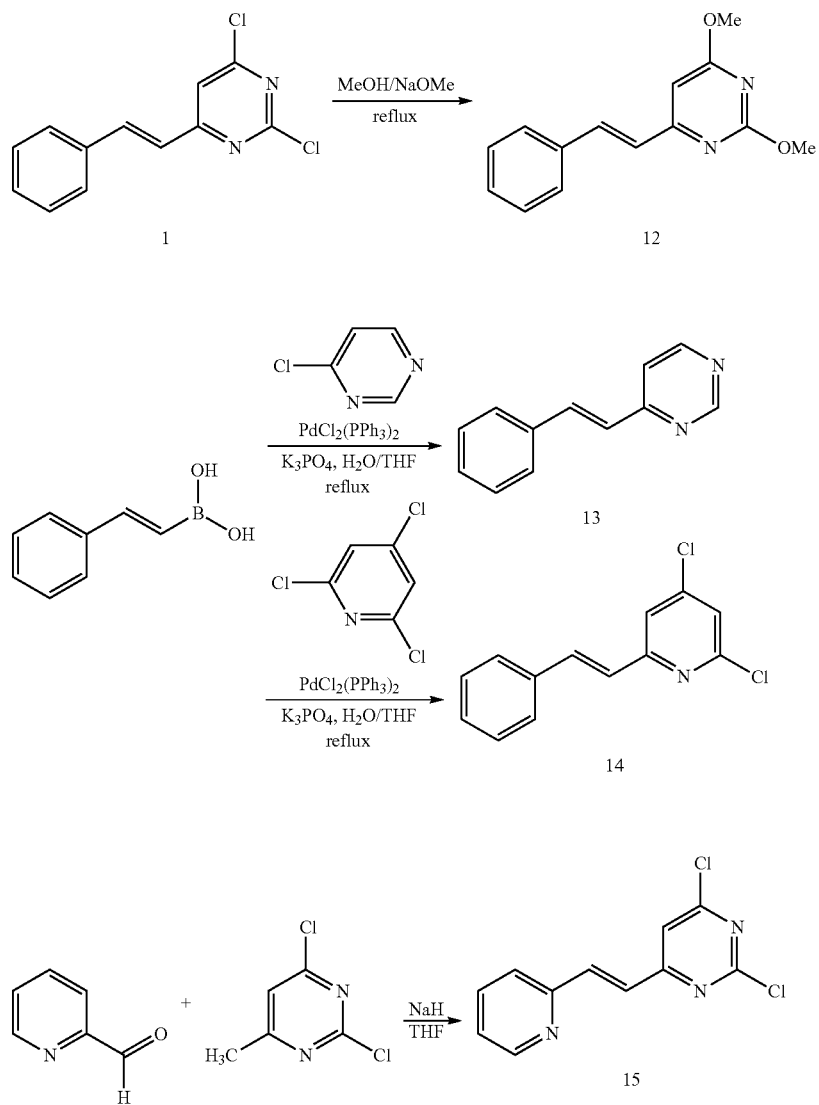

Scheme 2. Synthesis of azastilbene derivatives.

-continued

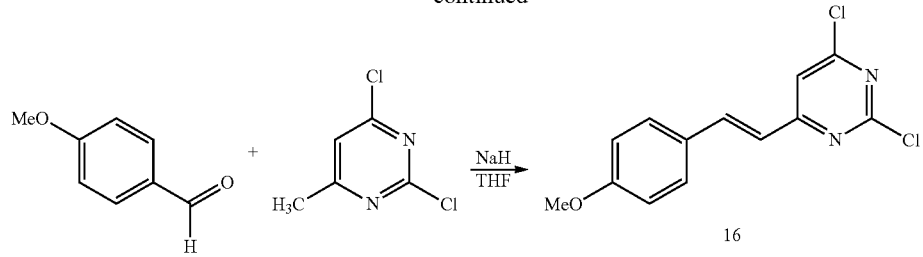

16

To adequately probe the relationship between π system polarization and topochemically-controlled reactivity, we prepared an irradiation facility that provided uniform light intensity and temperature. Due to the relatively low melting point of some of the diazastilbenes, it was especially important to ensure even cooling of the reaction sample. Thus, a water-cooled borosilicate glass plate was created, upon which the ground, recrystallized sample was spread and then covered with a second borosilicate glass plate. To aid in cooling the reaction, we selected a 'cool' light source of comparable intensity to that of the 250 W sun lamp commonly used in irradiations: A 68 W compact fluorescent light (300 W incandescent equivalent, 2700 K color temperature). This source converted 50 mg of 1 into 2 in less than 30 minutes.[38,39] When performed in an aluminum foil-encased enclosure, this simple reaction set-up allows for an approximately room temperature irradiation in which the air temperature does not exceed 30° C. and the surface of the water-cooled plate has a constant temperature of 23-25° C.

Figure 29:
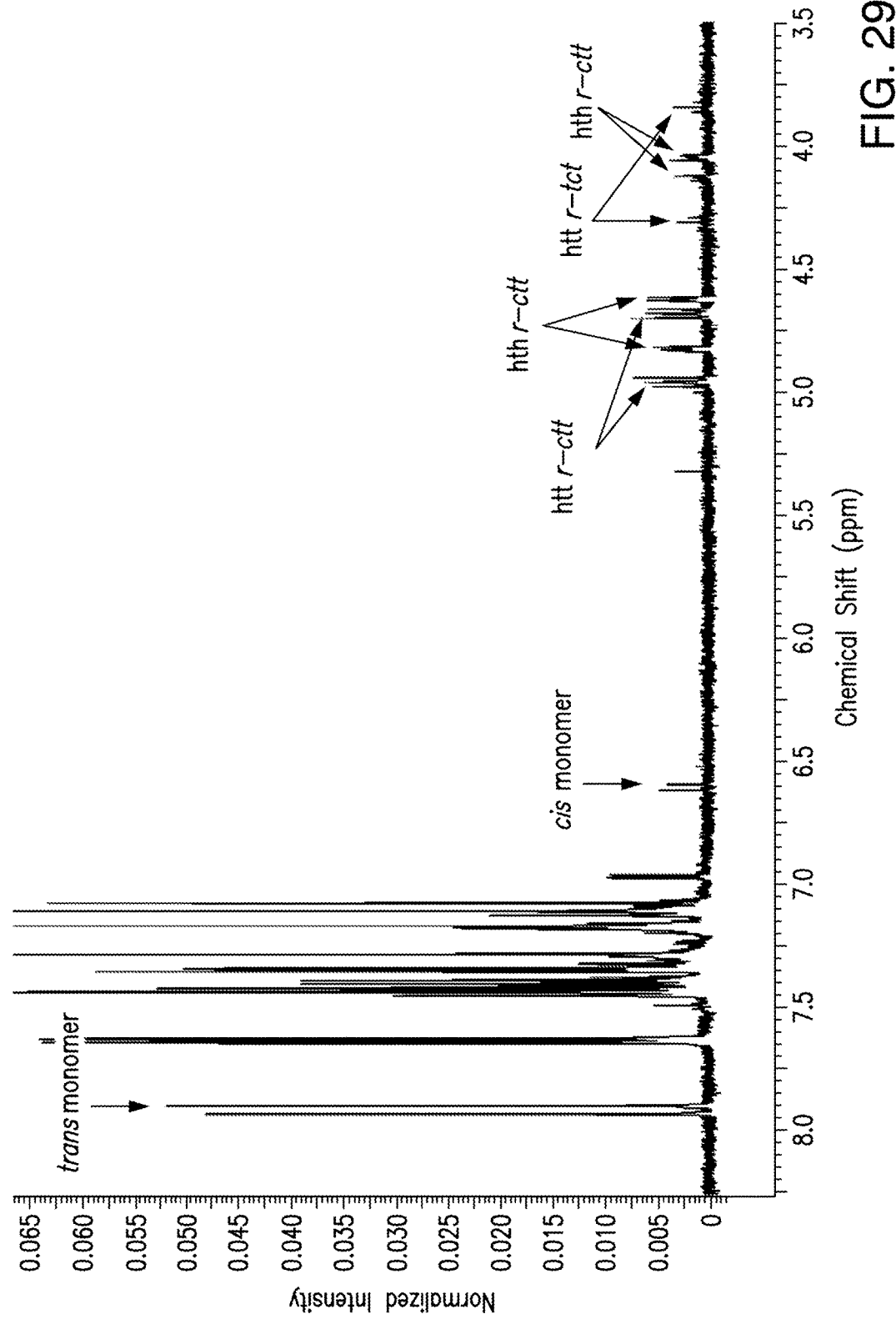
FIG. 29 is a $^1$H NMR (500 MHz, CDCl$_3$) spectrum of a crude reaction mixture for the solid-state irradiation of compound 13 of Example III at 24 h.
Figure 30A:
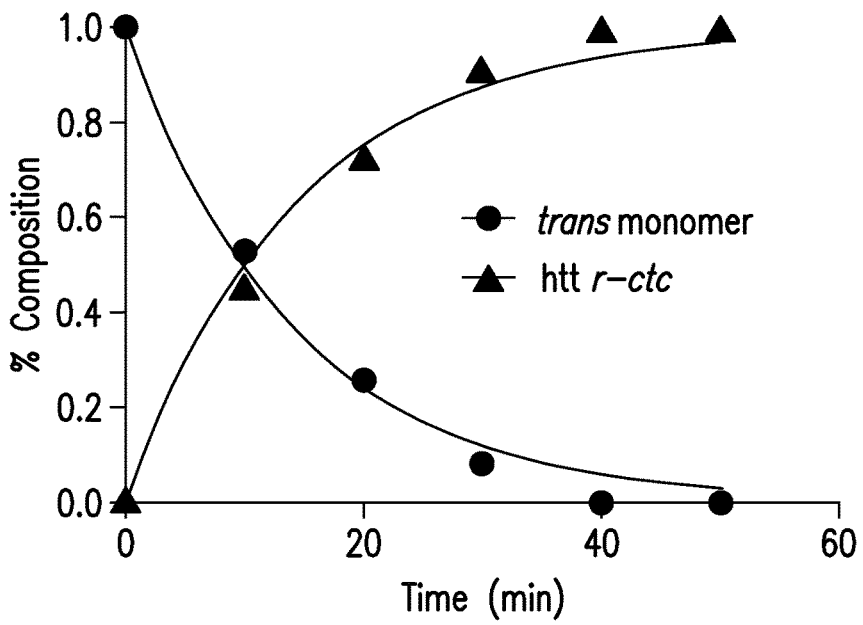
FIGS. 30A and 30B depict photolysis time courses with fitted exponential curves for (a) trans-2,4,-dichloro-6-styrylpyrimidine (compound 1 of Example III) and (b) trans-2,4-dichloro-6-(2-(pyridin-2-yl)vinyl)pyrimidine (compound 15 of Example III).
Figure 30B:
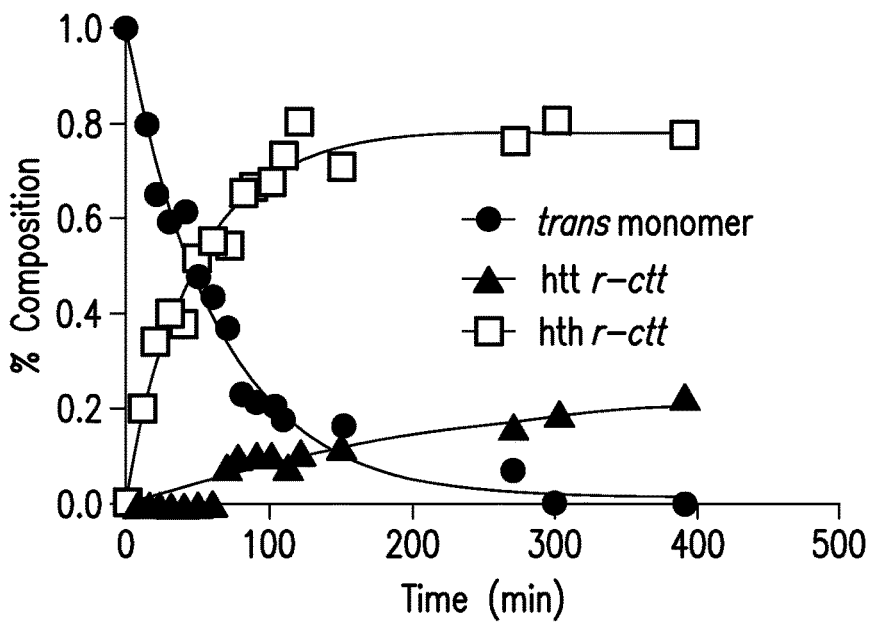

Using this set-up, we performed irradiations on 45-50 mg of recrystallized material for each of the six trans-azastilbenes (1, 12-16), as well as on cis-2,4-dichloro-6-styrylpyrimidine, cis-1, with time points taken at 10 minute intervals for the first 2 hours, and at 0.5-1 h intervals thereafter. Each sample was analyzed by $^1$H NMR, and in most cases, the eight expected cyclobutane isomers could be differentiated, based on the $^1$H NMR assignments made previously for the various isomers of compound 2. An example of peak assignment for the crude irradiation spectrum of compound 13, showcasing the ability to distinguish between photoproducts using $^1$H NMR, is shown in FIG. 29. For each photolysis, the percent composition of every component in the reaction mixture was determined from the peaks arising from the vinylic protons of the starting material (cis and trans vinylic as well as cyclobutyl peaks). These values were then plotted vs. time, and an exponential least-squares curve was fitted to each data set (see FIGS. 30A and 30B for example photolysis curves of 1 and 15).

The half-lives ($t_{1/2}$) for the formation of each component in the final photolysis mixture, along with the associated values for all combined cyclobutane isomers, are shown in Table 2. Table 3 lists the percent composition of each component of the reactions mixtures at the final time point for each photolysis. Study of these tables reveals somewhat contradictory trends. Based on our initial hypothesis, we expected those systems that are adequately polarized (i.e., having one electron-withdrawing and one electron-donating ring) would provide the htt r-ctt isomer preferentially. Additionally, we expected that the more polarized the azastilbene, the more rapid the reaction (smaller $t_{1/2}$). While the dichlorostryrylpyridine 14 reacted exclusively to form the htt r-ctt isomer with a satisfactory rate ($t_{1/2}$ ca. 4 times that for the similar reaction of 1), it was unique among the set of derivatives. Even the highly polarized, 4'-methoxystyrylpyrimidine 16 failed to selectively produce the htt r-ctt isomer (ca. 39% conversion, $t_{1/2}$ ca. 33 times that of 1), and instead formed the hth r-ctt compound as the major product. The photolysis of the significantly less-polarized triazastilbene 15 proceeded four times as quickly as that of 16, although it did favor formation of the hth dimer more strongly (81.3 vs. 18.7% for the hth and htt r-ctt dimers, respectively).

TABLE 2

$t_{1/2}$'s for the photoproducts of the solid-state irradiation of azastilbenes 1 and 12-16.

| | | $t_{1/2}$ (min) of formation[a] | | | | |
|---|---|---|---|---|---|---|
| azastilbene | cis[b] | comb. CBs[c] | htt r-ctt | htt r-tct | hth r-ctt | hth r-tct |
| 1 | — | 9.8 | 9.8 | — | — | — |
| 12 | — | 14200 | 28800 | — | 28400 | — |
| 13 | 498 | 1994 | 6730 | >10$^5$ | 3850 | 19700 |
| 14 | — | 39.1 | 39.1 | — | — | — |
| 15 | — | 45.4 | 160 | — | 34.2 | — |
| 16 | — | 201 | 331 | — | 243 | — |
| cis-1[d] | N/A | 213 | 213 | — | — | — |

[a]Isomers not reported in the table were not observed upon photolysis.
[b]Respective cis-azastilbene.
[c]$t_{1/2}$ calculated from curve formed by total % composition of all cyclobutanes in the reaction mixture.
[d]cis-2,4,-dichloro-6-styrylpyrimidine.

TABLE 3

Percent composition of the photoproducts of the solid-state irradiation of azastilbenes 1 and 12-16.

| | | | | % composition at end of irradiation[a] | | | | |
|---|---|---|---|---|---|---|---|---|
| azastilbene | time (min) | trans | cis[b] | comb. CBs[c] | htt r-ctt | htt r-tct | hth r-ctt | hth r-tct |
| 1 | 40 | 0 | 0 | 100 | 100 | 0 | 0 | 0 |
| 12 | 1440 | 90.5 | 0 | 9.5 | 4.7 | 0 | 4.8 | 0 |
| 13 | 1440 | 55.9 | 6.5 | 37.5 | 15.4 | 5.8 | 10.4 | 6.0 |
| 14 | 180 | 0 | 0 | 100 | 100 | 0 | 0 | 0 |
| 15 | 300 | 0 | 0 | 100 | 18.7 | 0 | 81.3 | 0 |
| 16 | 540 | 4.0 | 0 | 96.0 | 38.7 | 0 | 57.3 | 0 |
| cis-1[d] | 420 | 0 | 0 | 100 | 100 | 0 | 0 | 0 |

[a]Isomers not reported in the table were not observed upon photolysis.
[b]Respective cis-azastilbene.
[c]Percent composition of all cyclobutanes in the reaction mixture.
[d]cis-2,4,-dichloro-6-styrylpyrimidine.

In contrast to the solid-state irradiations with the highly-polarized stilbene systems, the azastilbenes designed to have reduced polarity across the conjugated π system (12 and 13) reacted with very little conversion to the htt r-ctt dimer, even with extended irradiation times. The dimethoxy-substituted compound, 12, was especially inert to photolysis, forming the htt r-ctt dimer in only 4.7% yield after 24 h. As with the initial irradiation of 1, essentially no cis/trans isomerization took place in the crystalline material. Only photolysis of 13 produced a small amount of the cis-styrylpyrimidine (6.5%) after 24 h.

Molecular Modeling of Azastilbene Interactions

While chemical intuition allows for ordering of the azastilbenes based on polarity across the π-system (16>1>14>15>13>12), π-stacking is an effect mediated by more subtle electronic effects than simply oppositely-paired electrostatic charge.[40,41] Consequently, it is more difficult to predict how increasing the electron withdrawing and/or donating nature of the aryl rings would affect the π-stacking of the azastilbenes. To provide a more quantitative understanding of this stabilization of the azastilbenes, M06-2X density functional and correlated ab initio (MP2) calculations were performed. All geometries were optimized with the M06-2X functional and 6-31G(d,p) basis set in Gaussian 09[42] using an ultrafine integration grid[43] in the gas phase. Monomers and π-stacking 'dimers' were oriented in either a head-to-tail or head-to-head manner, with the crystal structures described below acting as the starting point for the dimer geometry optimizations. All stationary points were verified as minima by vibrational normal mode inspection. Energies reported are M06-2X/6-311+G(2d,p)//M06-2X/6-31G(d,p). Interaction energies reported are relative to separated monomers and are corrected for basis-set superposition error. Spin component scaled MP2 (SCS-MP2) energies were computed by scaling the αβ and αα/ββ MP2 correlation energies by 1/3 and 6/5, respectively.[44]

The M062X and SCS-MP2 interaction energies for the azastilbene dimers are listed in Table 4, and differ by an average of only 0.8 kcal/mol. The trends and relative changes in binding energy across the two basis sets are nearly identical.

TABLE 4

Azastilbene interaction energies.

| azastilbene | interaction energies (kcal/mole) | |
| --- | --- | --- |
| | M062X | SCS-MP2 |
| 1 | −15.8 | −17.0 |
| 12 | −6.4 | −6.3 |
| 13 | −11.8 | −12.4 |
| 14 | −14.8 | −15.9 |
| 15 | −14.2 | −15.2 |
| 16 | −17.8 | −18.9 |

Figure 31A:
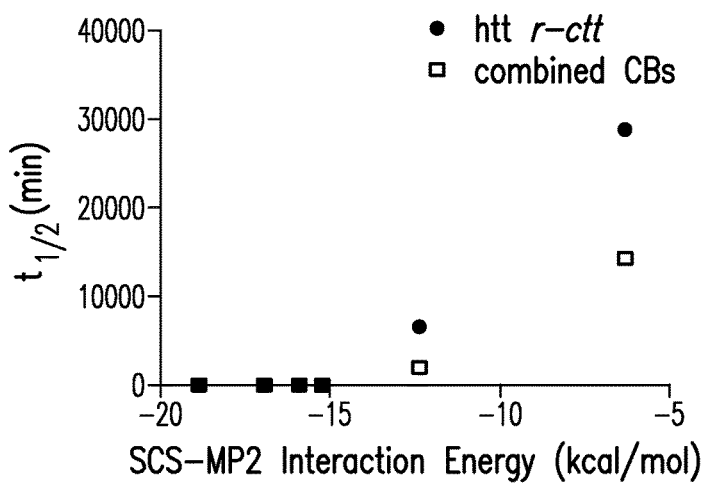
FIGS. 31A, B, and C show the correlation between spin-component-scaled SCS-MP2 energy calculation interaction energies and the formation of cyclobutanes under solid-state irradiation conditions.
Figure 31B:
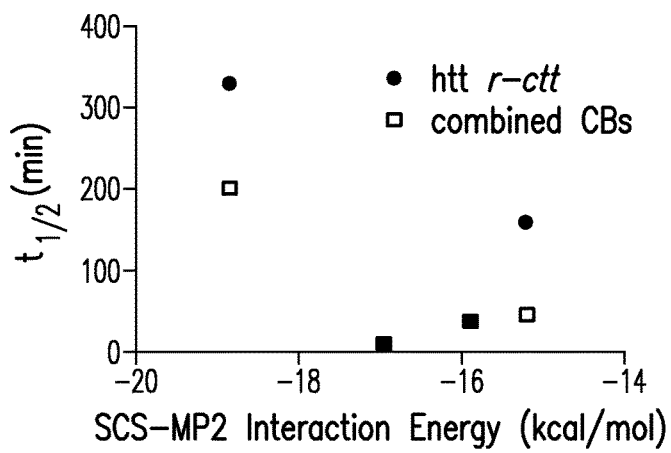
FIG. 31B is a blow-up of plot showing t½ vs. interaction energy with only first four points shown.
Figure 31C:
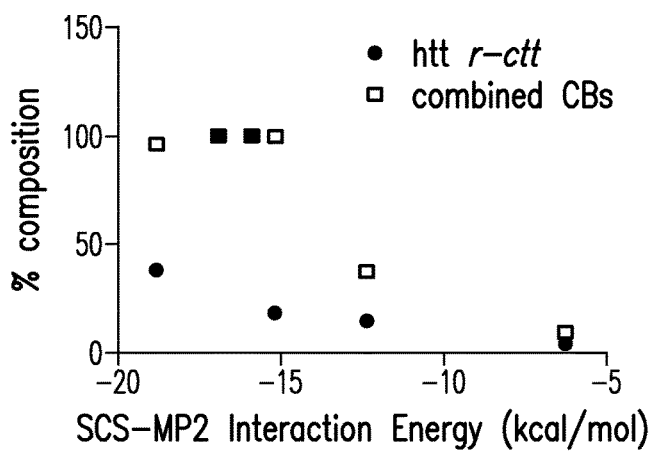
FIG. 31C shows the percent composition of the cyclobutane inhibitors at final irradiation time vs. interaction energy.

FIGS. 31A, B, and C show plots of the $t_{1/2}$'s of htt r-ctt dimer formation versus the SCS-MP2 interaction energies of the six azastilbenes. Based on the presumption that compounds which exhibit a higher binding energy should pack more tightly in the head-to-tail configuration, one would expect that azastilbenes that release more energy upon interaction would produce the htt r-ctt cyclobutane more rapidly and in greater yield. While this holds true for compounds 1, 12, 13, and 14, monomers 15 and 16 do not react as expected in the solid-state (FIGS. 31B and 31C). Due to the large interaction energy of azastilbene 16 (−18.8 kcal/mol), we anticipated that the reaction rate and yield for the htt r-ctt dimer would be comparable or higher than that of compound 1 (interaction energy=−17.0 kcal/mol). Nonetheless, the opposite is true: The solid-state photolysis of 16 forms the htt r-ctt dimer with a rate 300 times slower than that of 1, and provides the htt r-ctt dimer in only 39% yield, whereas 1 undergoes quantitative conversion to 2. Furthermore, based on the close binding energies exhibited by 14 and 15, one could postulate these two to have similar $t_{1/2}$'s for the formation of the htt r-ctt dimers. As with 16, compound 15 reacts to form the htt dimer with a rate six times slower than does 14. A lack of regioselectivity is observed in the irradiation of 15, which produces the htt dimer in only 19% yield, while 14 is quantitatively converted to the htt r-ctt cyclobutane.

Figure 32:
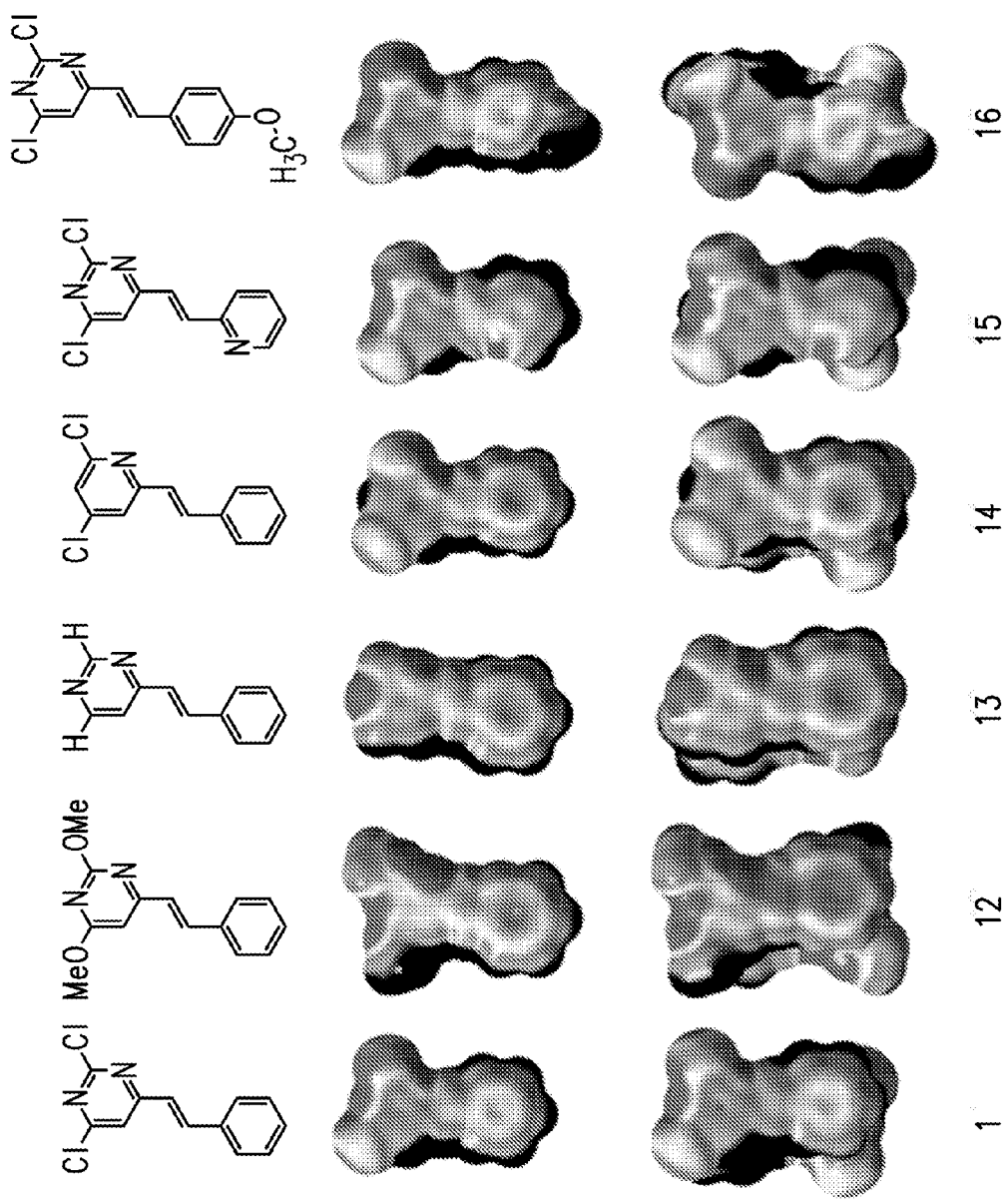
FIG. 32 depicts electrostatic potential surfaces of azastilbenes (middle row) and the head-to-tail interacting dimers (bottom row).

In addition to binding energies, electrostatic potentials were calculated for each monomer and head-to-tail π-stacking pair, and these are projected on an isodensity surface in FIG. 32—energy data ranges from +0.02 hartrees in the darker regions to −0.02 hartrees in the lighter regions. Visual inspection of these surfaces does not provide significant insight into which systems are more polarized; while a difference in electrostatic potential exists across the aromatic rings of each compound, from the ESPs it is not possible to grade this level of polarity. More visually satisfying is the increase of polarity observed across monomers as they interact in the htt dimer formation (bottom row of FIG. 32). This change in electrostatic potential is seen as the π-systems begin to feed into one another, accentuating the charge differential across the azastilbene.

Crystal Analysis and Photoreactivity of Trans-Azastilbenes

Figure 33:
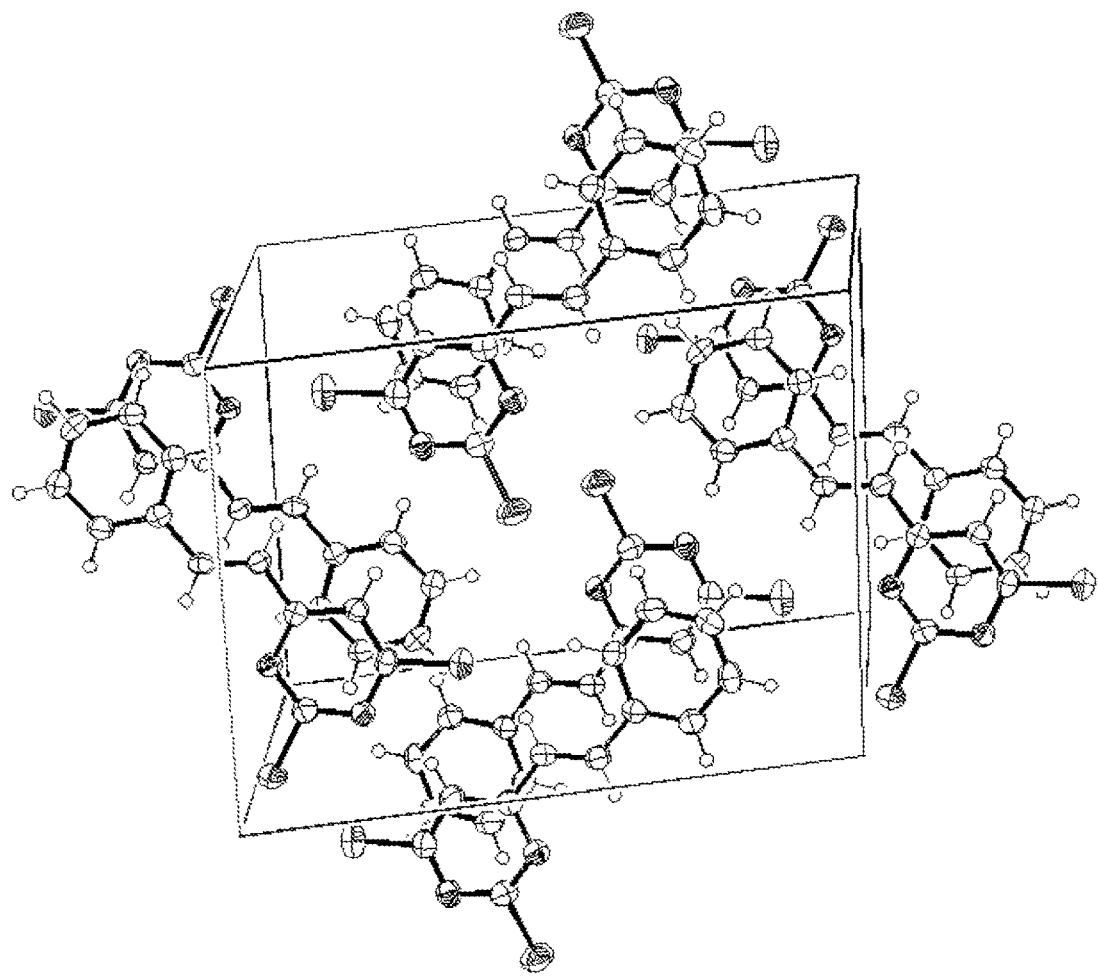
FIG. 33 depicts an X-ray crystal structure of trans-2,4-dichloro-6-styrylpyrimidine (compound 1 of Example III).

To understand the disconnect between the binding energies and reactivity of compounds 15 and 16, single-crystal X-ray structures of the azastilbene monomers 1 and 16 were obtained and compared. As anticipated from both the experimental results and computation work, 2,4-dichloro-6-styrylpyrimidine 1 packs in an array of infinite columns in a head-to-tail manner (FIG. 33). There are two unique columns contained in each unit cell; these alternate with distances between the monomers being either 3.543 Å or 3.775 Å. The short distance and planarity between the alkene double bonds suggest that the [2+2] photocycloaddition between monomers of 1 should proceed under topochemical control, and this is indeed the case (as described above).

Figure 34:
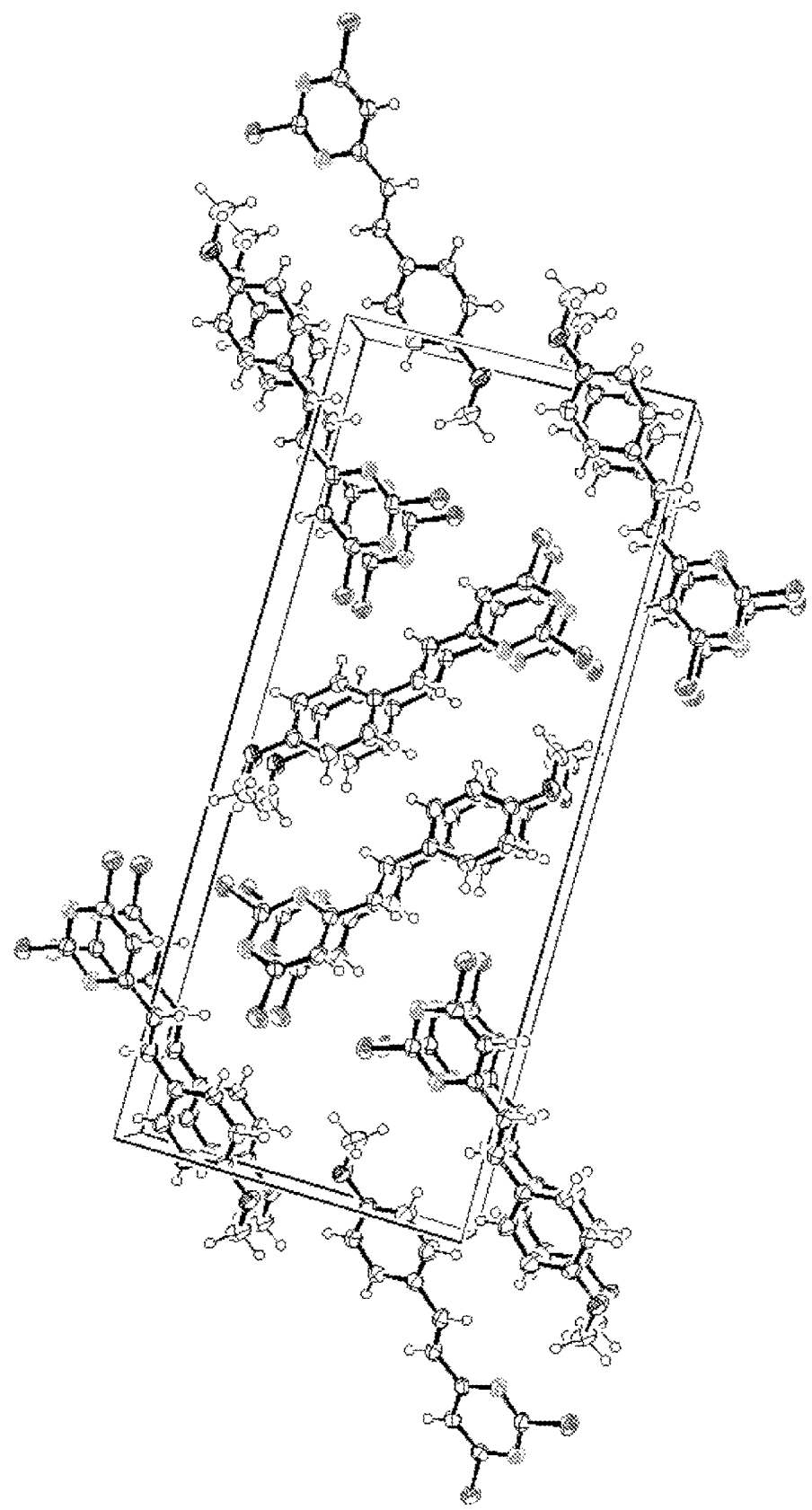
FIG. 34 depicts an X-ray crystal structure of trans-2,4-dichloro-6-(4-methoxystyryl)pyrimidine (compound 16 of Example III).

The X-ray crystal structure of azastilbene 16 is more intriguing. Based on the push-pull nature of the aromatic rings and the large interaction energy exhibited by the head-to-tail dimer of 16, we expected crystal packing to mimic that of 1. Nevertheless, the 4'-methoxyazastilbene packs in a head-to-head array with multiple infinite columns contributing to the unit cell (FIG. 34). The crystal analysis of 16 displays only a single inter-alkene distance of 4.164 Å. This places the reacting double bonds at the limits of the distance in which the topochemical principles are considered to operate (4.2 Å). Nonetheless, with the crystal structure of 16 in hand, the regio and stereochemistry observed upon its solid-state irradiation can readily be explained. Indeed, it appears that photolysis of 16 also proceeds under quasi-topochemical control, producing the hth r-ctt dimer preferentially (57.3% conversion).

Crystal Structure of Cis-2,4-Dichloro-6-Styrylpyrimidine

As shown in Tables 2 and 3, the solid-state irradiation of cis-2,4-dichloro-6-styrylpyrimidine (cis-1) produces 2 in yields equivalent to that from the irradiation of the trans-2,4-dichloro-6-styrylpyrimidine 1, albeit at a significantly decreased rate ($t_{1/2}$ of 213 min. vs 9.8 min. for the trans isomer). There are two possible routes for formation of the htt r-ctt dimer from the crystalline cis-azastilbene: cis-1 might crystallize in such a manner that the reacting double bonds are parallel to each other, with the aryl rings of each alternating monomer oriented away from one another; if the [2+2] photocycloaddition then proceeded under topochemical control, cyclobutane 2 would be formed selectively (top pathway of Scheme 3). Alternatively, crystalline cis-1 might first undergo light-initiated cis/trans isomerization to 1, which then reorients to form microcrystals that give rise to 2 (bottom pathway of Scheme 3).

Scheme 3. Formation of cyclobutane 2 from cis-2,4-dichloro-6-styrylpyrimidine.

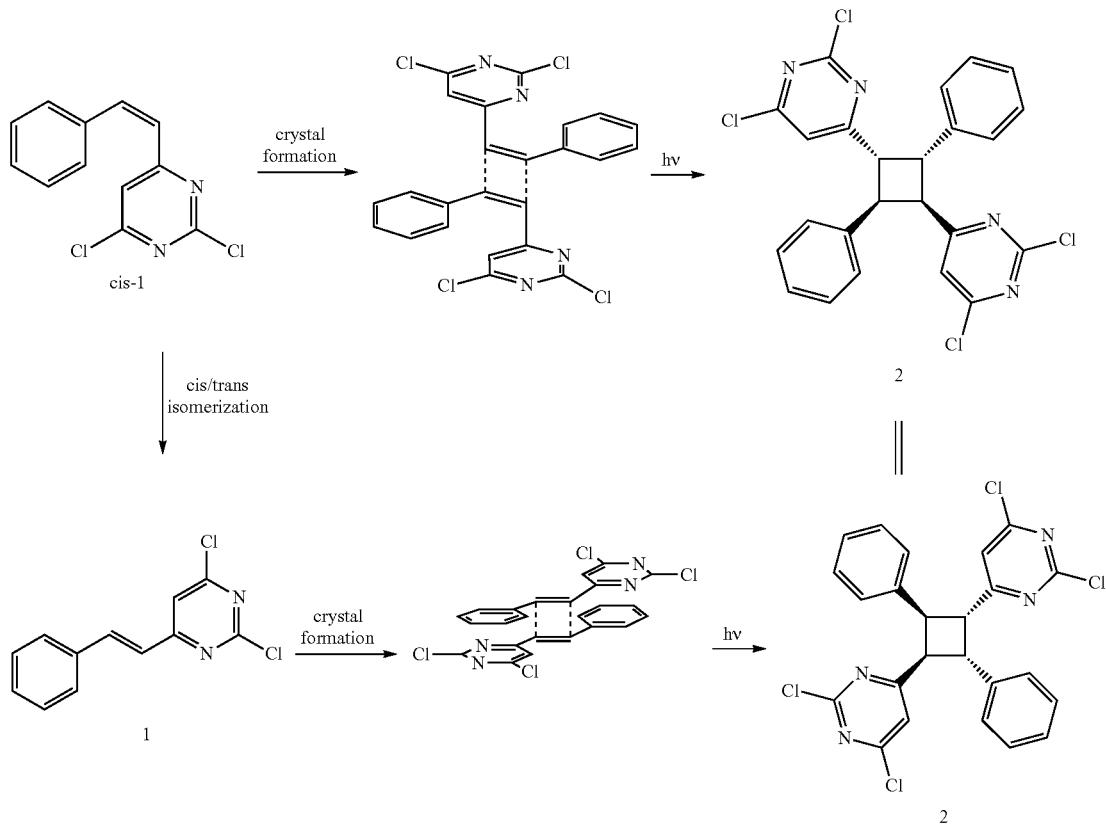

Figure 35:
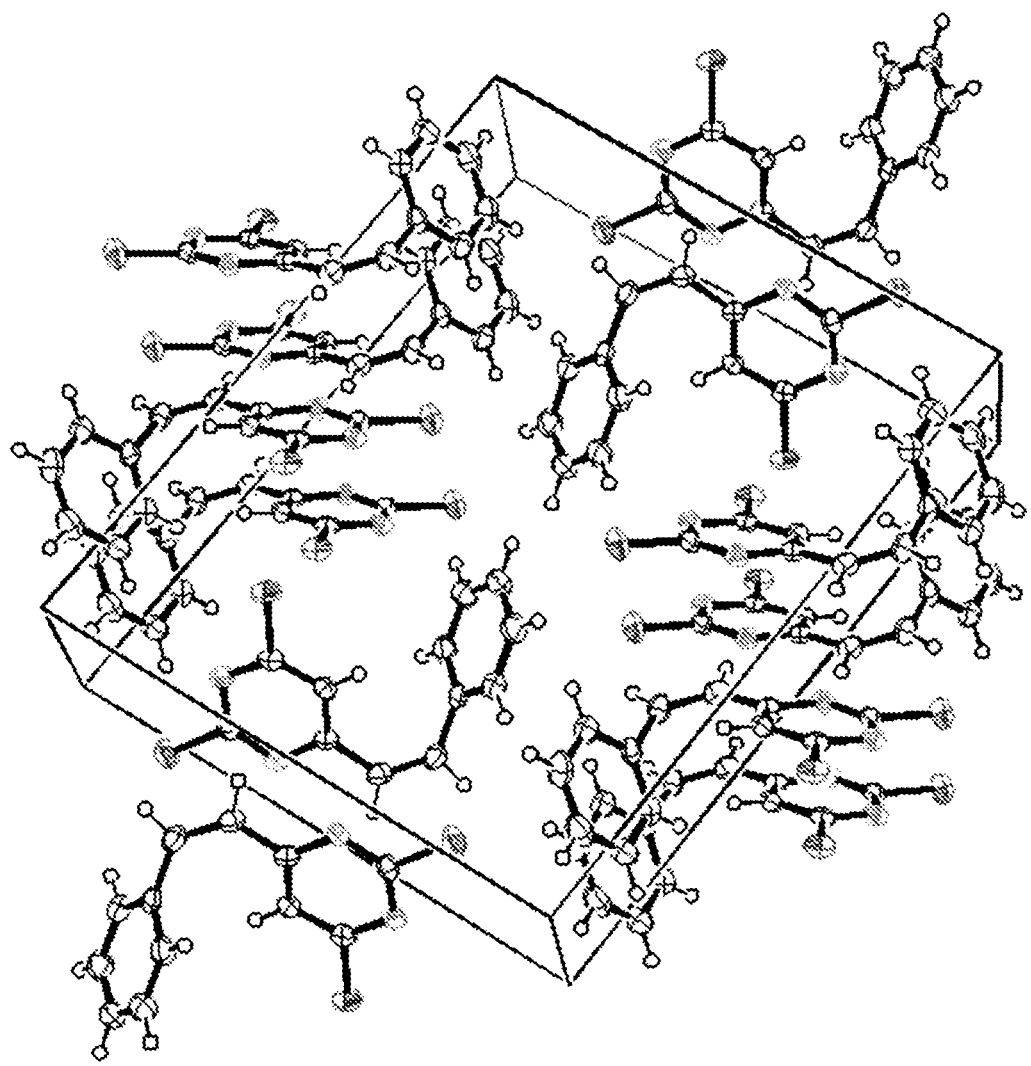
FIG. 35 depicts an X-ray crystal structure of cis-2,4-dichloro-6-styrylpyrimidine (the cis form of compound 1 from Example III).

To differentiate between these two pathways, we obtained an X-ray crystal structure of the cis-1 starting material. As shown in FIG. 35, the unit cell of cis-1 also contains multiple infinite columns which are packed in such a manner that the alkenyl double bonds are parallel to one another. Nonetheless, if the stereochemistry of the photoproducts was determined by the solid-state molecular packing, one would expect the hth r-ccc isomer to be produced, not the htt r-ctt cyclobutane. Additionally, measurement of the space between the reacting double bonds in the cis-1 crystal shows that they are separated by 5.131 Å, too large for cycloaddition without significant perturbation of the crystal lattice. Thus, formation of 2 from cis-1 cannot be proceeding under topochemical control, so the alternate pathway must be considered.

Additional evidence for cis/trans isomerization in the solid-state photolysis of cis-1 is apparent in the presence of trans isomer 1 in the reaction mixture after as little as 20 minutes of irradiation. The amount of 1 remains at a fairly constant level (3-10%) throughout the irradiation, but disappears near the completion of the reaction. The absence of crystal packing suitable for formation of the htt r-ctt cyclobutane, and the confirmed presence of 1 in the reaction mixture, strongly suggest that the conversion of cis-1 to 2 proceeds through the trans-azastilbene intermediate. While visual inspection throughout the water-cooled irradiation of cis-1 shows no observable solid-to-liquid transformation, it is possible that the initial cis/trans isomerization is expedited by microscopic melting, facilitated by the relatively low melting point of cis-1 (47-48° C.).

Solution-State Irradiation of Azastilbene Derivatives

From the X-ray crystal structure of 16, it became clear that the stereo and regiochemistry observed upon irradiation of this compound were due to its molecular packing in the solid state. This packing overcame the inherent polarity and associated energetic preference for head-to-tail interaction demonstrated in the gas phase calculations of the 4'-methoxyazastilbene (similar considerations likely apply to the triazastilbene, 15). We wanted to investigate whether this bias towards head-to-head photoproducts for 15 and 16 could be reversed by irradiation in solution, which would eliminate the constraints enforced by the structured crystal lattice. To this end, 40 mM solutions of each azastilbene in CDCl$_3$ were prepared and subsequently irradiated in sealed borosilicate NMR tubes. Photolysis was accomplished using the same arrangement as described for the solid-state irradiations, and all of the azastilbene samples were irradiated simultaneously so as to minimize variability. The percent composition of each sample after 24 h of photolysis is shown in Table 5.

TABLE 5

Percent composition of solution-state irradiation mixture of azastilbenes at 24 h.

| | | | | | % composition | | | | | | | |
|---|---|---|---|---|---|---|---|---|---|---|---|---|
| Aza-stilbene | trans[a] | cis[b] | htt r-ctt | htt r-cct + r-ctc | htt r-tct | htt r-ccc | hth r-ctt | hth r-tcc + r-ctc | hth r-tct | hth r-ccc | Peri-cyclic pdt[c] | comb CBs[d] |
| 1 | 29.9 | 30.6 | 21.3 | 1.9 | 5.2 | 0.0 | 4.9 | 0.0 | 4.0 | 2.3 | 0.0 | 39.5 |
| 12 | 32.5 | 61.2 | 1.9 | 0.1 | 0.0 | 0.0 | 0.5 | 0.6 | 0.0 | 0.0 | 3.1 | 3.2 |
| 13 | 35.0 | 57.2 | 4.3 | 0.5 | 0.3 | 0.0 | 1.1 | 0.0 | 0.1 | 1.6 | 0.0 | 8.0 |
| 14 | 39.9 | 49.2 | 7.4 | 0.0 | 0.6 | 0.6 | 1.3 | 0.0 | 0.0 | 1.0 | 0.0 | 10.9 |
| 15[e] | 65.5 | 22.9 | 0.0 | 0.0 | 3.5 | 0.0 | 2.3 | 0.0 | 4.3 | 1.5 | 0.0 | 11.6 |
| 16 | 27.3 | 14.0 | 46.3 | 1.7 | 5.0 | 0.0 | 4.6 | 0.0 | 1.1 | 0.0 | 0.0 | 58.7 |

[a]respective trans azastilbene.
[b]respective cis-azastilbene.
[c]respective benzo[f]quinolone or benzo[f]quinazoline.
[d]Percent composition of all cyclobutanes in the reaction mixture.
[e]decomposition/precipitation of SM/pdt upon irradiation.

The solution-state irradiations resulted predominantly in trans/cis isomerization of the azastilbene rather than cycloaddition. For all compounds except 15 and 16, the cis monomer was the predominant component of the reaction mixture at 24 h. Additionally, there was a loss of regio and stereoselectivity for most of the azastilbene samples. This was especially striking for 1 and 14, which, in the solid-state, were quantitatively converted to the htt r-ctt isomer. While the htt r-ctt isomer continues to be the major cyclobutane product, the formation of multiple other isomers attests to the role that topochemical control plays for these compounds in the solid-state. In addition to the htt r-tct and hth r-ctt and r-tct dimers observed as products of the solid-state irradiations, the solution-state irradiations also produced varying amounts of the previously identified htt r-cct and r-ctc, and hth r-tcc and r-ctc isomers. Because the $^1$H NMR peaks of the hth r-cct and r-ctc isomers, as well as the htt r-cct and r-ctc isomers overlap, the percent composition of these compounds in Table 5 are combined. Intriguingly, in four of the six samples a ninth cyclobutane dimer, the hth r-ccc isomer, was found. This assignment is based on the presence of two distinct doublets located between δ 3.9 and 4.3 in the $^1$H NMR of the product mixture of four of the six azastilbenes (in the photolysis of 13 these peaks presumably overlap to form an apparent quartet at δ 4.04). The assignment of the htt r-ccc isomer to these peaks is negated by the splitting pattern (doublet vs. triplet). The presence of multiple methoxy peaks in the spectra of the product mixture from irradiation of 12 and 16 makes it impossible to confirm or deny the presence of the hth r-ccc dimer. It should be noted that irradiation of triazastilbene 15 leads to formation of insoluble photoproducts which preclude the accurate measurement of the reaction components by NMR. Two additional products of note include the possible formation of the htt r-ccc dimer from 14 (based on an otherwise unexplained singlet at δ 4.01) and a benzo[f]quinazoline, formed upon the irradiation of 12. Benzo[f]quinazoline is a well-known irradiation product of diazastilbenes.[45-48]

Regardless of the presence of multiple cyclobutane isomers in the solution-state irradiation mixtures, in every instance except for compound 15, the predominant product was the htt r-ctt isomer. The percent composition of the htt r-ctt adducts as well as of the total combined cyclobutane products from the azastilbene solution irradiations are displayed, plotted against the SCS-MP2 binding energy calculated for each compound in FIG. 36 (compound 15 has been excluded from this analysis based on the insolubility of its photoproducts). In contrast to the solid state photolysis, the solution irradiations display a consistent relationship between the binding energy of the azastilbenes and the yield of the htt r-ctt dimer, and an exponential least-squares curve fitting provides a coefficient of determination ($R^2$-value) of 0.96. A similar analysis of the percent composition of all the combined cyclobutanes in each reaction mixture produces a somewhat worse fit, with an $R^2$-value of 0.83, reflecting the expectation that the head-to-tail binding energy provides a better predictive measure of htt r-ctt dimer formation than that of cyclobutane formation as a whole.

The range of solid-state photochemical results we have presented here are generally consistent with the conclusions made by Schmidt and coworkers when they first presented their topochemical postulates.[8-11,49] Namely, the crystal structure of trans-2,4-dichloro-6-styrylpyrimidine 1 displays a molecular packing in which the double bonds undergoing [2+2] photocycloaddition are parallel to one another and separated by less than 4.0 Å. The htt r-ctt dimer 2 is formed in quantitative yield in a short amount of time with even moderate-intensity light sources ($t_{1/2}$ of less than 10 min). When azastilbenes of similar or increased polarity across the π-system were irradiated in the solid state, the results initially proved contradictory. While the less polarized trans-2,4-dichloro-6-styrylpyridine 14 also quantitatively produced the htt r-ctt cyclobutane, albeit with a longer half-life than for the reaction of 1, the similarly polar triazastilbene 15 and significantly more polarized 4'-methoxystyrylpyrimidine 16 preferentially produced the hth r-ctt dimer.

X-ray structural analysis of 16 sheds light on these results, as it shows a consistent head-to-head arrangement of infinite columns of azastilbene monomers with an inter-alkene distance just under 4.2 Å. Further inspection of the crystal structure reveals multiple weak hydrogen bonds stabilizing this arrangement. Most notable of these are the intra-columnar methoxy C—H to O (2.613 Å) and methoxy C—H to π (2.860 Å) interactions. There are two additional inter-columnar weak hydrogen bonds: pyrimidinyl C—H to N (2.719 Å) and phenyl C—H to O (2.67 Å). Weak hydrogen bonding has been studied extensively through crystal structure analysis as well as computationally (see the reviews by Steiner and Desiraju).[50-52] The distances measured for the weak interactions in the crystal structure of 16 (all <3 Å) suggest structurally significant bonding, and while it is difficult to assign energy values to any single interaction, other examples of C—H to O, C—H to π, and C—H to N bonds have been calculated to range from ≤1 to >2 kcal/mol.

Consequently, it is not surprising that these weak hydrogen bonds in aggregate are able to overcome the energetically less favorable head-to-head π-stacking conformation (15.1 vs. 18.9 kcal/mol binding energy for the hth vs. htt dimers).

Although the topochemical postulate can be used to explain the hth r-ctt isomer as the major photoproduct of solid-state 16 (57.3% conversion), It is more difficult to justify the large amount of the htt r-ctt isomer formed from this reaction (38.7%). Two main explanations for the loss of topochemical control have been presented in the literature.[8,30] Both argue that non-topochemical isomers are produced at defects in the crystal. In one view these defects are present in the crystal at the beginning of irradiation and are continually propagated as the non-topochemical isomer forms. The other argument concludes that formation of topochemical dimers causes local disruption in the crystal lattice. This eventually produces defects in which a new crystal phase is formed during the photolysis, from which the non-topochemical isomer arises. The presence of the htt isomer upon irradiation of 16 could be justified according to either of these posits.

Extension of this reasoning to compounds 14 and 15 suggests that photoproduct formation proceeds from the head-to-tail and head-to-head crystal forms, respectively. Although the absence of a methoxy group on 14 and 15 negate the possibility of the intra-columnar C—H to O and methoxy C—H to t bonds pertinent to 16, the unique presence of a pyridine in these compounds may predispose to stronger C—H to N hydrogen bonds, leading to unanticipated packing orientations and the observed irradiation results.

As described here, we have attempted to correlate the polarity of interacting π-systems with their photoreactivity in the solid-state. To better gauge the effect of different aryl substituents on polarization of the azastilbenes, DFT and MP2 calculations were performed in both the monomer and 'dimer' states. These calculations provided interaction or binding energies which could then be correlated to the azastilbene photoreactivity. Gratifyingly, the trends in binding energy mimicked those that would have been predicted from an intuitive analysis of the stilbenes, based on generally accepted electron withdrawing and electron donating properties of the aryl rings. More importantly, these calculations provide quantitative values that can be compared to the rates and percent compositions obtained from the various photolysis reactions.

We hypothesized that compounds exhibiting greater interaction energies (i.e., had more polarized π-systems) would have crystal packing in which the monomers were more closely oriented in a head-to-tail manner. As a consequence of this presumed tight head-to-tail packing, we anticipated that the rate of formation of and the selectivity for the htt r-ctt dimers would be greater for those proceeding from more polar starting material. This hypothesis, however, failed to predict the outcomes of the solid state irradiation of six azastilbenes. While these results can be rationalized from the crystal structures of the starting materials, the unexpected crystal packing of 15 and 16 highlights the unpredictability associated with rational crystal engineering and the limits that this unpredictability places on the use of solid-state photochemistry to produce synthetically useful products with good control over stereo and regioselectivity. Indeed, there has been great interest in this field recently, and significant advances have been made in the use of intermolecular templating agents to increase photoreactivity and selectivity in the solid state.[53] These include the use of hydrogen-bonding, metal-lone pair interactions, halogen-bonding, and encapsulation approaches.[54,55] There has been less work in the direct design of molecules that in-and-of-themselves pack in a specific and reactive manner. While examples exist of hydrogen-bonding enforced diastereoselective solid-state photochemical reactions,[56] the majority of these examples focus on engineering a push-pull system in which one arene ring of the diarylethylene system preferentially interacts with the oppositely polarized ring or alkene.[21,22,57,58] Undoubtedly, this 'neat' approach to crystal engineering involving designed hydrogen-bonding or π-π interactions, in which no secondary organizing agent is required, is more efficient. Unfortunately, as described here, efforts to design crystals in this manner can be frustratingly unfruitful, and it may prove that templating techniques are more versatile in their application and hence more useful.[59] For recent overviews of crystal engineering and 2+2 photocycloadditions see the reviews by Natarajan, Biradha, and Elacqua.[18,54,55]

To our knowledge, this is the first attempt to correlate photoreactivity in the solid-state with calculated π-system to π-system interaction energies. Similar comparisons of irradiation results and the polarity of extended π-systems have been made, but only in a generalized fashion.[24,33,60] Our work in this area was only partially successful, largely due to the unexpected crystal packing of 15 and 16. If these compounds are excluded from the analysis shown in FIGS. 31A, B, and C, the hypothesized relationship between binding energy and the percent composition of the htt r-ctt dimer in the reaction mixture and the inverse relationship between interaction energy and $t_{1/2}$ become apparent. Indeed, as molecular orientation inside the crystal controls the outcome of irradiation for crystalline solids and prediction of crystal packing remains an un-mastered problem, it seems unlikely that the stereoselective synthesis of cyclobutane derivatives through this approach will remain little more than a hit-and-miss situation for the foreseeable future.

Figure 36:
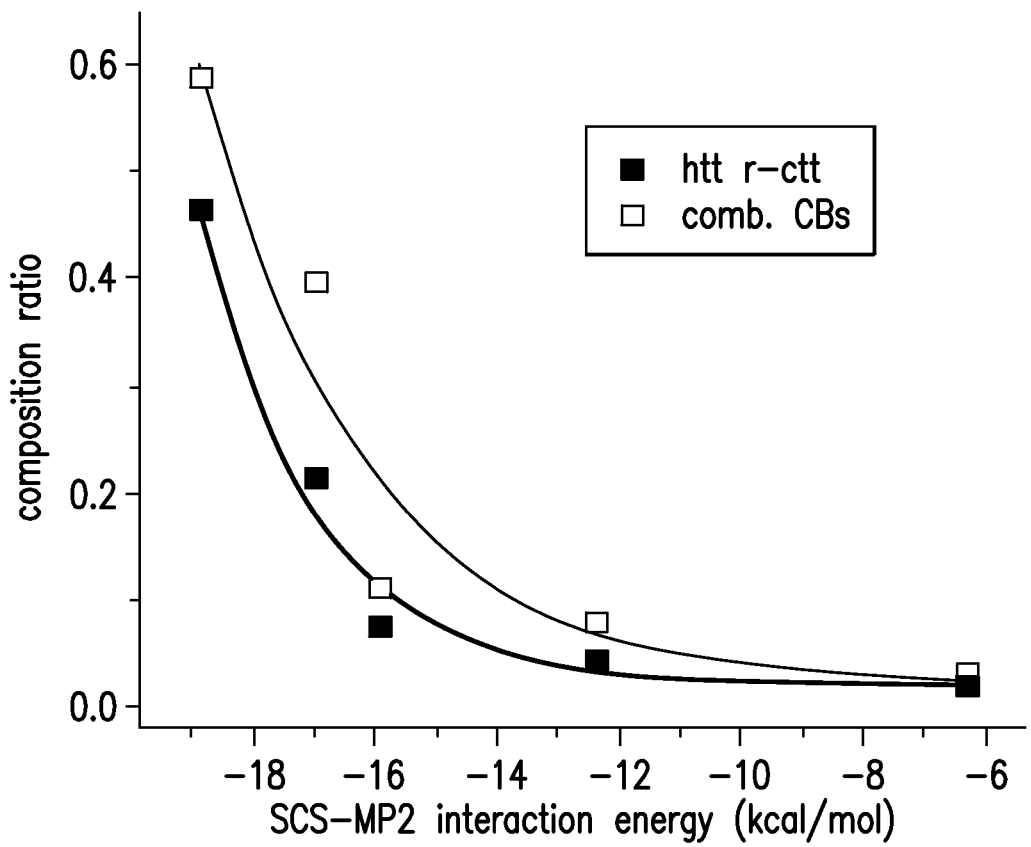
FIG. 36 depicts the correlation between SCS-MP2 interaction energies and the formation of cyclobutanes under solution-state irradiation at 24 h.

Unlike the solid-state irradiations, the solution reactions show a consistent exponential relationship between the percent composition of the htt r-ctt dimer in the photolysis mixture and binding energy of the azastilbenes (FIG. 36). Of special note is the observation that the cyclobutane formed preferentially from azastilbene 16, which has the highest calculated htt interaction energy of the six irradiated compounds, switches from the hth r-ctt dimer formed in the solid-state to the anticipated htt r-ctt dimer in solution. The excellent correlation observed for selective solution-state formation of the htt r-ctt dimer and binding energy suggests that designing stilbene-type compounds that exhibit sufficiently large computational binding energies may be a generally applicable method for attaining solution [2+2] photocycloadditions that proceed in synthetically useful regio and stereochemical yields. Further experimental work would do much to confirm the generality of solution reactivity based on interaction energies.

Here, we reported the discovery of a solid-state topochemically controlled [2+2] photocycloaddition between two molecules of trans-2,4-dichloro-6-styrylpyrimidine 1 to form in quantitative yield the associated htt r-ctt cyclobutane dimer. Through solution irradiations, eight of the ten possible cyclobutane isomers formed from the dimerization of 1 were isolated and identified. The spectral assignments from this analysis were applied to the solid and solution-state photochemical reactions of 1 and five other azastilbene derivatives (compounds 12-16) that contained varying degrees of polarization across their extended π-systems. Interaction energies between two azastilbene monomers were calculated for each compound using DFT and correlated ab initio calculations. While it proved difficult to predict the preferential formation of the htt r-ctt dimer in the solid-state based on these calculations, due to unpredictable crystal packing of two of the azastilbenes (15 and 16), there was a strong correlation between binding energies and htt r-ctt cyclobutane formation for all starting materials in solution. It is proposed that the calculation of interaction energies may be a good general tool for the prediction of successful stereo and regioselective photocycloaddition in solution for stilbene-type compounds.

EXPERIMENTAL

General Synthetic Methods.

All reagents were used as purchased. THF, Ether, $CH_2Cl_2$, and DMF used in reactions were dried using a solvent delivery system (neutral alumina column).[61] All reactions were run under dry $N_2$ atmosphere except where noted. Flash column chromatography[62] was performed on flash silica gel (40-64 μM, 60 Å) or using an MPLC system equipped with silica gel columns. $^1$H NMR, $^{13}$C NMR, and NOE spectra were obtained on 500 MHz FT-NMR spectrometers. Except where noted, both low and high resolution mass spectra were obtained using electrospray ionization.

trans-2,4-Dichloro-6-styryl-pyrimidine 1.

Based on the coupling described by Tan et al.[63] trans-2-Phenylvinylboronic acid (2.546 g, 17.2 mmol), $K_3PO_4$ (7.307 g, 34.4 mmol), and $PdCl_2(PPh_3)_2$ (0.362 g, 0.52 mmol) were dissolved in 100 mL THF. To this mixture, 2,4,6-trichloropyrimidine (3.156 g, 17.2 mmol) dissolved in 20 mL THF was added producing a cloudy yellow suspension. $H_2O$ (15 mL) were added, and the now clear solution was heated at reflux for 7 h. Approximately 100 mL of $H_2O$ were added, and the biphasic mixture was extracted three times with ether. The combined organic layers were washed with brine, dried over anhydrous $MgSO_4$, and the solvent removed with a rotary evaporator. The product purified by column chromatography (5-10% EtOAc in hexanes) to provide 1 (3.161 g, 73%). $^1$H NMR (500 MHz, $CDCl_3$) δ 6.95 (d, J=15.87 Hz, 1H), 7.22 (s, 1H), 7.41 (m, 3H), 7.59 (dd, J=7.45, 2.08 Hz, 2H), 7.96 (d, J=15.87 Hz, 1H). $^{13}$C NMR (500 MHz, $CDCl_3$) δ 117.1, 123.0, 128.2, 129.2, 130.6, 134.8, 140.9, 160.7, 162.8, 166.6. HRMS (ESI$^+$) m/z calcd for $C_{12}H_9N_2Cl_2^+$ 251.0143. found 251.0101. mp 119-121° C. (recryst. from EtOAc/hex).

Solution Irradiations of trans-2,4-dichloro-6-styrylpyrimidine 1 in Benzene, Acetonitrile, and Methanol.

Solutions of 750 mg (2.98 mmol) of 1 were prepared in 150 mL of benzene, acetonitrile, or methanol. The resulting solution was placed in a photochemical reaction assembly consisting of a water-cooled borosilicate immersion well and surrounding photochemical reactor, and was subsequently degassed with vigorous bubbling of $N_2$ gas for 1.5 h. Irradiation was performed using a 450 W medium-pressure mercury arc-lamp for 4-5 hours, with mixing of the solution accomplished by continuous bubbling of $N_2$ through the reaction mixture.

cis-2,4-Dichloro-6-styryl-pyrimidine cis-1.

Isolated from solution irradiations of 1 in benzene, acetonitrile, or methanol. $^1$H NMR (500 MHz, $CDCl_3$) δ 6.49 (d, J=12.22 Hz, 1H), 7.01 (s, 1H), 7.15 (d, J=12.43 Hz, 1H), 7.27-7.33 (m, 2H), 7.33-7.38 (m, 3H). $^{13}$C NMR (500 MHz, $CDCl_3$) δ 118.7, 126.2, 128.6, 128.7, 129.1, 134.8, 140.6, 160.6, 161.8, 167.3. HRMS (ESI$^+$) m/z calcd for $C_{12}H_9N_2Cl_2^+$ 251.0143. found 251.0140. mp 47-48° C. (recryst. from hexanes).

Isolation of 1,3-bis(2,4-dichloropyrimid-6-yl)-2,4-diphenylcyclobutanes 2-5 and 7-10.

The reaction mixtures from the preceding solution-state irradiations of 1 were combined, and separation of the photoproducts accomplished by multiple rounds of flash column chromatography using EtOAc/hexanes. Additional separations involving preparative thin-layer chromatography were necessary to isolate some of the lower yielding photoproducts (developed with EtOAc/hexanes or $CH_2Cl_2$/EtOAc).

r-1,t-3-Bis(2,4-dichloropyrimid-6-yl)-c-2,t-4-diphenylcyclobutane 2 (htt r-ctt isomer).

$^1$H NMR (500 MHz, $CDCl_3$) δ 4.64 (dd, J=10.30, 7.30 Hz, 2H), 4.84 (dd, J=10.25, 7.32 Hz, 2H), 6.93 (s, 2H), 7.15-7.19 (m, 6H), 7.25 (d, J=7.50 Hz, 4H). $^{13}$C NMR (500 MHz, $CDCl_3$) δ 44.9, 47.3, 119.2, 127.2, 127.5, 128.4, 137.1, 160.1, 161.8, 172.7. HRMS (ESI$^+$) m/z calcd for $C_{24}H_{17}N_4Cl_4^+$ 501.0207. found 501.0211.

r-1,c-3-Bis(2,4-dichloropyrimid-6-yl)-c-2,t-4-diphenylcyclobutane 3 (htt r-cct isomer).

$^1$H NMR (500 MHz, $CDCl_3$) δ 4.36 (t, J=10.13 Hz, 2H), 4.63 (t, J=9.64 Hz, 1H), 5.22 (t, J=10.74 Hz, 1H), 6.92 (d, J=6.84 Hz, 2H), 6.97 (s, 2H), 7.02-7.10 (m, 3H), 7.32 (t, J=7.08 Hz, 1H), 7.40 (t, J=7.32 Hz, 2H), 7.44 (d, J=7.08 Hz, 2H). $^{13}$C NMR (500 MHz, $CDCl_3$) δ 42.9, 48.5, 48.8, 118.6, 121.6, 126.7, 127.43, 127.45, 128.36, 128.9, 129.3, 134.7, 160.3, 162.0, 172.3. HRMS (ESI$^+$) m/z calcd for $C_{24}H_{17}N_4Cl_4^+$ 501.0207. found 501.0207.

r-1,t-3-Bis(2,4-dichloropyrimid-6-yl)-c-2,c-4-diphenylcyclobutane 4 (htt r-ctc isomer).

$^1$H NMR (500 MHz, $CDCl_3$) δ 4.40 (t, J=8.68 Hz, 1H), 4.63 (t, J=9.43 Hz, 2H), 5.25 (t, J=10.29 Hz, 1H), 6.90 (s, 1H), 7.13 (d, J=7.29 Hz, 6H), 7.22 (t, J=7.93 Hz, 4H), 7.49 (s, 1H). $^{13}$C NMR (500 MHz, $CDCl_3$) δ 45.8, 46.7, 50.2, 119.0, 120.8, 126.2, 127.1, 128.3, 136.8, 159.2, 161.2, 162.0, 162.8, 172.0, 173.8. HRMS (ESI$^+$) m/z calcd for $C_{24}H_{17}N_4Cl_4^+$ 501.0207. found 501.0220.

r-1,c-3-Bis(2,4-dichloropyrimid-6-yl)-t-2,t-4-diphenylcyclobutane 5 (htt r-tct isomer).

$^1$H NMR (500 MHz, $CDCl_3$) δ 3.78 (t, J=9.54 Hz, 2H), 4.20 (t, J=9.65 Hz, 2H), 7.14 (s, 2H), 7.27 (d, J=6.86 Hz, 4H), 7.31 (d, J=7.29 Hz, 2H), 7.37 (t, J=7.90 Hz, 4H). $^{13}$C NMR (500 MHz, $CDCl_3$) δ 47.7, 52.1, 118.5, 124.9, 126.8, 127.7, 129.0, 139.7, 162.6. 173.2. HRMS (ESI$^+$) m/z calcd for $C_{24}H_{17}N_4Cl_4^+$ 501.0207. found 501.0202.

r-1,c-2-Bis(2,4-dichloropyrimid-6-yl)-t-3,t-4-diphenylcyclobutane 7 (hth r-ctt isomer).

$^1$H NMR (500 MHz, $CDCl_3$) δ 3.97 (AA'BB', 2H), 4.09 (AA'BB', 2H), 7.13 (s, 2H), 7.30 (d, J=7.07 Hz, 6H), 7.37 (t, J=7.07 Hz, 4H). $^{13}$C NMR (500 MHz, $CDCl_3$) δ 49.2, 50.2, 118.8, 127.0, 127.6, 128.9, 140.2, 161.1, 162.6, 172.7. HRMS (ESI$^+$) m/z calcd for $C_{24}H_{17}N_4Cl_4^+$ 501.0207. found 501.0201.

r-1,t-2-Bis(2,4-dichloropyrimid-6-yl)-c-3,c-4-diphenylcyclobutane 8 (hth r-tcc isomer).

$^1$H NMR (500 MHz, $CDCl_3$) δ 4.27-4.33 (q, J=8.55 Hz. 2H), 4.49 (t, J=8.79 Hz, 1H), 5.13 (t, J=10.74 Hz, 1H), 6.87 (s, 1H), 7.13 (t, J=8.06 Hz, 4H), 7.21 (t, J=7.57 Hz, 2H), 7.37 (d, J=4.15 Hz, 4H), 7.44 (s, 1H). HRMS (ESI$^+$) m/z calcd for $C_{24}H_{17}N_4Cl_4^+$ 501.0207. found 501.0208.

r-1,c-2-Bis(2,4-dichloropyrimid-6-yl)-t-3,c-4-diphenylcyclobutane 9 (hth r-ctc isomer).

$^1$H NMR (500 MHz, $CDCl_3$) δ 4.57 (quin, J=9.46 Hz, 2H), 4.76 (t, J=9.77 Hz, 1H), 4.97 (dd, J=10.62, 8.91 Hz, 1H), 6.79 (d, J=0.49 Hz, 1H), 6.83 (dd, J=7.57, 1.71 Hz, 2H), 6.95 (d, J=8.06 Hz, 2H), 6.98-7.03 (m, 3H), 7.08 (t, J=7.08 Hz, 1H), 7.15 (t, J=7.57 Hz, 2H), 7.57 (s, 1H). HRMS (ESI$^+$) m/z calcd for $C_{24}H_{17}N_4Cl_4^+$ 501.0207. found 501.0195.

r-1,t-2-Bis(2,4-dichloropyrimid-6-yl)-c-3,t-4-diphenylcyclobutane 10 (hth r-tct isomer).

$^1$H NMR (500 MHz, CDCl$_3$) δ 3.95-3.98 (AA'BB' q, 2H) 4.07-4.11 (AA'BB' q, 2H) 7.12 (s, 2H) 7.28-7.32 (m, 6H) 7.35-7.39 (m, 4H). $^{13}$C NMR (500 MHz, CDCl$_3$) δ 46.4, 47.0, 119.4, 126.8, 127.7, 128.4, 137.9, 160.2, 162.8, 173.0. HRMS (ESI$^+$) m/z calcd for $C_{24}H_{17}N_4Cl_4^+$ 501.0207. found 501.0200.

trans-2,4-Dimethoxy-6-styrylpyrimidine 12.

Dissolved 0.500 g (1.99 mmol) of trans-2,4-dichloro-6-styrylpyrimidine 1 in 10 mL of 25%, by weight, NaOMe/MeOH. The resulting solution was heated at reflux for 12 h. After being cooled to room temperature, the reaction was extracted from water three times with Et$_2$O. The combined organic layers were washed with saturated NaCl solution and dried over anhydrous MgSO$_4$, and solvent removed with a rotary evaporator. The crude solid was recrystallized from EtOAc/hexanes to give 0.174 g (0.72 mmol, 36% yield) of pure 12. $^1$H NMR (500 MHz, CDCl$_3$) δ 4.00 (s, 3H), 4.07 (s, 3H), 6.35 (s, 1H), 6.95 (d, J=15.63 Hz, 1H), 7.34 (t, J=7.57 Hz, 1H), 7.39 (t, J=7.32 Hz, 2H), 7.59 (d, J=7.32 Hz, 2H), 7.87 (d, J=15.87 Hz, 1H). $^{13}$C NMR (500 MHz, CDCl$_3$) δ 53.7, 54.6, 99.5, 125.5, 127.4, 128.7, 128.9, 135.8, 136.1, 164.0, 165.1, 172.3. HRMS (ESI$^+$) m/z calcd for $C_{14}H_{15}N_2O_2^+$ 243.1134. found 243.1127. mp 47-48° C. (recryst. from EtOAc/hexanes).

trans-4-Styrylpyrimidine 13.

Samples of 0.400 g (3.5 mmol) 4-chloropyrimidine, 0.516 g (3.5 mmol) trans-2-phenylvinylboronic acid, 0.074 g (0.105 mmol) Pd(Cl$_2$)(PPh$_3$)$_2$, and 2.23 g (10.5 mmol) K$_3$PO$_4$ were combined in 26 mL THF. To this heterogeneous mixture, 3.24 mL of H$_2$O were added. The resulting solution was heated at reflux overnight. The reaction was allowed to cool to room temperature, and approximately 50 mL of water were added. The resulting biphasic mixture was extracted three times with ether. The combined organic layers were washed with brine, dried over anhydrous MgSO$_4$, and the solvent removed with a rotary evaporator. The product purified by column chromatography (25% EtOAc in hexanes) to provide pure 13 (0.442 g, 70% yield). $^1$H NMR (500 MHz, CDCl$_3$) δ 7.02 (d, J=15.87 Hz, 1H), 7.26 (d, J=5.15 Hz, 1H), 7.30-7.41 (m, 3H), 7.56 (d, J=7.07 Hz, 2H), 7.86 (d, J=15.86 Hz, 1H), 8.63 (d, J=5.15 Hz, 1H), 9.15 (s, 1H). $^{13}$C NMR (500 MHz, CDCl$_3$) δ 118.4, 125.5, 127.6, 128.7, 129.3, 135.5, 137.4, 157.2, 158.8, 162.1. HRMS (ESI$^+$) m/z calcd for $C_{12}H_{11}N_2^+$ 183.0922. found 183.0919. mp 70-71° C. (recryst. from EtOAc/hexanes).

trans-2,4-Dichloro-6-styrylpyridine 14.

Samples of 0.500 g (2.74 mmol) 2,4,6-trichloropyridine, 0.487 g (3.29 mmol) trans-2-phenylvinylboronic acid, 0.057 g (0.082 mmol) Pd(Cl$_2$)(PPh$_3$)$_2$, and 1.17 g (5.48 mmol) K$_3$PO$_4$ were combined in 20 mL THF. To this heterogeneous mixture, 2.5 mL of H$_2$O were added. The resulting solution was heated at reflux for 20 h. After being cooled to room temperature, the resulting residue was extracted from water with three times with ether. The combined organic layers were washed with brine, dried over anhydrous MgSO$_4$, and the solvent removed with a rotary evaporator. The product was purified by column chromatography (5-10% EtOAc in hexanes) to provide pure 14 (0.323 g, 47% yield). $^1$H NMR (500 MHz, CDCl$_3$) δ 7.01 (d, J=16.08 Hz, 1H), 7.19 (s, 1H), 7.25 (s, 1H), 7.34 (t, J=7.07 Hz, 1H), 7.40 (t, J=7.50 Hz, 2H), 7.57 (d, J=7.29 Hz, 2H), 7.70 (d, J=15.87 Hz, 1H). $^{13}$C NMR (500 MHz, CDCl$_3$) δ 120.6, 121.9, 125.1, 127.4, 128.8, 129.0, 135.6, 135.7, 145.8, 151.7, 157.1. HRMS (ESI$^+$) m/z calcd for $C_{13}H_{10}NCl_2^+$ 250.0190. found 250.0188. mp 36-38° C. (recryst. from EtOAc/hexanes).

trans-2,4-Dichloro-6-(2-(pyridin-2-yl)vinyl)pyrimidine 15.

A sample of 27 mg of NaH (0.67 mmol, 60% dispersion in mineral oil) was added to 4 mL THF. To this suspension, 2,4-dichloro-6-methylpyrimide (0.100 g, 0.61 mmol) dissolved in 2 mL THF was added. The resulting cloudy yellow solution was stirred for 10 minutes at room temperature, after which 140 μL (1.23 mmol) of 2-pyridylcarboxaldehyde was added dropwise. Upon complete addition of the aldehyde, the reaction mixture turned from a cloudy yellow to a clear orange. The reaction was stirred at room temperature for 30 minutes, quenched with H$_2$O, and extracted three times with ether. The combined organic layers were washed with saturated NaCl solution, and dried over anhydrous magnesium sulfate. After removal of solvent by rotary evaporator, the resulting residue was purified by MPLC on a silica gel column using a 0-50%, 1% TEA in EtOAc/hexanes gradient elution to provide 46 mg (0.18 mmol, 30% yield) of 15. $^1$H NMR (500 MHz, CDCl$_3$) δ 7.26 (s, 1H), 7.29 (ddd, J=7.56, 4.77, 1.18 Hz, 1H), 7.46 (d, J=7.72 Hz, 1H), 7.56 (d, J=15.44 Hz, 1H), 7.75 (td, J=7.66, 1.82 Hz, 1H), 8.00 (d, J=15.22 Hz, 1H), 8.67 (d, J=3.65 Hz, 1H). $^{13}$C NMR (500 MHz, CDCl$_3$) δ 118.2, 124.2, 125.1, 126.7, 137.0, 139.0, 150.2, 152.9, 160.6, 163.0, 165.9. HRMS (ESI$^+$) m/z calcd for $C_{11}H_8N_3Cl_2^+$ 252.0095. found 252.0095. mp 153-154° C. (recryst. from EtOAc/hexanes).

trans-2,4-Dichloro-6-(4-methoxystyryl)pyrimidine 16.

A sample of 108 mg of NaH (2.70 mmol, 60% dispersion in mineral oil) was added to 8 mL THF. To this suspension, 2,4-dichloro-6-methylpyrimide (0.200 g, 1.22 mmol) dissolved in 4 mL THF was added. The resulting cloudy yellow solution was stirred for 5 minutes at room temperature, after which 150 μL (1.23 mmol) 4-methoxybenzaldehyde was added dropwise. The reaction stirred at room temperature under a constant weak stream of nitrogen with the N$_2$ efflux passing directly from the flask through a needle fitted with a Drierite drying tube. Under these conditions, the solvent was allowed to slowly evaporate, leaving behind a reddish orange solid. The residue was dissolved in CH$_2$Cl$_2$ and extracted from water three times. The combined organic layers were washed with saturated NaCl solution, and dried over anhydrous magnesium sulfate. After removal of solvent by rotary evaporation, the resulting residue was purified by MPLC on a silica gel column using a 35%-100% CH$_2$Cl$_2$/hexanes gradient elution to provide 54 mg (0.19 mmol, 15% yield) of 16. $^1$H NMR (500 MHz, CDCl$_3$) δ 3.86 (s, 3H), 6.81 (d, J=15.65 Hz, 1H), 6.94 (d, J=8.79 Hz, 2H), 7.18 (s, 1H), 7.55 (d, J=8.79 Hz, 2H), 7.92 (d, J=15.86 Hz, 1H). $^{13}$C NMR (500 MHz, CDCl$_3$) δ 55.4, 114.5, 116.4, 120.5, 127.5, 129.8, 140.5, 160.4, 161.5, 162.3, 166.8. HRMS (ESI$^+$) m/z calcd for $C_{13}H_{11}N_2OCl_2^+$ 281.0248. found 281.0249. mp 127-128° C. (recryst. from EtOAc/hexanes).

Solid-State Irradiations/Rate Studies.

Irradiations were accomplished using a 68 W compact fluorescent light bulb (300 W incandescent equivalent, 2700 K color temperature) placed in a 0.5 m$^3$ box that was completely encased in aluminum foil. With this set-up the air-temperature in the irradiation box did not rise above 30° C., and the temperature on the water-cooled plate was a constant 23-25° C. Prior to irradiation of each sample, the bulb was allowed to warm up for at least 30 minutes. For each irradiation 45 to 50 mg of azastilbene (compounds 1, 12-16, each recrystallized from EtOAc/hexanes) was ground to a fine powder using a mortar and pestle. The powder was then spread evenly on a water-cooled borosilicate glass plate over an area approximately 9×9 cm. The sample was then covered with a borosilicate glass plate, which was firmly pressed into place to further ensure an even distribution of the solid. The samples were placed approximately 7-8 cm beneath the 68 W bulb and irradiated for times ranging from 2 to 24 h, depending on the rate of photocycloaddition. Time points were taken every 10 minutes for the first 2 hours and generally every 30 to 60 minutes thereafter. Time-point samples were obtained using a microspatula after brisk removal of the cover slide, and efforts were made to ensure that these samples were representative of a broad area of the irradiated solid. The crude irradiation samples were dissolved in $CDCl_3$, and analyzed for relative integration of proton signals using a 500 MHz narrow-bore spectrometer.

Solution-State Irradiations/Rate Studies.

The same irradiation set-up used for the solid-state rate studies was used for the solution-state rate studies with the exception that the samples were not water-cooled. For each sample, 40 mM solutions of each azastilbene (compounds 2, 12-16) in $CDCl_3$ were placed in sealed borosilicate NMR tubes. The samples were irradiated simultaneously for 24 hours, removed from the light source, and directly analyzed by $^1H$ NMR using a 500 MHz narrow-bore spectrometer. Evaporated solvent was replaced, and the samples were irradiated for an additional 24 h. This was repeated 5 times for a total of 120 h of irradiation.

Data Analysis.

Data analysis for the solid-state reactions was accomplished using Graphpad Prism 5.0, fitted to a first order exponential decay curve. Data analysis for solution-state reactions was performed using OriginPro 8.5, with data fitted to an exponential least-squares fit curve.

Crystallography

Cyclobutane 2 was recrystallized from MeOH. The azastilbenes 1, cis-1 and 16 were recrystallized from EtOAc/hexanes.

REFERENCES

The references numbers cited in Example III correspond to the references listed at the end of this Example III.

(1) Liebermann, C.; Bergami, O. *Berichte der Deutschen Chemischen Gesellschaft* 1889, 22, 782.
(2) Marckwald, W. *Zeitschrift fuer Physikalische Chemie, Stoechiometrie und Verwandtschaftslehre* 1899, 30, 140.
(3) Ciamician, G.; Silber, P. *Ber Dtsch. chem. Ges.* 1901, 34, 2040.
(4) Senier, A.; Shepheard, F. G. *Journal of the Chemical Society, Transactions* 1909, 95, 1943.
(5) Kohlschutter, V.; Haenni, P. *Zeitschrift fuer Anorganische und Allgemeine Chemie* 1919, 105, 121.
(6) Stobbe, H.; Steinberger, F. K. *Berichte der Deutschen Chemischen Gesellschaft [Abteilung]B: Abhandlungen* 1922, 55B, 2225.
(7) Bernstein, H. I.; Quimby, W. C. *Journal of the American Chemical Society* 1943, 65, 1845.
(8) Schmidt, G. M. J. *Pure and Applied Chemistry* 1971, 27, 647.
(9) Cohen, M. D.; Schmidt, G. M. *J. Journal of the Chemical Society* 1964, 1996.
(10) Cohen, M. D.; Schmidt, G. M. J.; Sonntag, F. I. *Journal of the Chemical Society* 1964, 2000.
(11) Schmidt, G. M. *J. Journal of the Chemical Society* 1964, 2014.
(12) Cohen, M. D. *Angewandte Chemie* 1975, 87, 439.
(13) Gnanaguru, K.; Ramasubbu, N.; Venkatesan, K.; Ramamurthy, V. *Journal of Organic Chemistry* 1985, 50, 2337.
(14) Bhadbhade, M. M.; Murthy, G. S.; Venkatesan, K.; Ramamurthy, V. *Chemical Physics Letters* 1984, 109, 259.
(15) Murthy, G. S.; Arjunan, P.; Venkatesan, K.; Ramamurthy, V. *Tetrahedron* 1987, 43, 1225.
(16) Ramdas, S.; Jones, W.; Thomas, J. M.; Desvergne, J. P. *Chemical Physics Letters* 1978, 57, 468.
(17) Natarajan, A.; Ramamurthy, V. *Chemistry of Cyclobutanes* 2005, 2, 807.
(18) Natarajan, A.; Bhogala, B. R. *Supramolecular Photochemistry* 2011, 175.
(19) Ito, Y.; Kajita, T.; Kunimoto, K.; Matsuura, T. *Journal of Organic Chemistry* 1989, 54, 587.
(20) Syamala, M. S.; Ramamurthy, V. *Journal of Organic Chemistry* 1986, 51, 3712.
(21) Papagni, A.; Del Buttero, P.; Bertarelli, C.; Miozzo, L.; Moret, M.; Pryce, M. T.; Rizzato, S. *New Journal of Chemistry* 2010, 34, 2612.
(22) Coates, G. W.; Dunn, A. R.; Henling, L. M.; Ziller, J. W.; Lobkovsky, E. B.; Grubbs, R. H. *Journal of the American Chemical Society* 1998, 120, 3641.
(23) Stegemeyer, H. *Chimia* 1965, 19, 536.
(24) Ulrich, H.; Rao, D. V.; Stuber, F. A.; Sayigh, A. A. R. *Journal of Organic Chemistry* 1970, 35, 1121.
(25) Williams, J. L. R.; Webster, S. K.; Van Allan, J. A. *Journal of Organic Chemistry* 1961, 26, 4893.
(26) Williams, J. L. R. *Journal of Organic Chemistry* 1960, 25, 1839.
(27) Williams, J. L. R.; Carlson, J. M.; Reynolds, G. A.; Adel, R. E. *Journal of Organic Chemistry* 1963, 28, 1317.
(28) Homer, M.; Huenig, S. *Liebigs Annalen der Chemie* 1982, 1183.
(29) Yamada, S.; Uematsu, N.; Yamashita, K. *Journal of the American Chemical Society* 2007, 129, 12100.
(30) Vansant, J.; Toppet, S.; Smets, G.; Declercq, J. P.; Germain, G.; Van Meerssche, M. *Journal of Organic Chemistry* 1980, 45, 1565.
(31) Mondal, B.; Captain, B.; Ramamurthy, V. *Photochemical & Photobiological Sciences* 2011, 10, 891.
(32) Chung, C.; Nakamura, F.; Hashimoto, Y.; Hasegawa, M. *Chemistry Letters* 1991, 779.
(33) Kaupp, G.; Frey, H.; Behmann, G. *Chemische Berichte* 1988, 121, 2135.
(34) Kato, T.; Katagiri, N.; Takahashi, T.; Katagiri, Y. *Journal of Heterocyclic Chemistry* 1979, 16, 1575.
(35) Hasegawa, M.; Endo, Y.; Aoyama, M.; Saigo, K. *Bulletin of the Chemical Society of Japan* 1989, 62, 1556.
(36) *Pure and Applied Chemistry* 1976, 45, 11.
(37) Whitten, D. G.; Lee, Y. *J. J. Amer Chem. Soc.* 1972, 94, 9142.
(38) Dudek, R. C.; Anderson, N. T.; Donnelly, J. M. *Chemical Educator* 2011, 16, 76.

(39) Vaske, Y. S. M.; Mahoney, M. E.; Konopelski, J. P.; Rogow, D. L.; McDonald, W. J. *Journal of the American Chemical Society* 2010, 132, 11379.

(40) Wheeler, S. E.; Houk, K. N. *Journal of the American Chemical Society* 2008, 130, 10854.

(41) Wheeler, S. E.; Houk, K. N. *Journal of Chemical Theory and Computation* 2009, 5, 2301.

(42) Frisch, M. J. T., G. W.; Schlegel, H. B.; Scuseria, G. E.; Robb, M. A.; Cheeseman, J. R.; Scalmani, G.; Barone, V.; Mennucci, B.; Petersson, G. A.; Nakatsuji, H.; Caricato, M.; Li, X.; Hratchian, H. P.; Izmaylov, A. F.; Bloino, J.; Zheng, G.; Sonnenberg, J. L.; Hada, M.; Ehara, M.; Toyota, K.; Fukuda, R.; Hasegawa, J.; Ishida, M.; Nakajima, T.; Honda, Y.; Kitao, O.; Nakai, H.; Vreven, T.; Montgomery, Jr., J. A.; Peralta, J. E.; Ogliaro, F.; Bearpark, M.; Heyd, J. J.; Brothers, E.; Kudin, K. N.; Staroverov, V. N.; Kobayashi, R.; Normand, J.; Raghavachari, K.; Rendell, A.; Burant, J. C.; Iyengar, S. S.; Tomasi, J.; Cossi, M.; Rega, N.; Millam, N. J.; Klene, M.; Knox, J. E.; Cross, J. B.; Bakken, V.; Adamo, C.; Jaramillo, J.; Gomperts, R.; Stratmann, R. E.; Yazyev, O.; Austin, A. J.; Cammi, R.; Pomelli, C.; Ochterski, J. W.; Martin, R. L.; Morokuma, K.; Zakrzewski, V. G.; Voth, G. A.; Salvador, P.; Dannenberg, J. J.; Dapprich, S.; Daniels, A. D.; Farkas, Ö.; Foresman, J. B.; Ortiz, J. V.; Cioslowski, J.; Fox, D. J. *Gaussian, Inc., Wallingford Conn.* 2009.

(43) Zhao, Y.; Truhlar, D. G. *Accounts of Chemical Research* 2008, 41, 157.

(44) Grimme, S. *Journal of Chemical Physics* 2003, 118, 9095.

(45) Loader, C. E.; Timmons, C. J. *Journal of the Chemical Society [Section]C: Organic* 1967, 1343.

(46) Hazai, L.; Hornyak, G. *ACH—Models in Chemistry* 1998, 135, 493.

(47) Perkampus, H. H.; Bluhm, T. *Tetrahedron* 1972, 28, 2099.

(48) Fehn, H.; Perkampus, H. H. *Tetrahedron* 1978, 34, 1971.

(49) Leiserowitz, L.; Schmidt, G. M. J. *Acta Crystallographica* 1965, 18, 1058.

(50) Steiner, T. *NATO Science Series, Series E: Applied Sciences* 1999, 360, 185.

(51) Desiraju, G. R. *Accounts of Chemical Research* 2002, 35, 565.

(52) Desiraju, G. R. *Journal of the American Chemical Society* 2013, 135, 9952.

(53) Nagarathinam, M.; Peedikakkal, A. M. P.; Vittal, J. J. *Chemical Communications* (Cambridge, United Kingdom) 2008, 5277.

(54) Biradha, K.; Santra, R. *Chemical Society Reviews* 2013, 42, 950.

(55) Elacqua, E.; Laird, R. C.; MacGillivray, L. R. *Supramolecular Chemistry: From Molecules to Nanomaterials* 2012, 6, 3153.

(56) Feldman, K. S.; Campbell, R. F. *Journal of Organic Chemistry* 1995, 60, 1924.

(57) Marras, G.; Metrangolo, P.; Meyer, F.; Pilati, T.; Resnati, G.; Vij, A. *New Journal of Chemistry* 2006, 30, 1397.

(58) Liu, J.; Wendt, N. L.; Boarman, K. J. *Organic Letters* 2005, 7, 1007.

(59) Bhogala, B. R.; Captain, B.; Parthasarathy, A.; Ramamurthy, V. *Journal of the American Chemical Society* 2010, 132, 13434.

(60) Song, Q.-H.; Wang, H.-B.; Li, X.-B.; Hei, X.-M.; Guo, Q.-X.; Yu, S.-Q. *Journal of Photochemistry and Photobiology, A: Chemistry* 2006, 183, 198.

(61) Pangborn, A. B.; Giardello, M. A.; Grubbs, R. H.; Rosen, R. K.; Timmers, F. J. *Organometallics* 1996, 15, 1518.

(62) Still, W. C.; Kahn, M.; Mitra, A. *Journal of Organic Chemistry* 1978, 43, 2923.

(63) Tan, J.; Chang, J.; Deng, M. *Synthetic Communications* 2004, 34, 3773.

Example IV. Cyclobutane-Core Androgen Receptor Antagonists: Mutant-Selective Inhibitors for Treatment of Hormone-Refractory Prostate Cancer The references numbers cited in Example IV correspond to the references listed at the end of this Example IV. The Scheme, Table, and Compound Numbers recited in this Example IV are with respect to this Example IV. Note: In the following Example IV for the Figures and Tables, compound 1 is the same as CB22 of Example VI. Other compound number substitutions are as outlined in the tables below.

The androgen receptor (AR), a member of the nuclear hormone receptor superfamily of small molecule-modulated transcription factors, plays an integral role in male sexual development. While deficiencies in AR signaling leads to male infertility and feminization, excessive AR activity can drive benign prostatic hyperplasia and prostate cancer (1). Both of these diseases respond to endocrine-based treatments that suppress AR activity by administration of AR antagonists or by 'chemical castration' that decreases gonadal production of testosterone. While treatment with traditional AR antagonists initially suppresses prostate tumor growth, with time (a few months to years) cellular modifications, including AR mutations, up-regulation of AR and coactivators, changes in the post-translational modification of AR and accessory proteins, as well as increased androgen production by the suprarenal glands and in the tumors themselves, result in an endocrine-treatment refractory state in which cancer progression occurs despite the presence of an antagonist (2).

Bicalutamide, flutamide, nilutamide, and cyproterone acetate are the four traditional antiandrogens in clinical use for the treatment of prostate cancer (3), and while they all show some benefit when used either alone and/or in combination with castration, each has major side effects, including gynecomastia, loss of libido, decreased bone mineral density and muscle mass, and hot flashes. Additionally, their efficacy is only of limited duration, after which the tumors cease to respond (4, 5). More recently, the new, higher affinity antiandrogen enzalutamide (previously MDV3100) has shown considerable promise in phase I-III clinical trials and was recently FDA approved for treatment of advanced-stage prostate cancer (6-8). Nonetheless, resistance to enzalutamide has already been reported (9), further stressing the need for continued efforts to develop new, more effective agents for treating castration-resistant prostate cancer.

One intriguing therapeutic approach would be to selectively target mutant forms of AR known to arise in prostate tumors exposed to hormone therapy, such as the LNCaP mutation. This T877A point mutation in the AR ligand binding domain (LBD), which is estimated to appear in as many as 30% of prostate cancer patients previously treated with flutamide (10), alters the ligand response of AR, so that nominal antagonists, such as flutamide, behave as agonists. Ideally, if a mutant-specific antiandrogen could be developed, it would block signaling through the mutant AR, thereby affording effective anticancer therapy, but would only minimally disrupt normal androgen action through wild-type AR present in non-cancerous tissues. Thus, the side effects associated with conventional hormone therapy (impaired sexual activity, muscle wasting, etc.) might be avoided in this important subset of prostate cancer patients.

As with other nuclear receptors, androgen action through AR involves ligand binding to the LBD, which causes a characteristic conformational change in this domain that is accompanied by release of AR from heat shock proteins, dimerization, movement to the nucleus, binding to specific androgen response elements, and recruitment of coregulator proteins needed to form a transcriptionally active complex (11-18). The last of these events is thought to involve interaction of the LDB with the N-terminal domain (NTD) of AR. In this paper, we describe the discovery and exploration of a tetra-aryl cyclobutane scaffold as the basis for developing mutant-selective antiandrogens. These cyclobutane compounds act as competitive inhibitors of AR agonism and inhibit androgen-mediated gene transcription in multiple models of hormone-refractory disease, including LNCaP and W741C mutant ARs and wild type AR overexpression. The cyclobutanes cause a conformational change in AR similar to that adopted by apo-receptor, and effectively inhibit both DNA binding and LBD/NTD interaction. Notably, the most potent cyclobutanes have a 10 to 100-fold increased potency for T877A (LNCaP), W741C, and F876L AR over wild type receptor, suggesting the possibility for selective targeting of mutant AR signaling that is associated with previously-treated hormone-refractory prostate cancer.

Library Synthesis

As part of a major effort to identify modulators of nuclear receptors having distinctive activity and selectivity profiles, we screened an in-house library containing unique small-molecule scaffolds for suppression of AR-dependent endogenous gene expression. After eliminating compounds with unsatisfactory toxicity profiles, the tetra-aryl cyclobutane compound 1 emerged as a promising lead (Compound 1 and Scheme 1), providing complete suppression of AR-dependent gene transcription at concentrations well below those associated with cellular toxicity. Based upon this initial finding, an expanded library of cyclobutanes appended with a variety of substituted arenes was synthesized (Schemes 1 and 2).

Initial Lead Compound, Tetramethoxy-Substituted Tetra-Aryl Cyclobutane Compound 1

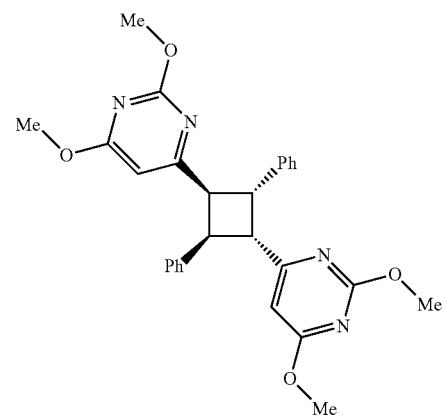 [SMILES: COc1cc([C@H]2[C@H](c3ccccc3)[C@H](c3cc(OC)nc(OC)n3)[C@H]2c2ccccc2)nc(OC)n1]

Compound 1
(also referred to as CB22 of Example VI.

Scheme 1. Synthesis of tetra-aryl cyclobutanes stemming from the symmetric dichloride 3.

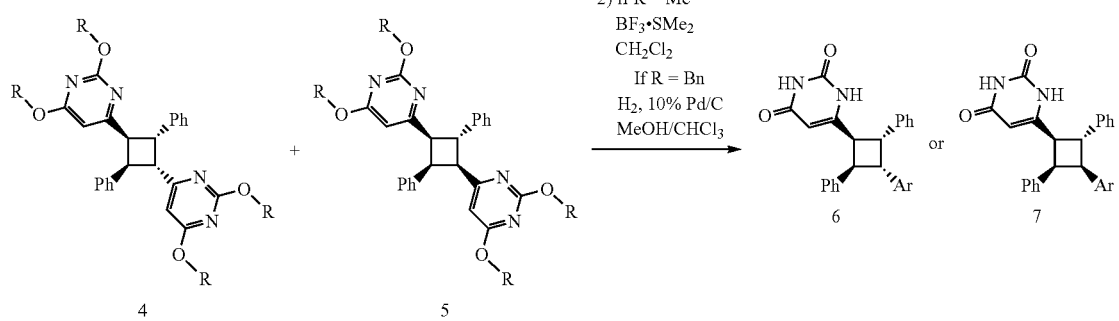

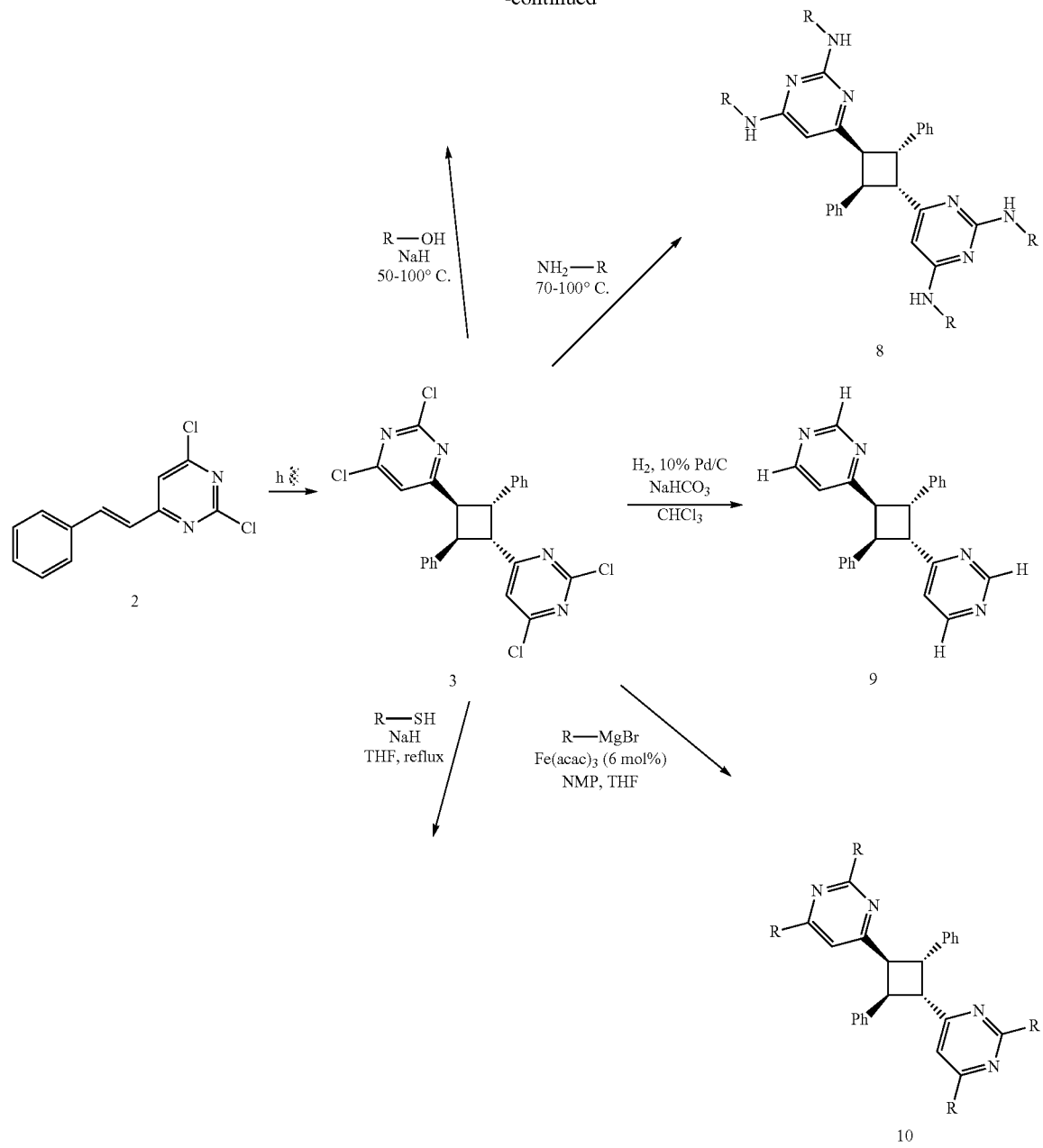

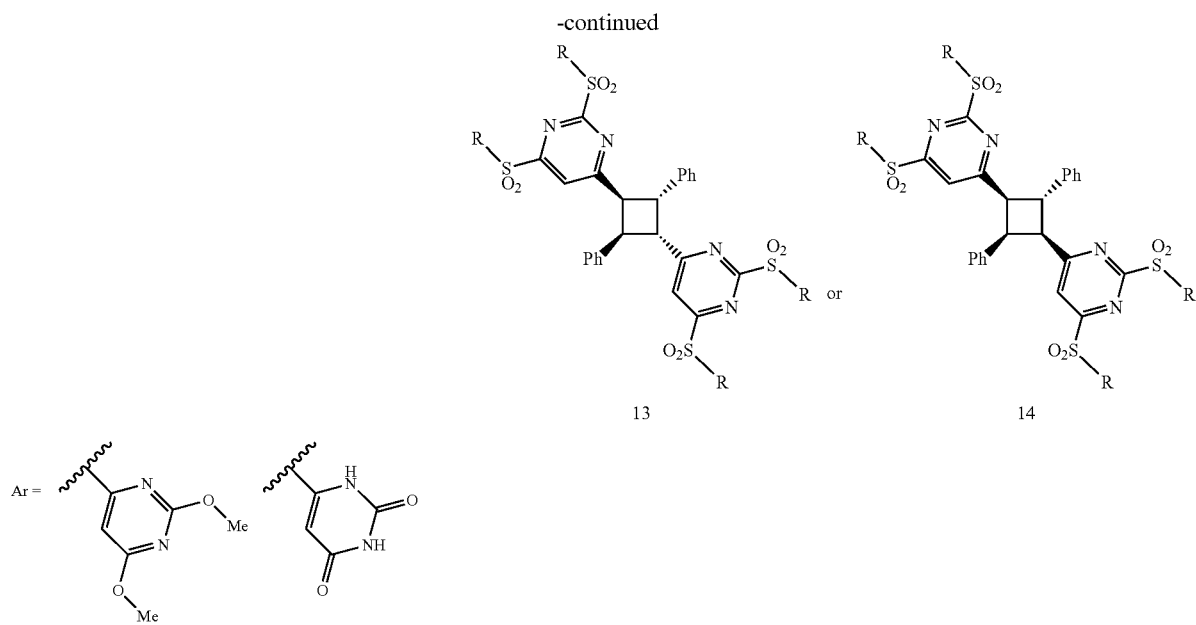
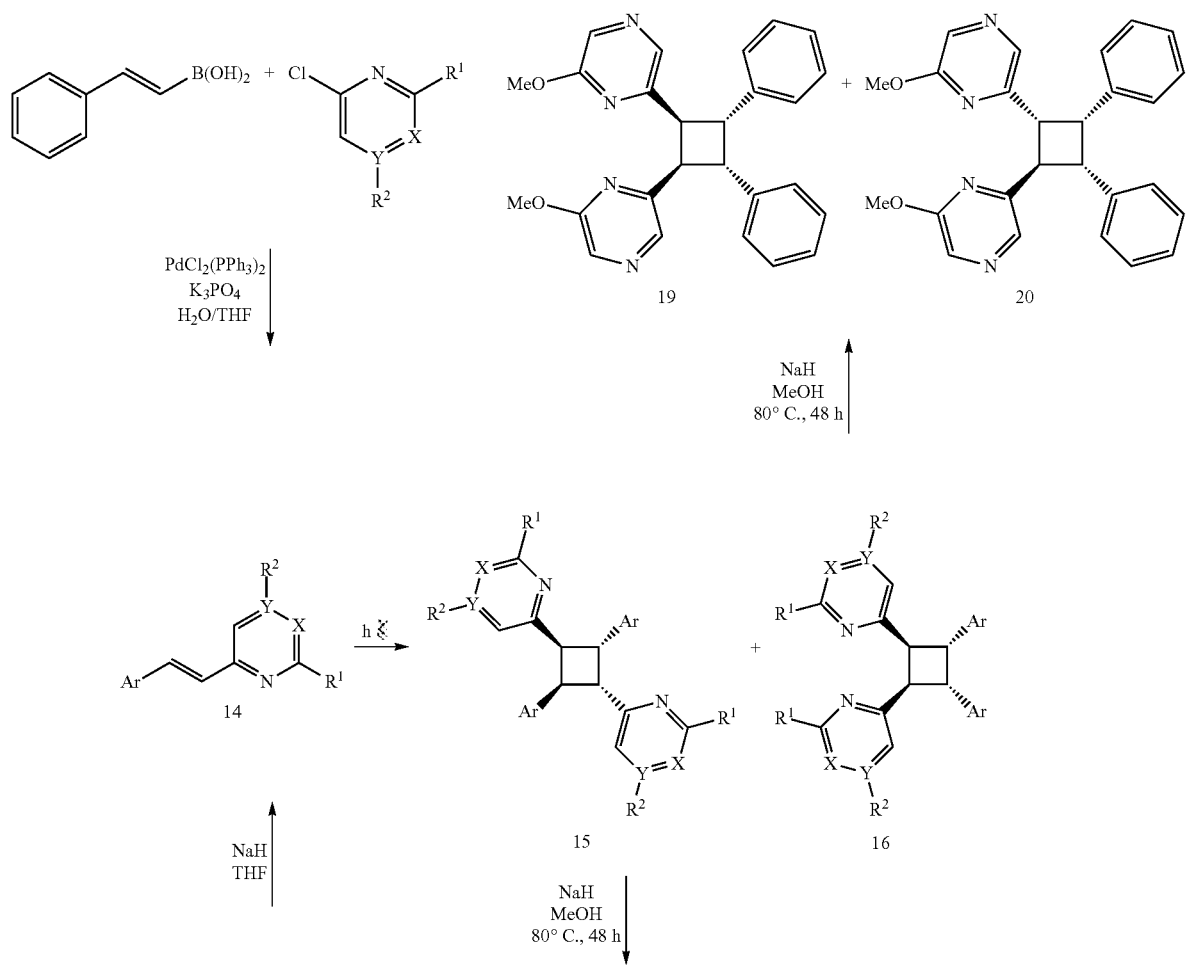

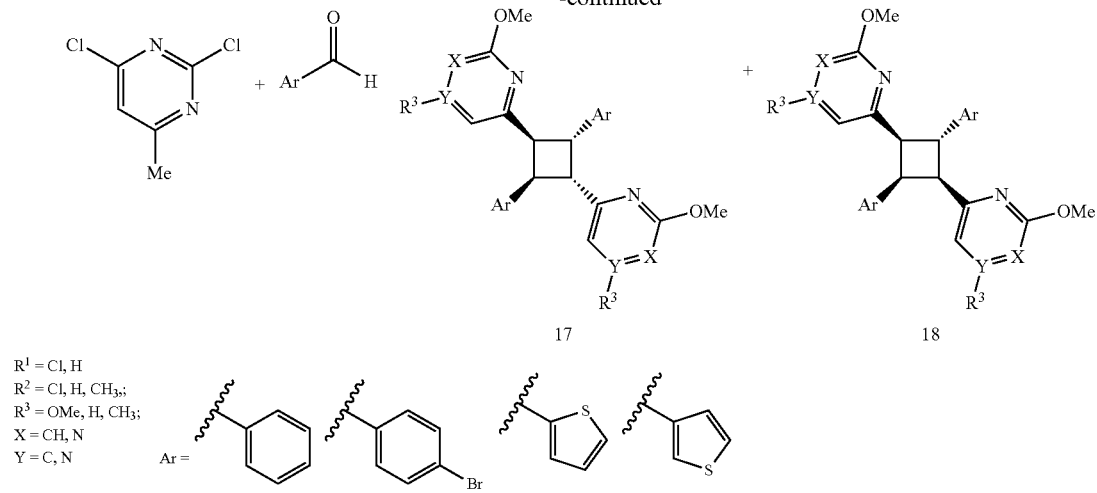

R[1] = Cl, H
R[2] = Cl, H, CH$_3$,;
R[3] = OMe, H, CH$_3$;
X = CH, N
Y = C, N

The synthesis of the lead compound 1 proceeded readily in two steps from the previously described diazastilbene 2 (19, 20), and involved a regio and stereoselective solid-state light-initiated 2+2 cycloaddition followed by S$_N$Ar addition of methoxylate anion to the aryl tetrachloride 3. In addition to the cis-trans-cis isomer 1, the strongly alkaline nature of the alkoxylation reaction produced the epimeric peralkylated epimer 5a through proton abstraction alpha to the pyrimidine ring. In a similar manner, six other alkoxy-substituted epimeric pairs were formed to explore the effects of both size and electronic properties of the alkyl substituent (compounds 4b-g and 5b-g in Scheme 1 and Table 1). Additionally, the separated methyl ethers 1 and 5a were deprotected with BF$_3$.SMe$_2$ to give the monopyrimidinediones 6b and 7b without further epimerization, and hydrogenolytic removal of the benzyl groups of 4e and 5e gave the dipyrimidinedione-substituted cyclobutanes 6a and 7a (top pathway in Scheme 1).

TABLE 4

Percent conversion and isomeric ratios of the photolysis of diarylethylenes, 1, 14a-l

| Cmpd # | Structure of monomer | % conversion, time (h) | htt:hth isomers |
|---|---|---|---|
| 2 | | 100%, 1 h[a] | 1:0 |
| 14a | | 100%, 1 h[a] | 1:0 |
| 14b | | 80%, 16 h[b] | 5:1 |

TABLE 4-continued
Percent conversion and isomeric ratios of the photolysis of diarylethylenes, 1, 14a-l
| Cmpd # | Structure of monomer | % conversion, time (h) | htt:hth isomers |
|---|---|---|---|
| 14c | 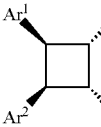 | 40%, 1 h[a] | 1:1 |
| 14d |  | 100%, 1 h[a] | 4:1 |
| 14e | 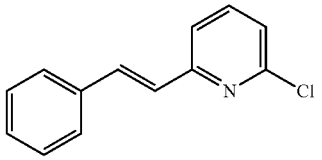 [SMILES: Clc1cccc(/C=C/c2ccccc2)n1] | 81%, 1 h[a] | 12:1 |
| 14f | 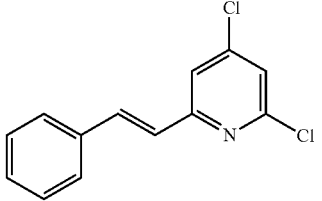 [SMILES: Clc1cc(Cl)nc(/C=C/c2ccccc2)c1] | 100%, 1 h[a] | 1:1 |
| 14g | 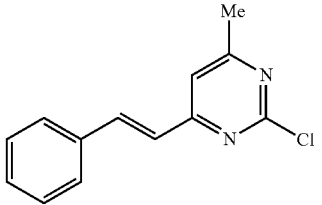 | 100%, 1 h[a] | 5:2 |
| 14h | 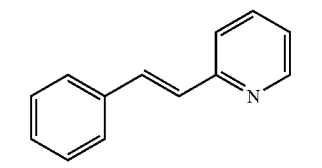 [SMILES: C(=C\c1ccccn1)/c1ccccc1] | 63%, 1 h[a] | 2:1 |

TABLE 4-continued

Percent conversion and isomeric ratios of the photolysis of diarylethylenes, 1, 14a-l

| Cmpd # | Structure of monomer | % conversion, time (h) | htt:hth isomers |
|---|---|---|---|
| 14i | | 98%, 18 h[b] | 1:2 |
| 14j | | 80%, 1 h[a] | 2:1 |
| 14k | | 98%, 18 h[b] | 1:2 |
| 14l | | 100%, 18 h[b] | 2:1 |

[a] Irradiations using a 450-W mercury vapor lamp.
[b] Irradiations using a 68-W compact fluorescent light bulb.

In addition to the alkoxy-containing derivatives described above, a focused set of compounds with proteo and N, C, and S-linked substituents stemming from the tetrachloro cyclobutane 3 was synthesized. Proceeding clockwise from compound 3, the tetra-aminocyclobutanes 8a-f were formed under simple $S_NAr$ conditions by heating in neat amine. As shown in Scheme 1 (second arrow clockwise from 3), this reaction was not sufficiently basic to cause epimerization, and only the cis-trans-cis product is obtained. The hydro-dechlorinated cyclobutane 9 was formed under reducing conditions ($H_2$, 10% Pd/C) in the presence of excess sodium bicarbonate (third arrow clockwise from 3). To form the alkylated analogues 10a and 10b, cyclobutane 3 was subjected to a Kumada-type coupling with methyl and ethyl Grignard in the presence of Fe(acac)$_3$ and N-methyl-2-pyrrolidinone in THF (21). As with the peramination, these conditions are not basic enough to cause epimerization. Finally, the tetrasulfide derivatives 11a, 11b, 12a, and 12b were synthesized from 3 through sodium methyl and ethyl thiolate addition in refluxing THF (bottom left arrow). After separation of the two epimeric tetrasulfide products, thioether oxidation with mCPBA produced the final persulfonylation compounds 13b, 14a and 14b. See Table 2 for a complete list of the final compounds described above.

TABLE 5

Dipyrimidinyl cyclobutanes and suppression of AR-responsive endogenous genes

| Cmpd # at Duke | Cmpd # in paper | Ar₁, Ar₂ | isomer | Extent of AR-target gene expression Inhibition | | |
|---|---|---|---|---|---|---|
| | | | | FKBP51 | TMPRSS2 | PSA |
| CB53 | 3 | 2,4-dichloropyrimidine | r-ctc | | | |
| CB-22 | 1 | 2,4-dimethoxypyrimidine | r-ctc | Good at 12.5 and 25 µM | Good at 12.5 µM | |
| CB-31 | 5a | | r-cct | As good as CB22 | As good as CB22 | As good as CB22 |
| CB-25 | 4b | 2,4-diethoxypyrimidine | r-ctc | None at 25 µM | None at 25 µM | |
| CB-25 | 5b | | t-cct | None at 25 µM | None at 25 µM | |
| CB-27 | 4c | 2,4-dipropoxypyrimidine | r-ctc | None at 25 µM | None at 25 µM | |
| CB-28 | 5c | | t-cct | Superagonist at 25 µM | None at 25 µM | |
| CB-29 | 4d | 2,4-diisopropoxypyrimidine | r-ctc | None at 25 µM | None at 25 µM | |
| CB-30 | 5d | | t-cct | None at 25 µM | None at 25 µM | |
| CB-32 | 4e | 2,4-bis(benzyloxy)pyrimidine | r-ctc | no inhibition | no inhibition | no inhibition |
| CB-33 | 5e | | t-cct | no inhibition | no inhibition | no inhibition |

TABLE 5-continued

Dipyrimidinyl cyclobutanes and suppression of AR-responsive endogenous genes

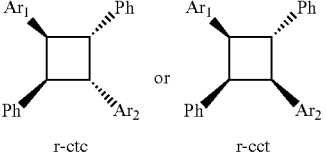

| Cmpd # at Duke | Cmpd # in paper | Ar₁, Ar₂ | isomer | Extent of AR-target gene expression Inhibition | | |
|---|---|---|---|---|---|---|
| | | | | FKBP51 | TMPRSS2 | PSA |
| CB-41 | 4f | 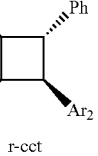 | r-ctc | no inhibition | no inhibition | no inhibition |
| CB-42 | 5f | | t-cct | no inhibition | no inhibition | no inhibition |
| CB-43 | 4g | 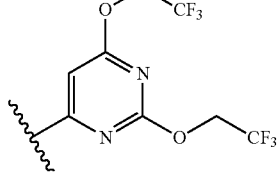 | r-ctc | no inhibition | no inhibition | no inhibition |
| CB-44 | 5g | | t-cct | no inhibition | no inhibition | no inhibition |
| CB-47 | 6a | 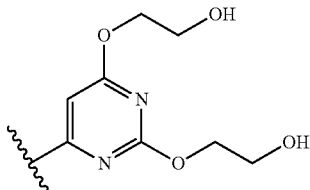 | r-ctc | | | |
| CB-48 | 7a | | t-cct | no inhibition | no inhibition | no inhibition |
| CB-45 | 6b | 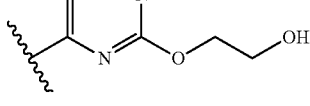 | r-ctc | Moderate | Moderate | Moderate |
| CB-46 | 7b | | t-cct | Moderate | Moderate | Moderate |
| CB-51 | 8a | 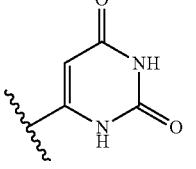 | r-ctc | | | |
| CB-8 | 8b | 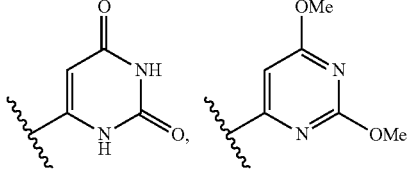 | r-ctc | good at 5 μM | good at 5 μM | |

TABLE 5-continued

Dipyrimidinyl cyclobutanes and suppression of AR-responsive endogenous genes

|  |  |  |  | Extent of AR-target gene expression Inhibition | | |
|---|---|---|---|---|---|---|
| Cmpd # at Duke | Cmpd # in paper | Ar₁, Ar₂ | isomer | FKBP51 | TMPRSS2 | PSA |
| CB-1 | 8c | HN—propyl on pyrimidine with NH—propyl | r-cct | good at 5 μM | good at 5 μM | |
| CB-11 | 8d | HN—butyl on pyrimidine with NH—butyl | r-ctc | | | |
| CB-52 | 8e | H₃C,CH₃-N on pyrimidine with N(CH₃)₂ | r-ctc | | | |
| CB-12 | 8f | HN—iPr on pyrimidine with NH—iPr | r-ctc | | | |
| CB-54 | 9 | pyrimidine (unsubstituted) | r-ctc | | | |
| CB-49 | 10a | 2,6-dimethylpyrimidine | r-ctc | As good as CB22 | As good as CB22 | As good as CB22 |

TABLE 5-continued

Dipyrimidinyl cyclobutanes and suppression of AR-responsive endogenous genes

| Cmpd # at Duke | Cmpd # in paper | Ar₁, Ar₂ | isomer | \multicolumn{3}{c}{Extent of AR-target gene expression Inhibition} |
|---|---|---|---|---|---|---|
| | | | | FKBP51 | TMPRSS2 | PSA |
| CB-50 | 10b | 2-ethyl-pyrimidin-4-yl | r-ctc | As good as CB22 | As good as CB33 | As good as zCB22 |
| CB-34 | 11a | 2-(methylthio)pyrimidin-4-yl | r-ctc | Moderate | Mild | Moderate |
| CB-35 | 12a | | r-cct | Moderate | Mild | moderate |
| CB-36 | 11b | 2-(ethylthio)pyrimidin-4-yl | r-ctc | No inhibition | No inhibition | No inhibition |
| CB-37 | 12b | | r-cct | No inhibition | No inhibition | No inhibition |
| CB-38 | 14a | 2-(methylsulfonyl)pyrimidin-4-yl | r-cct | No inhibition | No inhibition | No inhibition |
| CB-39 | 13b | 2-(ethylsulfonyl)pyrimidin-4-yl | r-ctc | No inhibition | No inhibition | No inhibition |
| CB-40 | 14b | | r-cct | No inhibition | No inhibition | No inhibition |

A number of additional diaryl alkenes were synthesized and irradiated to explore more fully the effects that the electronic nature and ring size have on biological activity of the tetraaryl cyclobutanes. Two different approaches were used to produce the azastilbene-like precursor compounds (Scheme 2): The straightforward Suzuki-Miyaura coupling of 2-phenylvinylboronic acid with a pyrimidinyl, pyridinyl, or pyryzinyl chloride (top arrow, compounds 14a-h in Scheme 2 and Table 1), and condensation of 2,4-dichloro-6-methylpyrimidine with an aryl aldehyde (bottom arrow, compounds 14i-l in Scheme 2 and Table 1). Solid-state photolysis of the trans-diaryl alkenes with a medium-pressure mercury arc lamp provided a mixture of the head-to-tail (htt) and head-to-head (hth) cis-trans-cis isomers in ratios ranging from 1:0 to 1:2, htt:hth (see Table 1 for specific product ratios). After separation of regioisomers, the htt (15a-g) and hth (16a-g) chloro-substituted cyclobutanes were subjected to methoxylation conditions as described above to form the epimeric pairs 17a-e and 18a-e, and 19 and 20 (See Table 3 for a complete list of compound structures).

Biological Activity

To examine the efficacy of the tetra-aryl cyclobutanes in hormone-refractory prostate cancer, we utilized both VCaP and LNCaP cell lines. The VCaP cell line was isolated from a prostate tumor vertebral metastasis and is distinguished by basal overexpression of wild type AR (22), whereas the LNCaP cell line contains a mutant T877A AR and is representative of conditions that arise upon long-term treatment with the traditional anti-androgen flutamide and its active metabolite hydroxyflutamide (OHF) (10). The T877A mutation creates a more promiscuous receptor in which androgen activity is bestowed on many weakly androgenic ligands, including OHF. Together, these provide excellent, although somewhat different models for hormone-refractory prostate cancer.

The selection of cyclobutane 1 as a lead compound occurred following a multi-stage set of tiered assays in which a library of small molecules was initially screened for general toxicity in both the LNCaP and VCaP cell lines, with subsequent screening of the non-toxic compounds for inhibitory activity in single (VCaP) or double-point (LNCaP) endogenous gene expression assays. Following this approach, the methoxylated tetra-aryl cyclobutane 1 stood out due to its ability to suppress AR-mediated transcription comparably to enzalutamide across both cell lines and genes. Due to this activity, coupled with its complete lack of toxicity at concentrations as high as 25 µM, compound 1 was selected for further study.

Figure 37A:
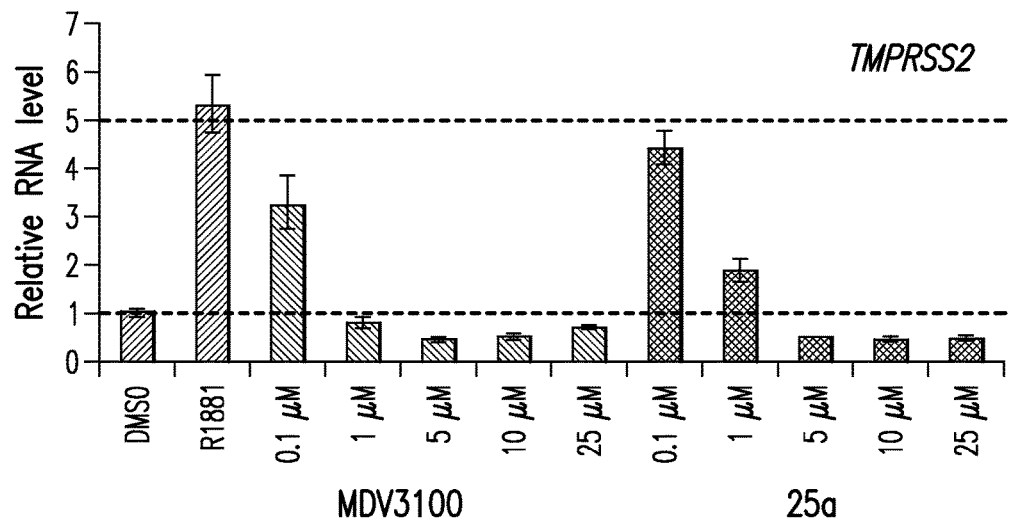
FIGS. 37A and B depict data for the dose response suppression of endogenous gene expression by compound 1 of Example IV in LNCaP cells on the presence of 0.1 nM R1881.
Figure 37B:
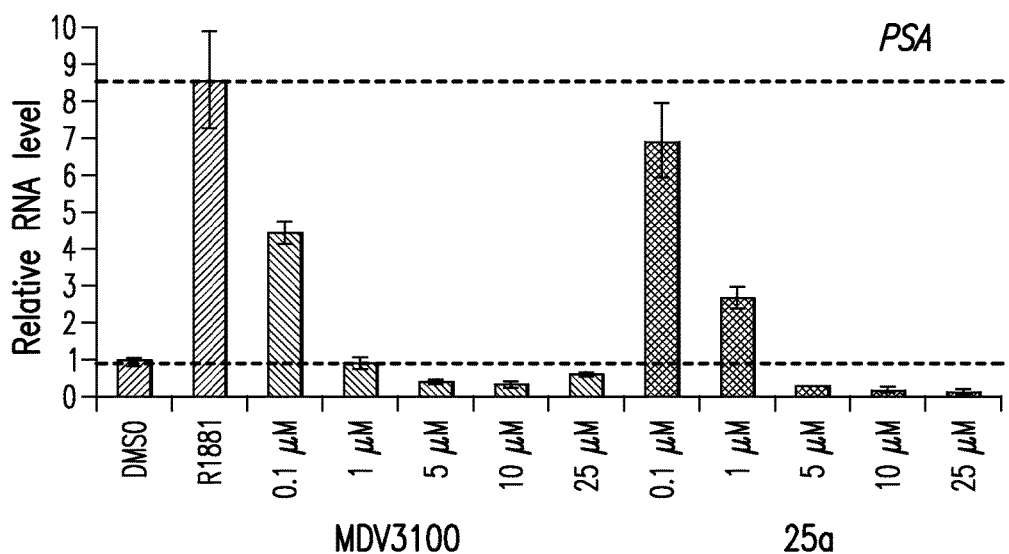
Figure 38:
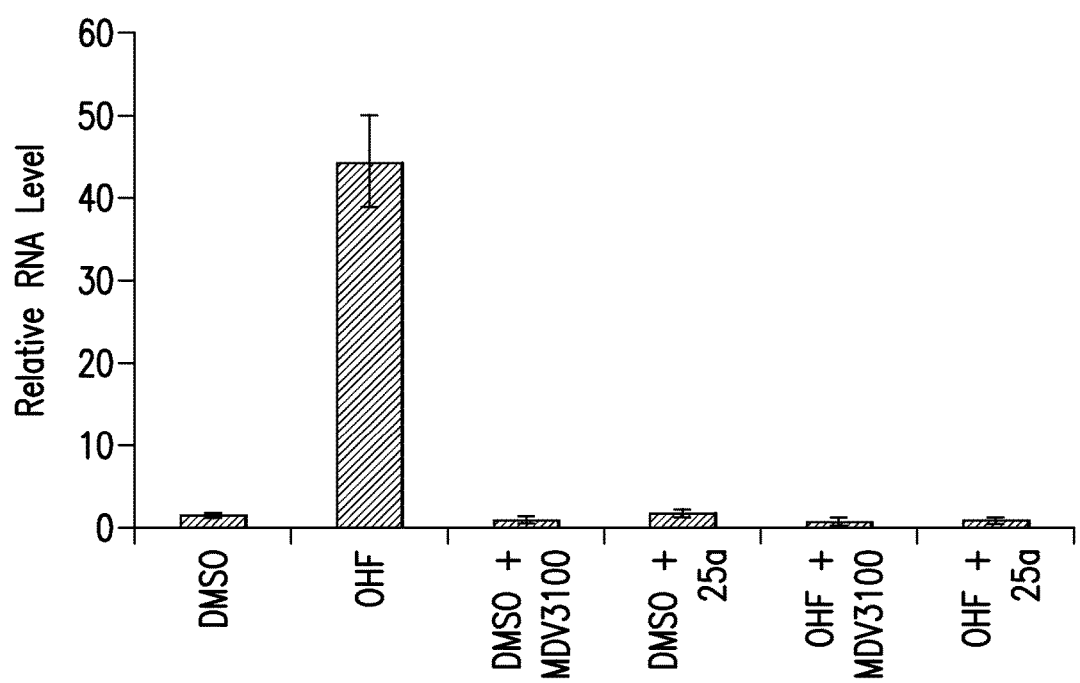
FIG. 38 depicts data for the suppression of hydroxyflutamide (OHF)-stimulated FKBP51 expression by compound 1 of Example IV in LNCaP cells.
Figure 39A:
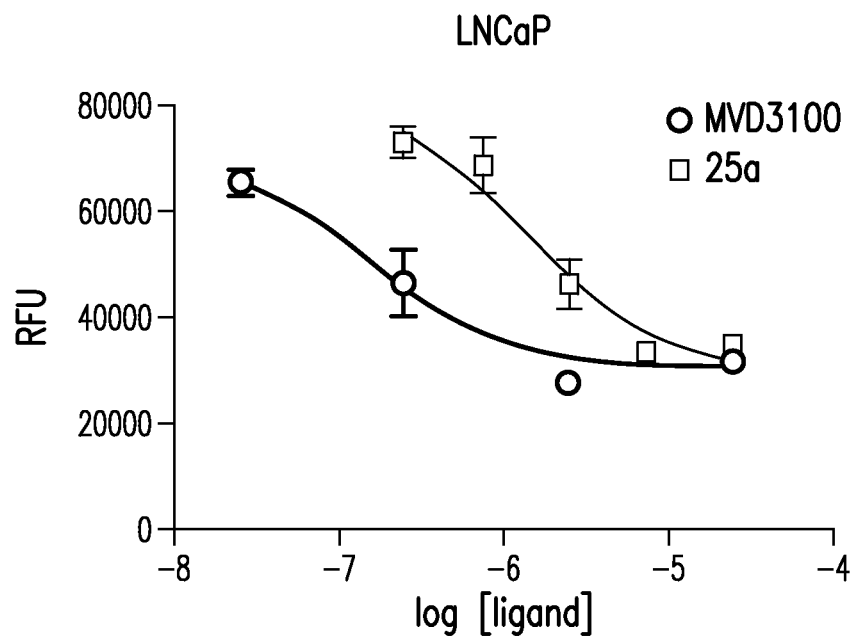
FIGS. 39A and B depict data showing the dose-dependent inhibition of LNCaP and VCaP cell proliferation by compound 1 of Example IV.
Figure 39B:
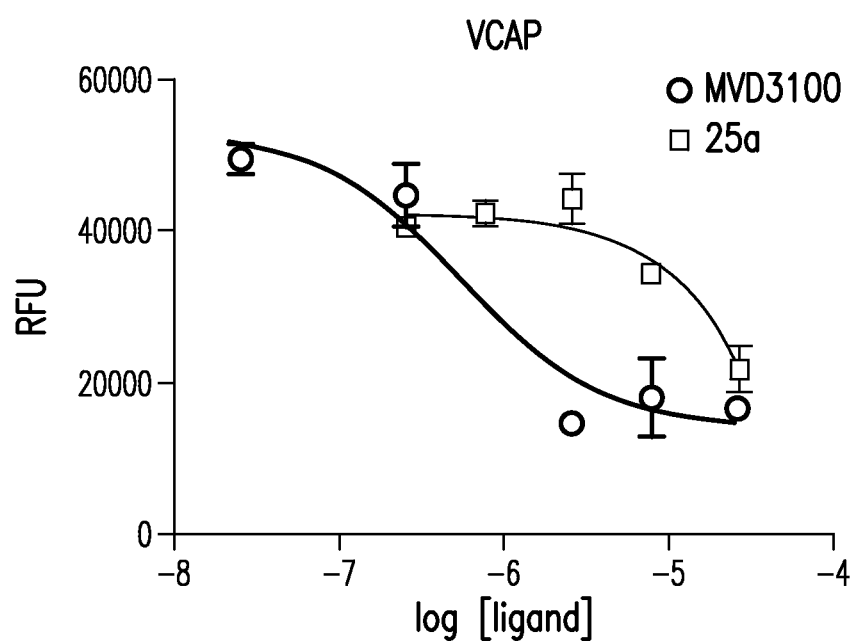

As shown in FIGS. 37A and B, compound 1 is capable of suppressing R1881-induced expression of TMPRSS2 and PSA, two AR-responsive genes known to play a role in prostate cancer. As noted above, these compounds are particularly effective at inhibiting resistant mutant ARs that arise after prior hormone treatment, as demonstrated with flutamide (T877A) or bicalutamide (W741C) resistant mutants with an $IC_{50}$ value of approximately 1 µM in LNCaP cells. The level of suppression obtained by 5 µM of 1 is comparable to that obtained by enzalutamide at its maximally effective concentration. Additionally, compound 1 is able to overcome the LNCaP expression of FKBP51 stimulated by OHF (which functions as an AR agonist in this cell type), providing further support that compound 1-induced inhibition of AR may translate to hormone-resistant tumors. FIG. 38 shows the suppression of OHF-stimulated FKBP51 expression by compound 1 in LNCaP cells. Finally, in both LNCaP and VCaP models of cell-proliferation, compound 1 is able to slow cell-growth in a dose-dependent manner (FIGS. 39A and B). In all of these assays, 1 has a potency approximately 10-fold lower than enzalutamide.

Mechanism of AR Inhibition.

Figure 40A:
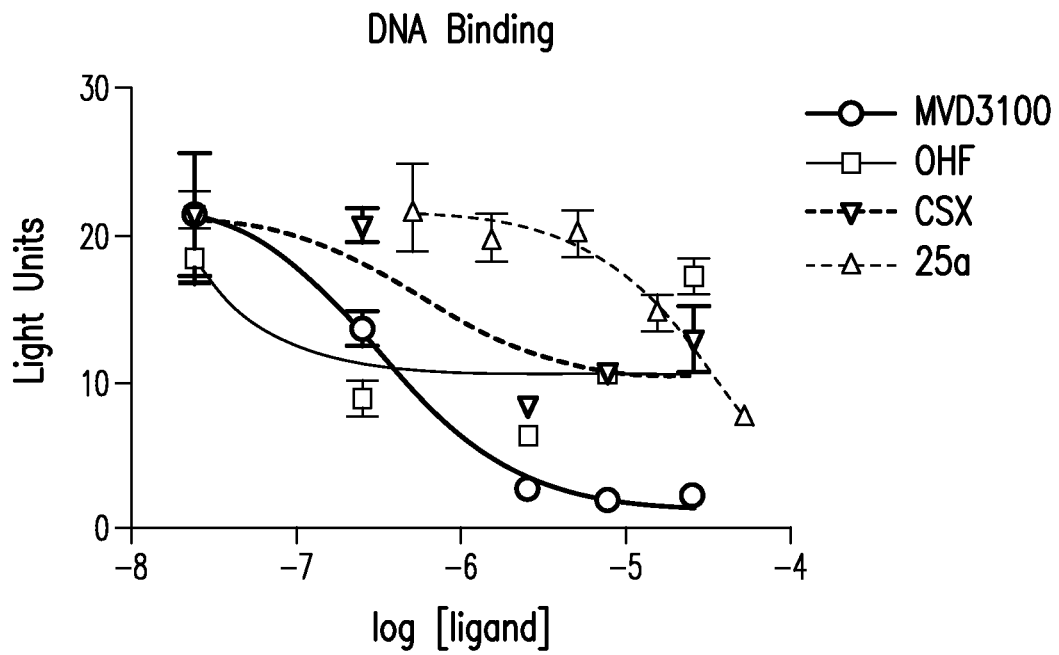
FIG. 40A depicts data from a (murine mammary tumor virus) MMTV-luciferase reporter gene assay with AR-VP16 construct demonstrating inhibition of AR/DNA binding by compound 1 of Example IV.
Figure 40B:
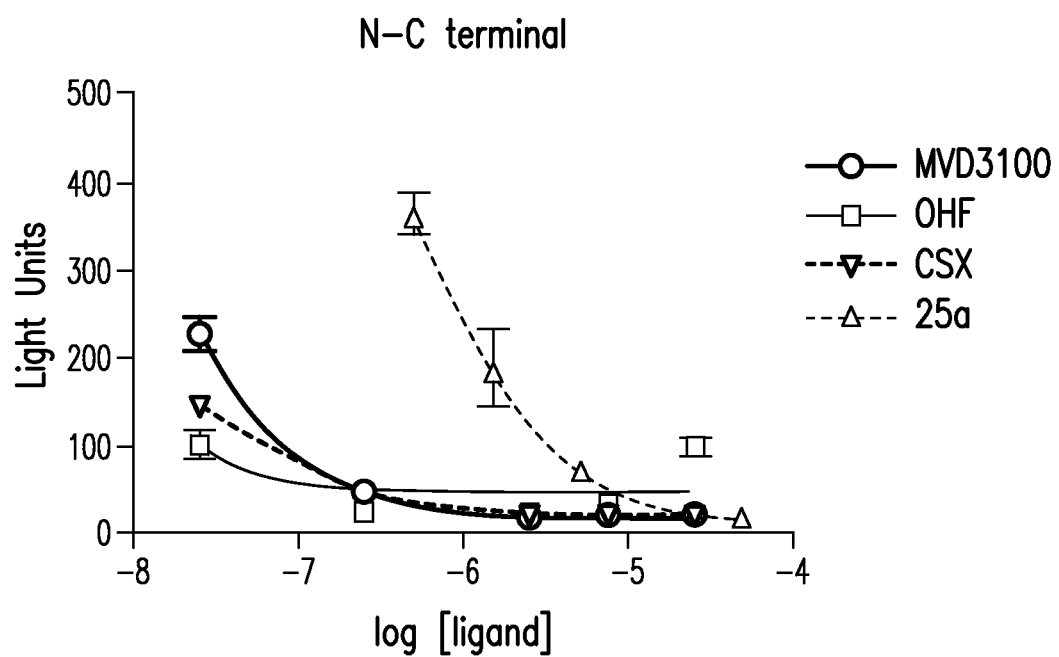
FIG. 40B depicts data from a (murine mammary tumor virus) MMTV-luciferase reporter gene assay demonstrating inhibition of the NTD/LBD interaction by compound 1 of Example IV.
Figure 40C:
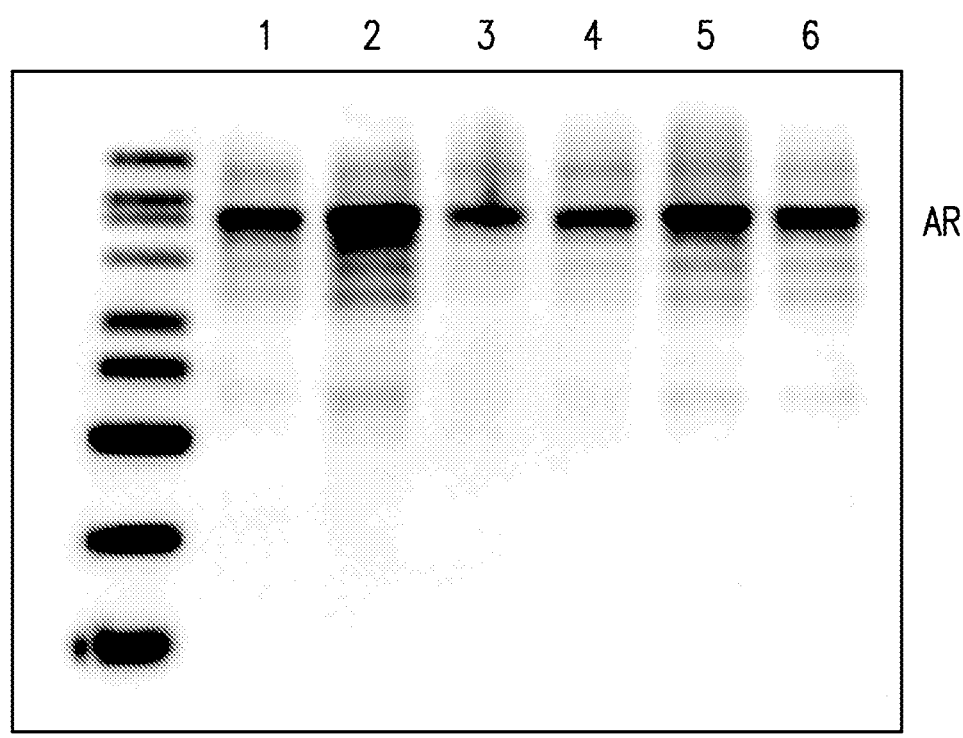
FIG. 40C depicts a Western blot analysis showing lack of androgen receptor degradation upon administration of compound 1 of Example IV.
Figure 41A:
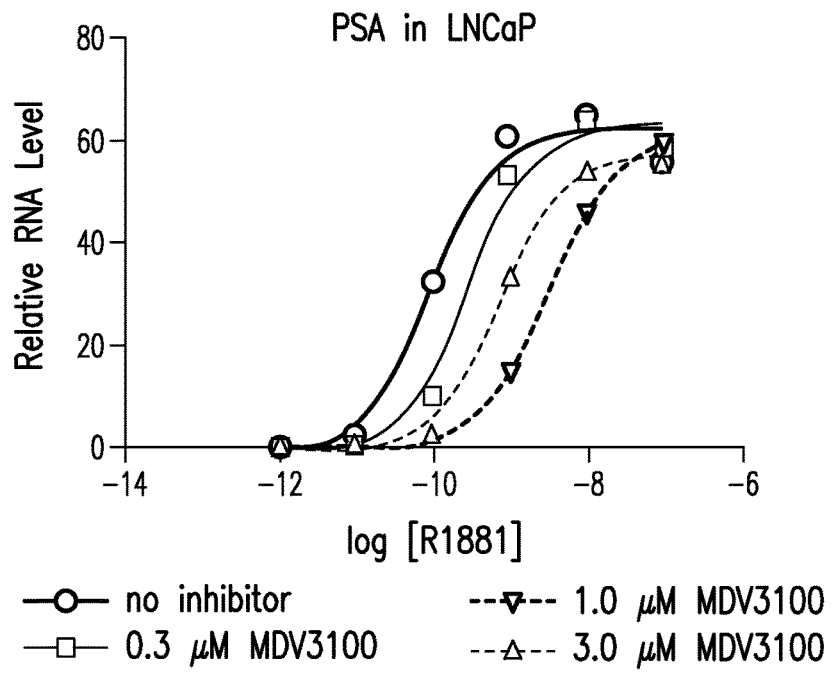
FIGS. 41A and B depict data from endogenous gene assays showing a right-shift in R1881-stimulated PSA expression caused by increasing concentrations of inhibitor [enzalutamide (MDV3100) and compound 1 of Example IV].
Figure 41B:
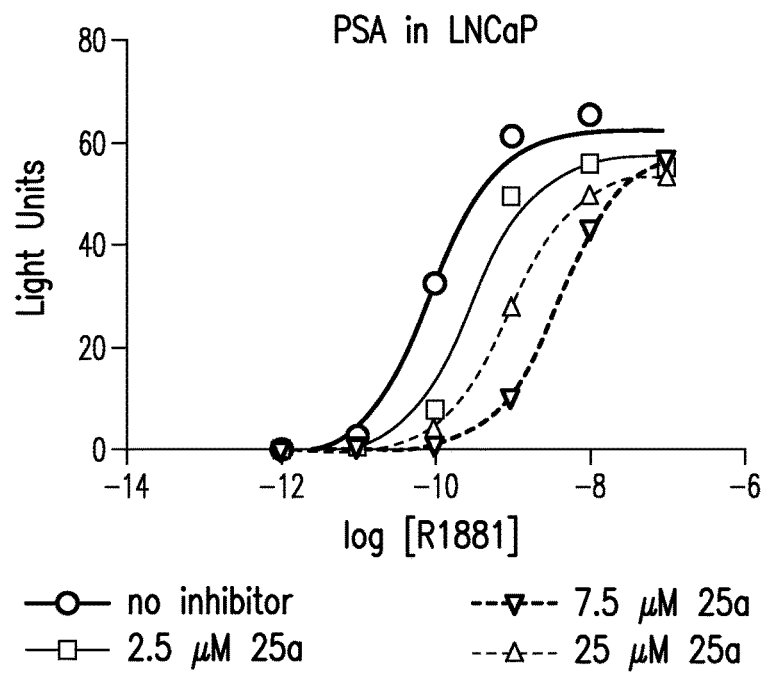

Next, we set out to gain greater insight into the mode of compound 1-associated AR inhibition. Accordingly, we analyzed the disruption of AR/DNA binding using a luciferase reporter gene assay transfected with an AR-VP16 construct that is constitutively active upon DNA binding, regardless of the ability of AR to recruit transcriptional machinery (FIG. 40A). Simultaneously, we examined CV-1 cells transfected with an AR construct that is only transcriptionally active when there is a positive interaction between the NTD and C-terminal LBD (AF-1) (FIG. 40B). Although compound 1 shows inhibitory activity in both assays, disruption of AR DNA binding requires higher concentrations than disturbance of the NTD/LBD interaction. This suggests that the primary mode of inhibition is likely through modulation of the AF-2 binding groove and not antagonism at the AR/DNA interface. Additionally, Western blot analysis of AR reveals that 1 does not influence the rate of receptor proteolysis (FIG. 40C). Furthermore, we observed direct competition of compound 1 with the AR agonist R1881 in endogenous PSA, TMPRSS2, and FKBP51 expression assays (FIG. 41A). The right shift in R1881-mediated transcription mirrors the action of the known direct competitor MDV3100 (FIG. 41B), suggesting a similar mechanism of action. Together, these results provide strong evidence for direct or allosteric competition of compound 1 for agonist ligand binding.

Conformational Profiling of Compound 1-Bound AR.

Figure 42:
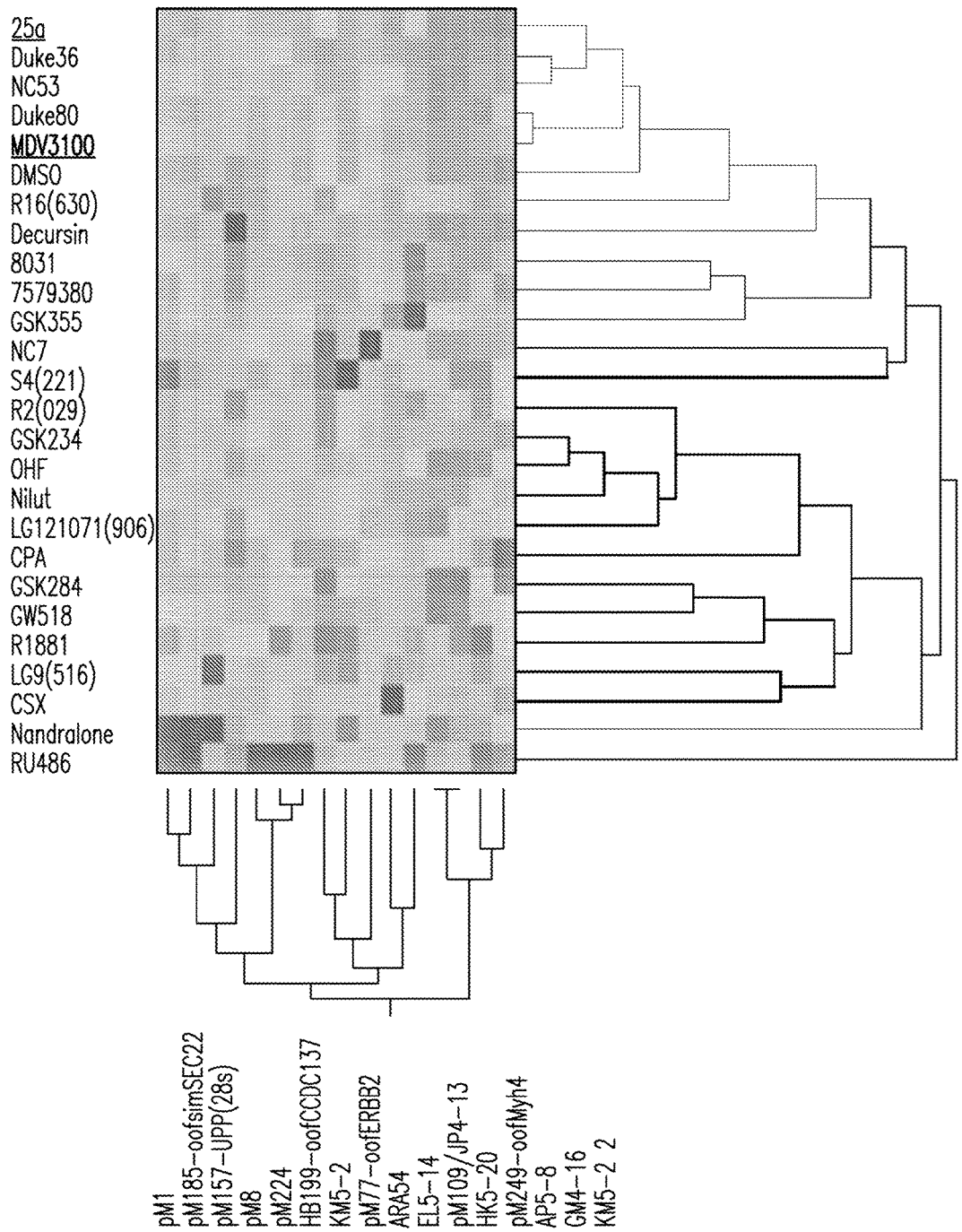
FIG. 42 depicts a conformational profiling heat map of ligand-dependent androgen receptor interaction with various androgen receptor-binding proteins as measured in mammalian two-hybrid assays. The darker the shading the higher the recruitment. Compound 1 of Example IV (25a) and enzalutamide (MDV3100) are underlined.

Conformational profiling was performed on the complex between compound 1 and AR using a subset of AR-interacting proteins previously identified (23, 24). As seen in FIG. 42, compound 1 clusters with ligands associated with the apo conformation of the receptor, including DMSO vehicle, and Duke 36 and Duke 80, two compounds previously reported to prevent AR/gelsolin interaction (24). Notably, enzalutamide also induces a conformation similar to that of the apo-protein. The success of enzalutamide in clinical trials suggests that compounds with this protein recruitment profile maintain their activity against hormone-resistant tumors in vivo and further supports the viability of 1 as a drug lead (7).

Screening of Focused Cyclobutane Library.

As described in the synthetic section above, based on the activity of 1, a set of dipyrimidinyl cyclobutane derivatives was synthesized and the compounds screened for their ability to inhibit AR-dependent PSA, TMPRSS2, and FKBP51 endogenous gene expression. A complete list of compounds and associated AR-dependent FKBP51 suppression is shown in Table 2, and these values are representative of the results obtained with all three genes. From these results a strict size-limitation becomes apparent, and regardless of the linking atom (O, S, or C), all cyclobutane derivatives bearing pyrimidinyl substituents longer than three non-hydrogen atoms failed to show inhibition of AR-dependent transcription. Only slightly larger than the methoxy variants, the methyl sulfides 11a and 12a only produce inhibition at a level of about 50% of cyclobutane 1. Conversely, the methyl and ethyl-substituted pyrimidines 10a and 10b exhibited AR inhibition equivalent to 1. Interestingly, this general size preference was not followed by the partially demethylated cyclobutanes 6b and 7b, which only suppress PSA expression to a level approximately 75% that of 1. Presumably, the significantly increased hydrophilicity of the pyrimidinedione negatively affects ligand binding. This was supported by the lack of activity of the bispyrimidinedione 6a. Of note is the fact that there appeared to be no preference between the two epimeric forms of the cyclobutanes, and in instances where the r-ctt isomers are active the r-cct isomers showed comparable inhibition (isomeric pairs: 1 and 5a, 6b and 7b, 11a and 12a).

In spite of the range of derivatives synthesized and tested in Table 2, only the methyl and ethyl compounds 10a and 10b gave inhibition comparable to that achieved with the initial lead compound, 1. Accordingly, an expanded set of tetra-aryl cyclbutanes was designed and synthesized, maintaining the apparently optimal methoxy substitution, while varying the size and electronic nature of the rings (as described in Scheme 2). These compounds were screened using an AR-responsive MMTV transcription assay in CV-1 cells, utilizing both wild type and T877A (LNCaP) AR. As listed in Table 3, a number of these compounds had activity profiles comparable or better than that of 1.

TABLE 6

Tetra-aryl cyclobutanes and suppression of AR-responsive endogenous genes

| Cmpd # at Duke | Cmpd # in paper | Ar₁, Ar₂ | isomer | MMTV transcription assay in CV-1 cells WT | T877A |
|---|---|---|---|---|---|
| CB-22 | 1 | (phenyl), (2,4-dimethoxypyrimidin-6-yl) | htt r-ctc | 18 µM | 1.1 µM |
| DPM-21 | 15a | (phenyl), (2-chloropyrimidin-4-yl) | htt r-ctc | IC50~10^−5 | IC50~10^−7 |
| DPM-26 | 15b | (phenyl), (4-chloropyrimidin-6-yl) | htt r-ctc | Incomplete inhibition at 10^−5 | IC50 9 µM |
| DPM-30 | 15c | (phenyl), (4-methyl-2-chloropyrimidin-6-yl) | htt r-ctc | IC50 17 µM | IC50 2.89 µM |
| DMP-13 | 15d | (phenyl), (pyridin-2-yl) | htt r-ctc | No inhibition | IC50~10^−5 |
| DPM-14 | 16d | | hth r-ctc | No inhibition | No inhibition |
| DPM-11/20 | 15e | (phenyl), (pyrazin-2-yl) | htt r-ctc | No inhibition | Mild inhibition at~10^−5 |
| DPM-12 | 16e | | hth r-ctc | No inhibition | No inhibition |

TABLE 6-continued

Tetra-aryl cyclobutanes and suppression of AR-responsive endogenous genes

| Cmpd # at Duke | Cmpd # in paper | Ar₁, Ar₂ | isomer | MMTV transcription assay in CV-1 cells | |
|---|---|---|---|---|---|
| | | | | WT | T877A |
| DPM-27 | 15f | [4-Ph-phenyl], [2,4-dichloropyrimidin-6-yl] | htt r-ctc | No inhibition | No inhibition |
| DMP-28 | 15g | [thiophen-2-yl], [2-chloropyrimidin-4-yl] | htt r-ctc | Incomplete inhibition at 10^−5 | IC50 2.6 μM |
| DPM-29 | 16g | | hth r-ctc | Incomplete inhibition at 10^−5 | Incomplete inhibition at 10^−5 |
| DPM-5 | 17a | [phenyl], [2-methoxypyrimidin-4-yl] | htt r-ctc | No inhibition | No inhibition |
| DMP-6 | 18a | | htt r-cct | No inhibition | No inhibition |
| DPM-18 | 17b | [phenyl], [6-methoxypyrazin-2-yl] | htt r-ctc | No inhibition | IC50~10^−5 |
| DPM-17 | 18b | | htt r-cct | IC50~10^−5 | IC50~10^−6 |
| DPM-16 | 19 | | hth r-ctc | No inhibition | Slight inhibition at 10^−5 |
| DPM-15 | 20 | | hth r-cct | No inhibition | IC50~10^−5 |
| DPM-19 | 17c | [phenyl], [4-methyl-2-methoxypyrimidin-6-yl] | htt r-ctc + htt r-cct | IC50~10^−5 | IC50~10^−6 |
| DMP-10 | 17d | [4-Br-phenyl], [2,4-dimethoxypyrimidin-6-yl] | htt r-ctc | No inhibition | No inhibition |

TABLE 6-continued

Tetra-aryl cyclobutanes and suppression of AR-responsive endogenous genes

[Structures showing four cyclobutane isomers with Ar1 and Ar2 substituents: htt r-ctc, htt r-cct, hth r-ctc, and hth r-cct]

| Cmpd # at Duke | Cmpd # in paper | Ar1, Ar2 | hth r-cct isomer | MMTV transcription assay in CV-1 cells WT | T877A |
|---|---|---|---|---|---|
| DPM-8 | 17e | [thiophene], [pyrimidine with OMe at 4-position and OMe at 2-position] | htt r-ctc | Incomplete inhibition at 10^−5 | IC50~10^−6 |
| DPM-9 | 18e | [thiophene], [pyrimidine with OMe at 4-position and OMe at 2-position] | htt r-cct | Incomplete inhibition at 10^−5 | IC50~10^−6 |

In general, deleterious effects were observed with loss of both substituents on the aryl ring, and the pan-proteo compounds 15d-e and 16d-e displayed almost a complete loss of activity. Decreasing the number of substituents on the pyrimidine ring to a single chloride or methoxy group gave variable effects on potency: Selective substitution with chloride at the 2-position (compound 15a) produced the most potent AR inhibitor, with an $IC_{50}$ approximately 10-fold lower than 1 ($IC_{50}$=~$10^{-7}$ M vs. ~1 mM for 1 for T877A AR). Conversely, monochloro substitution at the 6-position (compound 15b) produced a compound of decreased potency, and surprisingly, the 2-methoxy compound 17 displayed no inhibition at concentrations as high as 20 μM. The 2-chloro and 2-methoxy-6-methylpyrimidine substituted cyclobutanes 15c and 17c had comparable potency to 1, while the mono-substituted pyrazines with either head-to-tail (compounds 17b and 18b) or head-to-head (19 and 20) orientations all exhibited decreased activity. Additionally, efforts were made to explore the affect that alteration of the phenyl ring has on AR antagonism. Substitution of the phenyl ring at the para position with either a benzene or bromine produced inactive compounds (15f and 17d), while replacement of the phenyl ring with the smaller thiophene provides cyclobutanes that retained parent compound potency (15g, 16g, 17e and 18e).

Selective Inhibition of Mutant LNCaP (T877A) AR Over Wild Type Receptor.

Figure 43A:
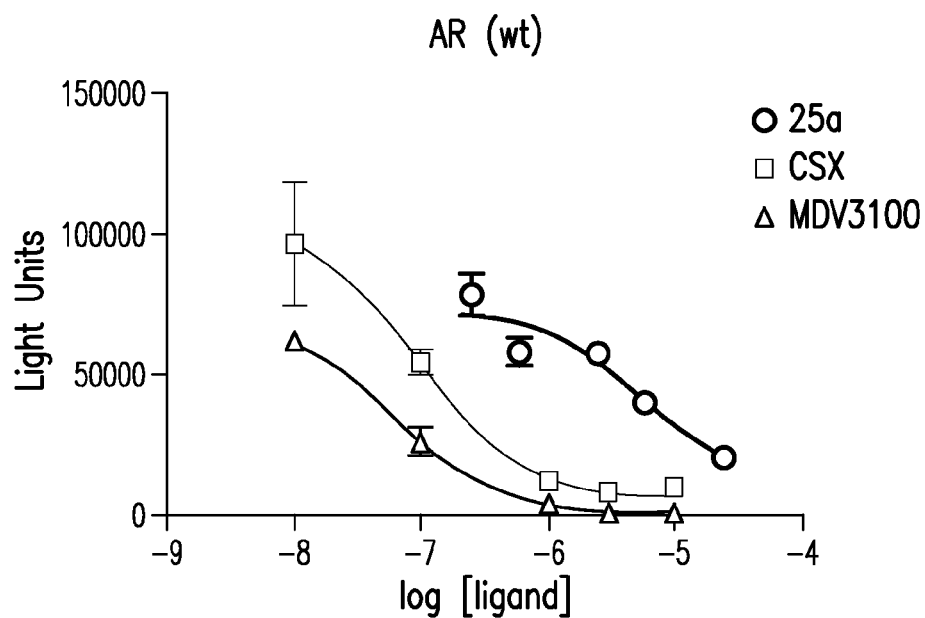
FIGS. 43A and B depict data for an androgen receptor-dependent luciferase transcription assay performed in CV-1 cells with transfected wild type (FIG. 43A) and mutant T877A androgen receptor (FIG. 43B), demonstrating the decreased affinity of compound 1 of Example IV for wild type receptor.
Figure 43B:
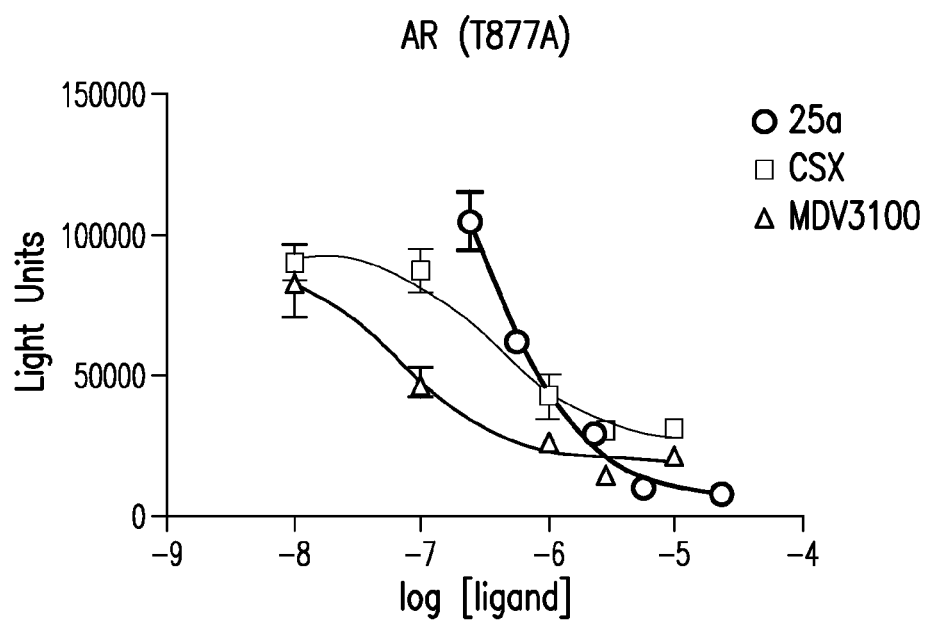
Figure 44:
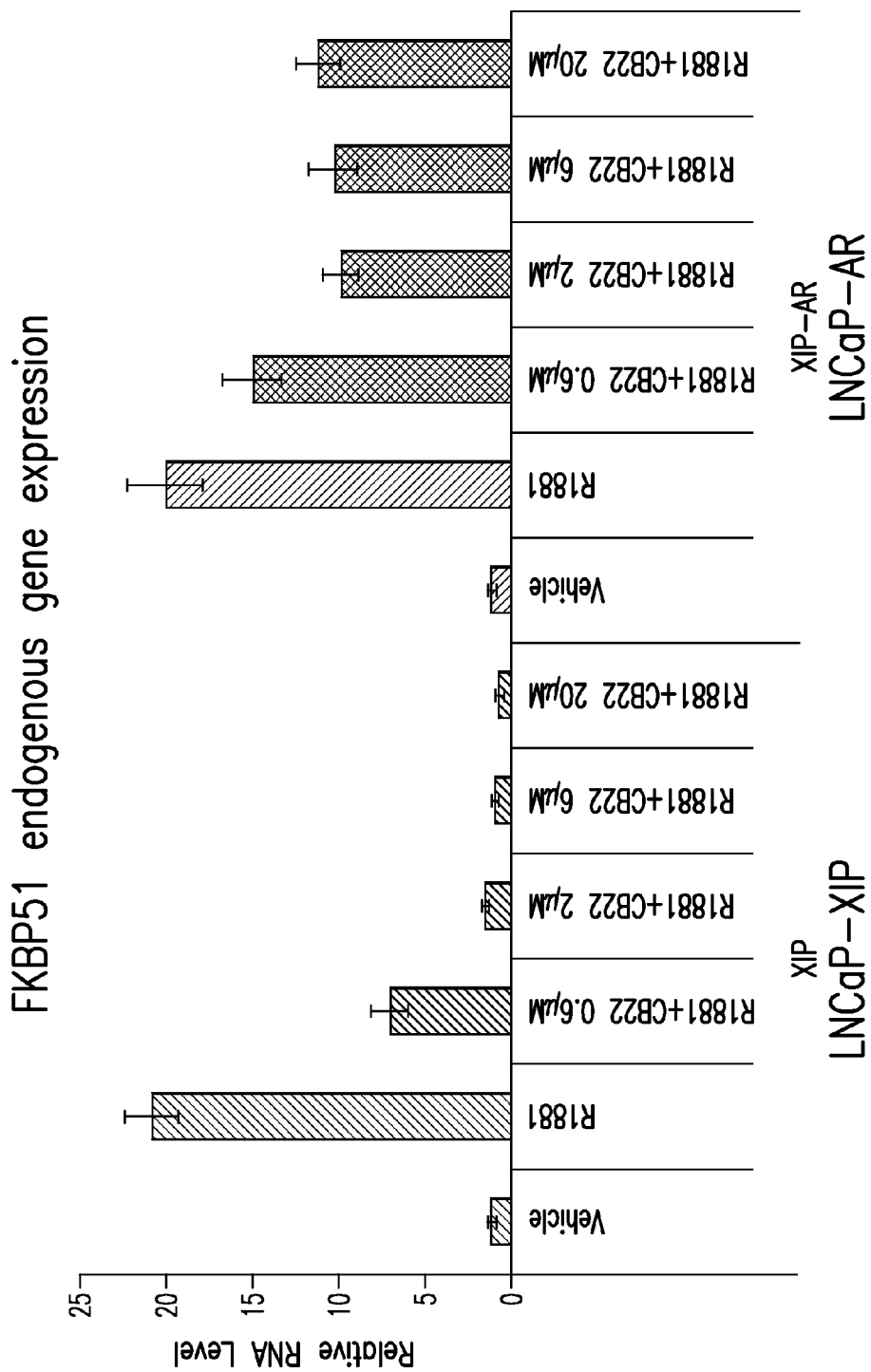
FIG. 44 depicts data for dose-dependent inhibition of androgen receptor-dependent endogenous gene expression of FKBP51 by Compound 1 of Example IV in LNCaP cells producing exclusively T877A mutant androgen receptor (LNCaP-XIP) and LNCaP cells transfected with wild type androgen receptor (LNCaP-androgen receptor, ratio of wild type to T877A receptor is ca. 3:1).

As shown in FIGS. 9A and B above, cyclobutane 1 exhibited anti-proliferative activity in both the LNCaP and VCaP prostate tumor cells, but was approximately 10-15 fold more potent in the LNCaP cells. To more fully characterize the selectivity of compound 1 for the mutant receptor, we measured its inhibitory potential against the WT and T877A mutant receptor in an AR-dependent luciferase transcription assay in CV-1 cells (FIGS. 43A and B). Here again, we observed an approximately 10-fold increase in potency for the T877A mutant over the WT. These results were further confirmed with endogenous gene expression. As shown in FIG. 44, when only the LNCaP receptor (T877A) was present in the prostate cancer cells (LNCaP-XIP), 2 μM of 1 resulted in complete inhibition of FKBP51 gene expression. Conversely, when WT receptor was overexpressed in addition to basal-level expression of mutant AR (LNCaP-AR), 1 was no longer able to fully suppress FKBP51 gene expression, and at concentrations as high as 20 M, only approximately 50% inhibition was observed.

Figure 45A:
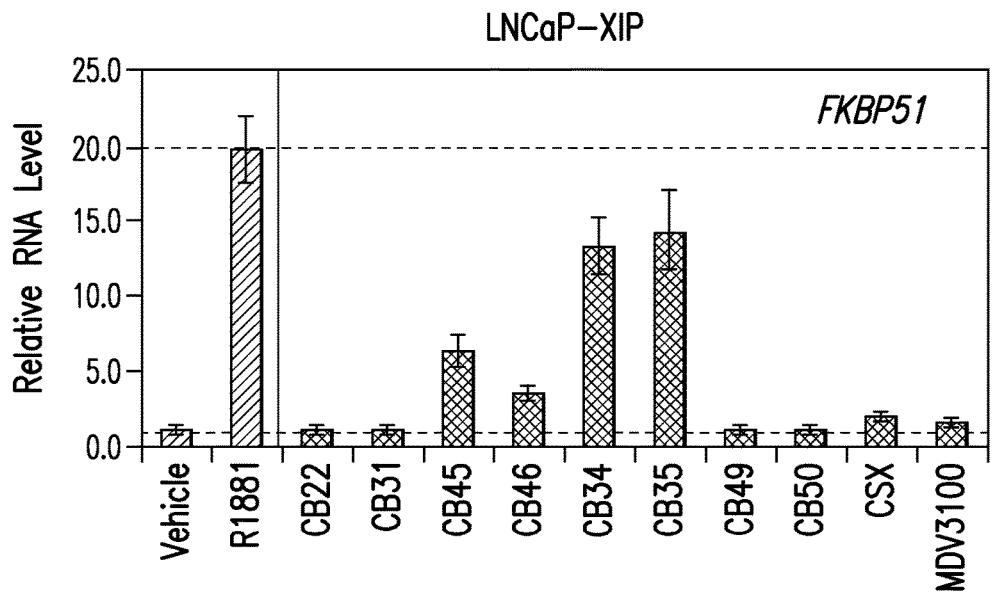
FIGS. 45A, B, C, and D depict data for the inhibition of androgen receptor—dependent endogenous gene expression of FKBP51 and TMPRSS2 by compound 1 of Example IV and derivatives in LNCaP cells producing exclusively T877A mutant androgen receptor (LNCaP-XIP) and LNCaP cells transfected with wild type androgen receptor (LNCaP-androgen receptor, ratio of wild type to TA877A androgen receptor is ca. 3:1).
Figure 45B:
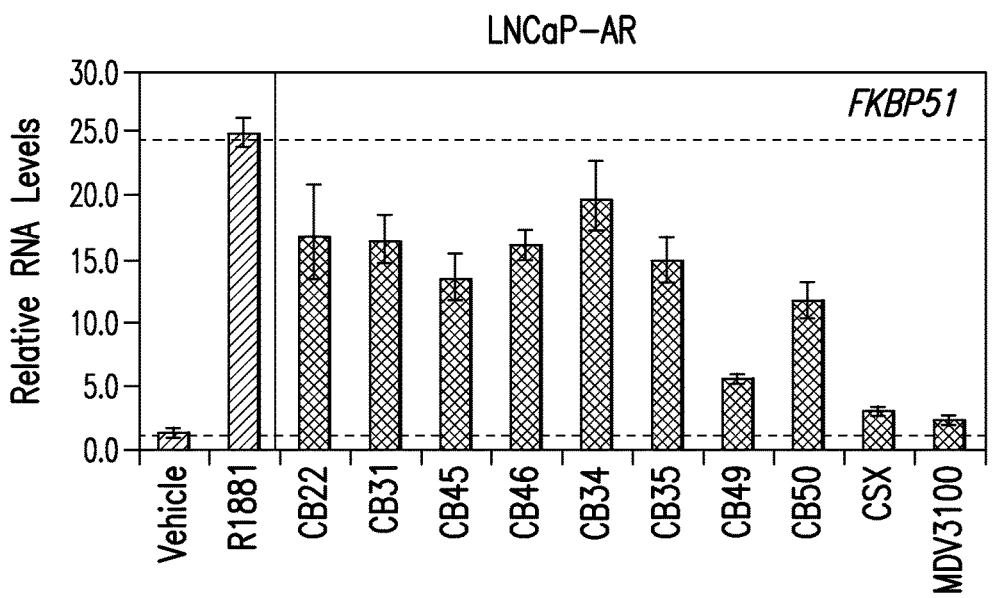
Figure 45C:
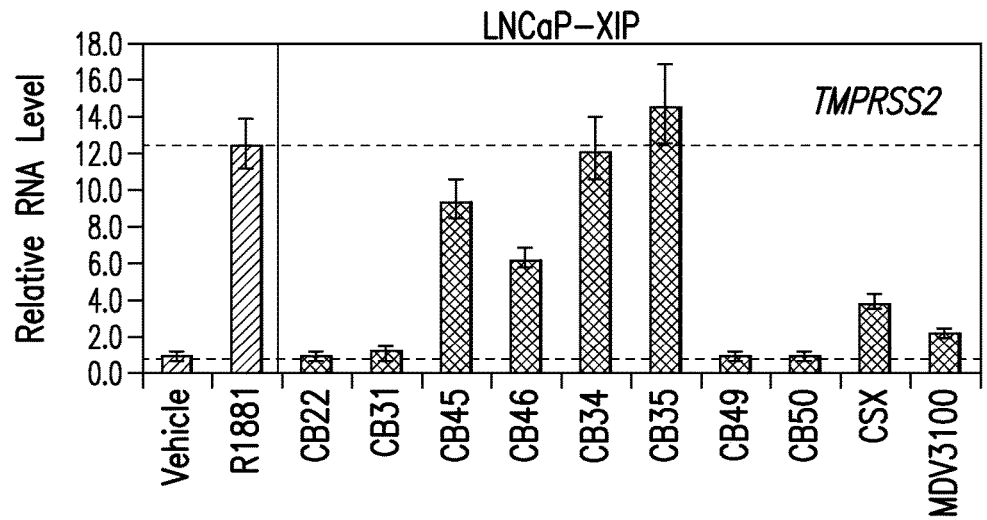
Figure 45D:
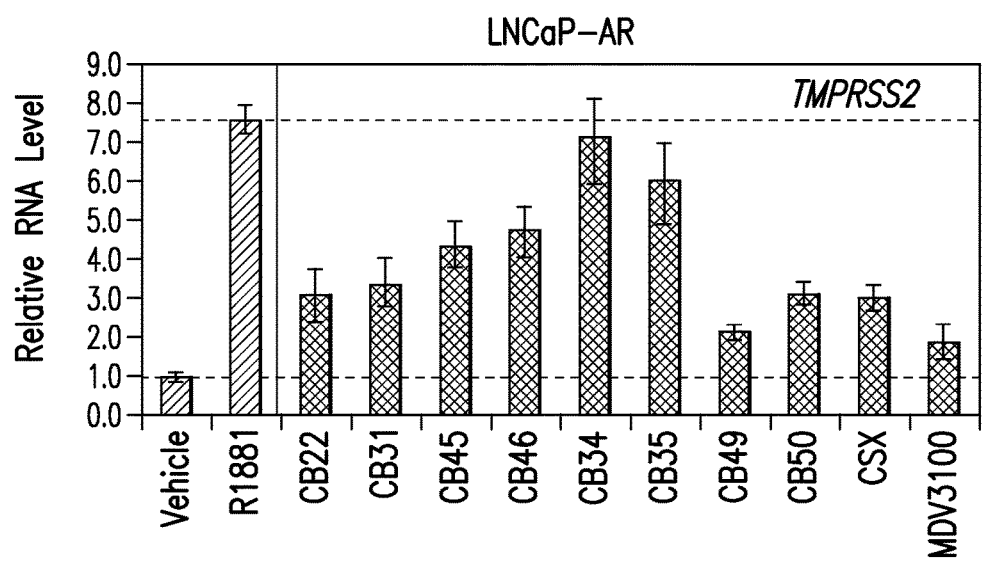
Figure 46:
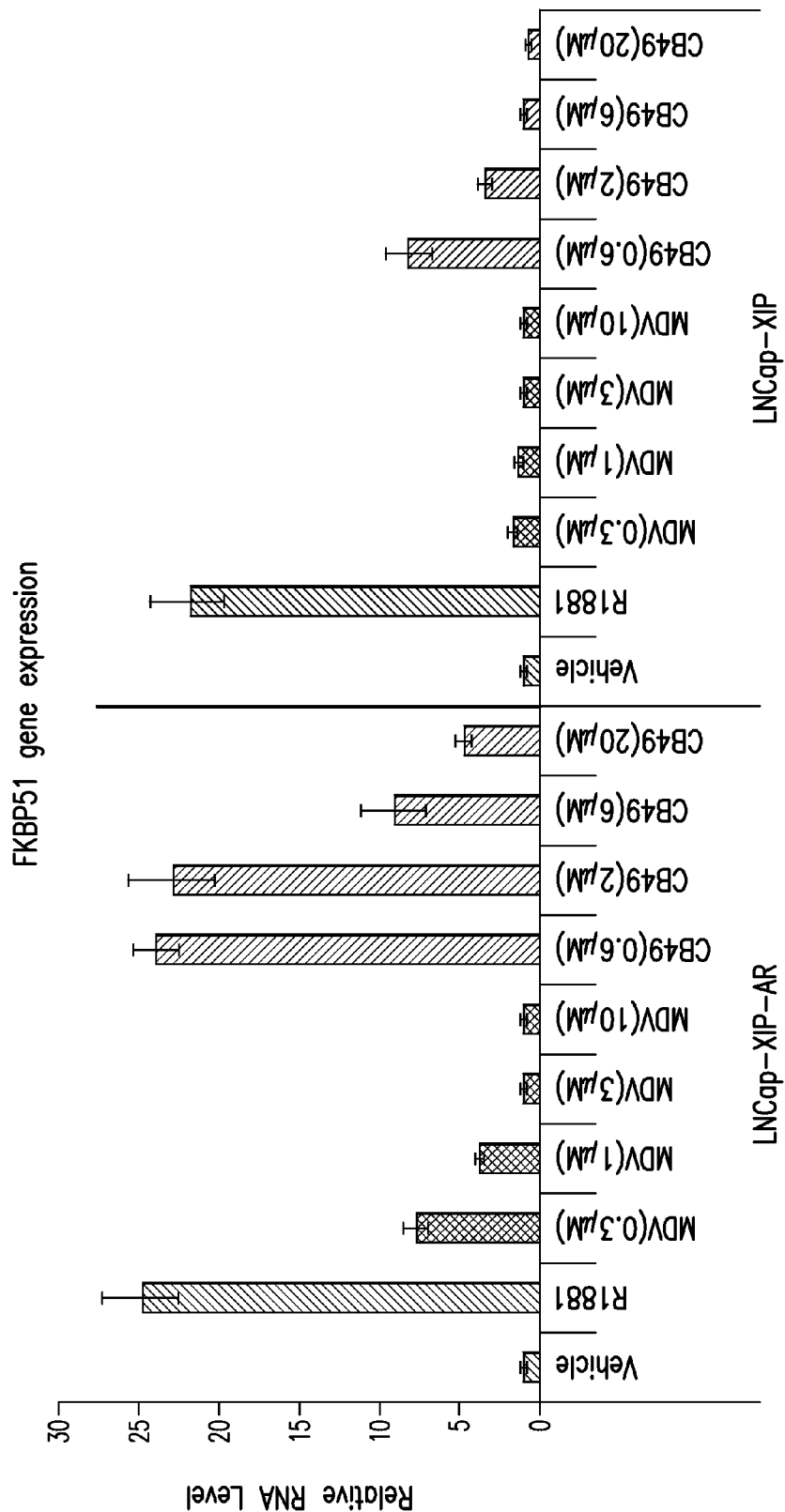
FIG. 46 depicts data for dose-dependent inhibition of androgen-receptor-dependent endogenous gene expression of FKBP51 by enzalutamide (MDV3100) and Compound CB49 of Example VI (also known as compound 10a in Example IV and compound u) in LNCaP cells producing exclusively T877A mutant androgen receptor (LNCaP-XIP) and LNCaP cells transfected with wild type androgen receptor (LNCaP-androgen receptor, ratio of wild type to T877A androgen receptor is ca. 3:1).

Further investigation of the other active cyclobutane derivatives showed similar selectivity for the mutant T877A receptor (FIGS. 45A, B, C, and D). Interestingly, the methylated compound 10a retained significant activity in both mutant and wild type settings. However, a dose-response titration of this compound in the same assay (FIG. 46) revealed that while it has lower potency for the T877A mutant receptor than does 1 (maximal inhibition with 10a (also known as compound CB49) obtained at 6 μM vs. 2 μM for 1, compare with FIG. 44), it retained greater activity in the LNCaP-AR system, achieving ca. 80% inhibition of FKBP51 expression at 20 M of compound. Additionally, comparison of the $IC_{50}$ values listed in Table 3 for the wild type vs. T877A mutant AR demonstrated a consistent preference of the tetra-aryl cyclobutanes for mutant receptor, with many compounds showing lack of activity at assayed concentrations in the wild type. This selectivity was especially striking for the potent dichloride antagonist 15a, which demonstrated an approximately 100-fold higher potency for the mutant receptor.

Figure 47A:
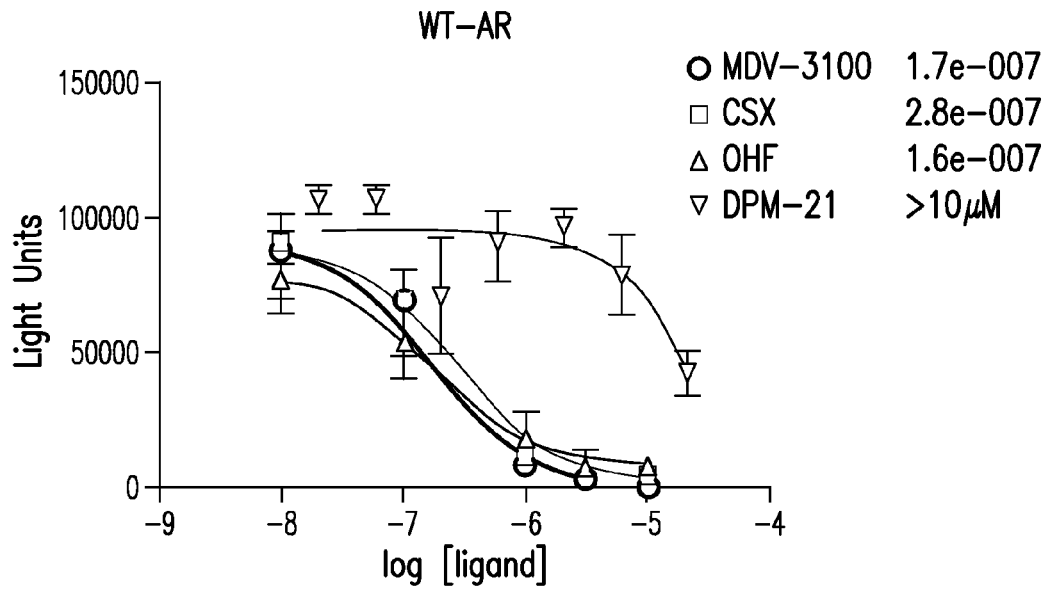
FIG. 47 depicts data for inhibition of wild type, T877A, and W741C androgen receptors by tetra-aryl cyclobutane Compound 15a of Example IV.
Figure 47B:
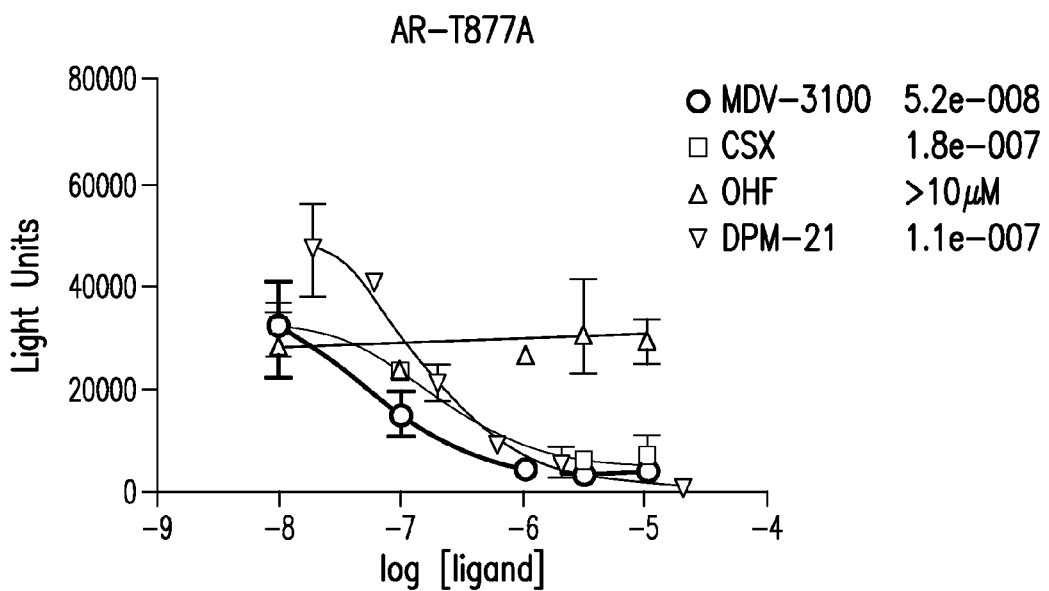
Figure 47C:
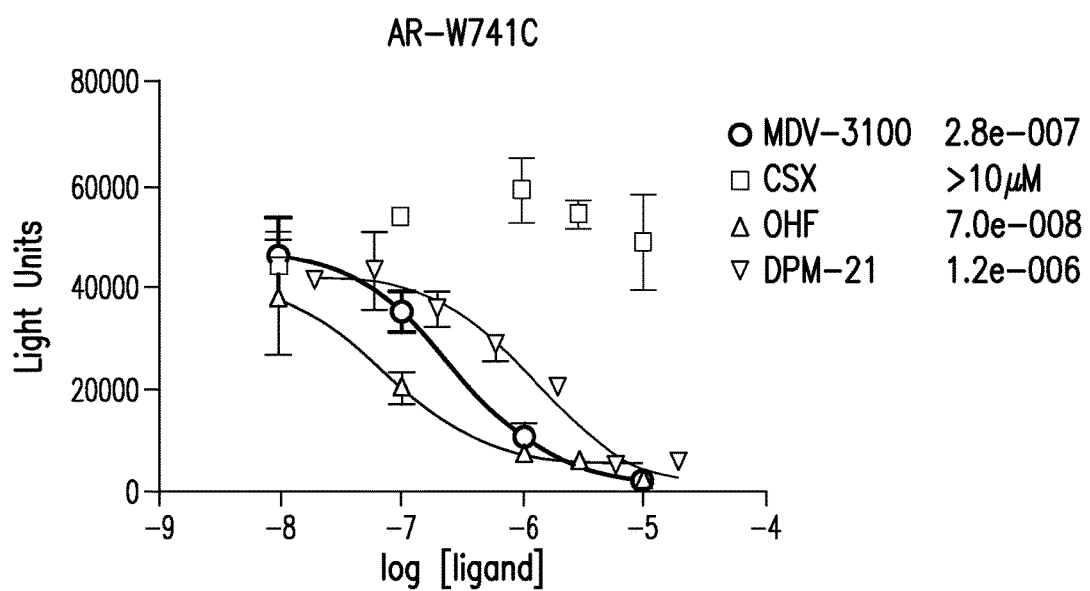

In an effort to determine whether the cyclobutane antiandrogens were selective for mutant receptors other than the LNCaP mutant found in flutamide-treated patients, AR-dependent luciferase transfection assays were performed using a W741C which has been observed in prostate cancer patients previously treated with the antiandrogen bicalutamide (25). As shown in FIGS. 47A, B, and C, although compound 15a had decreased activity in the W741C AR when compared to the LNCaP mutant, it retained an approximately 10-fold increase in potency over the WT receptor, suggesting that compounds of this class could be developed with selectivity for a range of prostate cancer-associated mutants.

TABLE 7

Activity and RBAs of AR-active cyclobutane ERDs.

| Cmpd # | Ar₁, Ar₂ | Stereochem | AR activity | AR RBA |
|---|---|---|---|---|
| 1 | OMe-pyrimidine-OMe | r-ctc | 100% | 0.056% |
| 5a | | r-cct | 100% of 1 | 0.046% |
| 7a | uracil | r-cct | none | 0.023% |
| 6b | uracil | r-ctc | 75% of 1 | 0.087% |
| 7b | OMe-pyrimidine-OMe | r-cct | 75% of 1 | 0.065% |
| 10a | CH₃-pyrimidine-CH₃ | r-ctc | Equal to 1 | 0.027% |
| 10b | Et-pyrimidine-Et | r-ctc | Equal to 1 | 0.029% |
| 11a | SMe-pyrimidine-SMe | r-ctc | 50% of 1 | 0.002% |
| 12a | | r-cct | 50% of 1 | 0.027% |

The identification of novel modulators of AR function is essential in combating hormone-refractory prostate cancer, especially as resistance to clinically approved drugs continues to develop. Here, we have identified competitive AR antagonists with a novel structure that inhibit endogenous gene expression, slow cellular proliferation, and force an apo-like conformation of the receptor. These compounds are of particular interest because they are effective at inhibiting antiandrogen-resistant mutant ARs that arise after prior hormone treatment, as we demonstrate with mutant ARs resistant to flutamide (T877A) or bicalutamide (W741C). Previous work has focused on successfully inhibiting these mutant ARs, but it has resulted in compounds having comparable effects on the WT AR (26-28). We propose that the mutant-selective inhibitors we have developed might provide effective therapy for hormone-refractory prostate cancer, while in principle avoiding the negative side effects associated with androgen deprivation (impaired sexual activity, muscle wasting, etc.).

Specifically targeting a mutant form of a protein target in cancer has some precedent in the development of vemurafenib (PLX4032/RG7204, Plexxikon/Roche), a kinase inhibitor used for the treatment of a common form of metastatic melanoma linked to the BRAF V600E mutation; vemurafenib is not active on WT BRAF or on most other mutant forms (29-31). In the case of prostate cancer, however, the wild type form of AR is the original target for antiandrogen therapy, with mutant AR forms developing under the selective pressure of AR-suppressive therapy, the new result being that the initial antiandrogen coveys only the negative side effects through WT AR and no therapeutic benefit through the mutant AR. New mutant-selective antagonists such as those we have developed might be able to reverse this situation—giving effective therapy without side effects—which might provide a more optimized treatment of certain forms of advanced prostate cancer (23-25).

Our initial lead compound, cyclobutane 1, was obtained from a stilbene precursor prepared in connection with a different project; it was formed by a serendipitous photodimerization that occurred during storage on the bench top, a process we have studied in some detail (32). Natural products and other bioactive compounds that contain cyclobutanes as core structural components are relatively rare. Most of the naturally occurring molecules in this class are the result of a sunlight-initiated [2+2] cycloaddition of either a stilbene or cinnamic acid-like precursor, leading to a symmetric or quasi-symmetric tetra-substituted cyclobutane dimer (33-38). Examples of synthetically-derived bioactive cyclobutane-core compounds have also been isolated from the photodimerization of drug candidates containing photoactive π-systems (39, 40). Despite their rarity, substituted cyclobutanes are intriguing as scaffolds for molecular probes and drug candidates due to their inherent three-dimensionality. Recently, molecules with a cyclobutane core have shown promise as agonists of glucagon-like peptide-1 (GLP-1) receptor in vitro and in vivo (40, 41).

REFERENCES

The references numbers cited in Example IV correspond to the references listed at the end of this Example IV.
(1) Chatterjee, B. (2003) The role of the androgen receptor in the development of prostatic hyperplasia and prostate cancer, *Molecular and Cellular Biochemistry* 253, 89-101.
(2) Taplin, M.-E. (2007) Drug Insight: role of the androgen receptor in the development and progression of prostate cancer, *Nature Clinical Practice Oncology* 4, 236-244.
(3) Anderson, J. (2003) The role of antiandrogen monotherapy in the treatment of prostate cancer, *BJU International* 91, 455-461.
(4) Chodak, G., Gomella, L., and Phung, D. H. (2007) Combined Androgen Blockade in Advanced Prostate Cancer: Looking Back to Move Forward, *Clinical Genitourinary Cancer* 5, 371-378.
(5) Gillatt, D. (2006) Antiandrogen treatments in locally advanced prostate cancer: are they all the same?, *Journal of Cancer Research and Clinical Oncology* 132, 17-26.
(6) Tran, C., Ouk, S., Clegg, N. J., Chen, Y., Watson, P. A., Arora, V., Wongvipat, J., Smith-Jones, P. M., Yoo, D., Kwon, A., Wasielewska, T., Welsbie, D., Chen, C. D., Higano, C. S., Beer, T. M., Hung, D. T., Scher, H. I., Jung, M. E., and Sawyers, C. L. (2009) Development of a Second-Generation Antiandrogen for Treatment of Advanced Prostate Cancer, *Science* 324, 787-790.
(7) Scher, H. I., Beer, T. M., Higano, C. S., Anand, A., Taplin, M.-E., Efstathiou, E., Rathkopf, D., Shelkey, J., Yu, E. Y., Alumkal, J., Hung, D., Hirmand, M., Seely, L., Morris, M. J., Danila, D. C., Humm, J., Larson, S., Fleisher, M., and Sawyers, C. L. (2010) Antitumour activity of MDV3100 in castration-resistant prostate cancer: a phase 1?2 study, *The Lancet* 375, 1437-1446.
(8) Scher, H. I., Fizazi, K., Saad, F., Taplin, M.-E., Sternberg, C. N., Miller, K., de Wit, R., Mulders, P., Chi, K. N., Shore, N. D., Armstrong, A. J., Flaig, T. W., Fléchon, A., Mainwaring, P., Fleming, M., Hainsworth, J. D., Hirmand, M., Selby, B., Seely, L., and de Bono, J. S. (2012) Increased Survival with Enzalutamide in Prostate Cancer after Chemotherapy, *New England Journal of Medicine* 367, 1187-1197.
(9) Li, Y., Chan, S. C., Brand, L. J., Hwang, T. H., Silverstein, K. A. T., and Dehm, S. M. (2013) Androgen Receptor Splice Variants Mediate Enzalutamide Resistance in Castration-Resistant Prostate Cancer Cell Lines, *Cancer Research* 73, 483-489.
(10) Taplin, M.-E., Bubley, G. J., Ko, Y.-J., Small, E. J., Upton, M., Rajeshkumar, B., and Balk, S. P. (1999) Selection for Androgen Receptor Mutations in Prostate Cancers Treated with Androgen Antagonist, *Cancer Research* 59, 2511-2515.
(11) He, B., Kemppainen, J. A., and Wilson, E. M. (2000) FXXLF and WXXLF sequences mediate the NH2-terminal interaction with the ligand binding domain of the androgen receptor, *Journal of Biological Chemistry* 275, 22986-22994.
(12) He, B., Lee, L. W., Minges, J. T., and Wilson, E. M. (2002) Dependence of selective gene activation on the androgen receptor NH2- and COOH-terminal interaction, *Journal of Biological Chemistry* 277, 25631-25639.
(13) Callewaert, L., Van Tilborgh, N., and Claessens, F. (2006) Interplay between Two Hormone-Independent Activation Domains in the Androgen Receptor, *Cancer Research* 66, 543-553.
(14) He, B., Gampe, R. T., Jr., Kole, A. J., Hnat, A. T., Stanley, T. B., An, G., Stewart, E. L., Kalman, R. I., Minges, J. T., and Wilson, E. M. (2004) Structural basis for androgen receptor interdomain and coactivator interactions suggests a transition in nuclear receptor activation function dominance, *Molecular Cell* 16, 425-438.
(15) McEwan, I. J. (2004) Molecular mechanisms of androgen receptor-mediated gene regulation: structure-function analysis of the AF-1 domain, *Endocrine-Related Cancer* 11, 281-293.
(16) Gelmann, E. P. (2002) Molecular biology of the androgen receptor, *Journal of Clinical Oncology* 20, 3001-3015.
(17) Hanstein, B., Djahansouzi, S., Dall, P., Beckmann, M. W., and Bender, H. G. (2004) Insights into the molecular biology of the estrogen receptor define novel therapeutic targets for breast cancer, *European Journal of Endocrinology* 150, 243-255.
(18) Hall Julie, M., and McDonnell Donald, P. (2005) Coregulators in nuclear estrogen receptor action: from concept to therapeutic targeting, *Molecular Interventions* 5, 343-357.

(19) Gunther, J. R., Parent, A. A., and Katzenellenbogen, J. A. (2009) Alternative Inhibition of Androgen Receptor Signaling: Peptidomimetic Pyrimidines As Direct Androgen Receptor/Coactivator Disruptors, *ACS Chem. Biol.* 4, 435-440.

(20) Parent, A. A., Gunther, J. R., and Katzenellenbogen, J. A. (2008) Blocking Estrogen Signaling After the Hormone: Pyrimidine-Core Inhibitors of Estrogen Receptor-Coactivator Binding, *J. Med. Chem.* 51, 6512-6530.

(21) Fuerstner, A., and Leitner, A. (2002) Iron-catalyzed cross-coupling reactions of alkyl-Grignard reagents with aryl chlorides, tosylates, and triflates, *Angew. Chem., Int. Ed.* 41, 609-612.

(22) Korenchuk, S., Lehr, J. E., L, M. C., Lee, Y. G., Whitney, S., Vessella, R., Lin, D. L., and Pienta, K. J. (2001) VCaP, a cell-based model system of human prostate cancer, *In Vivo.* 15, 163-168.

(23) Norris, J. D., Joseph, J. D., Sherk, A. B., Juzumiene, D., Tumbull, P. S., Rafferty, S. W., Cui, H., Anderson, E., Fan, D., Dye, D. A., Deng, X., Kazmin, D., Chang, C.-Y., Willson, T. M., and McDonnell, D. P. (2009) Differential Presentation of Protein Interaction Surfaces on the Androgen Receptor Defines the Pharmacological Actions of Bound Ligands, *Chem. Biol.* (Cambridge, Mass., U.S.) 16, 452-460.

(24) Joseph, J. D., Wittmann, B. M., Dwyer, M. A., Cui, H., Dye, D. A., McDonnell, D. P., and Norris, J. D. (2009) Inhibition of prostate cancer cell growth by second-site androgen receptor antagonists, *Proc. Natl. Acad. Sci. U.S.A* 106, 12178-12183, S12178/12171-S12178/12113.

(25) Hara, T., Miyazaki, J.-i., Araki, H., Yamaoka, M., Kanzaki, N., Kusaka, M., and Miyamoto, M. (2003) Novel Mutations of Androgen Receptor: A Possible Mechanism of Bicalutamide Withdrawal Syndrome, *Cancer Research* 63, 149-153.

(26) Wakabayashi, K., Imai, K., Miyachi, H., Hashimoto, Y., and Tanatani, A. (2008) 4-(Anilino)pyrrole-2-carboxamides: Novel non-steroidal/non-anilide type androgen antagonists effective upon human prostate tumor LNCaP cells with mutated nuclear androgen receptor, *Bioorg Med Chem* 16, 6799-6812.

(27) Oh, S., Nam, H. J., Park, J., Beak, S. H., and Park, S. B. (2010) Development of a benzopyran-containing androgen receptor antagonist to treat antiandrogen-resistant prostate cancer, *ChemMedChem* 5, 529-533.

(28) Yamamoto, S., Kobayashi, H., Kaku, T., Aikawa, K., Hara, T., Yamaoka, M., Kanzaki, N., Hasuoka, A., Baba, A., and Ito, M. (2013) Design, synthesis, and biological evaluation of 3-aryl-3-hydroxy-1-phenylpyrrolidine derivatives as novel androgen receptor antagonists, *Bioorg Med Chem* 21, 70-83.

(29) Bollag, G., Hirth, P., Tsai, J., Zhang, J., Ibrahim, P. N., Cho, H., Spevak, W., Zhang, C., Zhang, Y., Habets, G., Burton, E. A., Wong, B., Tsang, G., West, B. L., Powell, B., Shellooe, R., Marimuthu, A., Nguyen, H., Zhang, K. Y., Artis, D. R., Schlessinger, J., Su, F., Higgins, B., Iyer, R., D'Andrea, K., Koehler, A., Stumm, M., Lin, P. S., Lee, R. J., Grippo, J., Puzanov, I., Kim, K. B., Ribas, A., McArthur, G. A., Sosman, J. A., Chapman, P. B., Flaherty, K. T., Xu, X., Nathanson, K. L., and Nolop, K. (2010) Clinical efficacy of a RAF inhibitor needs broad target blockade in BRAF-mutant melanoma, *Nature* 467, 596-599.

(30) Flaherty, K., Puzanov, I., Sosman, J., Kim, K., Ribas, A., McArthur, G., Lee, R. J., Grippo, J. F., Nolop, K., and Chapman, P. (2009) Phase I study of PLX4032: Proof of concept for V600E BRAF mutation as a therapeutic target in human cancer, *Journal of Clinical Oncology* 27.

(31) Flaherty, K. T., Puzanov, I., Kim, K. B., Ribas, A., McArthur, G. A., Sosman, J. A., O'Dwyer, P. J., Lee, R. J., Grippo, J. F., Nolop, K., and Chapman, P. B. (2010) Inhibition of mutated, activated BRAF in metastatic melanoma, *N Engl J Med* 363, 809-819.

(32) Parent, A. A., Ess, D. H., and Katzenellenbogen, J. A. (2013) π-π Interaction Energies as Determinants of the Photodimerization of Mono-, Di- and Triazastilbenes *Photochemistry Photobiology*.

(33) Pearce, A. N., Chia, E. W., Berridge, M. V., Maas, E. W., Page, M. J., Harper, J. L., Webb, V. L., and Copp, B. R. (2008) Orthidines A-E, tubastrine, 3,4-dimethoxyphenethyl-β-guanidine, and 1,14-sperminedihomovanillamide: potential anti-inflammatory alkaloids isolated from the New Zealand ascidian Aplidium orthium that act as inhibitors of neutrophil respiratory burst, *Tetrahedron* 64, 5748-5755.

(34) Watanabe, K., Kubota, T., Shinzato, T., Ito, J., Mikami, Y., and Kobayashi, J. i. (2007) Sarusubine A, a new dimeric Lythraceae alkaloid from *Lagerstroemia subcostata*, *Tetrahedron Lett.* 48, 7502-7504.

(35) Davis, R. A., Carroll, A. R., Duffy, S., Avery, V. M., Guymer, G. P., Forster, P. I., and Quinn, R. J. (2007) Endiandrin A, a Potent Glucocorticoid Receptor Binder Isolated from the Australian Plant Endiandra anthropophagorum, *J. Nat. Prod.* 70, 1118-1121.

(36) Lu, Y., and Foo, L. Y. (1999) Rosmarinic acid derivatives from *Salvia officinalis*, *Phytochemistry* 51, 91-94.

(37) Dembitsky, V. M. (2008) Bioactive cyclobutane-containing alkaloids, *J. Nat. Med.* 62, 1-33.

(38) Sagawa, T., Takaishi, Y., Fujimoto, Y., Duque, C., Osorio, C., Ramos, F., Garzon, C., Sato, M., Okamoto, M., Oshikawa, T., and Ahmed, S. U. (2005) Cyclobutane dimers from the Colombian medicinal plant Achyrocline bogotensis, *J. Nat. Prod.* 68, 502-505.

(39) Hockemeyer, J., Burbiel, J. C., and Mueller, C. E. (2004) Multigram-Scale Syntheses, Stability, and Photoreactions of A2A Adenosine Receptor Antagonists with 8-Styrylxanthine Structure: Potential Drugs for Parkinson's Disease, *J. Org. Chem.* 69, 3308-3318.

(40) Chen, D., Liao, J., Li, N., Zhou, C., Liu, Q., Wang, G., Zhang, R., Zhang, S., Lin, L., Chen, K., Xie, X., Nan, F., Young, A. A., and Wang, M.-W. (2007) A nonpeptidic agonist of glucagon-like peptide 1 receptors with efficacy in diabetic db/db mice, *Proc. Natl. Acad. Sci. U.S.A* 104, 943-948.

(41) Liu, Q., Li, N., Yuan, Y., Lu, H., Wu, X., Zhou, C., He, M., Su, H., Zhang, M., Wang, J., Wang, B., Wang, Y., Ma, D., Ye, Y., Weiss, H. C., Gesing, E. R., Liao, J., and Wang, M. W. (2012) Cyclobutane derivatives as novel nonpeptidic small molecule agonists of glucagon-like peptide-1 receptor, *J Med Chem* 55, 250-267.

Example V: Cyclobutane-Core Androgen Receptor Antagonists: Inhibitors for Treatment of Ezalutamide Resistant Prostate Cancer The references numbers cited in Example V correspond to the references listed at the end of this Example V. The Scheme, Table, and Compound Numbers recited in this Example V are with respect to this Example V. CB compound numbers are also found in Example VI.

Prostate cancer is the most commonly diagnosed cancer among males in the United States with more than 29,000 men estimated to die from it in 2014[1]. The critical driver of prostate tumor progression is the androgen receptor (AR), and when the cancer has progressed past definitive local therapy, antagonists of the receptor are employed as therapeutics. The suppression of AR function by anti-androgens is initially effective, but a large number of tumors develop resistance resulting in a more aggressive tumor known as castration-resistant prostate cancer (CRPC). CRPC has sustained AR signaling through over expression of the wild type AR, upregulation of intratumoral androgen production, alternative mRNA splicing resulting in truncated receptors, or mutations within AR that result in altered ligand binding and activation characteristics[2]. Recent sequencing of advanced prostate cancers revealed that 44% of CRPCs had genomic alterations involving AR, with 20% containing an AR point mutation[3]. Mutations in the ligand-binding domain of AR often convert the anti-androgens from antagonists to agonists. For example, the first generation drugs flutamide (OHF) and bicalutamide (CSX) confer agonist activity against the AR common mutations of T877A and W741C, respectively[4,5]. The second generation anti-androgens enzalutamide (MDV3100, MDV) and ARN-509 were developed to retain antagonist activity against acquired resistance including cancers comprising the aforementioned mutants and overexpressing the wild type receptor[6,7]. Despite the impressive clinical activity of these anti-androgens, recent studies have revealed that acquired resistance has emerged; this resistance has been linked to a new, F876L mutation within the ligand binding domain of AR[8,9].

We describe the tetra-aryl cyclobutane scaffold as a core building block for the development of mutant-selective anti-androgens. It is believed these cyclobutane compounds act as competitive inhibitors of androgren receptor (AR) agonism and are able to inhibit androgen-mediated gene transcription in multiple models of hormone-refractory disease, including mutant (F876L, T877A, and W741C) AR and wild type AR overexpression. Notably, the most potent cyclobutanes have a 10 to 30-fold increased affinity for the F876L AR over wild type receptor, suggesting the possibility for selective targeting of mutant androgen receptor AR signaling that is associated with previously-treated hormone-refractory prostate cancer.

Results:
Potent Antagonists of AR Mutants

In an effort to identify inhibitors that overcome MDV resistance, we utilized a CV1 transient transfection system (MMTV-Luciferase reporter gene) expressing AR-F876L to screen an in-house library containing unique small-molecule scaffolds. After eliminating compounds with unsatisfactory toxicity profiles, the tetra-aryl cyclobutane (CB) compound 1 emerged as a promising lead (Table 1), providing effective inhibition of AR activation without cellular damage, with an $IC_{50}$ of 1.64 µM. Based upon this initial finding, an expanded library of cyclobutanes appended with a variety of substituted arenes was synthesized via an efficient and in some cases regioselective solid state photodimerization[10].

TABLE 1

| | AR ligand | | | $IC_{50}$ (µM) | | | |
|---|---|---|---|---|---|---|---|
| CB | $R_1$ | $R_2$ | Ar | F876L | WT | T877A | W741C |
| 1 | OMe | OMe | $C_6H_4$ | 1.64 | 20.0 | 0.81 | 2.36 |
| 2 | OEt | OEt | $C_6H_4$ | >20 | >20 | >20 | >20 |
| 3 | OPr | OPr | $C_6H_4$ | >20 | >20 | >20 | >20 |
| 4 | Oi-Pr | Oi-Pr | $C_6H_4$ | >20 | >20 | >20 | >20 |
| 5 | OBn | OBn | $C_6H_4$ | >20 | >20 | >20 | >20 |
| 6 | H | H | $C_6H_4$ | >20 | >20 | 11.42 | >20 |
| 7 | Me | Me | $C_6H_4$ | 1.04 | >20 | 2.83 | 8.69 |
| 8 | Et | Et | $C_6H_4$ | 1.95 | >20 | 1.02 | 6.33 |
| 9 | Cl | Cl | $C_6H_4$ | 10.4 | >20 | >20 | 14.7 |
| 10 | Cl | H | $C_6H_4$ | 0.36 | 1.4 | 0.20 | 1.15 |
| 11 | H | Cl | $C_6H_4$ | 1.15 | >20 | 1.63 | 13.1 |
| 12 | Cl | Me | $C_6H_4$ | 0.96 | >20 | 0.90 | 3.56 |
| 13 | Cl | Cl | 4-Ph$C_6H_4$ | >20 | >20 | >20 | >20 |
| 14 | Cl | Cl | 3-thienyl | >20 | >20 | >20 | >20 |
| 15 | OMe | Me | $C_6H_4$ | 0.46 | 9.4 | 0.36 | 2.25 |
| 16 | H | OMe | $C_6H_4$ | 1.90 | >20 | >20 | >20 |
| 17 | OMe | OMe | 3-thienyl | 8.11 | >20 | 5.18 | >20 |
| 18 | SMe | SMe | $C_6H_4$ | >20 | >20 | >20 | >20 |
| 19 | $SO_2Et$ | $SO_2Et$ | $C_6H_4$ | >20 | >20 | >20 | >20 |
| 20 | NHMe | NHMe | $C_6H_4$ | Toxic | >20 | >20 | Toxic |
| | | MDV | | Agonist | 0.22 | 0.21 | 3.15 |
| | | CSX | | 0.26 | 0.18 | 0.34 | Agonist |
| | | OHF | | 0.07 | 0.01 | Agonist | 0.06 |

The inhibitory activity of the CBs was measured using the same CV1 transient transfection system expressing AR-F876L. Substitution of the methoxy group on CB 1 with larger alkoxy groups (CB 2, 3, 4, 5) along with removal of substitution on the pyrimidine ring (CB 6) abolished antagonist activity. However, replacement with a methyl or ethyl group (CB 7 and CB 8, respectively) retained activity. Although the tetra-chloro CB 9 was not potent, the presence of one chloro substituent increased activity (CB 10 and CB 11). Indeed, CB 10 showed sub-micromolar inhibition of AR-F876L. Addition of the methyl group on CB 12 and substitution of the chloro with a methoxy group (CB 15 and CB 16) retained activity. The exchange of the phenyl group with a diphenyl ring (CB 13) or a thienyl group (CB 14 and CB 17) was not tolerated well. Additionally, thioether, sulfonyl, and amino substitutions were not effective (CB 18, 19, 20).

To assess the therapeutic potential of the CBs, we expanded our studies to examine additional modes of resistance to current anti-androgens. We utilized the CV1 transient transfection assay to look at the antagonistic activity of the CBs against WT-AR and two additional mutants, T877A and W741C, developed after treatment with OHF and CSX, respectively (Table 1). The most potent inhibitors of AR-F876L (CB 1, 7, 10, 11, 12, 15) were equally effective at inhibiting AR-T877A and retained fairly potent inhibition of AR-W741C. To our surprise, the CBs did not inhibit WT-AR at the same concentrations, with only CB 10 and CB 15 having an $IC_{50}$ of less than 10 M. This unique 10-30 fold selectivity of the CBs for mutant ARs suggests that compounds of this class could be developed with selectivity for a range of prostate cancer-associated mutants.

Figure 48A:
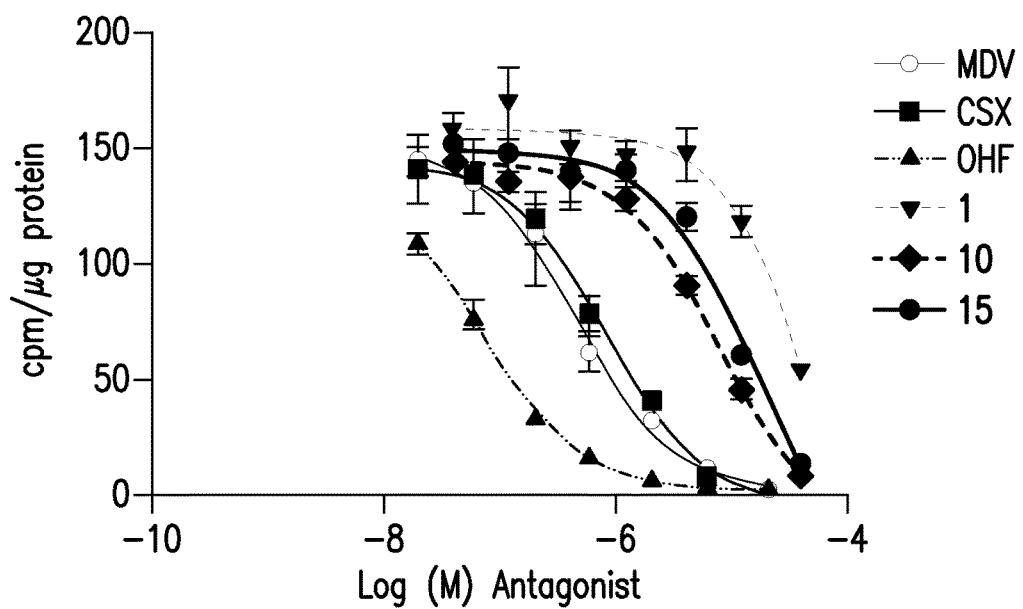
FIGS. 48A, B, C, and D depict whole-cell competition binding assays using $^3$H-R1881 for cyclobutane compounds 1, 10, and 15 of Example V, compared to MDV, bicalutamide (CSX), and OHF.
Figure 48B:
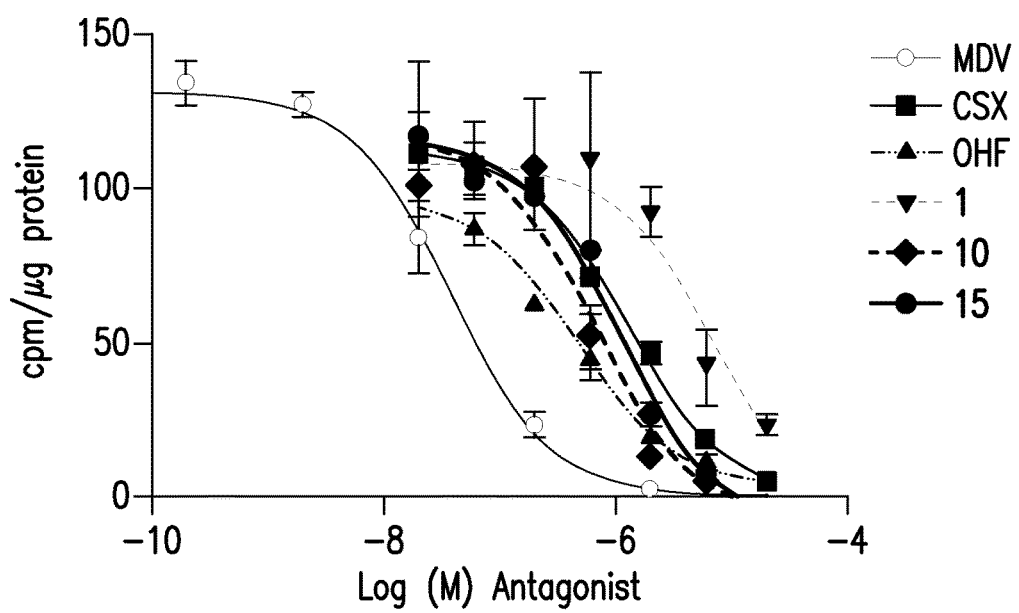
FIG. 48E depicts IC50 data for compounds 1, 10, and 15 of Example V, compared to MDV, CSX, and OHF for wild type and mutant F 876L, T877A, and W741C androgen receptors for a whole cell competition binding assay using $^3$H R1881.
Figure 48C:
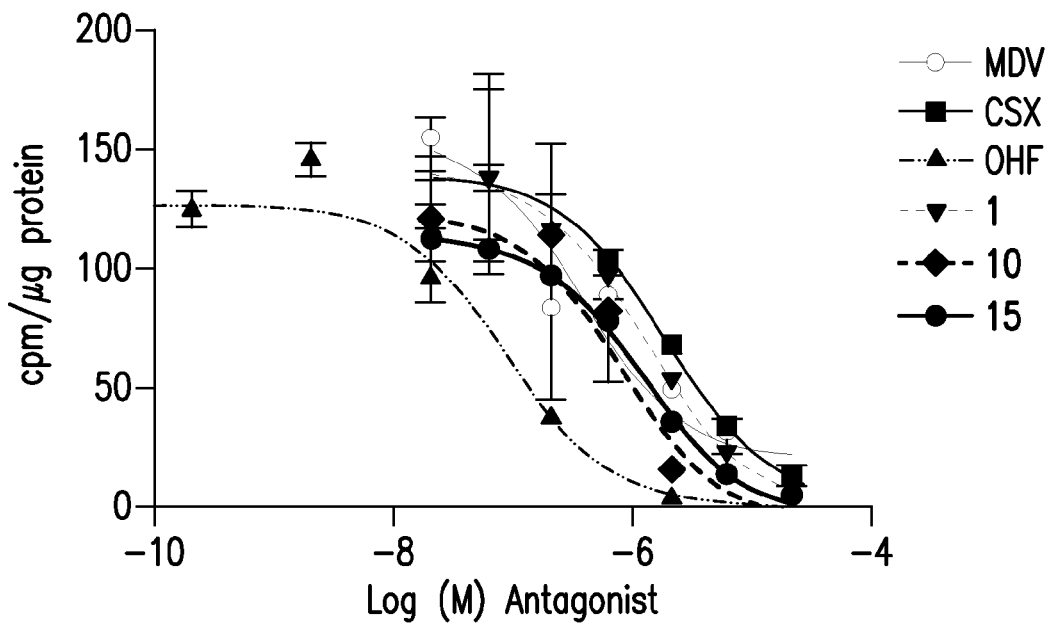
Figure 48D:
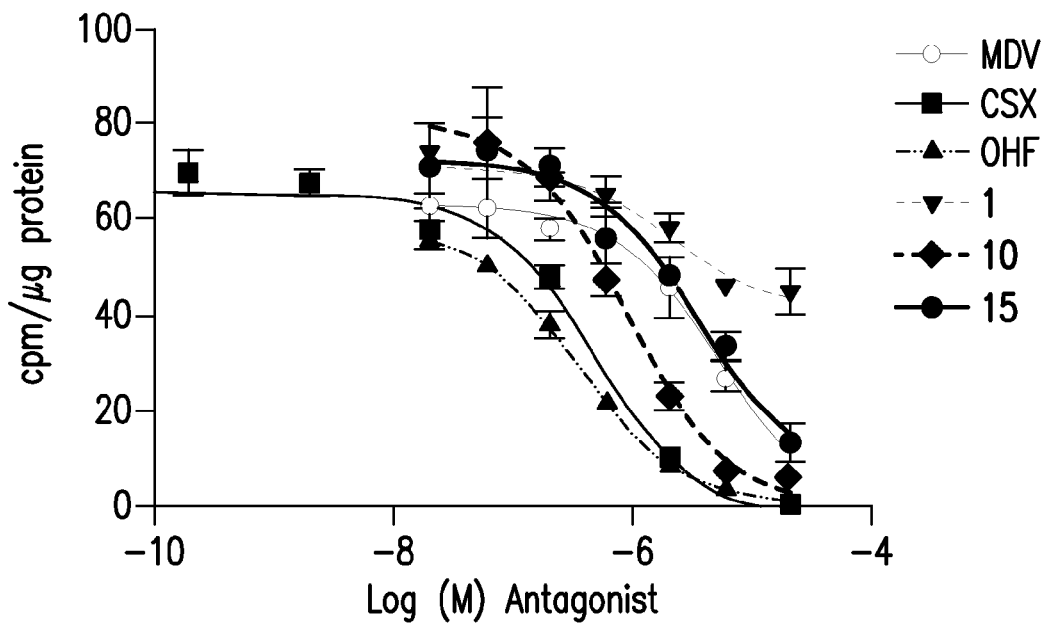

The structure of the CBs is not similar to known AR ligands; therefore, we set out to determine whether they have a unique mode of inhibition. Using $^3$H-R1881 whole-cell competition binding assays, we determined that they are able to disrupt agonist binding (FIGS. 48A-D) as unlabeled CB 1, 10, and 15 effectively compete against R1881 binding at concentrations near their predicted $IC_{50}$ for each mutant AR and WT-AR (FIG. 48E). We confirmed that CB 10 is a competitive antagonist of AR as it did not decrease the maximal R1881 stimulated response of the MMTV luciferase reporter but did decrease the apparent $EC_{50}$.

Figure 49:
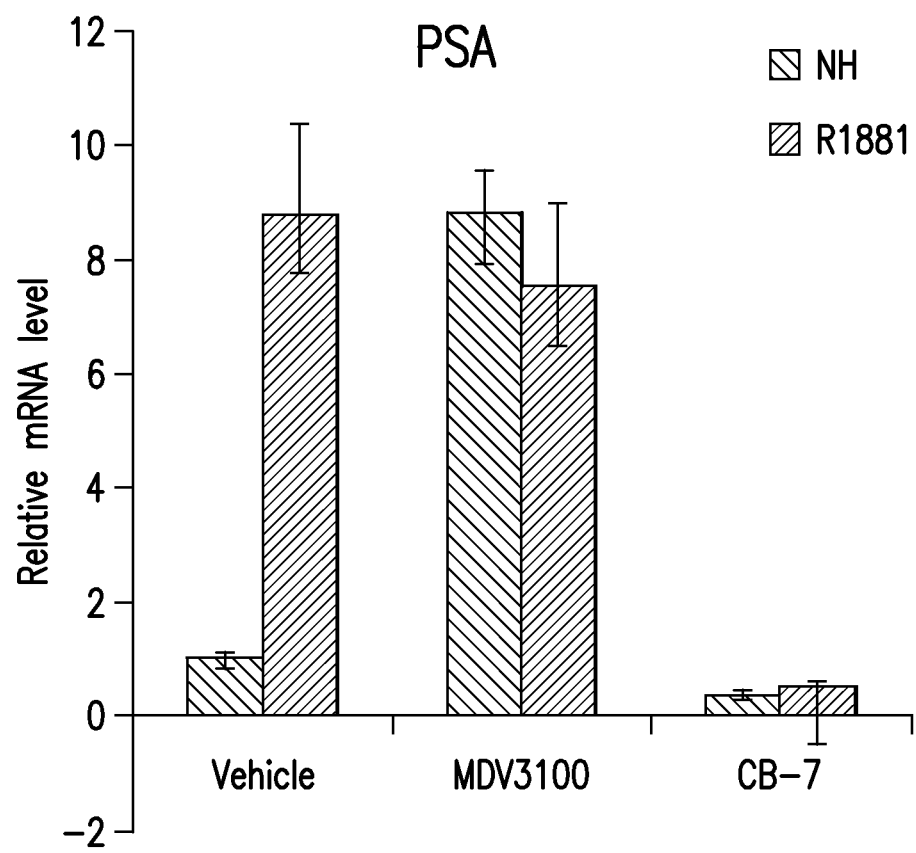
FIG. 49 depicts the mRNA levels of endogenous PSA after treatment of XIP-F876L cells with compound CB10 of Example V in the presence and absence of agonist R1881 compared to MDV.

We next sought to determine whether CB 10 could antagonize endogenous AR transcriptional activity in the prostate cancer cell line, LNCaP, which expresses AR-T877A. CB 10 inhibits R1881-mediated PSA, NKX3.1, and FKBP51 mRNA expression with the same efficacy as MDV. In addition, CB 10 inhibits androgen-stimulated proliferation of LNCaP cells equally as well as MDV (FIG. 20A). In order to examine the therapeutic potential of the CBs, we generated two prostate cancer cell lines that mimic mechanisms of CRPC; XIP-AR expresses a high level of AR and XIP-F876L expresses mutant AR resistant to MDV. In both cell lines, R1881, an AR agonist, induces cell proliferation. We then examined the ability of CB 1, 10, and 15 to inhibit AR transcriptional activity in these CRPC cell lines. CSX promotes expression of AR target genes in XIP-AR overexpressing cells while the CBs and MDV do not. In the presence of R1881, CB 10 and 15 reverse androgen stimulated gene expression similar to MDV. CB 1 is less effective in this context because it has a higher $IC_{50}$ for WT-AR. In the XIP-F876L cell line, MDV stimulates expression of AR target genes, but the CBs do not (FIG. 49). In addition, in antagonist mode, the CBs once again reverse R1881 stimulated gene expression while MDV fails (FIG. 49).

Figure 50:
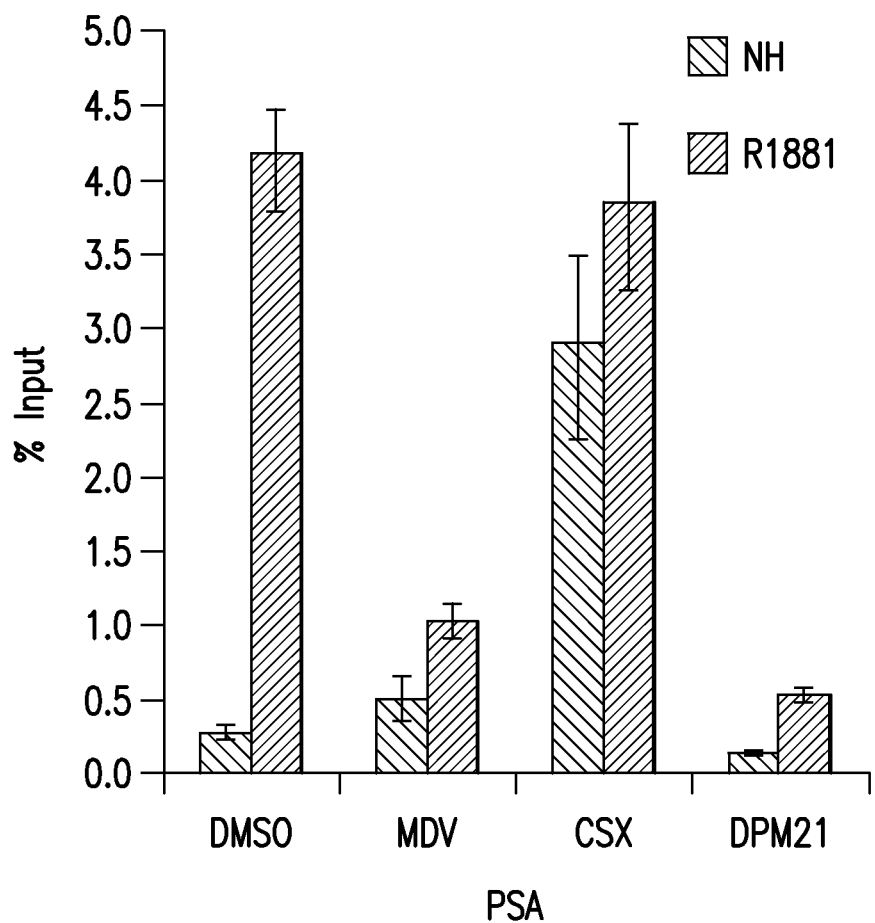
FIG. 50 depicts the percentage of androgen receptor recruited to the PSA ARE in XIP-AR cells after treatment with compound CB10 of Example V, MDV and CSX in the presence and absence of the agonist R1881.
Figure 51:
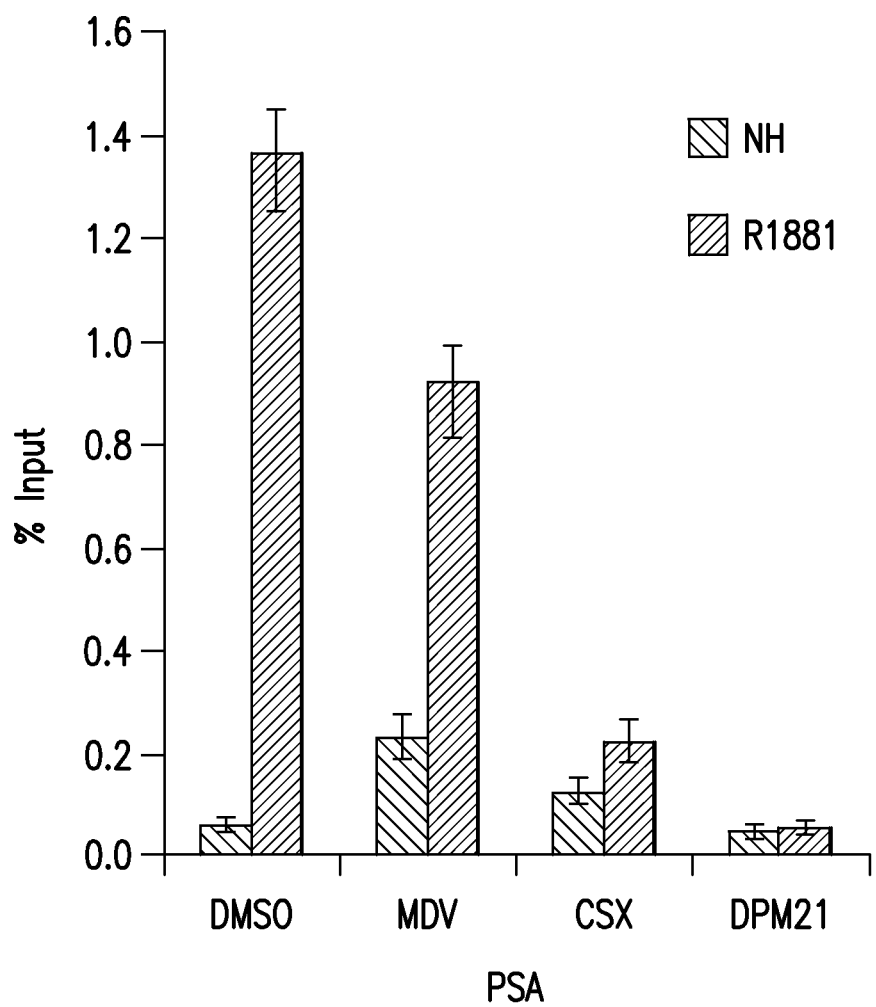
FIG. 51 depicts the percentage of androgen receptor recruited to the PSA ARE in XIP-F876L cells after treatment with compound CB10 of Example V, MDV, and CSX in the presence and absence of the agonist R1881.

To further discern the mechanism of action of the CBs, we performed chromatin immunoprecipitation in both XIP-AR and XIP-F876L cells and compared their ability to recruit AR to androgen-response elements of PSA and NKX3.1. In the XIP-AR cells, CSX induces AR recruitment similar to R1881 while MDV and CB 10 inhibit the recruitment (FIG. 50). In the XIP-F876L model, MDV fails to inhibit AR recruitment while CB 10 continues to be effective; CB 10 inhibits AR recruitment more effectively than CSX in this case as well (FIG. 51). Although the CBs do not promote AR degradation similar to geldanamycin, at high concentrations, they trend towards receptor turnover); perhaps future optimization of the CBs may uncover this activity more. These results indicate that the cyclobutanes bind to an apo conformation of the androgen receptor. In order to investigate this further, we examined the cellular location of AR after treatment with compound CB 10 using microscopy. After treatment with CB10, AR is primarily outside of the nucleus in stark contrast to MDV, CSX, and R1881 which each promote nuclear translocation.

Inhibition of Prostate Cancer Cell Proliferation

Figure 52A:
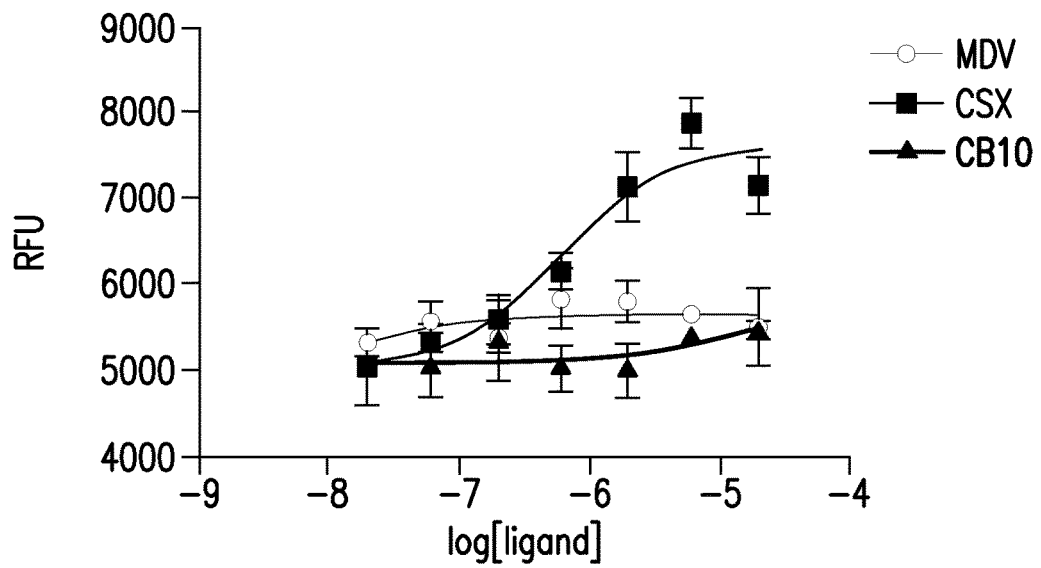
FIGS. 52A and B depict data for the growth effects of compound CB 10 of Example V on the XIP-AR and XIP-F876L cell lines.
Figure 52B:
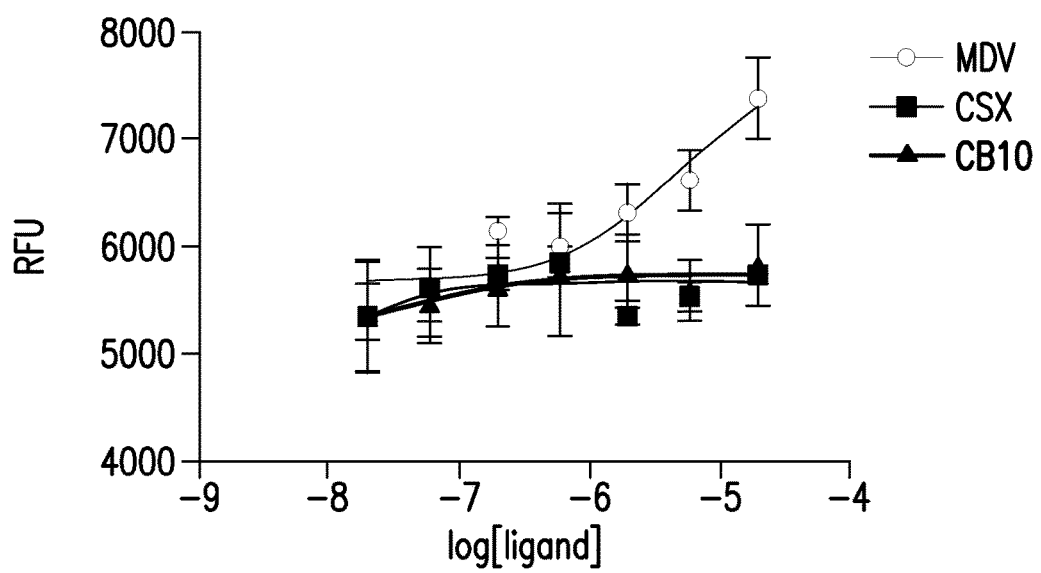

To further mimic CRPC, we assess the growth effects of CB 10 on the XIP-AR and XIP-F876L cell lines. CSX and OHF promote cell proliferation in XIP-AR overexpressing cells); however, MDV and CB 10 do not (FIG. 52A). Similarly, in XIP-F876L cells, MDV promotes cell proliferation, but CB 10 does not (FIG. 52B).

Animal Studies

Based on the above results, we further evaluated the effects of CB 10 in vivo. We generated a mouse xenograft of the XIP-F876L cell line that is resistant to MDV. We also utilized a traditional in vivo model of prostate cancer, the LNCaP xenograft model. For this study, intact male mice bearing LNCaP xenografts were treated with MDV (15 mpk) or an escalating dose of CB 10 (5 mpk to 100 mpk). Administration of CB 10 (50 mpk or 100 mpk) significantly inhibited androgen-responsive LNCaP human prostate cancer cell tumor growth (FIG. 24). Furthermore, an evaluation of tumor weight at the study termination indicated that there was a significant dose dependent inhibition of tumor growth with CB 10 treatment suggesting on-target activity of the drug.

The identification of novel modulators of AR function is essential in combating hormone-refractory prostate cancer, especially as resistance to clinically approved drugs continues to develop. Here we have identified competitive AR antagonists of novel structure that inhibit endogenous gene expression, slow cellular proliferation, and inhibit tumor formation. These compounds are of particular interest because they are effective at inhibiting resistant mutant ARs that arise after prior hormone treatment, as we demonstrate with MDV (F876L), OHF (T887A), and CSX (W741C) pertinent mutants. Although previous work has focused on successfully inhibiting these mutant receptors, it has resulted in compounds with comparable effects on the WT AR[11-13]. We propose that mutant-selective AR inhibitors that we have developed may provide effective therapy for hormone-refractory prostate cancer, while theoretically avoiding the negative side effects associated with androgen deprivation. This approach has proven valuable in targeting the mutant form of BRAF, and consequently, in 2011, the FDA approved vemurafenib (PLX4032/RG7204, Plexxikon/Roche) for the treatment of metastatic melanoma bearing the BRAF V600E mutation[14-16]. Therefore, we believe that these new mutant-selective antagonists might provide valuable insight for the development of therapeutics to treat advanced prostate cancer.

REFERENCES

The references numbers cited in Example V correspond to the references listed at the end of this Example V.

(1) Siegel, R., Ma, J., Zou, Z., and Jemal, A. (2014) Cancer statistics, 2014, *CA Cancer J Clin* 64, 9-29.

(2) Chen, C. D., Welsbie, D. S., Tran, C., Baek, S. H., Chen, R., Vessella, R., Rosenfeld, M. G., and Sawyers, C. L. (2004) Molecular determinants of resistance to antiandrogen therapy, *Nat Med* 10, 33-39.

(3) Beltran, H., Yelensky, R., Frampton, G. M., Park, K., Downing, S. R., MacDonald, T. Y., Jarosz, M., Lipson, D., Tagawa, S. T., Nanus, D. M., Stephens, P. J., Mosquera, J. M., Cronin, M. T., and Rubin, M. A. (2013) Targeted next-generation sequencing of advanced prostate cancer identifies potential therapeutic targets and disease heterogeneity, *Eur Urol* 63, 920-926.

(4) Hara, T., Miyazaki, J., Araki, H., Yamaoka, M., Kanzaki, N., Kusaka, M., and Miyamoto, M. (2003) Novel mutations of androgen receptor: a possible mechanism of bicalutamide withdrawal syndrome, *Cancer Res* 63, 149-153.

(5) Veldscholte, J., Ris-Stalpers, C., Kuiper, G. G., Jenster, G., Berrevoets, C., Claassen, E., van Rooij, H. C., Trapman, J., Brinkmann, A. O., and Mulder, E. (1990) A mutation in the ligand binding domain of the androgen receptor of human LNCaP cells affects steroid binding characteristics and response to anti-androgens, *Biochem Biophys Res Commun* 173, 534-540.

(6) Clegg, N. J., Wongvipat, J., Joseph, J. D., Tran, C., Ouk, S., Dilhas, A., Chen, Y., Grillot, K., Bischoff, E. D., Cai, L., Aparicio, A., Dorow, S., Arora, V., Shao, G., Qian, J., Zhao, H., Yang, G., Cao, C., Sensintaffar, J., Wasielewska, T., Herbert, M. R., Bonnefous, C., Darimont, B., Scher, H. I., Smith-Jones, P., Klang, M., Smith, N. D., De Stanchina, E., Wu, N., Ouerfelli, O., Rix, P. J., Heyman, R. A., Jung, M. E., Sawyers, C. L., and Hager, J. H. (2012) ARN-509: a novel antiandrogen for prostate cancer treatment, *Cancer Res* 72, 1494-1503.

(7) Tran, C., Ouk, S., Clegg, N. J., Chen, Y., Watson, P. A., Arora, V., Wongvipat, J., Smith-Jones, P. M., Yoo, D., Kwon, A., Wasielewska, T., Welsbie, D., Chen, C. D., Higano, C. S., Beer, T. M., Hung, D. T., Scher, H. I., Jung, M. E., and Sawyers, C. L. (2009) Development of a second-generation antiandrogen for treatment of advanced prostate cancer, *Science* 324, 787-790.

(8) Joseph, J. D., Lu, N., Qian, J., Sensintaffar, J., Shao, G., Brigham, D., Moon, M., Maneval, E. C., Chen, I., Darimont, B., and Hager, J. H. (2013) A clinically relevant androgen receptor mutation confers resistance to second-generation antiandrogens enzalutamide and ARN-509, *Cancer Discov* 3, 1020-1029.

(9) Korpal, M., Korn, J. M., Gao, X., Rakiec, D. P., Ruddy, D. A., Doshi, S., Yuan, J., Kovats, S. G., Kim, S., Cooke, V. G., Monahan, J. E., Stegmeier, F., Roberts, T. M., Sellers, W. R., Zhou, W., and Zhu, P. (2013) An F876L mutation in androgen receptor confers genetic and phenotypic resistance to MDV3100 (enzalutamide), *Cancer Discov* 3, 1030-1043.

(10) Parent, A. A., Halsell Ess, D., and Katzenellenbogen, J. A. (2014) pi-pi Interaction energies as determinants of the photodimerization of mono-, di- and triazastilbenes, *J Org Chem*.

(11) Wakabayashi, K., Imai, K., Miyachi, H., Hashimoto, Y., and Tanatani, A. (2008) 4-(Anilino)pyrrole-2-carboxamides: Novel non-steroidal/non-anilide type androgen antagonists effective upon human prostate tumor LNCaP cells with mutated nuclear androgen receptor, *Bioorg Med Chem* 16, 6799-6812.

(12) Oh, S., Nam, H. J., Park, J., Beak, S. H., and Park, S. B. (2010) Development of a benzopyran-containing androgen receptor antagonist to treat antiandrogen-resistant prostate cancer, *ChemMedChem* 5, 529-533.

(13) Yamamoto, S., Kobayashi, H., Kaku, T., Aikawa, K., Hara, T., Yamaoka, M., Kanzaki, N., Hasuoka, A., Baba, A., and Ito, M. (2013) Design, synthesis, and biological evaluation of 3-aryl-3-hydroxy-1-phenylpyrrolidine derivatives as novel androgen receptor antagonists, *Bioorg Med Chem* 21, 70-83.

(14) Bollag, G., Hirth, P., Tsai, J., Zhang, J., Ibrahim, P. N., Cho, H., Spevak, W., Zhang, C., Zhang, Y., Habets, G., Burton, E. A., Wong, B., Tsang, G., West, B. L., Powell, B., Shellooe, R., Marimuthu, A., Nguyen, H., Zhang, K. Y., Artis, D. R., Schlessinger, J., Su, F., Higgins, B., Iyer, R., D'Andrea, K., Koehler, A., Stumm, M., Lin, P. S., Lee, R. J., Grippo, J., Puzanov, I., Kim, K. B., Ribas, A., McArthur, G. A., Sosman, J. A., Chapman, P. B., Flaherty, K. T., Xu, X., Nathanson, K. L., and Nolop, K. (2010) Clinical efficacy of a RAF inhibitor needs broad target blockade in BRAF-mutant melanoma, *Nature* 467, 596-599.

(15) Flaherty, K., Puzanov, I., Sosman, J., Kim, K., Ribas, A., McArthur, G., Lee, R. J., Grippo, J. F., Nolop, K., and Chapman, P. (2009) Phase I study of PLX4032: Proof of concept for V600E BRAF mutation as a therapeutic target in human cancer, *Journal of Clinical Oncology* 27.

(16) Flaherty, K. T., Puzanov, I., Kim, K. B., Ribas, A., McArthur, G. A., Sosman, J. A., O'Dwyer, P. J., Lee, R. J., Grippo, J. F., Nolop, K., and Chapman, P. B. (2010) Inhibition of mutated, activated BRAF in metastatic melanoma, *N Engl J Med* 363, 809-819.

| Example VI. Detailed List of Currently Synthesized Cyclobutanes | |
|---|---|
| name | Structure |
| CB-1 | 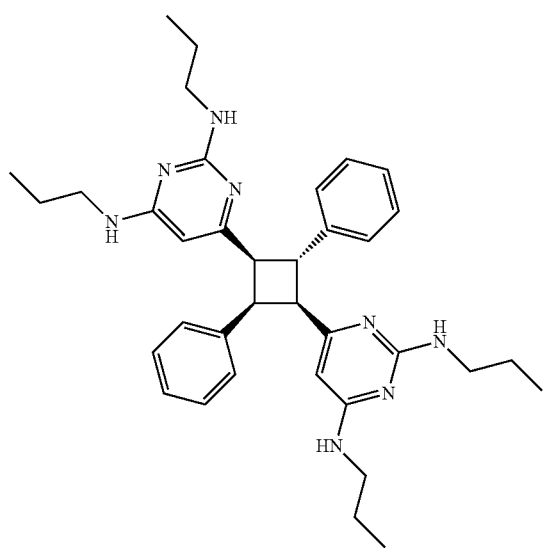 [SMILES: CCCNc1cc([C@H]2[C@H](c3ccccc3)[C@@H](c3cc(NCCC)nc(NCCC)n3)[C@H]2c2ccccc2)nc(NCCC)n1] |

Example VI. Detailed List of Currently Synthesized Cyclobutanes
| name | Structure |
|---|---|
| CB-2 | 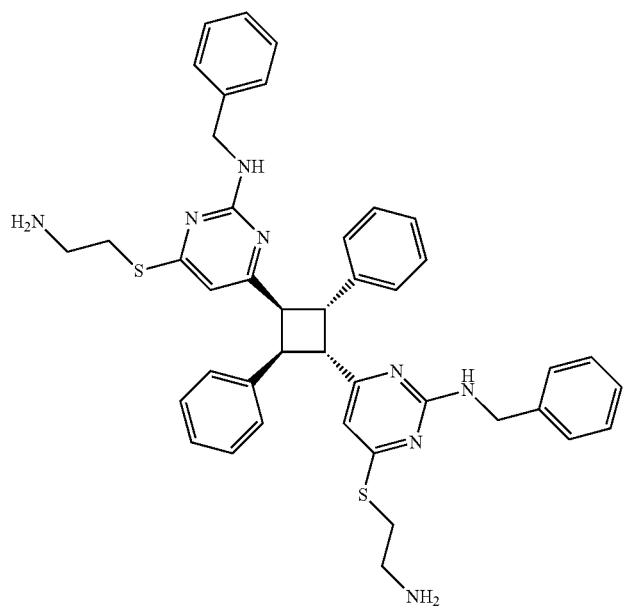 [SMILES: NCCSc1cc([C@H]2[C@H](c3ccccc3)[C@H](c3cc(SCCN)nc(NCc4ccccc4)n3)[C@H]2c2ccccc2)nc(NCc2ccccc2)n1] |
| CB-3 | 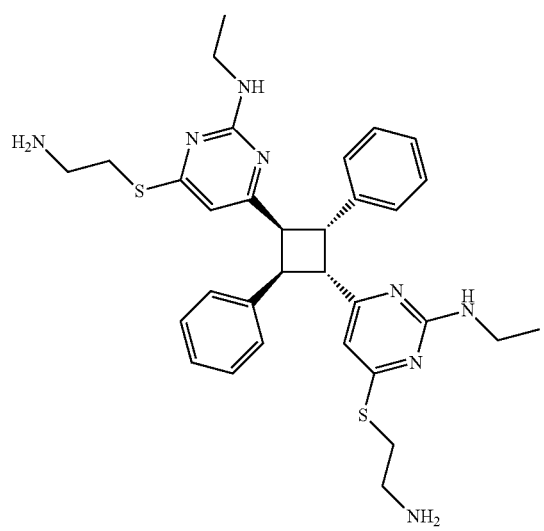 [SMILES: CCNc1nc(SCCN)cc([C@H]2[C@H](c3ccccc3)[C@H](c3cc(SCCN)nc(NCC)n3)[C@H]2c2ccccc2)n1] |

-continued
Example VI. Detailed List of Currently Synthesized Cyclobutanes
| name | Structure |
|---|---|
| CB-4 | 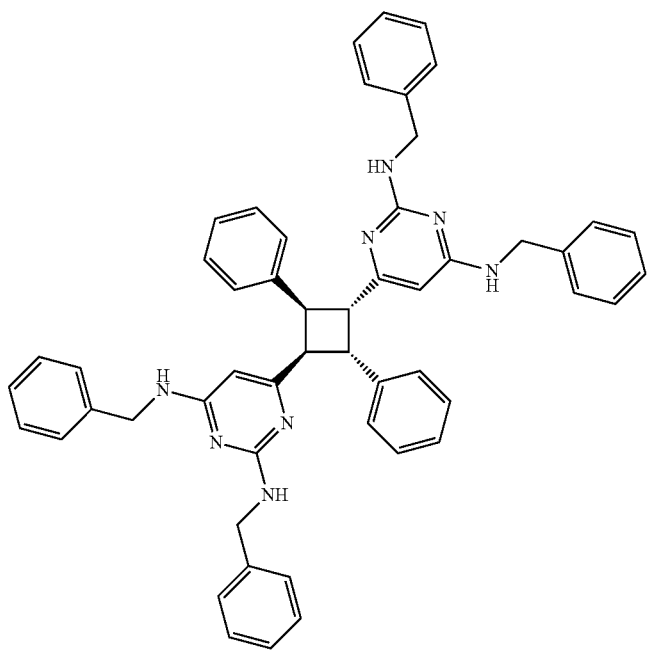 [SMILES: c1ccc(CNc2cc([C@H]3[C@H](c4ccccc4)[C@H](c4cc(NCc5ccccc5)nc(NCc5ccccc5)n4)[C@H]3c3ccccc3)nc(NCc3ccccc3)n2)cc1] |
| CB-5 | 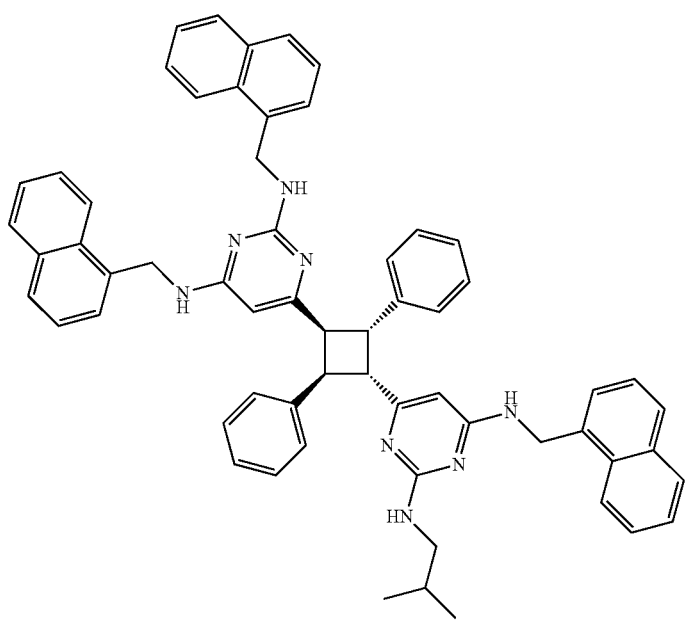 [SMILES: CC(C)CNc1nc(NCc2cccc3ccccc23)cc([C@H]2[C@@H](c3ccccc3)[C@H](c3cc(NCc4cccc5ccccc45)nc(NCc4cccc5ccccc45)n3)[C@@H]2c2ccccc2)n1] |

-continued
Example VI. Detailed List of Currently Synthesized Cyclobutanes
| name | Structure |
|---|---|
| CB-6 | 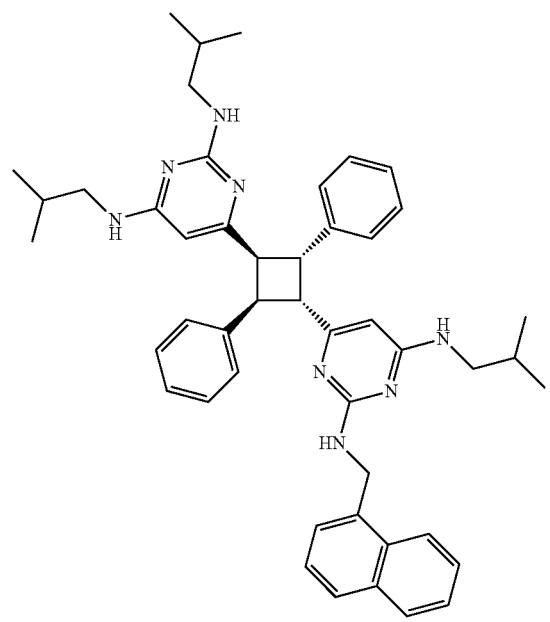 [SMILES: CC(C)CNc1cc([C@H]2[C@@H](c3ccccc3)[C@H](c3cc(NCC(C)C)nc(NCC(C)C)n3)[C@@H]2c2ccccc2)nc(NCc2cccc3ccccc23)n1] |
| CB-7 | 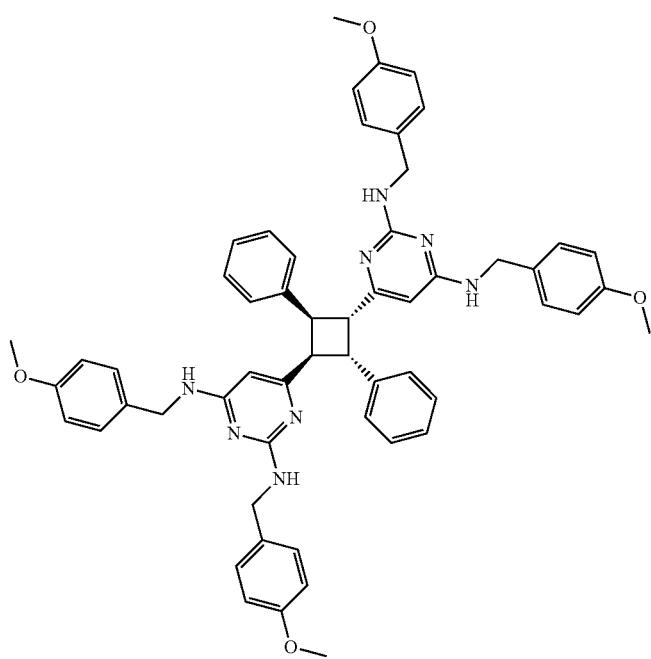 |

-continued
Example VI. Detailed List of Currently Synthesized Cyclobutanes
| name | Structure |
|---|---|
| CB-8 | 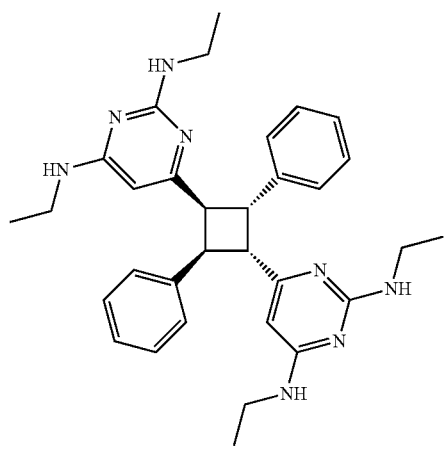 [SMILES: CCNc1cc([C@H]2[C@H](c3ccccc3)[C@H](c3cc(NCC)nc(NCC)n3)[C@H]2c2ccccc2)nc(NCC)n1] |
| CB-9 | 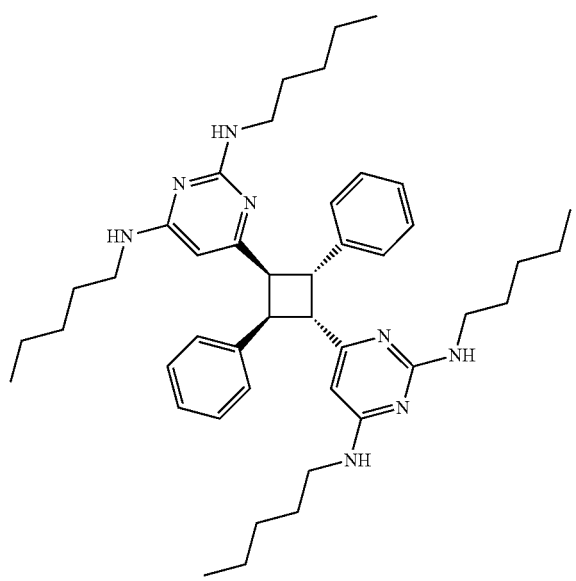 [SMILES: CCCCCNc1cc([C@H]2[C@H](c3ccccc3)[C@H](c3cc(NCCCCC)nc(NCCCCC)n3)[C@H]2c2ccccc2)nc(NCCCCC)n1] |

Example VI. Detailed List of Currently Synthesized Cyclobutanes
| name | Structure |
|---|---|
| CB-10 | 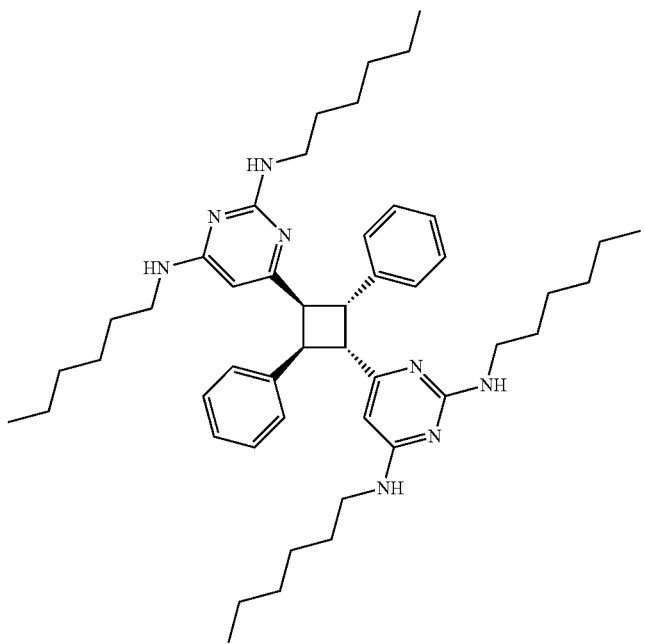 [SMILES: CCCCCCNc1cc([C@H]2[C@H](c3ccccc3)[C@H](c3cc(NCCCCCC)nc(NCCCCCC)n3)[C@H]2c2ccccc2)nc(NCCCCCC)n1] |
| CB-11 | 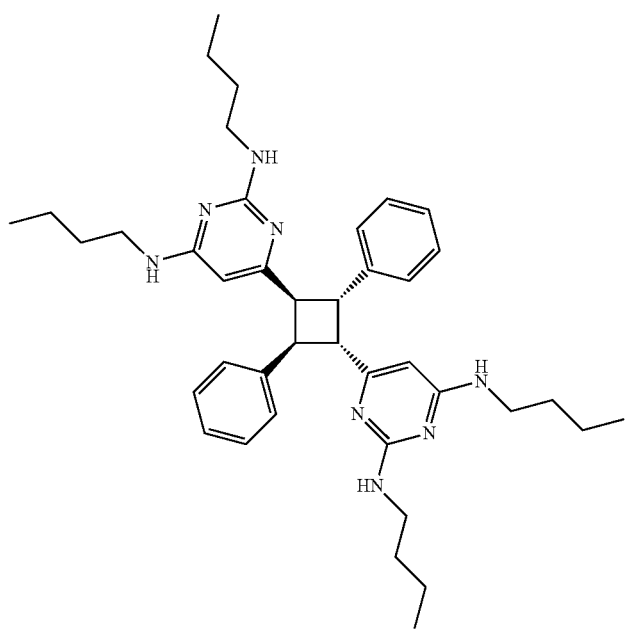 [SMILES: CCCCNc1cc([C@H]2[C@H](c3ccccc3)[C@H](c3cc(NCCCC)nc(NCCCC)n3)[C@H]2c2ccccc2)nc(NCCCC)n1] |

-continued
Example VI. Detailed List of Currently Synthesized Cyclobutanes
| name | Structure |
|---|---|
| CB-12 | 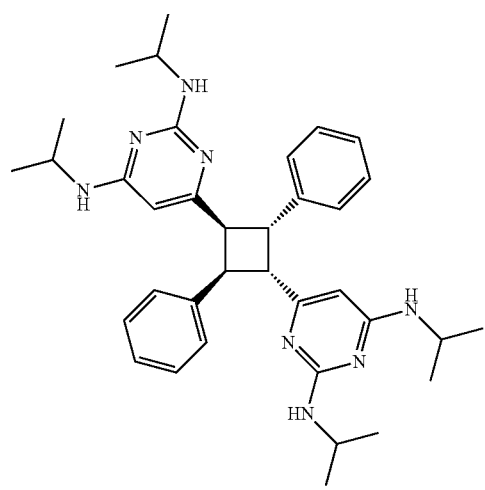 [SMILES: CC(C)Nc1cc([C@H]2[C@H](c3ccccc3)[C@H](c3cc(NC(C)C)nc(NC(C)C)n3)[C@H]2c2ccccc2)nc(NC(C)C)n1] |
| CB-13 | 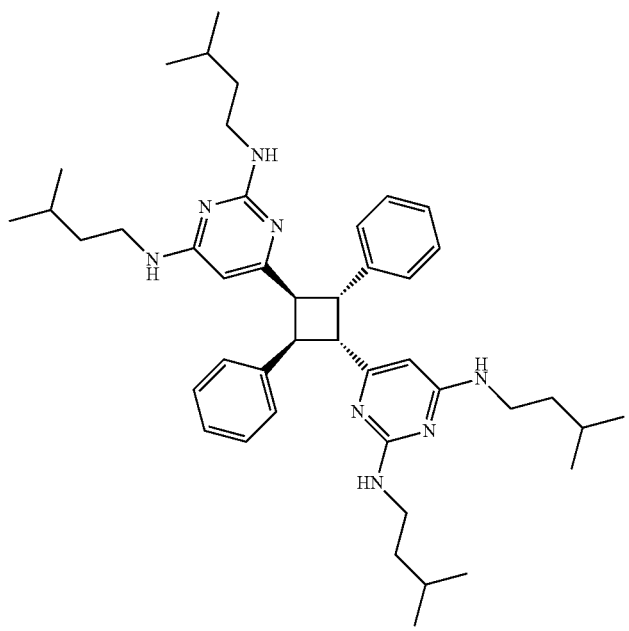 [SMILES: CC(C)CCNc1cc([C@H]2[C@H](c3ccccc3)[C@H](c3cc(NCCC(C)C)nc(NCCC(C)C)n3)[C@H]2c2ccccc2)nc(NCCC(C)C)n1] |

-continued
Example VI. Detailed List of Currently Synthesized Cyclobutanes
| name | Structure |
|------|-----------|
| CB-14 | 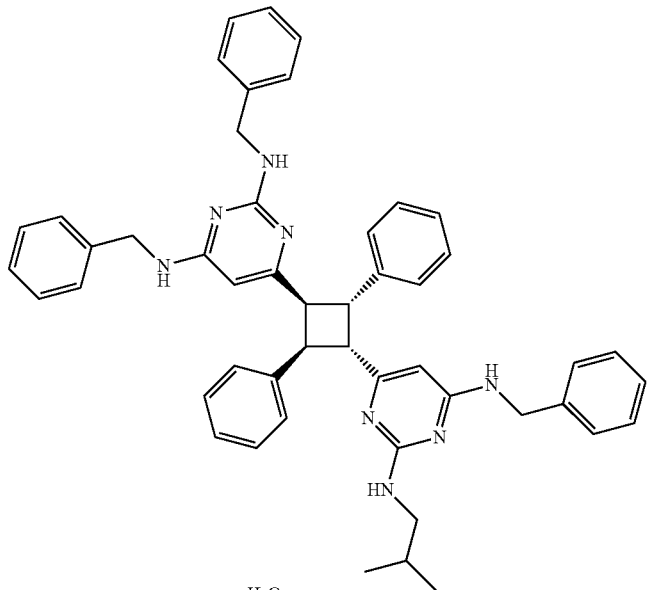 [SMILES: CC(C)CNc1nc(NCc2ccccc2)cc([C@H]2[C@@H](c3ccccc3)[C@H](c3cc(NCc4ccccc4)nc(NCc4ccccc4)n3)[C@@H]2c2ccccc2)n1] |
| CB-15 | 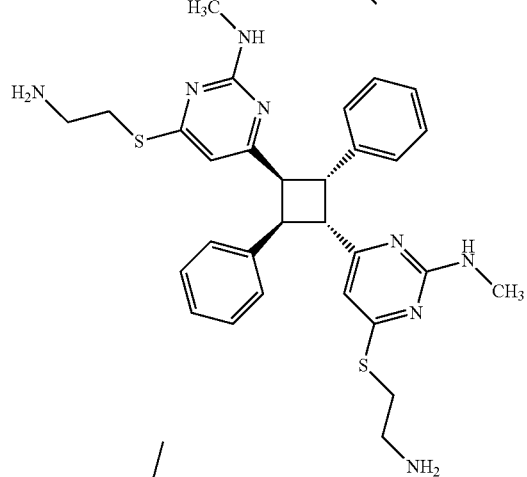 [SMILES: CNc1nc(SCCN)cc([C@H]2[C@H](c3ccccc3)[C@H](c3cc(SCCN)nc(NC)n3)[C@H]2c2ccccc2)n1] |
| CB-16 | 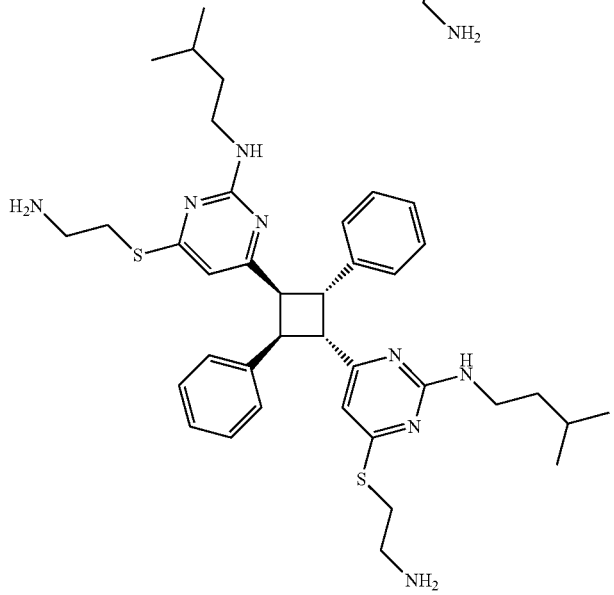 |

-continued
Example VI. Detailed List of Currently Synthesized Cyclobutanes
| name | Structure |
|---|---|
| CB-17 | 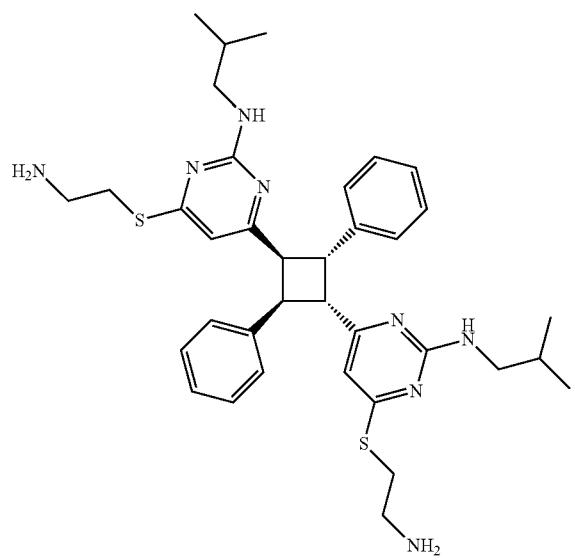 [SMILES: CC(C)CNc1nc(SCCN)cc([C@H]2[C@H](c3ccccc3)[C@H](c3cc(SCCN)nc(NCC(C)C)n3)[C@H]2c2ccccc2)n1] |
| CB-18 | 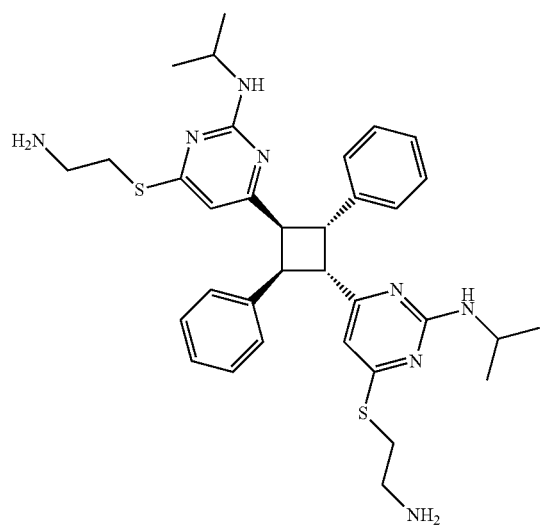 [SMILES: CC(C)Nc1nc(SCCN)cc([C@H]2[C@H](c3ccccc3)[C@H](c3cc(SCCN)nc(NC(C)C)n3)[C@H]2c2ccccc2)n1] |

Example VI. Detailed List of Currently Synthesized Cyclobutanes
| name | Structure |
|---|---|
| CB-19 | 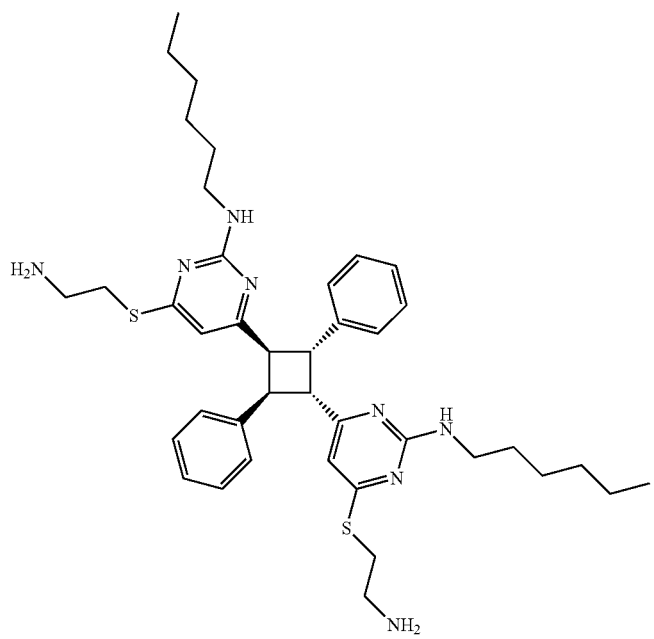 [SMILES: CCCCCCNc1nc(SCCN)cc([C@H]2[C@H](c3ccccc3)[C@H](c3cc(SCCN)nc(NCCCCCC)n3)[C@H]2c2ccccc2)n1] |
| CB-20 | 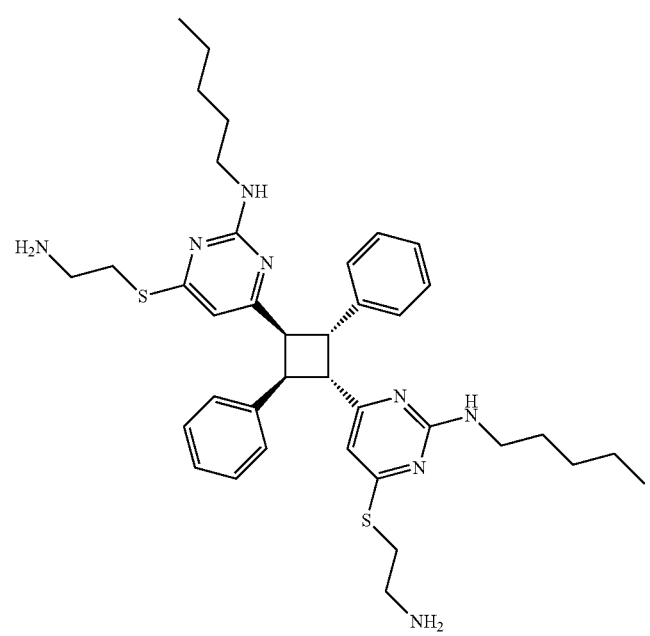 [SMILES: CCCCCNc1nc(SCCN)cc([C@H]2[C@H](c3ccccc3)[C@H](c3cc(SCCN)nc(NCCCCC)n3)[C@H]2c2ccccc2)n1] |

-continued
Example VI. Detailed List of Currently Synthesized Cyclobutanes
| name | Structure |
|---|---|
| CB-21 | 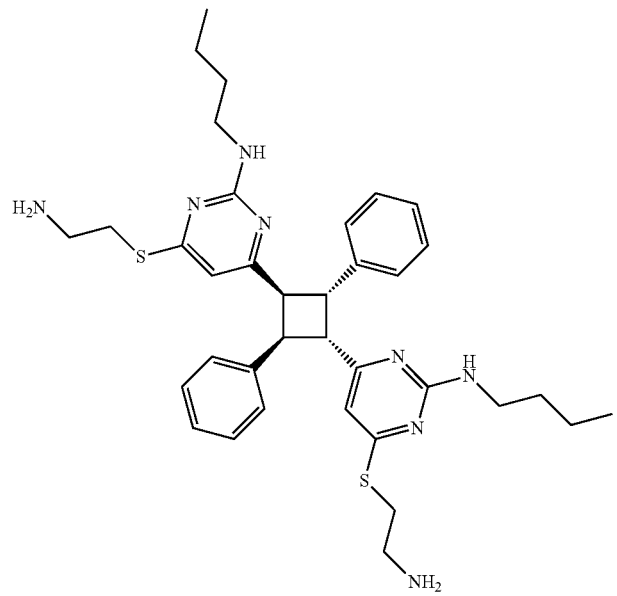 [SMILES: CCCCNc1nc(SCCN)cc([C@H]2[C@H](c3ccccc3)[C@H](c3cc(SCCN)nc(NCCCC)n3)[C@H]2c2ccccc2)n1] |
| CB-22 | 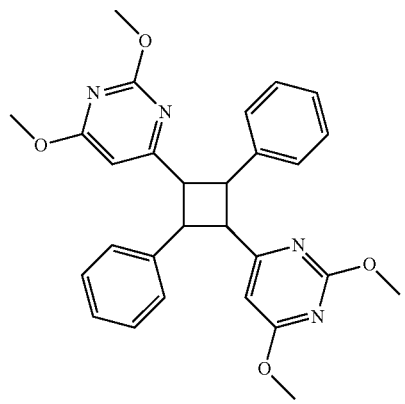 |
| CB-23 | 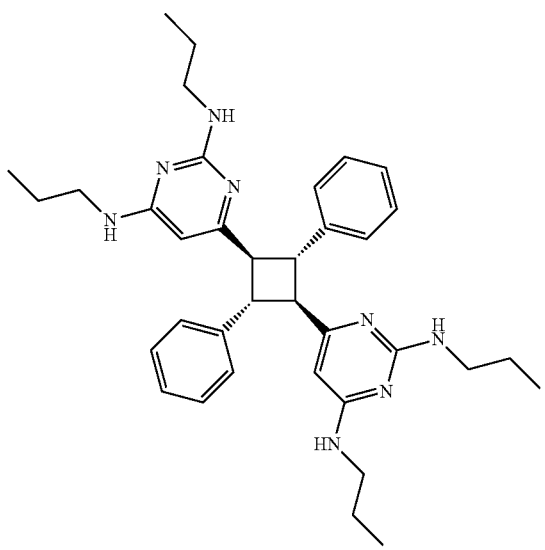 [SMILES: CCCNc1cc([C@H]2[C@H](c3ccccc3)[C@@H](c3cc(NCCC)nc(NCCC)n3)[C@@H]2c2ccccc2)nc(NCCC)n1] |

-continued
Example VI. Detailed List of Currently Synthesized Cyclobutanes
| name | Structure |
|---|---|
| CB-24 | 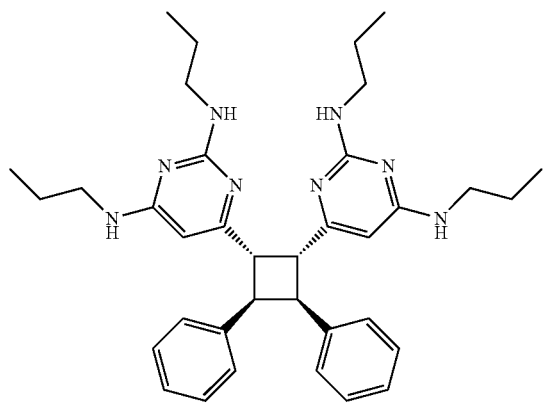 [SMILES: CCCNc1cc([C@@H]2[C@@H](c3ccccc3)[C@@H](c3ccccc3)[C@@H]2c2cc(NCCC)nc(NCCC)n2)nc(NCCC)n1] |
| CB-25 | 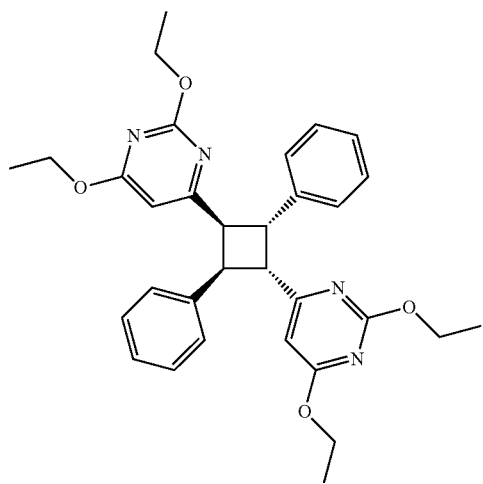 [SMILES: CCOc1cc([C@H]2[C@H](c3ccccc3)[C@H](c3cc(OCC)nc(OCC)n3)[C@H]2c2ccccc2)nc(OCC)n1] |
| CB-26 | 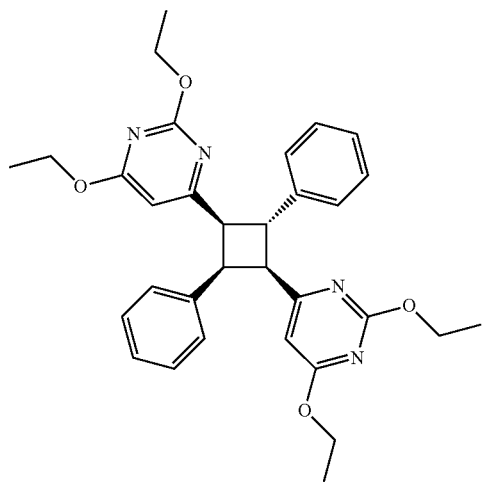 [SMILES: CCOc1cc([C@H]2[C@H](c3ccccc3)[C@@H](c3cc(OCC)nc(OCC)n3)[C@H]2c2ccccc2)nc(OCC)n1] |

Example VI. Detailed List of Currently Synthesized Cyclobutanes
| name | Structure |
|---|---|
| CB-27 | 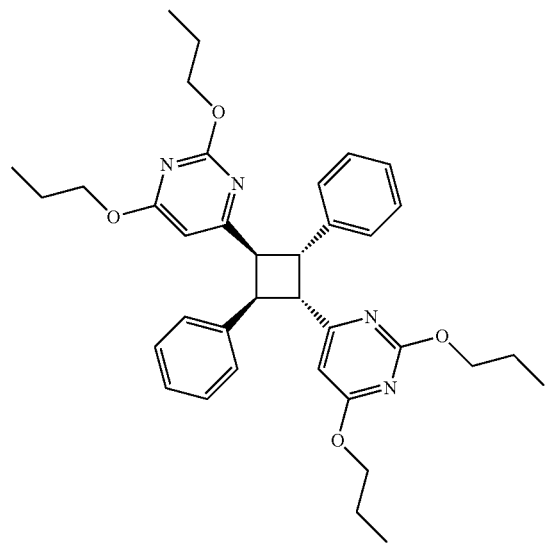 [SMILES: CCCOc1cc([C@H]2[C@H](c3ccccc3)[C@H](c3cc(OCCC)nc(OCCC)n3)[C@H]2c2ccccc2)nc(OCCC)n1] |
| CB-28 | 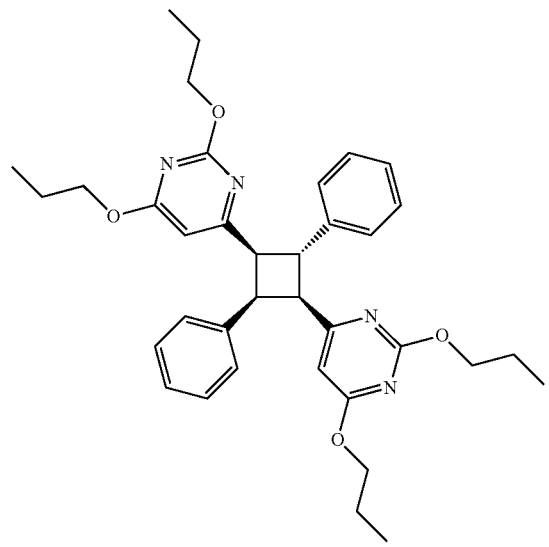 [SMILES: CCCOc1cc([C@H]2[C@H](c3ccccc3)[C@@H](c3cc(OCCC)nc(OCCC)n3)[C@H]2c2ccccc2)nc(OCCC)n1] |
| CB-29 | 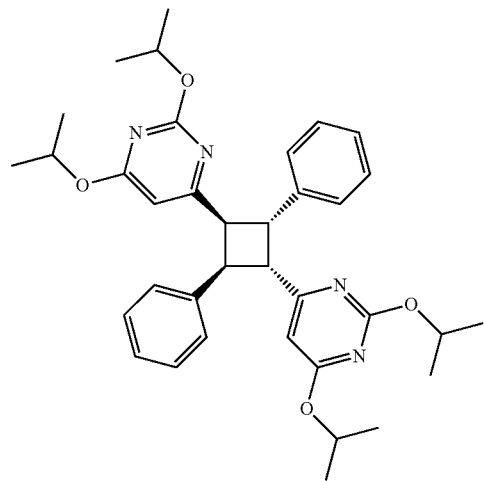 [SMILES: CC(C)Oc1cc([C@H]2[C@H](c3ccccc3)[C@H](c3cc(OC(C)C)nc(OC(C)C)n3)[C@H]2c2ccccc2)nc(OC(C)C)n1] |

Example VI. Detailed List of Currently Synthesized Cyclobutanes
| name | Structure |
|---|---|
| CB-30 | 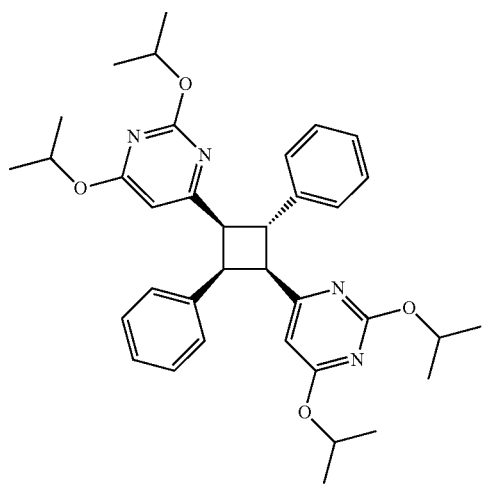 [SMILES: CC(C)Oc1cc([C@H]2[C@H](c3ccccc3)[C@@H](c3cc(OC(C)C)nc(OC(C)C)n3)[C@H]2c2ccccc2)nc(OC(C)C)n1] |
| CB-31 | 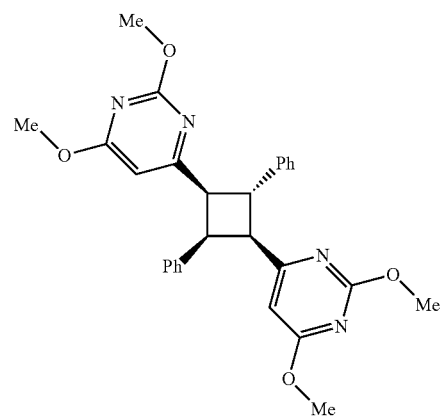 [SMILES: COc1cc([C@H]2[C@H](c3ccccc3)[C@@H](c3cc(OC)nc(OC)n3)[C@H]2c2ccccc2)nc(OC)n1] |
| CB-32 | 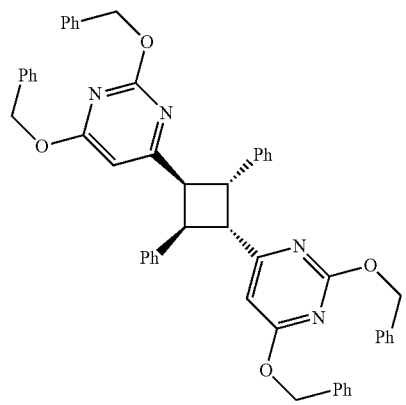 [SMILES: c1ccc(COc2cc([C@H]3[C@H](c4ccccc4)[C@H](c4cc(OCc5ccccc5)nc(OCc5ccccc5)n4)[C@H]3c3ccccc3)nc(OCc3ccccc3)n2)cc1] |

Example VI. Detailed List of Currently Synthesized Cyclobutanes
| name | Structure |
|---|---|
| CB-33 | 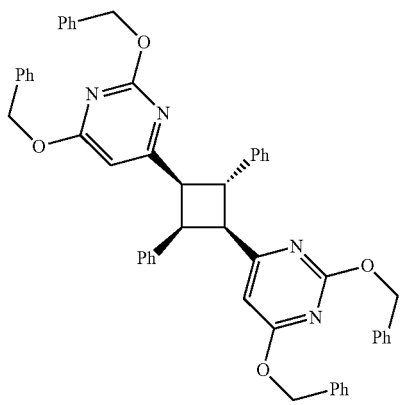 [SMILES: c1ccc(COc2cc([C@H]3[C@H](c4ccccc4)[C@@H](c4cc(OCc5ccccc5)nc(OCc5ccccc5)n4)[C@H]3c3ccccc3)nc(OCc3ccccc3)n2)cc1] |
| CB-34 | 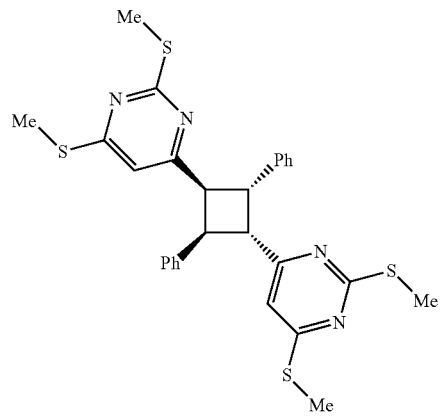 |
| CB-35 | 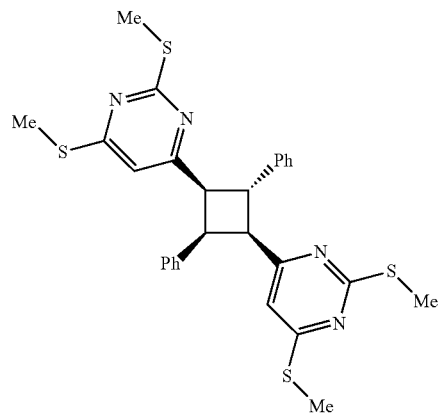 [SMILES: CSc1cc([C@H]2[C@H](c3ccccc3)[C@@H](c3cc(SC)nc(SC)n3)[C@H]2c2ccccc2)nc(SC)n1] |

Example VI. Detailed List of Currently Synthesized Cyclobutanes
| name | Structure |
|---|---|
| CB-36 | 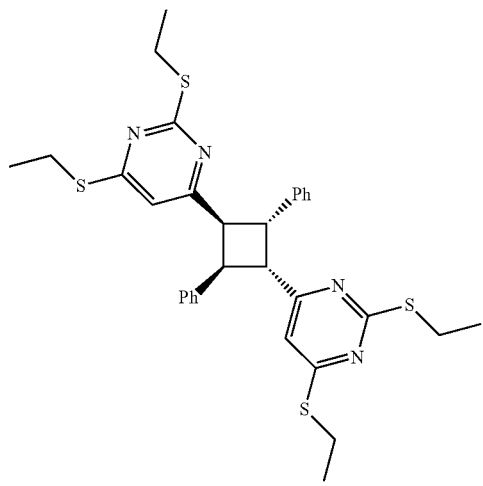 [SMILES: CCSc1cc([C@H]2[C@H](c3ccccc3)[C@H](c3cc(SCC)nc(SCC)n3)[C@H]2c2ccccc2)nc(SCC)n1] |
| CB-37 | 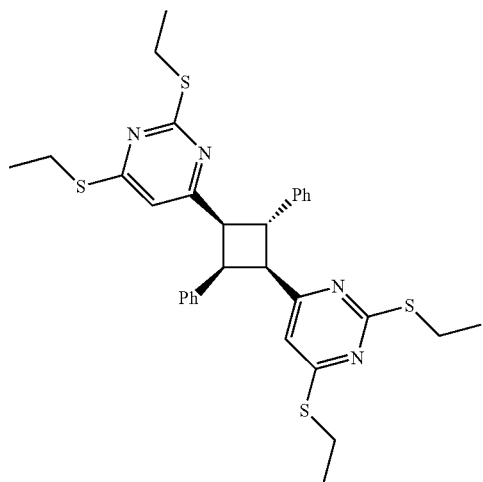 [SMILES: CCSc1cc([C@H]2[C@H](c3ccccc3)[C@@H](c3cc(SCC)nc(SCC)n3)[C@H]2c2ccccc2)nc(SCC)n1] |
| CB-38 | 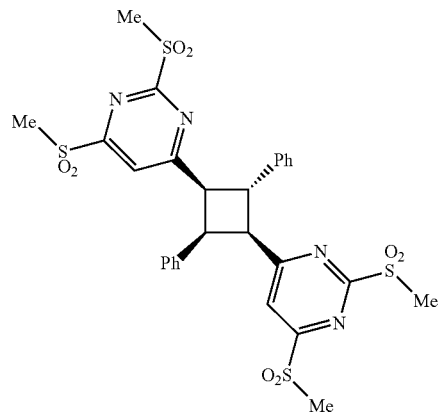 [SMILES: CS(=O)(=O)c1cc([C@H]2[C@H](c3ccccc3)[C@@H](c3cc(S(C)(=O)=O)nc(S(C)(=O)=O)n3)[C@H]2c2ccccc2)nc(S(C)(=O)=O)n1] |

-continued
Example VI. Detailed List of Currently Synthesized Cyclobutanes
| name | Structure |
|---|---|
| CB-39 | 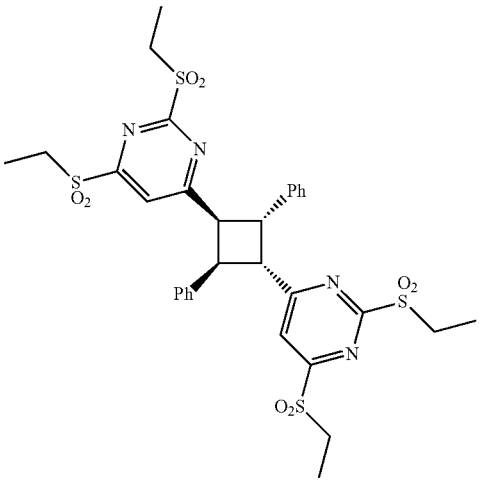 [SMILES: CCS(=O)(=O)c1cc([C@H]2[C@H](c3ccccc3)[C@H](c3cc(S(=O)(=O)CC)nc(S(=O)(=O)CC)n3)[C@H]2c2ccccc2)nc(S(=O)(=O)CC)n1] |
| CB-40 | 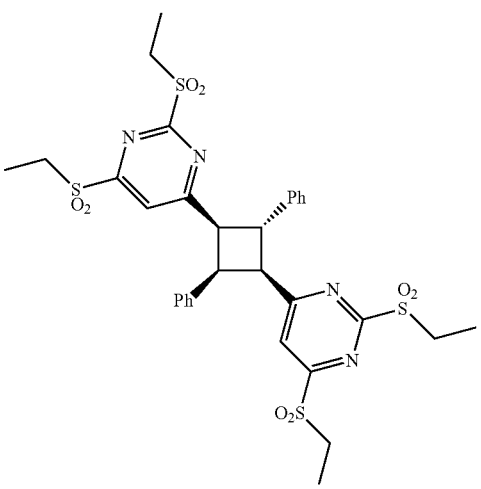 [SMILES: CCS(=O)(=O)c1cc([C@H]2[C@H](c3ccccc3)[C@@H](c3cc(S(=O)(=O)CC)nc(S(=O)(=O)CC)n3)[C@H]2c2ccccc2)nc(S(=O)(=O)CC)n1] |
| CB-41 | 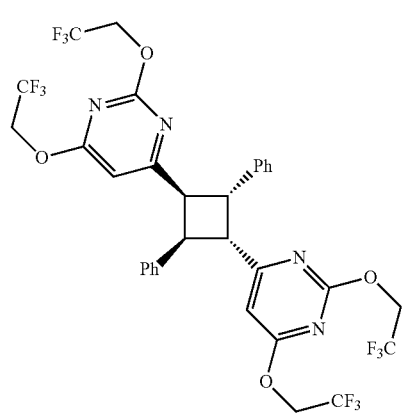 [SMILES: FC(F)(F)COc1cc([C@H]2[C@H](c3ccccc3)[C@H](c3cc(OCC(F)(F)F)nc(OCC(F)(F)F)n3)[C@H]2c2ccccc2)nc(OCC(F)(F)F)n1] |

-continued
Example VI. Detailed List of Currently Synthesized Cyclobutanes
| name | Structure |
|------|-----------|
| CB-42 | 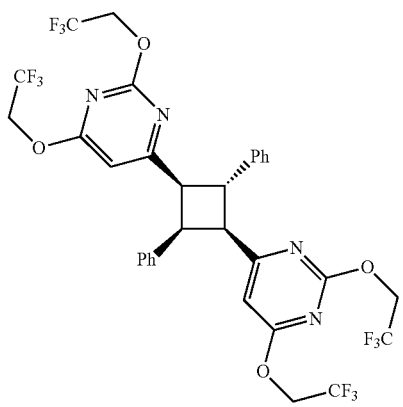 [SMILES: FC(F)(F)COc1cc([C@H]2[C@H](c3ccccc3)[C@@H](c3cc(OCC(F)(F)F)nc(OCC(F)(F)F)n3)[C@H]2c2ccccc2)nc(OCC(F)(F)F)n1] |
| CB-43 | 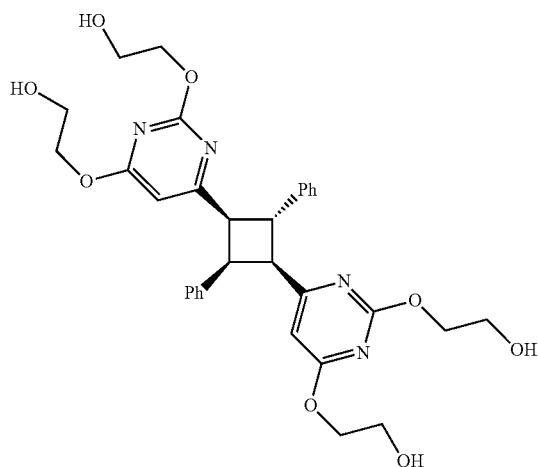 [SMILES: OCCOc1cc([C@H]2[C@H](c3ccccc3)[C@@H](c3cc(OCCO)nc(OCCO)n3)[C@H]2c2ccccc2)nc(OCCO)n1] |
| CB-44 | 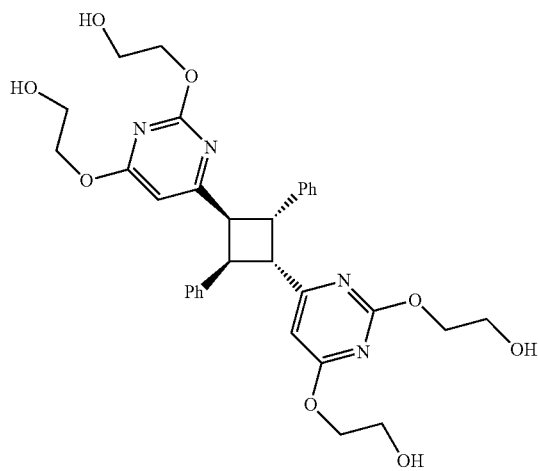 [SMILES: OCCOc1cc([C@H]2[C@H](c3ccccc3)[C@H](c3cc(OCCO)nc(OCCO)n3)[C@H]2c2ccccc2)nc(OCCO)n1] |

-continued
Example VI. Detailed List of Currently Synthesized Cyclobutanes
| name | Structure |
|---|---|
| CB-45 | 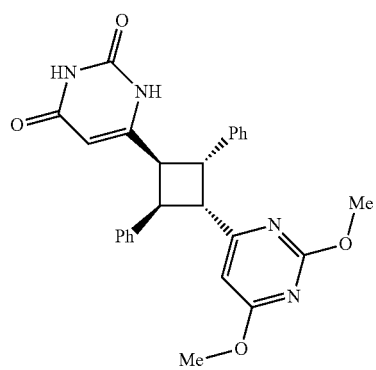 [SMILES: COc1cc([C@H]2[C@@H](c3ccccc3)[C@H](c3cc(=O)[nH]c(=O)[nH]3)[C@@H]2c2ccccc2)nc(OC)n1] |
| CB-46 | 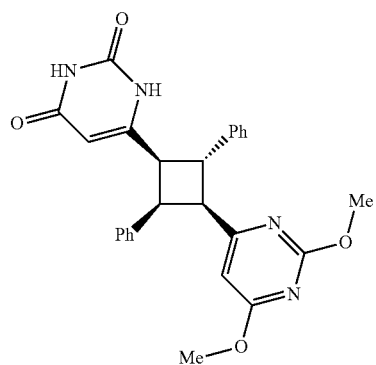 [SMILES: COc1cc([C@H]2[C@@H](c3ccccc3)[C@@H](c3cc(=O)[nH]c(=O)[nH]3)[C@@H]2c2ccccc2)nc(OC)n1] |
| CB-47 | 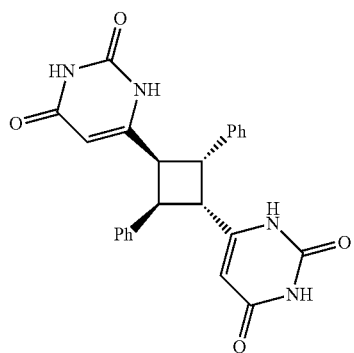 [SMILES: O=c1cc([C@H]2[C@H](c3ccccc3)[C@H](c3cc(=O)[nH]c(=O)[nH]3)[C@H]2c2ccccc2)[nH]c(=O)[nH]1] |
| CB-48 | 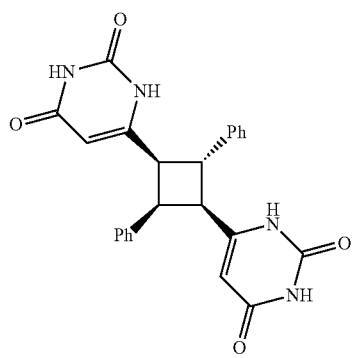 [SMILES: O=c1cc([C@H]2[C@H](c3ccccc3)[C@@H](c3cc(=O)[nH]c(=O)[nH]3)[C@H]2c2ccccc2)[nH]c(=O)[nH]1] |

-continued
Example VI. Detailed List of Currently Synthesized Cyclobutanes
| name | Structure |
|---|---|
| CB-49 | 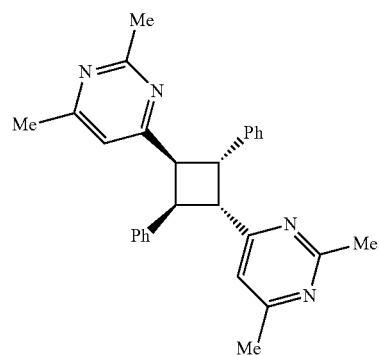 [SMILES: Cc1cc([C@H]2[C@H](c3ccccc3)[C@H](c3cc(C)nc(C)n3)[C@H]2c2ccccc2)nc(C)n1] |
| CB-50 | 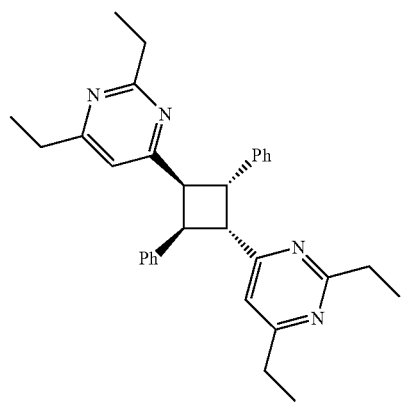 [SMILES: CCc1cc([C@H]2[C@H](c3ccccc3)[C@H](c3cc(CC)nc(CC)n3)[C@H]2c2ccccc2)nc(CC)n1] |
| CB-51 | 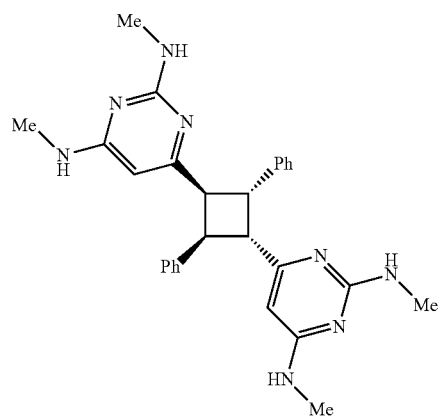 [SMILES: CNc1cc([C@H]2[C@H](c3ccccc3)[C@H](c3cc(NC)nc(NC)n3)[C@H]2c2ccccc2)nc(NC)n1] |

Example VI. Detailed List of Currently Synthesized Cyclobutanes
| name | Structure |
|---|---|
| CB-52 | 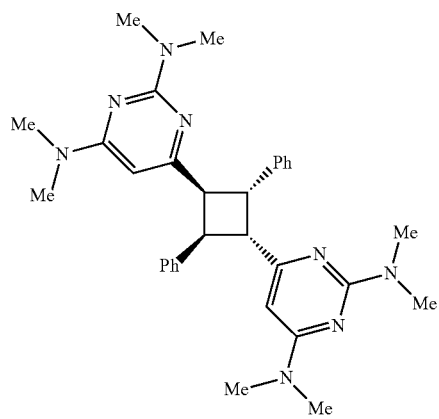 [SMILES: CN(C)c1cc([C@H]2[C@H](c3ccccc3)[C@H](c3cc(N(C)C)nc(N(C)C)n3)[C@H]2c2ccccc2)nc(N(C)C)n1] |
| CB-53 | 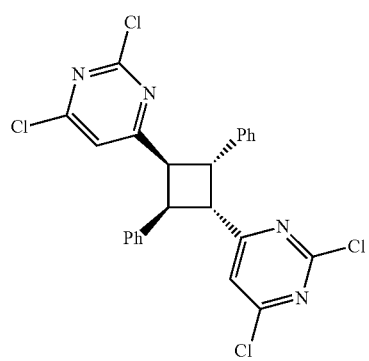 [SMILES: Clc1cc([C@H]2[C@H](c3ccccc3)[C@H](c3cc(Cl)nc(Cl)n3)[C@H]2c2ccccc2)nc(Cl)n1] |
| CB-54 | 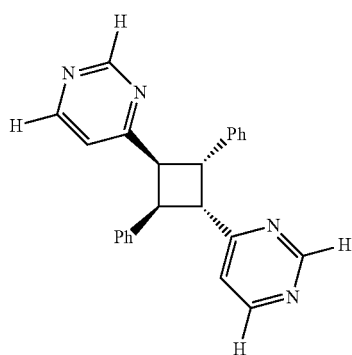 [SMILES: c1ccc([C@H]2[C@H](c3ccncn3)[C@H](c3ccccc3)[C@H]2c2ccncn2)cc1] |
| DPM-2012-05 | 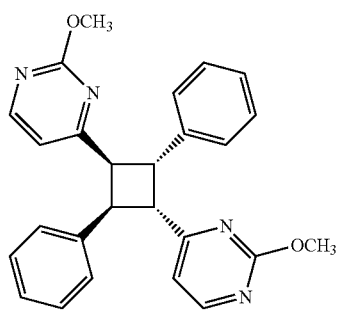 [SMILES: COc1nccc([C@H]2[C@H](c3ccccc3)[C@H](c3ccnc(OC)n3)[C@H]2c2ccccc2)n1] |

-continued
Example VI. Detailed List of Currently Synthesized Cyclobutanes
| name | Structure |
|---|---|
| DPM-2012-06 | 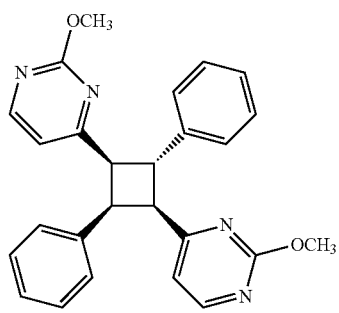 [SMILES: COc1nccc([C@H]2[C@H](c3ccccc3)[C@@H](c3ccnc(OC)n3)[C@H]2c2ccccc2)n1] |
| DPM-2012-07 | 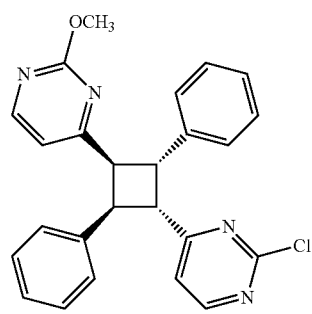 [SMILES: COc1nccc([C@H]2[C@H](c3ccccc3)[C@H](c3ccnc(Cl)n3)[C@H]2c2ccccc2)n1] |
| DPM-2012-08 | 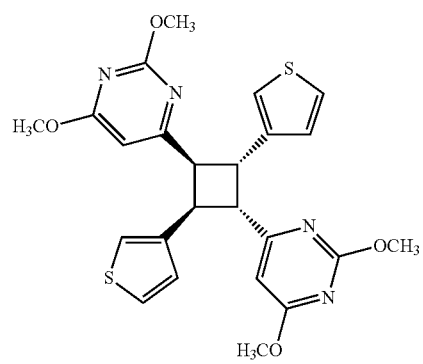 [SMILES: COc1cc([C@H]2[C@H](c3ccsc3)[C@H](c3cc(OC)nc(OC)n3)[C@H]2c2ccsc2)nc(OC)n1] |
| DPM-2012-09 | 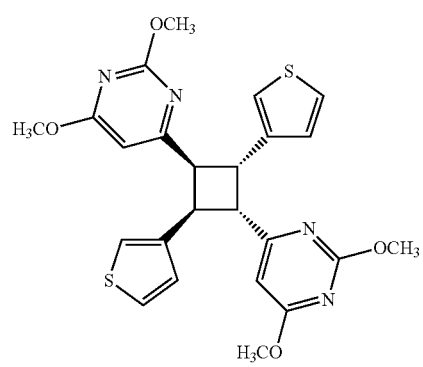 [SMILES: COc1cc([C@H]2[C@H](c3ccsc3)[C@H](c3cc(OC)nc(OC)n3)[C@H]2c2ccsc2)nc(OC)n1] |

-continued
Example VI. Detailed List of Currently Synthesized Cyclobutanes
| name | Structure |
|---|---|
| DPM-2012-10 | 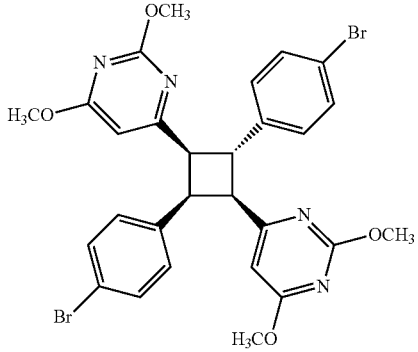 [SMILES: COc1cc([C@H]2[C@H](c3ccc(Br)cc3)[C@@H](c3cc(OC)nc(OC)n3)[C@H]2c2ccc(Br)cc2)nc(OC)n1] |
| DPM-2012-11 | 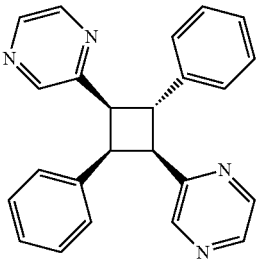 [SMILES: c1ccc([C@H]2[C@H](c3cnccn3)[C@H](c3ccccc3)[C@@H]2c2cnccn2)cc1] |
| DPM-2012-12 | 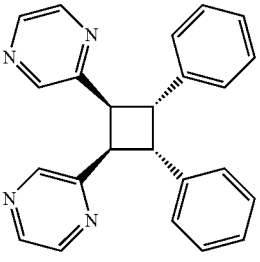 [SMILES: c1ccc([C@@H]2[C@H](c3ccccc3)[C@@H](c3cnccn3)[C@H]2c2cnccn2)cc1] |
| DPM-2012-13 | 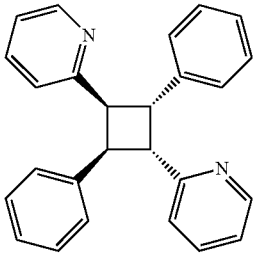 [SMILES: c1ccc([C@H]2[C@H](c3ccccn3)[C@H](c3ccccc3)[C@H]2c2ccccn2)cc1] |
| DPM-2012-14 | 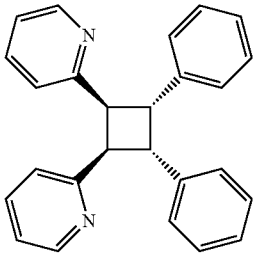 [SMILES: c1ccc([C@@H]2[C@H](c3ccccc3)[C@@H](c3ccccn3)[C@H]2c2ccccn2)cc1] |

-continued
Example VI. Detailed List of Currently Synthesized Cyclobutanes
| name | Structure |
|---|---|
| DPM-2012-15 | 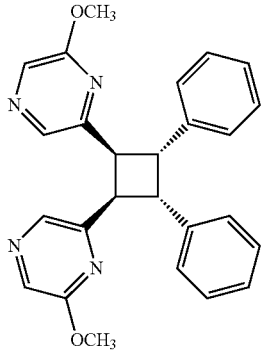 [SMILES: COc1cncc([C@@H]2[C@@H](c3ccccc3)[C@@H](c3ccccc3)[C@@H]2c2cncc(OC)n2)n1] |
| DPM-2012-16 | 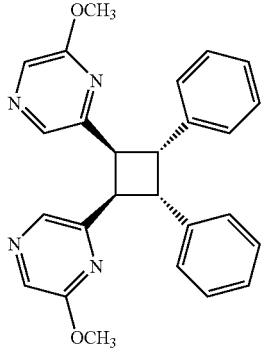 [SMILES: COc1cncc([C@@H]2[C@@H](c3ccccc3)[C@@H](c3ccccc3)[C@@H]2c2cncc(OC)n2)n1] |
| DPM-2012-17 | 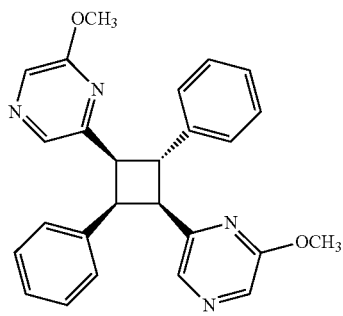 [SMILES: COc1cncc([C@H]2[C@H](c3ccccc3)[C@@H](c3cncc(OC)n3)[C@H]2c2ccccc2)n1] |
| DPM-2012-18 | 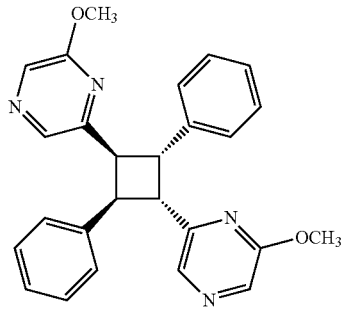 [SMILES: COc1cncc([C@H]2[C@H](c3ccccc3)[C@H](c3cncc(OC)n3)[C@H]2c2ccccc2)n1] |

Example VI. Detailed List of Currently Synthesized Cyclobutanes
| name | Structure |
|---|---|
| DPM-2012-19 | 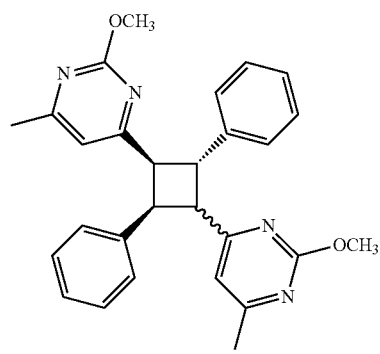 [SMILES: COc1nc(C)cc(C2[C@H](c3ccccc3)[C@@H](c3cc(C)nc(OC)n3)[C@H]2c2ccccc2)n1] |
| DPM-2012-20 | 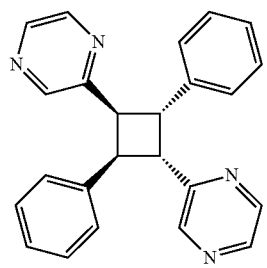 [SMILES: c1ccc([C@H]2[C@H](c3cnccn3)[C@H](c3ccccc3)[C@H]2c2cnccn2)cc1] |
| DPM-2012-21 | 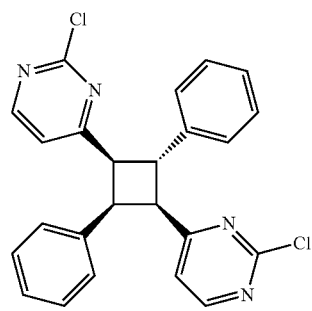 [SMILES: Clc1nccc([C@H]2[C@H](c3ccccc3)[C@@H](c3ccnc(Cl)n3)[C@H]2c2ccccc2)n1] |
| DPM-2012-26 | 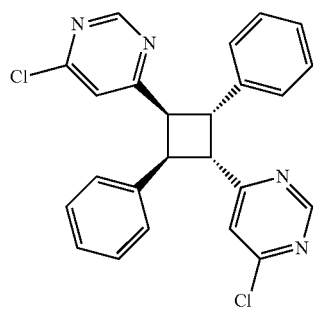 [SMILES: Clc1cc([C@H]2[C@H](c3ccccc3)[C@H](c3cc(Cl)ncn3)[C@H]2c2ccccc2)ncn1] |

Example VI. Detailed List of Currently Synthesized Cyclobutanes

| name | Structure |
|---|---|
| DPM-2012-27 | 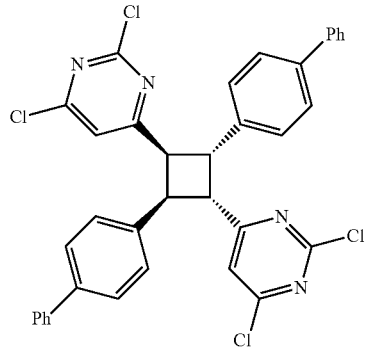 [SMILES: Clc1cc([C@H]2[C@H](c3ccc(-c4ccccc4)cc3)[C@H](c3cc(Cl)nc(Cl)n3)[C@H]2c2ccc(-c3ccccc3)cc2)nc(Cl)n1] |
| DPM-2012-28 | 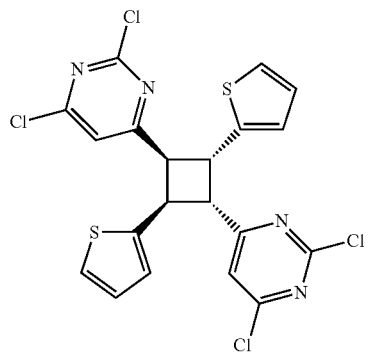 [SMILES: Clc1cc([C@H]2[C@H](c3cccs3)[C@H](c3cc(Cl)nc(Cl)n3)[C@H]2c2cccs2)nc(Cl)n1] |
| DPM-2012-29 | 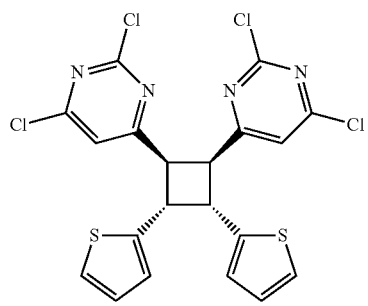 [SMILES: Clc1cc([C@@H]2[C@H](c3cc(Cl)nc(Cl)n3)[C@@H](c3cccs3)[C@H]2c2cccs2)nc(Cl)n1] |
| DPM-2012-30 | 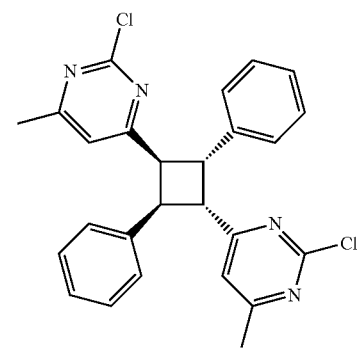 [SMILES: Cc1cc([C@H]2[C@H](c3ccccc3)[C@H](c3cc(C)nc(Cl)n3)[C@H]2c2ccccc2)nc(Cl)n1] |

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The foregoing embodiments are to be considered in all respects illustrative rather than limiting on the invention described herein. In the various embodiments of the methods and systems of the present invention, where the term comprises is used with respect to the recited steps or components, it is also contemplated that the methods and systems consist essentially of, or consist of, the recited steps or components. Further, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control. Combinations of one or more compounds of the present invention are also envisioned as within the scope herein.

The invention claimed is:

1. A compound having the formula:

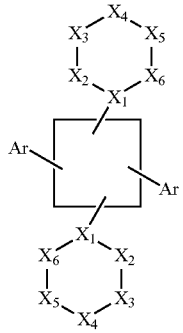

(X)

wherein each ring system,

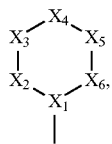

is

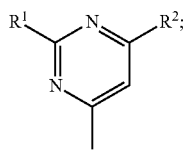

each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —$OR^3$, (o) —$NR^3R^3$, (p) —CN, (q) —$N_3$, (r) —$SR^3$, (s) —$SOR^3$, (t) —$SO_2R^3$, (u) —$COOR^3$, (v) —$COR^3$, (w) —$CONR^3R^3$, (x) —$NR^3COR^3$—, (y) —$NR^3CONR^3R^3$, (z) ($C_1$-$C_8$ alkyl)$OR^3$, (aa) —($C_1$-$C_8$ alkyl)$NR^3R^3$, (bb) —($C_1$-$C_8$ alkyl)$SR^3$, (cc) —($C_1$-$C_8$ alkyl)$SOR^3$, (dd) —($C_1$-$C_8$ alkyl)$SO_2R^3$, (ee) —($C_1$-$C_8$ alkyl)$COOR^3$, (ff) —($C_1$-$C_8$ alkyl)$COR^3$, (gg) —($C_1$-$C_8$ alkyl)$CONR^3R^3$, (hh) —($C_1$-$C_8$ alkyl)$NR^3COR^3$, and (ii) —($C_1$-$C_8$ alkyl)$NR^3CONR^3R^3$, wherein each of (e) through (j) immediately recited above is optionally substituted with one or more F, Cl, Br, I, —OH, —SH, —$NH_2$, —NH($C_1$-$C_8$ alkyl), or —N($C_1$-$C_8$ alkyl)$_2$ and wherein each of (k) through (l) immediately recited above is optionally substituted with one or more $R^4$ or $R^5$;

each $R^3$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (k) immediately recited above is optionally substituted with one or more $R^5$;

each $R^4$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, and (j) —$C_8$ cycloalkynyl, wherein each of (e) through (j) immediately recited above is optionally substituted with one or more $R^5$;

each $R^5$ is independently selected from (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^E$, (r) —$SO_2R^6$, (s) —$COOR^6$, (t) —$COR^6$, (u) —$CONR^6R^6$, (v) $NR^6COR^6$—, and (w) —$NR^6CONR^6R^6$, wherein each of (e) through (k) immediately recited above is optionally substituted with one or more F, Cl, Br, I, —OH, —SH, —$NH_2$, —NH($C_1$-$C_8$ alkyl), and —N($C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (i) immediately recited above is optionally substituted with one or more $R^7$; and each $R^7$ is independently selected from one or more (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$;

or an enantiomer, diastereomer, or tautomer of said compound, or a pharmaceutically acceptable, salt of said compound, of said enantiomer of said compound, of said diastereomer of said compound, or of said tautomer of said compound.

2. A compound having the formula:

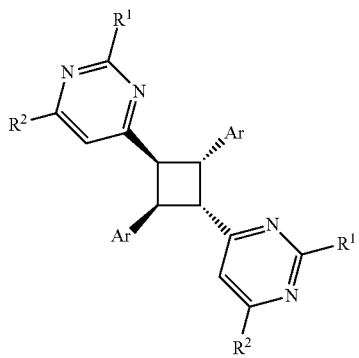

wherein each $R^1$ and $R^2$ is independently selected from (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, (j) —C$_8$ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —OR$^3$, (o) —NR$^3$R$^3$, (p) —CN, (q) —N$_3$, (r) —SR$^3$, (s) —SOR$^3$, (t) —SO$_2$R$^3$, (u) —COOR$^3$, (v) —COR$^3$, (w) —CONR$^3$R$^3$, (x) —NR$^3$COR$^3$—, (y) —NR$^3$CONR$^3$R$^3$, (z) —(C$_1$-C$_8$ alkyl)OR$^3$, (aa) —(C$_1$-C$_8$ alkyl)NR$^3$R$^3$, (bb) —(C$_1$-C$_8$ alkyl)SR$^3$, (cc) —(C$_1$-C$_8$ alkyl)SOR$^3$, (dd) —(C$_1$-C$_8$ alkyl)SO$_2$R$^3$, (ee) —(C$_1$-C$_8$ alkyl)COOR$^3$, (ff) —(C$_1$-C$_8$ alkyl)COR$^3$, (gg) —(C$_1$-C$_8$ alkyl)CONR$^3$R$^3$, (hh) —(C$_1$-C$_8$ alkyl)NR$^3$COR$^3$, and (ii) —(C$_1$-C$_8$ alkyl)NR$^3$CONR$^3$R$^3$, wherein each of (e) through (j) immediately recited above is optionally substituted with one or more F, Cl, Br, I, —OH, —SH, —NH$_2$, —NH(C$_1$-C$_8$ alkyl), or —N(C$_1$-C$_8$ alkyl)$_2$ and wherein each of (k) through (l) immediately recited above is optionally substituted with one or more $R^4$ or $R^5$;

each $R^3$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (k) immediately recited above is optionally substituted with one or more $R^5$;

each $R^4$ is independently selected from (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, and (j) —C$_8$ cycloalkynyl, wherein each of (e) through (j) immediately recited above is optionally substituted with one or more $R^5$;

each $R^5$ is independently selected from (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, (j) —C$_8$ cycloalkynyl, (k) phenyl, (l) —OR$^6$, (m) —NR$^6$R$^6$, (n) —CN, (o) —N$_3$, -(p) —SR$^6$, (q) —SOR$^6$, (r) —SO$_2$R$^6$, (s) —COOR$^6$, (t) —COR$^6$, (u) —CONR$^6$R$^6$, (v) —NR$^6$COR$^6$—, and (w) —NR$^6$CONR$^6$R$^6$, wherein each of (e) through (k) immediately recited above is optionally substituted with one or more F, Cl, Br, I, —OH, —SH, —NH$_2$, —NH(C$_1$-C$_8$ alkyl), and —N(C$_1$-C$_8$ alkyl)$_2$;

each $R^6$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (i) immediately recited above is optionally substituted with one or more $R^7$; and each $R^7$ is independently selected from one or more (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$;

or an enantiomer, diastereomer, or tautomer of said compound, or a pharmaceutically acceptable, salt of said compound, of said enantiomer of said compound, of said diastereomer of said compound, or of said tautomer of said compound.

3. A compound having the formula:

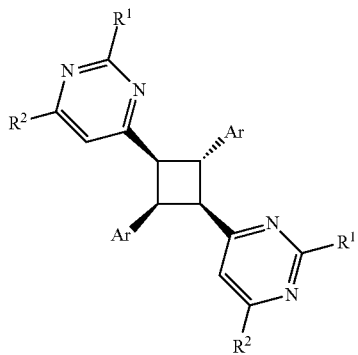

wherein each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —$OR^3$, (o) —$NR^3R^3$, (p) —CN, (q) —$N_3$, (r) —$SR^3$, (s) —$SOR^3$, (t) —$SO_2R^3$, (u) —$COOR^3$, (v) —$COR^3$, (w) —$CONR^3R^3$, (x) —$NR^3COR^3$—, (y) —$NR^3CONR^3R^3$, (z) —($C_1$-$C_8$ alkyl)$OR^3$, (aa) —($C_1$-$C_8$ alkyl)$NR^3R^3$, (bb) —($C_1$-$C_8$ alkyl)$SR^3$, (cc) —($C_1$-$C_8$ alkyl)$SOR^3$, (dd) —($C_1$-$C_8$ alkyl)$SO_2R^3$, (ee) —($C_1$-$C_8$ alkyl)$COOR^3$, (ff) —($C_1$-$C_8$ alkyl)$COR^3$, (gg) —($C_1$-$C_8$ alkyl)$CONR^3R^3$, (hh) —($C_1$-$C_8$ alkyl)$NR^3COR^3$, and (ii) —($C_1$-$C_8$ alkyl)$NR^3CONR^3R^3$, wherein each of (e) through (j) immediately recited above is optionally substituted with one or more F, Cl, Br, I, —OH, —SH, —$NH_2$, —$NH(C_1$-$C_8$ alkyl), or —$N(C_1$-$C_8$ alkyl)$_2$ and wherein each of (k) through (l) immediately recited above is optionally substituted with one or more $R^4$ or $R^5$;

each $R^3$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (k) immediately recited above is optionally substituted with one or more $R^5$;

each $R^4$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, and (j) —$C_8$ cycloalkynyl, wherein each of (e) through (j) immediately recited above is optionally substituted with one or more $R^5$;

each $R^5$ is independently selected from (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^6$, (r) —$SO_2R^6$, (s) —$COOR^6$, (t) —$COR^6$, (u) —$CONR^6R^6$, (v) —$NR^6COR^6$—, and (w) —$NR^6CONR^6R^6$, wherein each of (e) through (k) immediately recited above is optionally substituted with one or more F, Cl, Br, I, —OH, —SH, —$NH_2$, —$NH(C_1$-$C_8$ alkyl), and —$N(C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (i) immediately recited above is optionally substituted with one or more $R^7$; and each $R^7$ is independently selected from one or more (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$; and or an enantiomer, diastereomer, or tautomer of said compound, or a pharmaceutically acceptable, salt of said compound, of said enantiomer of said compound, of said diastereomer of said compound, or of said tautomer of said compound.

4. A compound having the formula:

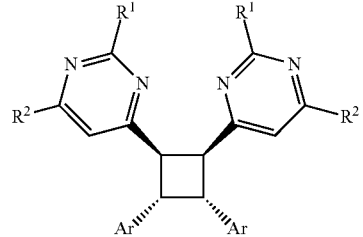

wherein each $R^1$ and $R^2$ is independently selected from (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —$OR^3$, (o) —$NR^3R^3$, (p) —CN, (q) —$N_3$, (r) —$SR^3$, (s) —$SOR^3$, (t) —$SO_2R^3$, (u) —$COOR^3$, (v) —$COR^3$, (w) —$CONR^3R^3$, (x) —$NR^3COR^3$—, (y) —$NR^3CONR^3R^3$, (z) —($C_1$-$C_8$ alkyl)OR³, (aa) —(C₁-C₈ alkyl)NR³R³, (bb) —(C₁-C₈ alkyl)SR³, (cc) —(C₁-C₈ alkyl)SOR³, (dd) —(C₁-C₈ alkyl)SO₂R³, (ee) —(C₁-C₈ alkyl)COOR³, (ff) —(C₁-C₈ alkyl)COR³, (gg) —(C₁-C₈ alkyl)CONR³R³, (hh) —(C₁-C₈ alkyl)NR³COR³, and (ii) —(C₁-C₈ alkyl)NR³CONR³R³, wherein each of (e) through (j) immediately recited above is optionally substituted with one or more F, Cl, Br, I, —OH, —SH, —NH₂, —NH(C₁-C₈ alkyl), or —N(C₁-C₈ alkyl)₂ and wherein each of (k) through (l) immediately recited above is optionally substituted with one or more R⁴ or R⁵;

each R³ is independently selected from (a) H, (b) —C₁-C₈ alkyl, (c) —C₂-C₈ alkenyl, (d) —C₂-C₈ alkynyl, (e) —C₃-C₈ cycloalkyl, (f) —C₃-C₈ cycloalkenyl, (g) —C₈ cycloalkynyl, (h) phenyl, (i) naphthyl, (j) —C₁-C₈ alkyl(phenyl), and (k) —C₁-C₈ alkyl(naphthyl), wherein each of (b) through (k) immediately recited above is optionally substituted with one or more R⁵;

each R⁴ is independently selected from (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, and (j) —C₈ cycloalkynyl, wherein each of (e) through (j) immediately recited above is optionally substituted with one or more R⁵;

each R⁵ is independently selected from (a) F, (b) Cl, (c) Br, (d) I, (e) —OH, (f) —NH₂, (g) —CN, (h) —SH, (i) —COOH, (j) —CHO, (k) —CONH₂, (l) —O(—C₁-C₈ alkyl), (m) —NH(—C₁-C₈ alkyl), (n) —N(—C₁-C₈ alkyl)₂, (o) —S(—C₁-C₈ alkyl), (p) —COO(—C₁-C₈ alkyl), (q) —CO(—C₁-C₈ alkyl), (r) —CONH(—C₁-C₈ alkyl), and (s) —CON(—C₁-C₈ alkyl)₂, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, (j) —C₈ cycloalkynyl, (k) phenyl, (l) —OR⁶, (m) —NR⁶R⁶, (n) —CN, (o) —N₃, -(p) —SR⁶, (q) —SOR⁶, (r) —SO₂R⁶, (s) —COOR⁶, (t) —COR⁶, (u) —CONR⁶R⁶, (v) —NR⁶COR⁶—, and (w) —NR⁶CONR⁶R⁶, wherein each of (e) through (k) immediately recited above is optionally substituted with one or more F, Cl, Br, I, —OH, —SH, —NH₂, —NH(C₁-C₈ alkyl), and —N(C₁-C₈ alkyl)₂;

each R⁶ is independently selected from (a) H, (b) —C₁-C₈ alkyl, (c) —C₂-C₈ alkenyl, (d) —C₂-C₈ alkynyl, (e) —C₃-C₈ cycloalkyl, (f) —C₃-C₈ cycloalkenyl, (g) —C₈ cycloalkynyl, (h) phenyl, (i) naphthyl, (j) —C₁-C₈ alkyl(phenyl), and (k) —C₁-C₈ alkyl(naphthyl), wherein each of (b) through (i) immediately recited above is optionally substituted with one or more R⁷; and each R⁷ is independently selected from one or more (a) F, (b) Cl, (c) Br, (d) I, (e) —OH, (f) —NH₂, (g) —CN, (h) —SH, (i) —COOH, (j) —CHO, (k) —CONH₂, (l) —O(—C₁-C₈ alkyl), (m) —NH(—C₁-C₈ alkyl), (n) —N(—C₁-C₈ alkyl)₂, (o) —S(—C₁-C₈ alkyl), (p) —COO(—C₁-C₈ alkyl), (q) —CO(—C₁-C₈ alkyl), (r) —CONH(—C₁-C₈ alkyl), and (s) —CON(—C₁-C₈ alkyl)₂;

or an enantiomer, diastereomer, or tautomer of said compound, or a pharmaceutically acceptable, salt of said compound, of said enantiomer of said compound, of said diastereomer of said compound, or of said tautomer of said compound.

5. A compound having the formula:

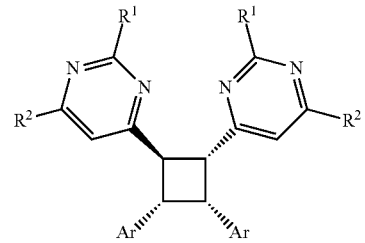

wherein
each R¹ and R² is independently selected from (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, (j) —C₈ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —OR³, (o) —NR³R³, (p) —CN, (q) —N₃, (r) —SR³, (s) —SOR³, (t) —SO₂R³, (u) —COOR³, (v) —COR³, (w) —CONR³R³, (x) —NR³COR³—, (y) —NR³CONR³R³, (z) —(C₁-C₈ alkyl)OR³, (aa) —(C₁-C₈ alkyl)NR³R³, (bb) —(C₁-C₈ alkyl)SR³, (cc) —(C₁-C₈ alkyl)SOR³, (dd) —(C₁-C₈ alkyl)SO₂R³, (ee) —(C₁-C₈ alkyl)COOR³, (ff) —(C₁-C₈ alkyl)COR³, (gg) —(C₁-C₈ alkyl)CONR³R³, (hh) —(C₁-C₈ alkyl)NR³COR³, and (ii) —(C₁-C₈ alkyl)NR³CONR³R³, wherein each of (e) through (j) immediately recited above is optionally substituted with one or more F, Cl, Br, I, —OH, —SH, —NH₂, —NH(C₁-C₈ alkyl), or —N(C₁-C₈ alkyl)₂ and wherein each of (k) through (l) immediately recited above is optionally substituted with one or more R⁴ or R⁵;

each R³ is independently selected from (a) H, (b) —C₁-C₈ alkyl, (c) —C₂-C₈ alkenyl, (d) —C₂-C₈ alkynyl, (e) —C₃-C₈ cycloalkyl, (f) —C₃-C₈ cycloalkenyl, (g) —C₈ cycloalkynyl, (h) phenyl, (i) naphthyl, (j) —C₁-C₈ alkyl(phenyl), and (k) —C₁-C₈ alkyl(naphthyl), wherein each of (b) through (k) immediately recited above is optionally substituted with one or more R⁵;

each R⁴ is independently selected from (a) F, (b) Cl, (c) Br, (d) I, (e) —C₁-C₈ alkyl, (f) —C₂-C₈ alkenyl, (g) —C₂-C₈ alkynyl, (h) —C₃-C₈ cycloalkyl, (i) —C₃-C₈ cycloalkenyl, and (j) —C₈ cycloalkynyl, wherein each of (e) through (j) immediately recited above is optionally substituted with one or more R⁵;

each R⁵ is independently selected from (a) F, (b) Cl, (c) Br, (d) I, (e) —OH, (f) —NH₂, (g) —CN, (h) —SH, (i) —COOH, (j) —CHO, (k) —CONH₂, (l) —O(—C₁-C₈ alkyl), (m) —NH(—C₁-C₈ alkyl), (n) —N(—C₁-C₈ alkyl)₂, (o) —S(—C₁-C₈ alkyl), (p) —COO(—C₁-C₈ alkyl), (q) —CO(—C$_1$-C$_8$ alkyl), (r) —CONH(—C$_1$-C$_8$ alkyl), and (s) —CON(—C$_1$-C$_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, (j) —C$_8$ cycloalkynyl, (k) phenyl, (l) —OR$^6$, (m) —NR$^6$R$^6$, (n) —CN, (o) —N$_3$, -(p) —SR$^6$, (q) —SOR$^6$, (r) —SO$_2$R$^6$, (s) —COOR$^6$, (t) —COR$^6$, (u) —CONR$^6$R$^6$, (v) —NR$^6$COR$^6$—, and (w) —NR$^6$CONR$^6$R$^6$, wherein each of (e) through (k) immediately recited above is optionally substituted with one or more F, Cl, Br, I, —OH, —SH, —NH$_2$, —NH(C$_1$-C$_8$ alkyl), and —N(C$_1$-C$_8$ alkyl)$_2$;

each R$^6$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (i) immediately recited above is optionally substituted with one or more R$^7$; and each R$^7$ is independently selected from one or more (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$;

or an enantiomer, diastereomer, or tautomer of said compound, or a pharmaceutically acceptable, salt of said compound, of said enantiomer of said compound, of said diastereomer of said compound, or of said tautomer of said compound.

6. A compound according to claim 1 wherein
each of R$^1$ and R$^2$ are independently selected from (a) F, (b) Cl, (c) —C$_1$-C$_8$ alkyl, (d) —C$_3$-C$_8$ cycloalkyl, (e) phenyl, (f) a 7 to 10-membered saturated, unsaturated, or aromatic fused bicyclic carbocyle, (g) a 3 to 10-membered saturated, unsaturated, or aromatic heterocycle or fused bicyclic heterocycle containing one or more heteroatoms selected from nitrogen, oxygen, sulfur, and combinations thereof, (h) —OR$^3$, (i) —NR$^3$R$^3$, (j) —CN, (k) —SR$^3$, (l) —SOR$^3$, (m) —SO$_2$R$^3$, (n) —COOR$^3$, (o) —COR$^3$, (p) —CONR$^3$R$^3$, (q) —NR$^3$COR$^3$—, (r) —NR$^3$CONR$^3$R$^3$, (s) —(C$_1$-C$_8$ alkyl)OR$^3$, (t) —(C$_1$-C$_8$ alkyl)NR$^3$R$^3$, (u) —(C$_1$-C$_8$ alkyl)SR$^3$, (v) —(C$_1$-C$_8$ alkyl)SOR$^3$, (w) —(C$_1$-C$_8$ alkyl)SO$_2$R$^3$, (x) —(C$_1$-C$_8$ alkyl)COOR$^3$, (y) —(C$_1$-C$_8$ alkyl)COR$^3$, (z) —(C$_1$-C$_8$ alkyl)CONR$^3$R$^3$, (aa) —(C$_1$-C$_8$ alkyl)NR$^3$COR$^3$, and (bb) —(C$_1$-C$_8$ alkyl)NR$^3$CONR$^3$R$^3$, wherein each of (c) or (d) immediately recited above is optionally substituted with one or more F, Cl, —OH, —SH, —NH$_2$, —NH(C$_1$-C$_8$ alkyl), or —N(C$_1$-C$_8$ alkyl)$_2$ and wherein each of (e) through (g) immediately recited above is optionally substituted with one more R$^4$ or R$^5$;

each R$^3$ is independently selected from (a) H, (b) —C$_1$-C$_8$ alkyl, (c) —C$_3$-C$_8$ cycloalkyl, (d) phenyl, (e) naphthyl, (f) —C$_1$-C$_8$ alkyl(phenyl), and (g) —C$_1$-C$_8$ alkyl(naphthyl), wherein each of (b) through (g) immediately recited above is optionally substituted with one or more R$^5$;

each R$^4$ is independently selected from one or more (a) F, (b) Cl, (c) —C$_1$-C$_8$ alkyl, and (d) —C$_3$-C$_8$ cycloalkyl, wherein each of (c) or (d) immediately recited above is optionally substituted with one or more R$^5$;

each R$^5$ is independently selected from one or more (a) F, (b) Cl, (c) —OH, (d) —NH$_2$, (e) —CN, (f) —SH, (g) —COOH, (h) —CHO, (i) —CONH$_2$, (j) —O(—C$_1$-C$_8$ alkyl), (k) —NH(—C$_1$-C$_8$ alkyl), (l) —N(—C$_1$-C$_8$ alkyl)$_2$, (m) —S(—C$_1$-C$_8$ alkyl), (n) —COO(—C$_1$-C$_8$ alkyl), (o) —CO(—C$_1$-C$_8$ alkyl), (p) —CONH(—C$_1$-C$_8$ alkyl), and (q) —CON(—C$_1$-C$_8$ alkyl)$_2$, or an enantiomer, diastereomer, or tautomer of said compound, or a pharmaceutically acceptable, salt of said compound, of said enantiomer of said compound, of said diastereomer of said compound, or of said tautomer of said compound.

7. A compound according to claim 6 wherein
each of R$^1$ and R$^2$ are independently selected from (a) F, (b) Cl, (c) —C$_1$-C$_8$ alkyl, (d) phenyl, (e) a 7 to 10-membered saturated, unsaturated, or aromatic fused bicyclic carbocyle, (f) a 3 to 10-membered saturated, unsaturated, or aromatic heterocycle or fused bicyclic heterocycle containing one or more heteroatoms selected from nitrogen, oxygen, sulfur, and combinations thereof, (g) —OR$^3$, (h) —NR$^3$R$^3$, (i) —SR$^3$, (j) —COOR$^3$, (k) —COR$^3$, and (l) —CONR$^3$R$^3$, wherein each (c) immediately recited above is optionally substituted with one or more F, Cl, —OH, —SH, —NH$_2$, —NH(C$_1$-C$_8$ alkyl), or —N(C$_1$-C$_8$ alkyl)$_2$ and wherein each (d) through (f) immediately recited above is optionally substituted with one more more R$^4$ or R$^5$;

each R$^3$ is independently selected from (a) H, (b) —C$_1$-C$_8$ alkyl, (c) phenyl, and (d) naphthyl, wherein each of (b) through (d) immediately recited above is optionally substituted with one or more R$^5$;

each R$^4$ is independently selected from one or more (a) F, (b) Cl, (c) —C$_1$-C$_8$ alkyl, (d) —C$_3$-C$_8$ cycloalkyl, wherein each of (c) or (d) immediately recited above is optionally substituted with one or more R$^5$;

each R$^5$ is independently selected from one or more (a) F, (b) Cl, (c) —OH, (d) —NH$_2$, (e) —SH, (f) —COOH, (g) —COCH$_3$, (h) —CHO, or (i) —CONH$_2$, or an enantiomer, diastereomer, or tautomer of said compound, or a pharmaceutically acceptable, salt of said compound, of said enantiomer of said compound, of said diastereomer of said compound, or of said tautomer of said compound.

8. A compound according to claim 7 wherein each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof nitrogen, wherein each of (a) through (d) immediately recited above is optionally substituted with one or more (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, (j) —C$_8$ cycloalkynyl, (k) phenyl, (l) —OR$^6$, (m) —NR$^6$R$^6$, (n) —CN, (o) —N$_3$, -(p) —SR$^6$, (q) —SOR$^6$, (r) —SO$_2$R$^6$, (s) —COOR$^6$, (t) —COR$^6$, (u) —CONR$^6$R$^6$, (v) —NR$^6$COR$^6$—, and (w) —NR$^6$CONR$^6$R$^6$, wherein each of (e) through (k) immediately recited above is optionally substituted with one or more F, Cl, Br, I, —OH, —SH, —NH$_2$, —NH(C$_1$-C$_8$ alkyl), and —N(C$_1$-C$_8$ alkyl)$_2$;

each R$^6$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (k) immediately recited above is optionally substituted with one or more R$^7$;

each R$^7$ is independently selected from one or more (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$, wherein each of (a) through (d) immediately recited above is optionally substituted with one or more (a) F, (b) Cl, (c) —C$_1$-C$_8$ alkyl, (d) —C$_3$-C$_8$ cycloalkyl, (e) phenyl, (f) —OR$^6$, (g) —NR$^6$R$^6$, (h) —CN, (i) —N$_3$, -(j) —SR$^6$, (k) —SOR$^6$, (l) —SO$_2$6$^3$, (m) —COOR$^6$, (n) —COR$^6$, (o) —CONR$^6$R$^6$, (p) —NR$^6$COR$^6$—, and (q) —NR$^6$CONR$^6$R$^6$, wherein each of (c) through (e) immediately recited above is optionally substituted with one or more F, Cl, —OH, —SH, —NH$_2$, —NH(C$_1$-C$_8$ alkyl), and —N(C$_1$-C$_8$ alkyl)$_2$;

each R$^6$ is independently selected from (a) H, (b) —C$_1$-C$_8$ alkyl, (c) —C$_3$-C$_8$ cycloalkyl, (d) phenyl, (e) naphthyl, (f) —C$_1$-C$_8$ alkyl(phenyl), and (g) —C$_1$-C$_8$ alkyl(naphthyl), wherein each of (b) through (g) immediately recited above is optionally substituted with one or more R$^7$;

each R$^7$ is independently selected from one or more (a) F, (b) Cl, (c) —OH, (d) —NH$_2$, (e) —CN, (f) —SH, (g) —COOH, (h) —CHO, (i) —CONH$_2$, (j) —O(—C$_1$-C$_8$ alkyl), (k) —NH(—C$_1$-C$_8$ alkyl), (l) —N(—C$_1$-C$_8$ alkyl)$_2$, (m) —S(—C$_1$-C$_8$ alkyl), (n) —COO(—C$_1$-C$_8$ alkyl), (o) —CO(—C$_1$-C$_8$ alkyl), (p) —CONH(—C$_1$-C$_8$ alkyl), and (q) —CON(—C$_1$-C$_8$ alkyl)$_2$, or an enantiomer, diastereomer, or tautomer of said compound, or a pharmaceutically acceptable, salt of said compound, of said enantiomer of said compound, of said diastereomer of said compound, or of said tautomer of said compound.

9. A compound according to claim 8 wherein each Ar is independently selected from (a) phenyl, (b) naphthyl, (c) pyridyl, (d) pyrimidyl (e) furanyl, (f) thienyl (g) pyrazolyl, (h) pyrazinyl (i) quinolyl, (j) oxazolyl, (k) isoxazolyl, (l) imidazolyl, (m) isothiazolyl, (n) thiazolyl, (o) triazolyl, (p) tetrazolyl, (q) indolyl, (r) benzofuranyl, (s) benzoxazolyl, (t) benzisoxazolyl, and (u) isoquinolinyl, wherein each of (a) through (u) immediately recited above is optionally substituted with one or more (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, (j) —C$_8$ cycloalkynyl, (k) phenyl, (l) —OR$^6$, (m) —NR$^6$R$^6$, (n) —CN, (o) —N$_3$, -(p) —SR$^6$, (q) —SOR$^6$, (r) —SO$_2$R$^6$, (s) —COOR$^6$, (t) —COR$^6$, (u) —CONR$^6$R$^6$, (v) —NR$^6$COR$^6$—, and (w) —NR$^6$CONR$^6$R$^6$, wherein each of (e) through (k) immediately recited above is optionally substituted with one or more F, Cl, Br, I, —OH, —SH, —NH$_2$, —NH(C$_1$-C$_8$ alkyl), and —N(C$_1$-C$_8$ alkyl)$_2$;

each R$^6$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (k) immediately recited above is optionally substituted with one or more R$^7$;

each R$^7$ is independently selected from one or more (a) F, (b) Cl, (c) Br, (d) I, (e) —OH, (f) —NH$_2$, (g) —CN, (h) —SH, (i) —COOH, (j) —CHO, (k) —CONH$_2$, (l) —O(—C$_1$-C$_8$ alkyl), (m) —NH(—C$_1$-C$_8$ alkyl), (n) —N(—C$_1$-C$_8$ alkyl)$_2$, (o) —S(—C$_1$-C$_8$ alkyl), (p) —COO(—C$_1$-C$_8$ alkyl), (q) —CO(—C$_1$-C$_8$ alkyl), (r) —CONH(—C$_1$-C$_8$ alkyl), and (s) —CON(—C$_1$-C$_8$ alkyl)$_2$, or an enantiomer, diastereomer, or tautomer of said compound, or a pharmaceutically acceptable, salt of said compound, of said enantiomer of said compound, of said diastereomer of said compound, or of said tautomer of said compound.

10. A compound according to claim 9 wherein each Ar is independently selected from (a) phenyl, (b) naphthyl, (c) pyridyl, (d) pyrimidyl (e) furanyl, (f) thienyl (g) pyrazolyl, (h) pyrazinyl (i) quinolyl, (j) oxazolyl, (k) isoxazolyl, (l) imidazolyl, (m) isothiazolyl, (n) thiazolyl, (o) triazolyl, (p) tetrazolyl, (q) indolyl, (r) benzofuranyl, (s) benzoxazolyl, (t) benzisoxazolyl, and (u) isoquinolinyl, wherein each of (a) through (d) immediately recited above is optionally substituted with one or more (a) F, (b) Cl, (c) —C$_1$-C$_8$ alkyl, (d) —C$_3$-C$_8$ cycloalkyl, (e) phenyl, (f) —OR$^6$, (g) —NR$^6$R$^6$, (h) —CN, (i) —N$_3$, -(j) —SR$^6$, (k) —SOR$^6$, (l) —SO$_2$6$^3$, (m) —COOR$^6$, (n) —COR$^6$, (o) —CONR$^6$R$^6$, (p) —NR$^6$COR$^6$—, and (q) —NR$^6$CONR$^6$R$^6$, wherein each of (c) through (e) immediately recited above is optionally substituted with one or more F, Cl, —OH, —SH, —NH$_2$, —NH(C$_1$-C$_8$ alkyl), and —N(C$_1$-C$_8$ alkyl)$_2$;

each R$^6$ is independently selected from (a) H, (b) —C$_1$-C$_8$ alkyl, (c) —C$_3$-C$_8$ cycloalkyl, (d) phenyl, (e) naphthyl, (f) —C$_1$-C$_8$ alkyl(phenyl), and (g) —C$_1$-C$_8$ alkyl(naphthyl), wherein each of (b) through (g) immediately recited above is optionally substituted with one or more R$^7$;

each R$^7$ is independently selected from one or more (a) F, (b) Cl, (c) —OH, (d) —NH$_2$, (e) —CN, (f) —SH, (g) —COOH, (h) —CHO, (i) —CONH$_2$, (j) —O(—C$_1$-C$_8$ alkyl), (k) —NH(—C$_1$-C$_8$ alkyl), (l) —N(—C$_1$-C$_8$ alkyl)$_2$, (m) —S(—C$_1$-C$_8$ alkyl), (n) —COO(—C$_1$-C$_8$ alkyl), (o) —CO(—C$_1$-C$_8$ alkyl), (p) —CONH(—C$_1$-C$_8$ alkyl), and (q) —CON(—C$_1$-C$_8$ alkyl)$_2$, or an enantiomer, diastereomer, or tautomer of said compound, or a pharmaceutically acceptable, salt of said compound, of said enantiomer of said compound, of said diastereomer of said compound, or of said tautomer of said compound.

11. A compound according to claim 10 wherein each Ar is independently selected from (a) phenyl, (b) naphthyl, (c) 2-thienyl, (d) 3-thienyl (e) 2-furanyl, and (f) 3-furanyl wherein
each of (a) through (f) immediately recited above is optionally substituted with one or more (a) F, (b) Cl, (c) —$C_1$-$C_8$ alkyl, (d) —$C_3$-$C_8$ cycloalkyl, (e) phenyl, (f) —$OR^6$, (g) —$NR^6R^6$, (h) —CN, -(i) —$SR^6$, (j) —$SOR^6$, (k) —$SO_2 6^3$, (l) —$COOR^6$, (m) —$COR^6$, (n) —$CONR^6R^6$, (o) —$NR^6COR^6$—, and (p) —$NR^6CONR^6R^6$,
wherein each of (c) through (e) immediately recited above is optionally substituted with one or more F, Cl, —OH, —SH, —$NH_2$, —NH($C_1$-$C_8$ alkyl), and —N($C_1$-$C_8$ alkyl)$_2$;
each $R^6$ is independently selected from (a) H, (b) —$C_1$-$C_8$ alkyl, (c) —$C_3$-$C_8$ cycloalkyl, (d) phenyl, (e) naphthyl, (f) —$C_1$-$C_8$ alkyl(phenyl), and (g) —$C_1$-$C_8$ alkyl(naphthyl), wherein each of (b) through (g) immediately recited above is optionally substituted with one or more $R^7$;

each $R^7$ is independently selected from one or more (a) F, (b) Cl, (c) —OH, (d) —$NH_2$, (e) —CN, (f) —SH, (g) —COOH, (h) —CHO, (i) —$CONH_2$, (j) —O(—$C_1$-$C_8$ alkyl), (k) —NH(—$C_1$-$C_8$ alkyl), (l) —N(—$C_1$-$C_8$ alkyl)$_2$, (m) —S(—$C_1$-$C_8$ alkyl), (n) —COO(—$C_1$-$C_8$ alkyl), (o) —CO(—$C_1$-$C_8$ alkyl), (p) —CONH(—$C_1$-$C_8$ alkyl), and (q) —CON(—$C_1$-$C_8$ alkyl)$_2$,
or an enantiomer, diastereomer, or tautomer of said compound, or a pharmaceutically acceptable, salt of said compound, of said enantiomer of said compound, of said diastereomer of said compound, or of said tautomer of said compound.

12. A compound according to claim 1 wherein the following provisos (I) and (II) apply:
(I) the compound is not selected from any of the following compounds (a) through (qq):

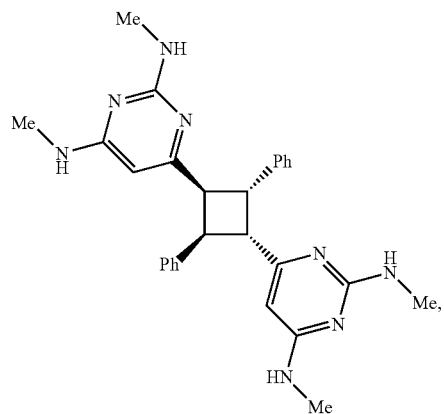

(a)

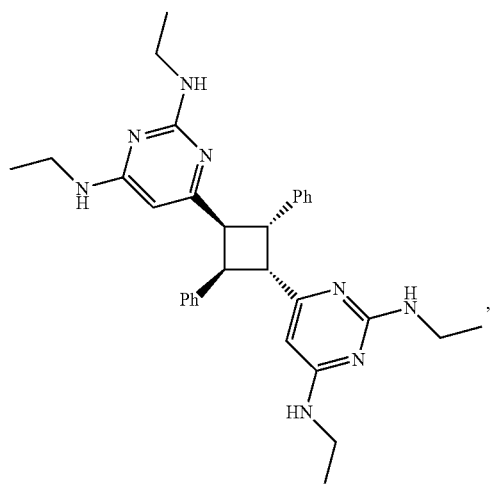

(b)

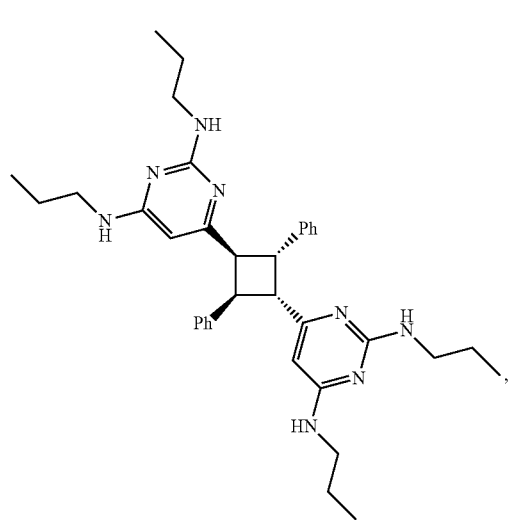

(c)

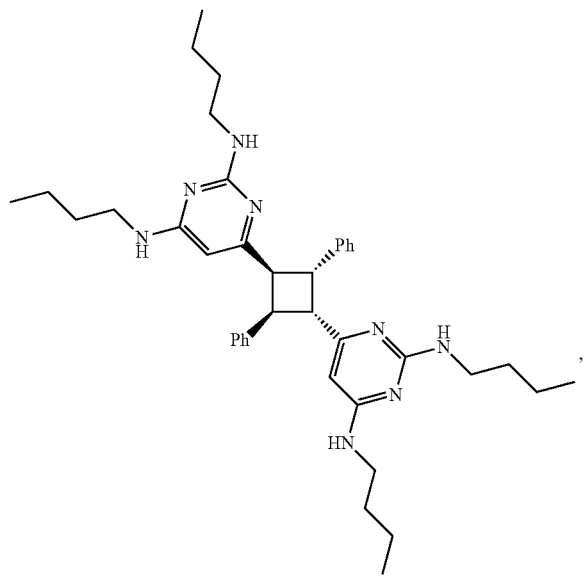

(d)

-continued
(e)
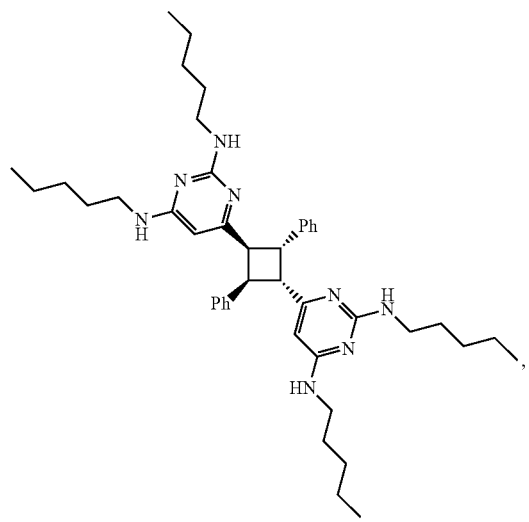
(f)
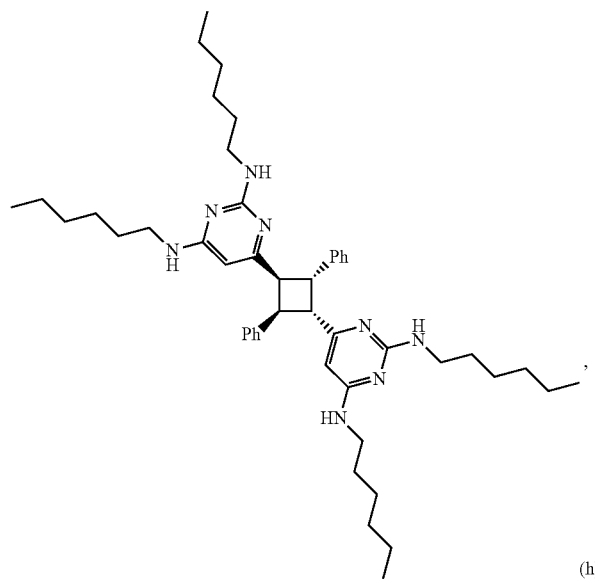
(g)
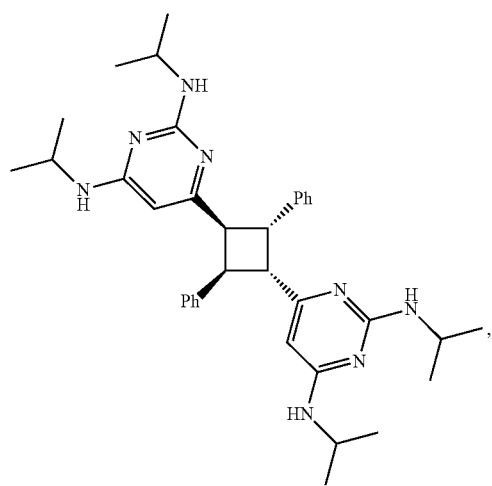
(h)
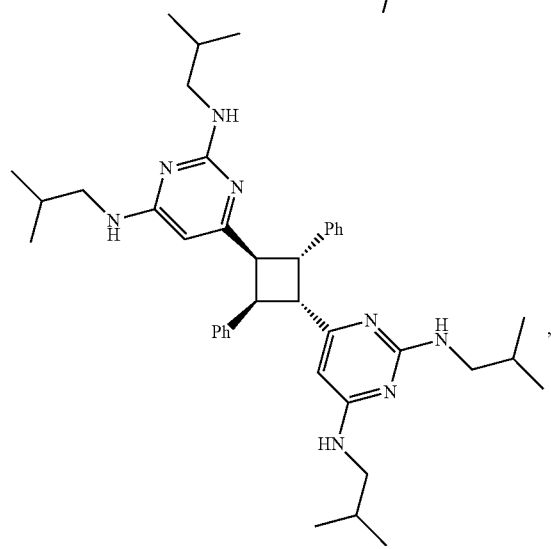
(i)
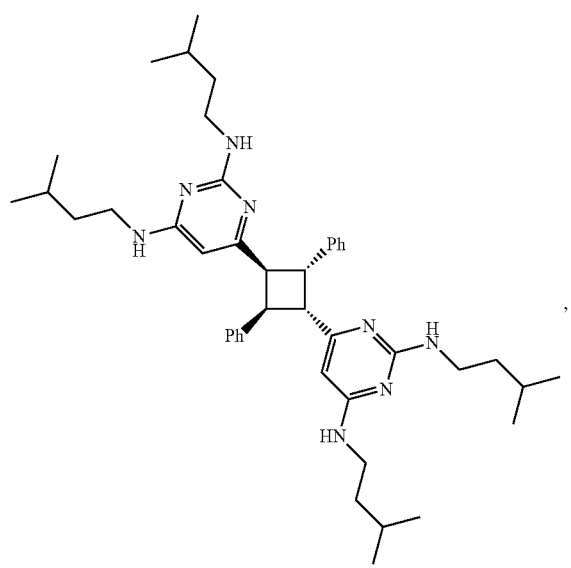
(j)
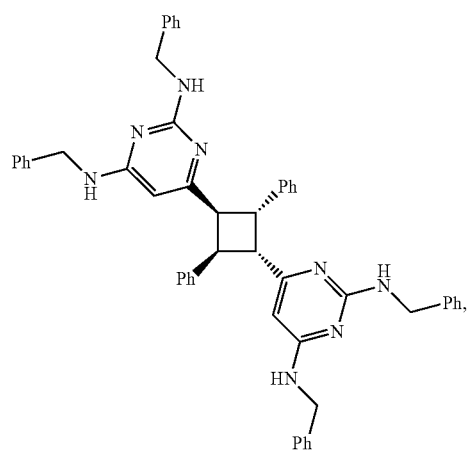

-continued
(k)
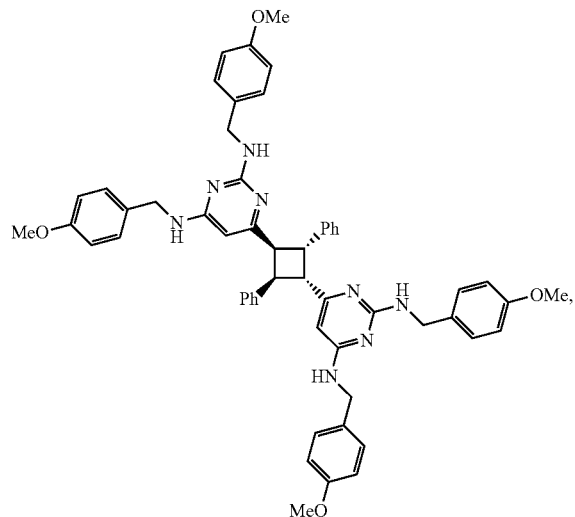
(l)
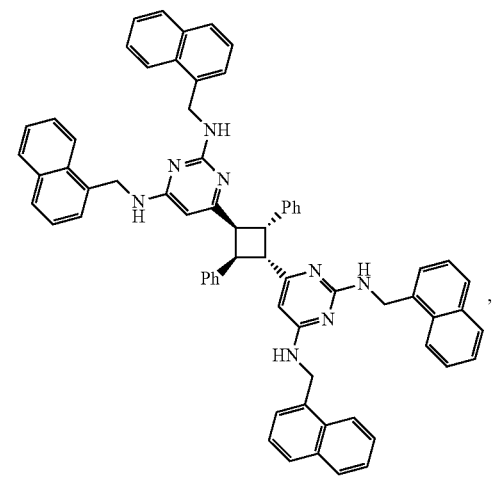
(m)
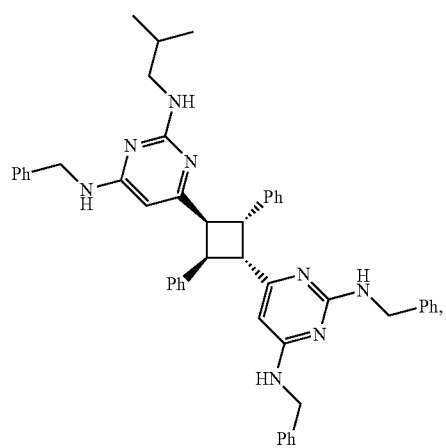
(n)
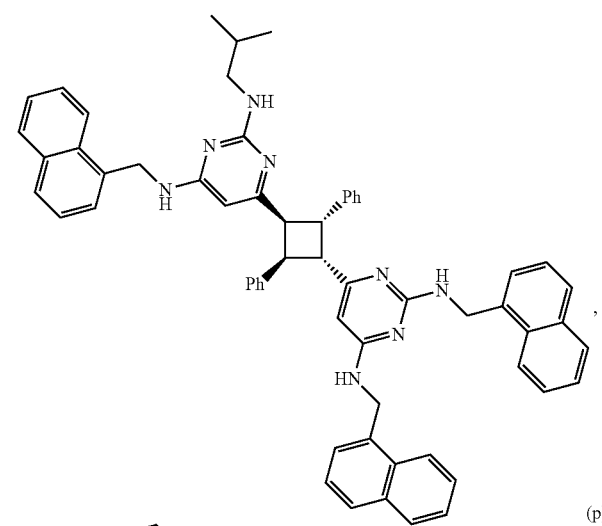
(o)
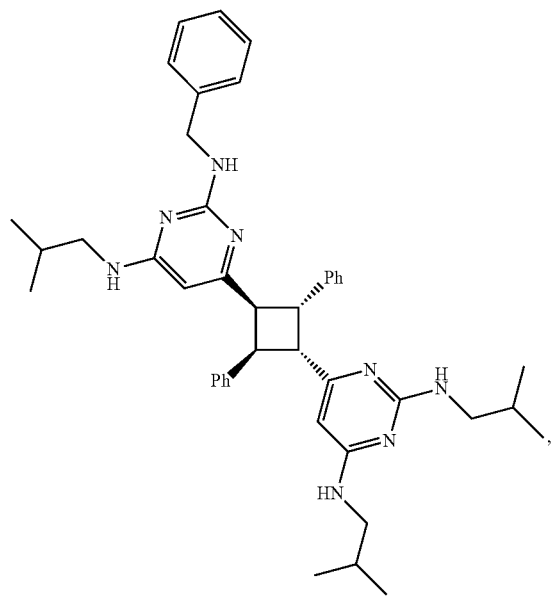
(p)
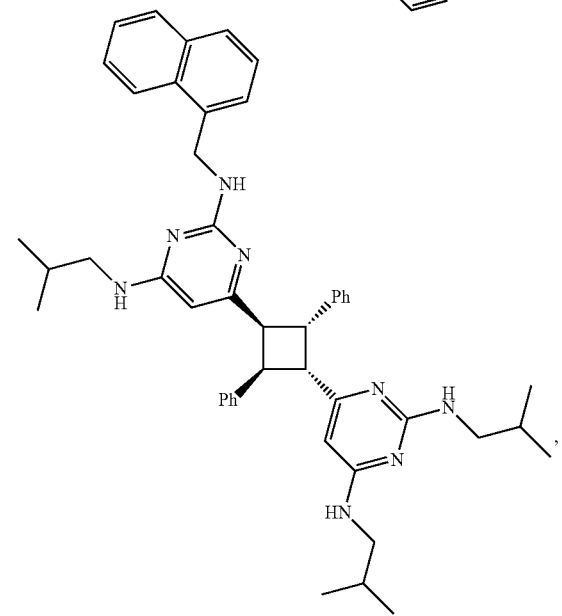

-continued
(q)
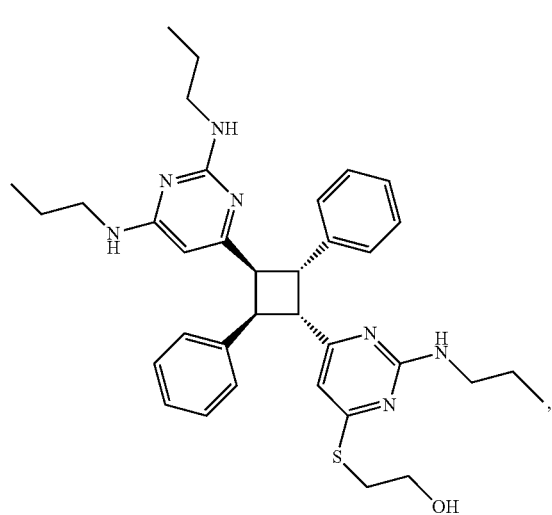
(r)
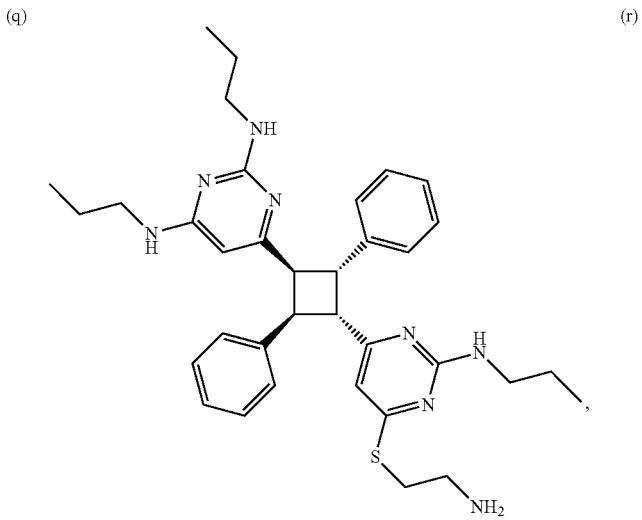
(s)
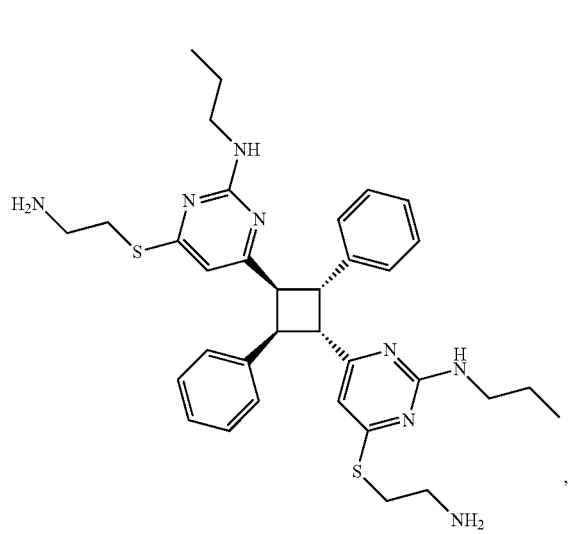
(t)
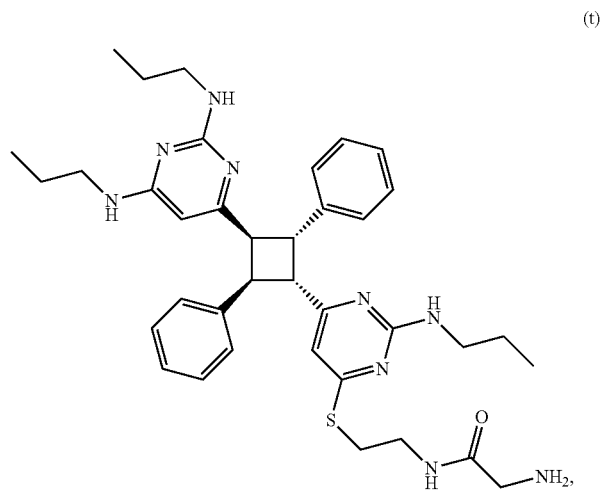
(u)
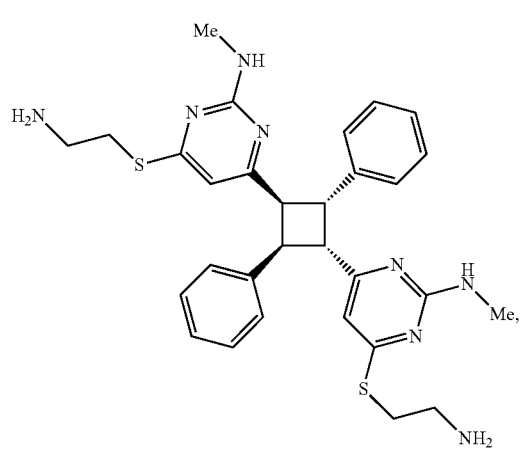
(v)
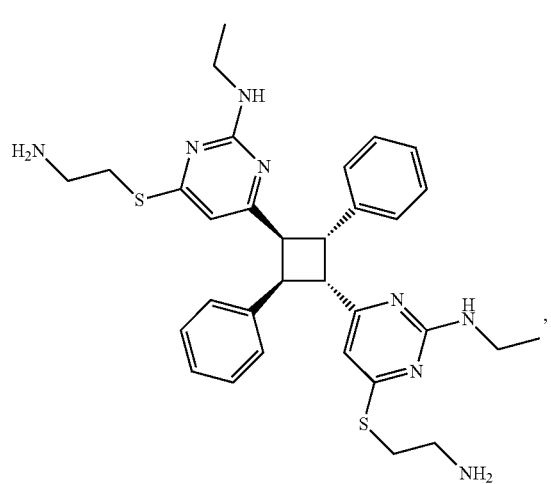

(w)
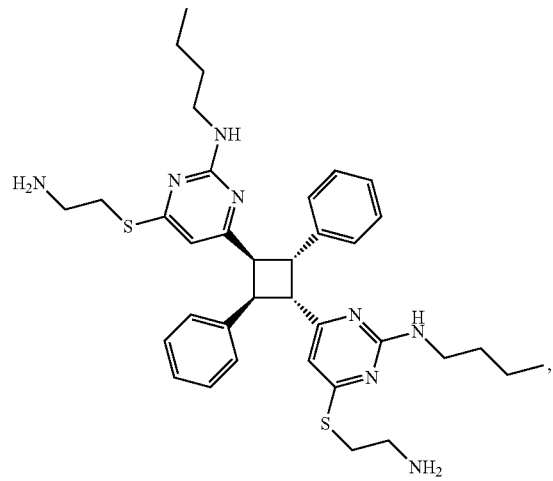
(x)
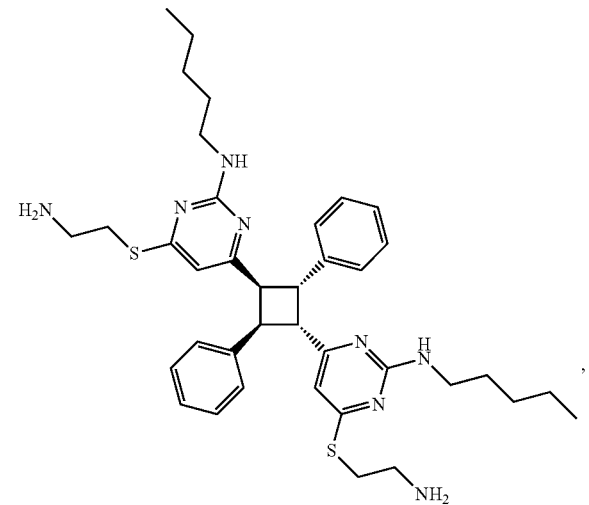
(y)
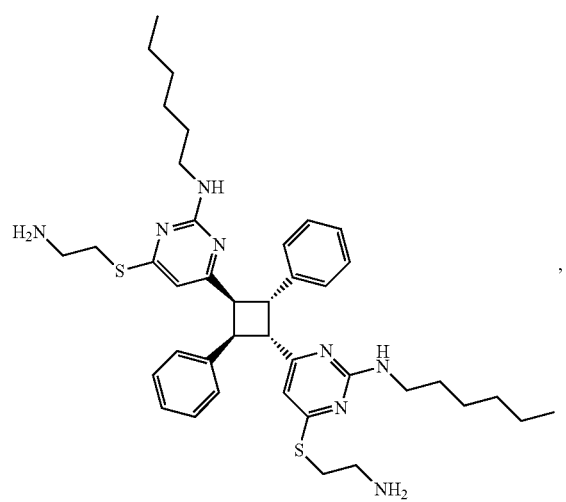
(z)
(aa)
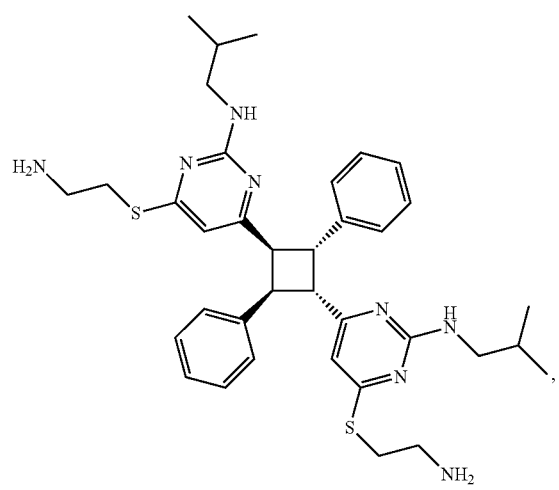
(bb)
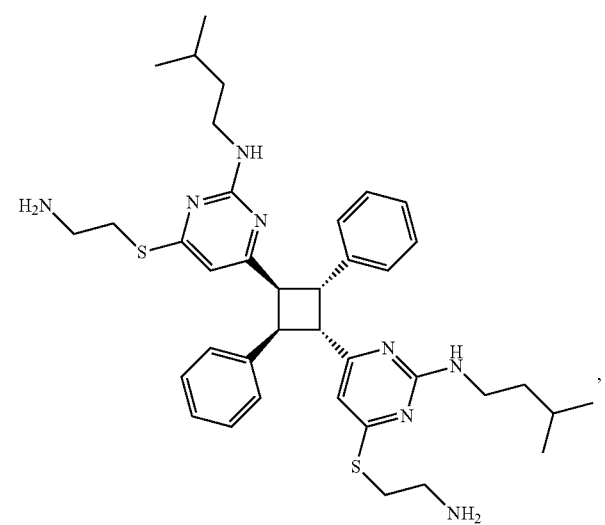

(cc)
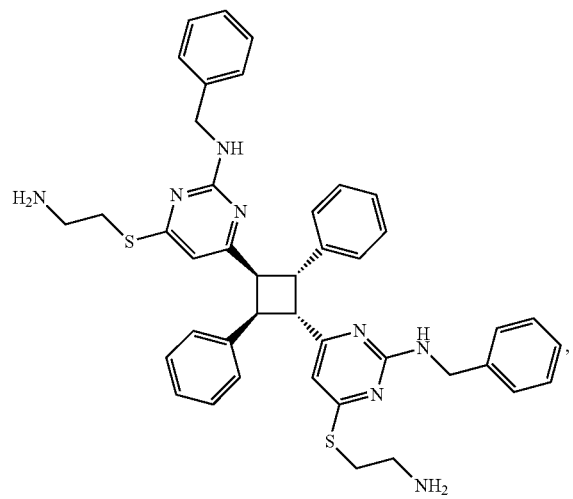
(dd)
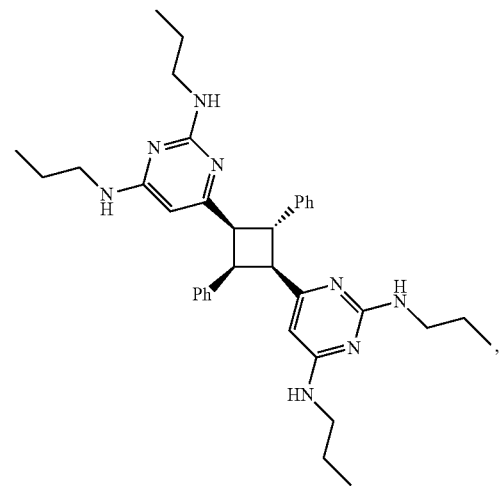
(ee)
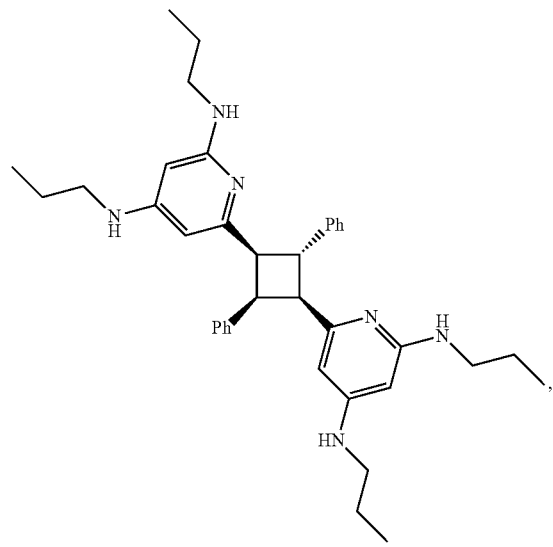
(ff)
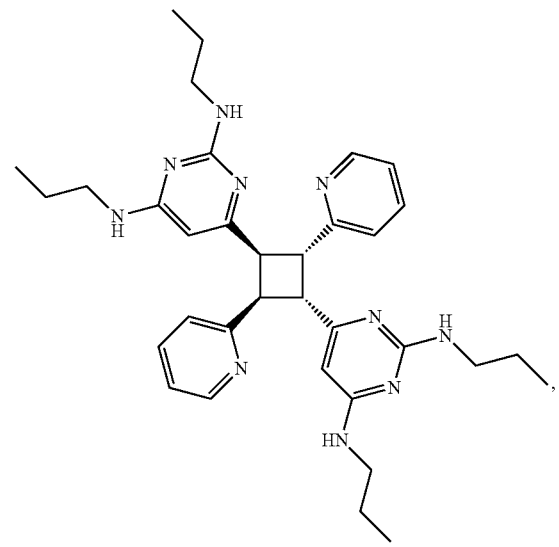
(gg)
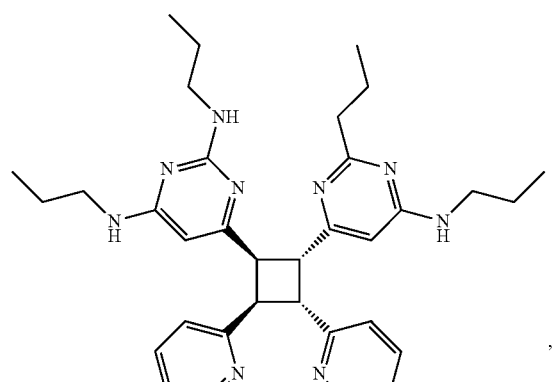
(hh)
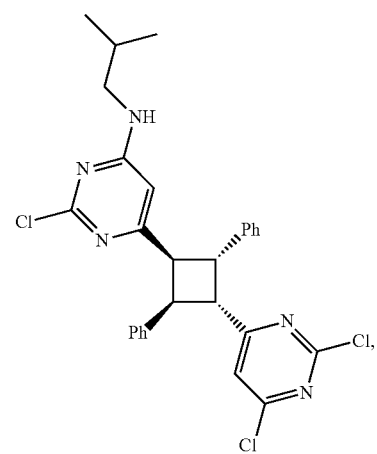

-continued
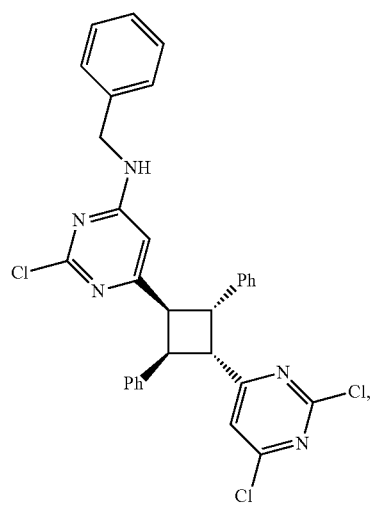 (ii)
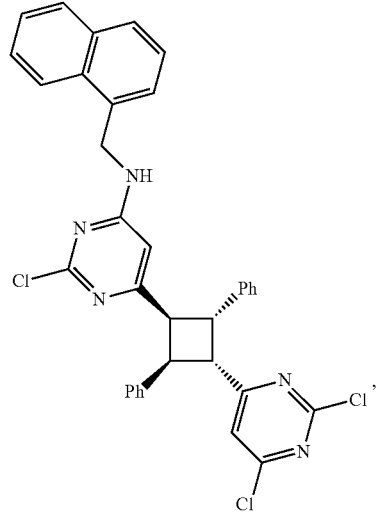 (jj)
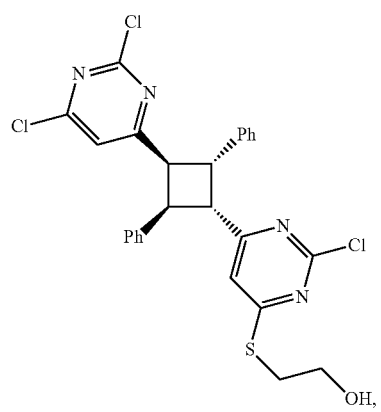 (kk)
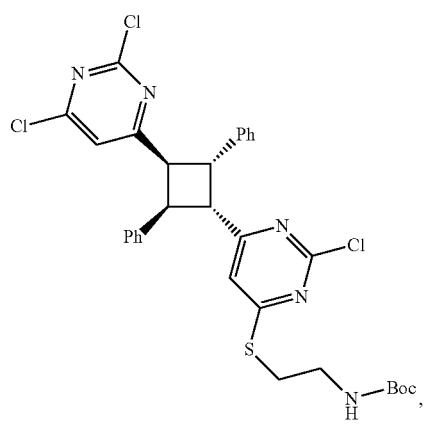 (ll)
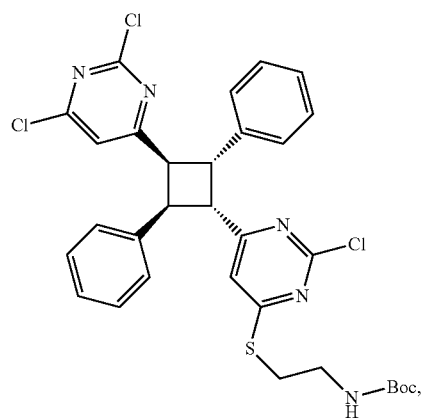 (mm)
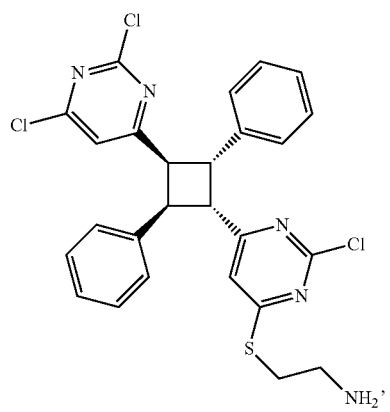 (nn)

(oo)
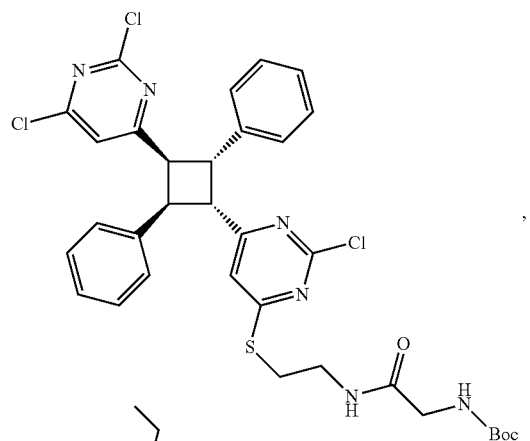
,
(pp)
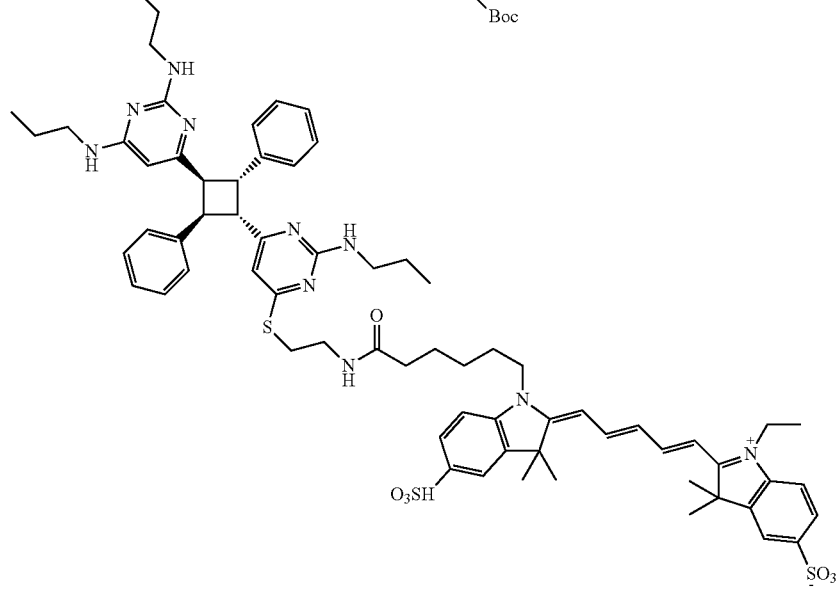
, or (qq)
or an enantiomer or diastereomer of any of the immediately foregoing compounds;
and
(II) the compound is not selected from a compound represented by the following formula
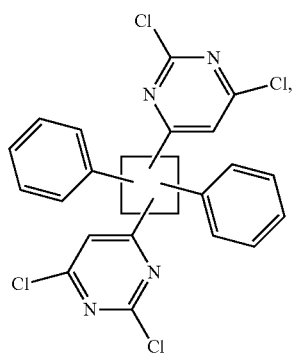
or stereoisomers, enantiomers or diastereoisomers of compounds represented by the foregoing formula.
13. A compound selected from
(a)
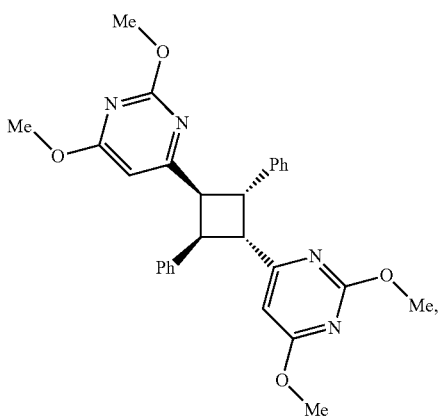

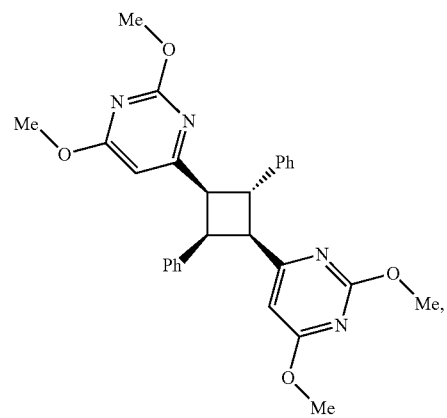
(b)
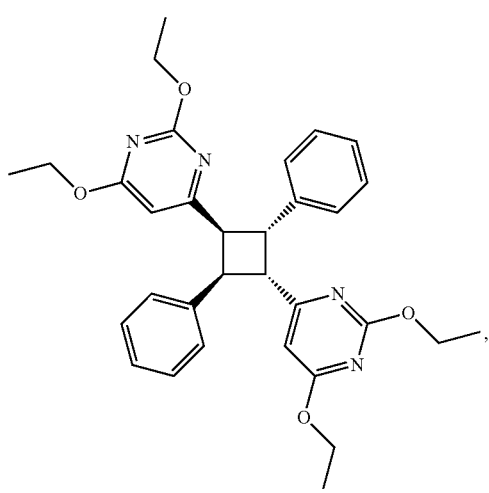
(c)
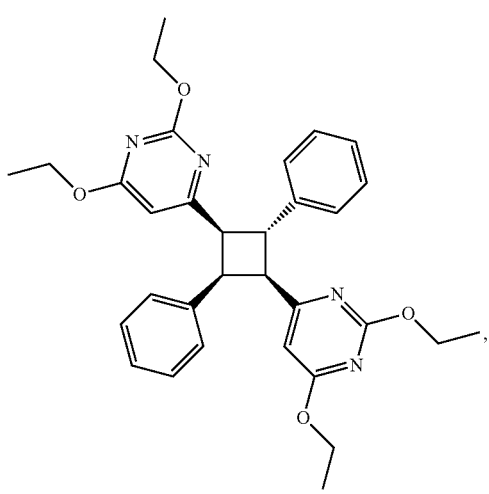
(d)
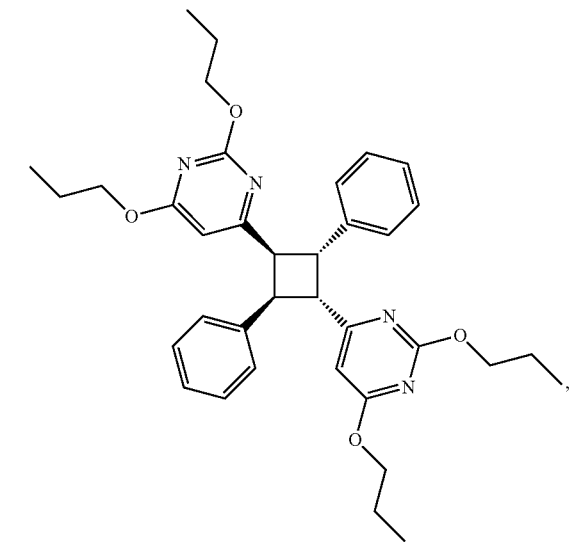
(e)
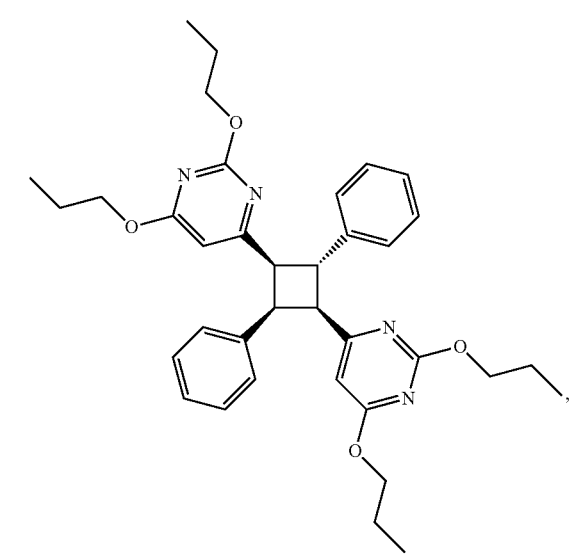
(f)
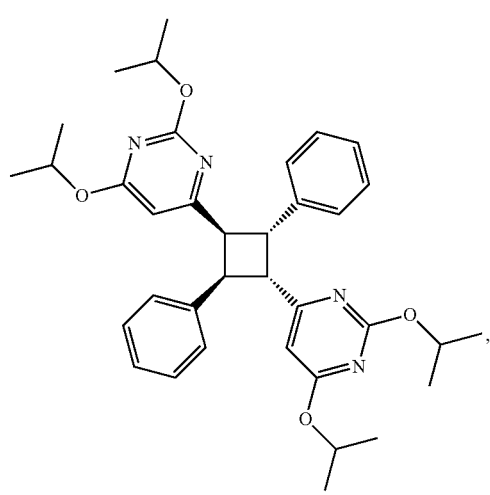
(g)

-continued
(h)
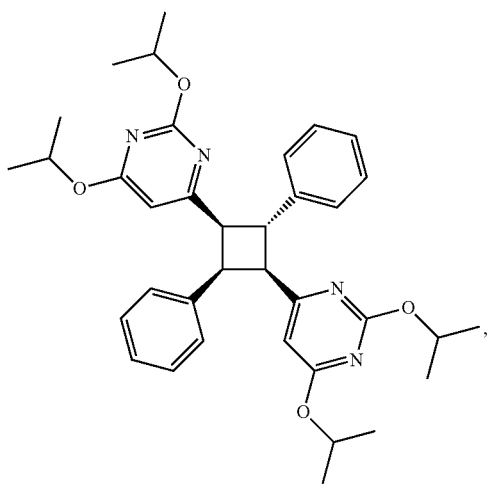
(i)
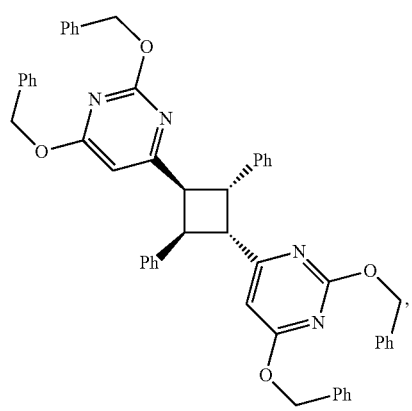
(j)
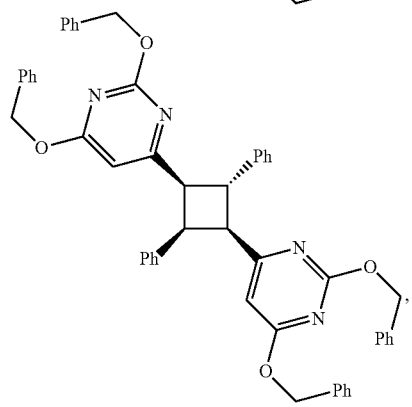
(k)
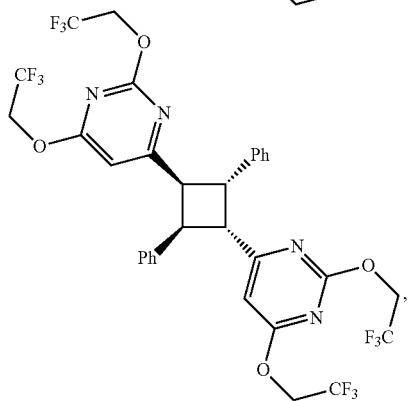
-continued
(l)
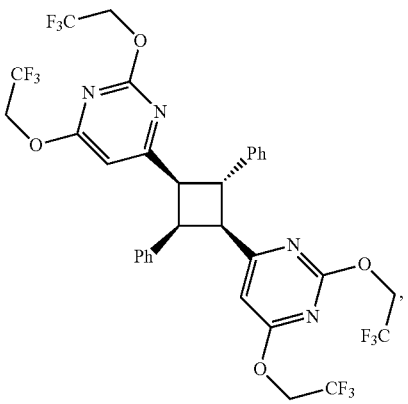
(m)
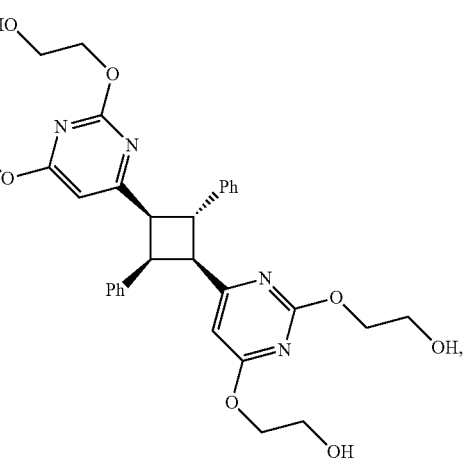
(n)
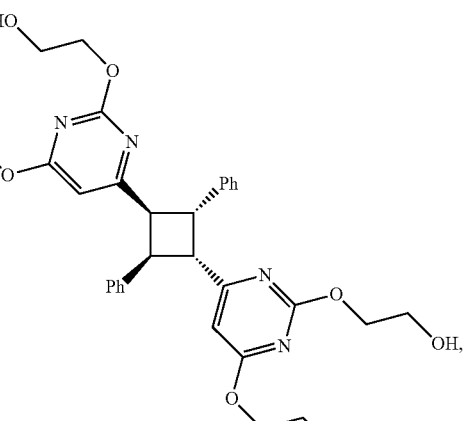
(o)
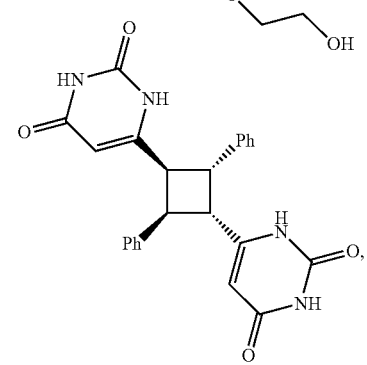

-continued
(p) 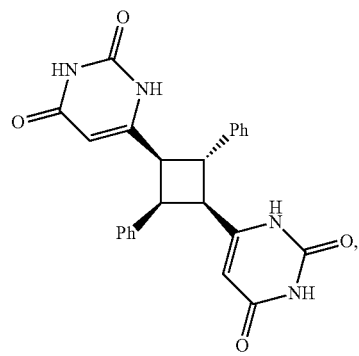
(q) 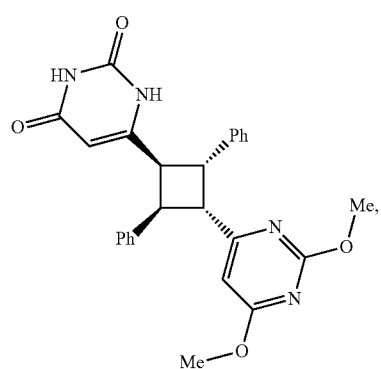
(r) 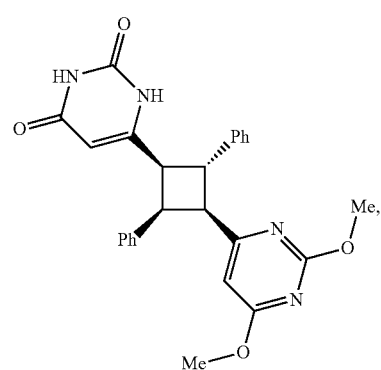
(s) 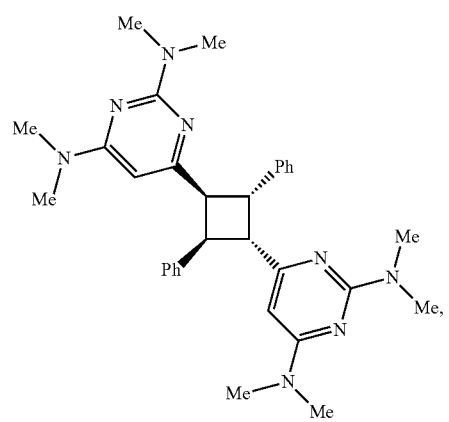
-continued
(t) 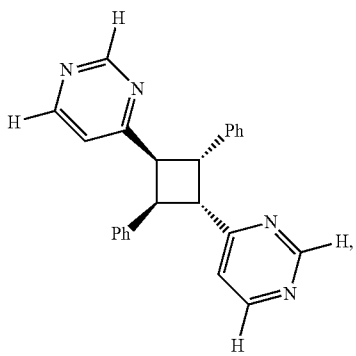
(u) 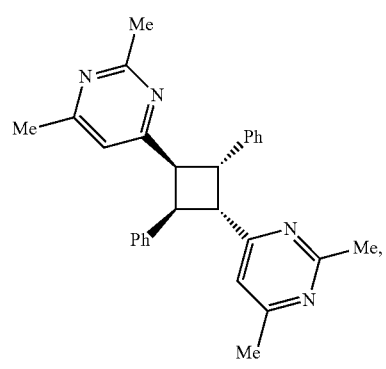
(v) 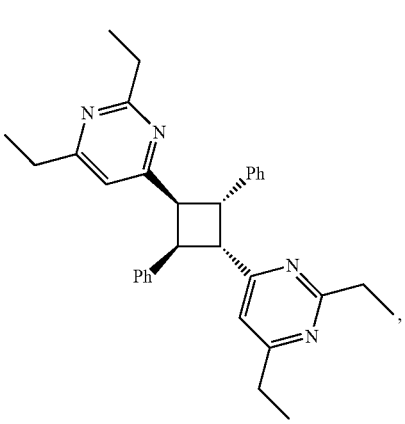
(w) 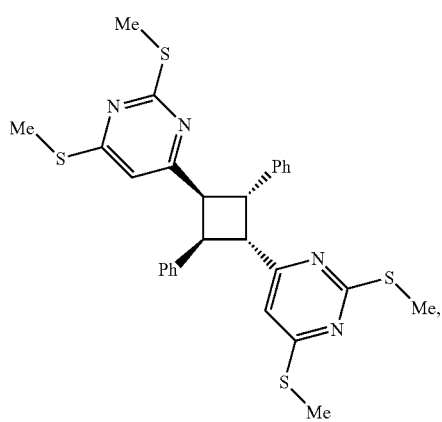

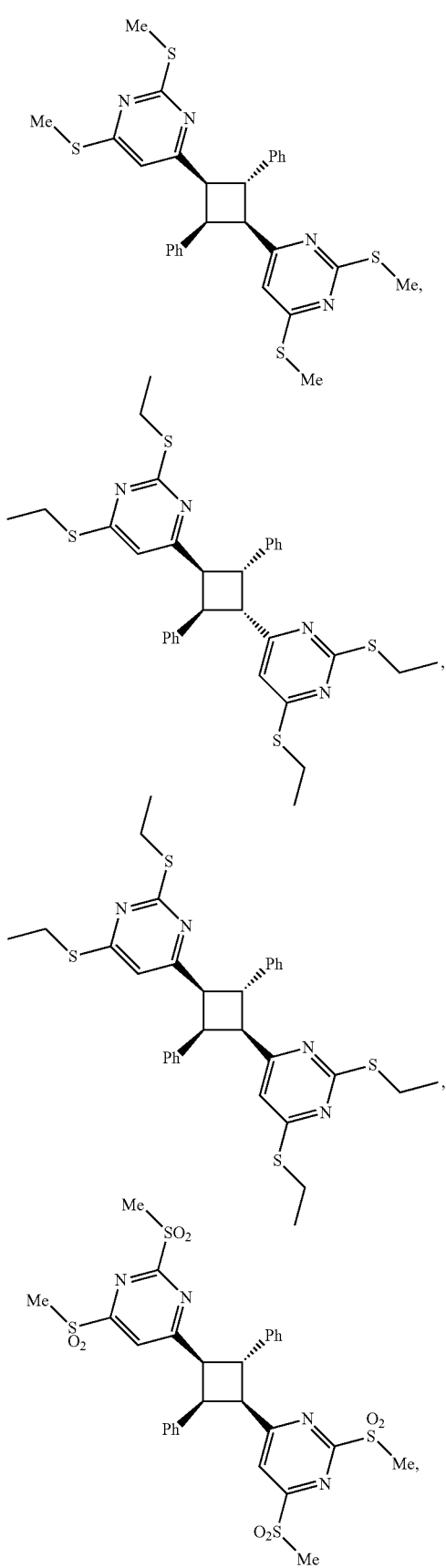
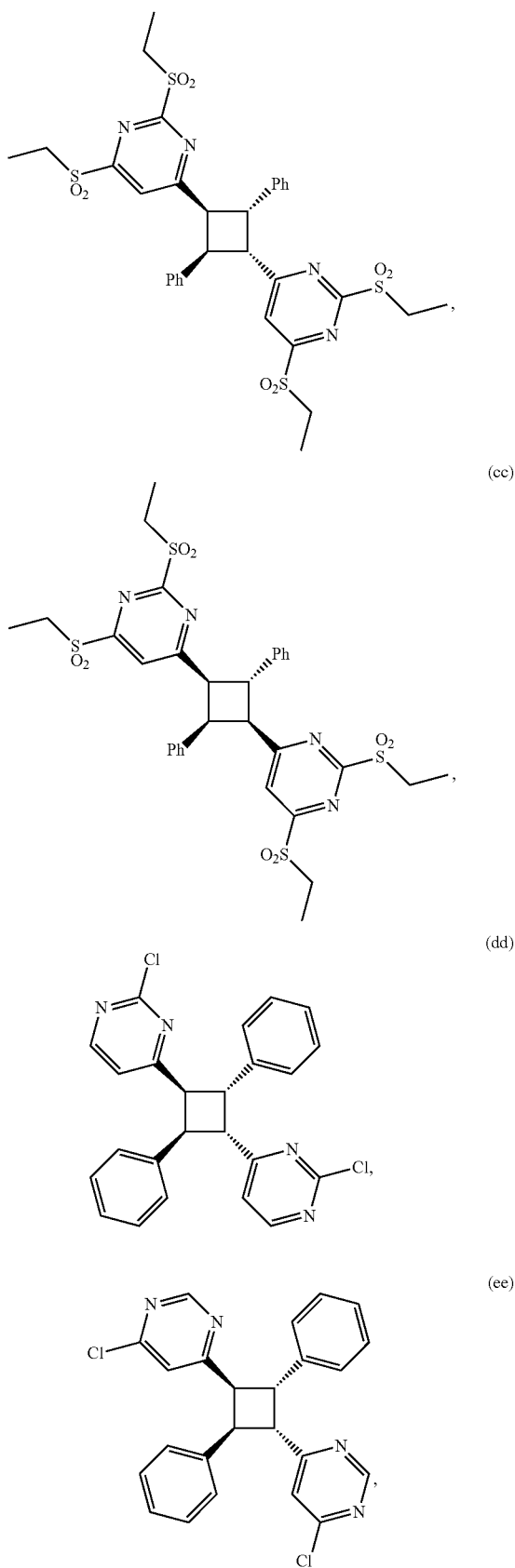

239
-continued
(ff)
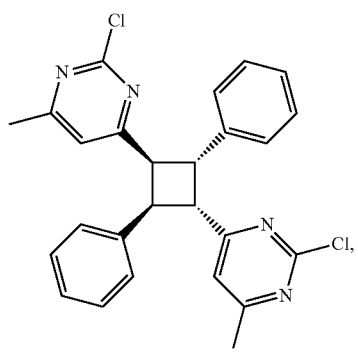
(gg)
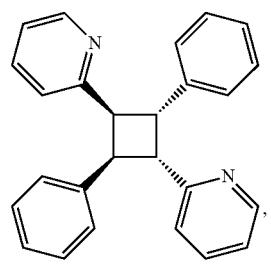
(hh)
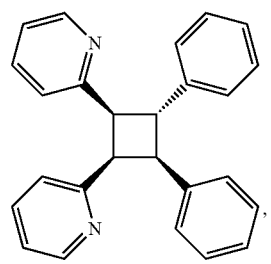
(ii)
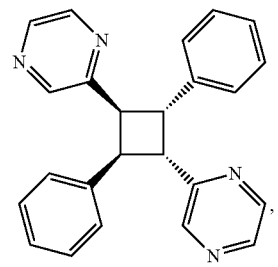
(jj)
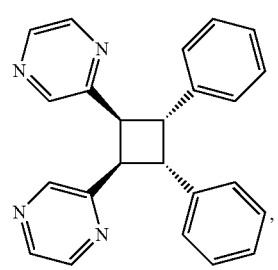
240
-continued
(kk)
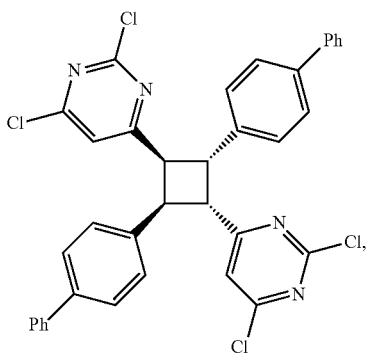
(ll)
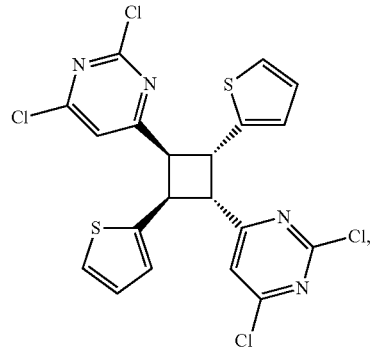
(mm)
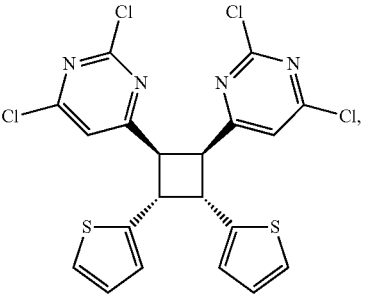
(nn)
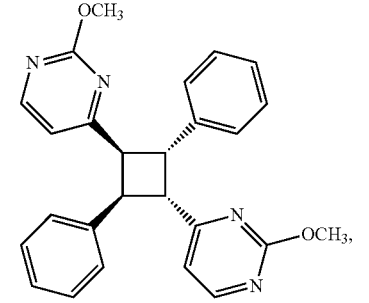
(oo)
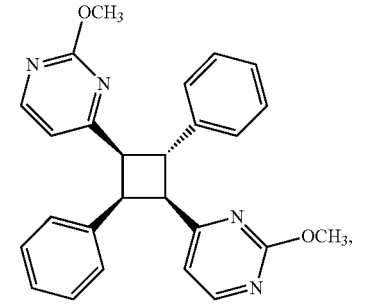

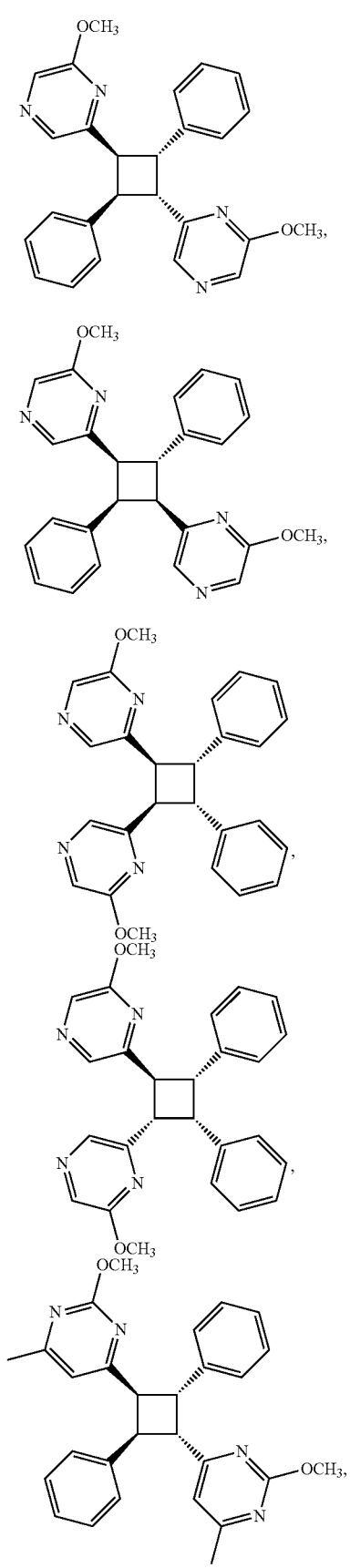
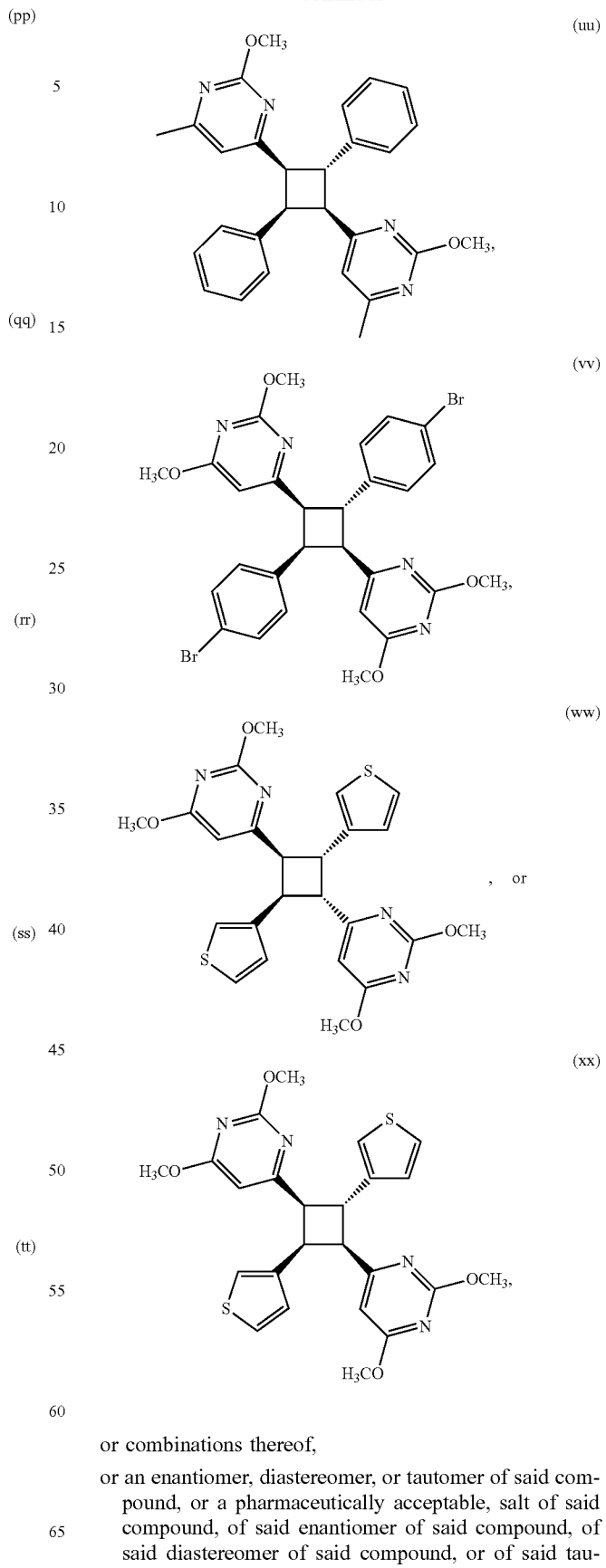
or combinations thereof,
or an enantiomer, diastereomer, or tautomer of said compound, or a pharmaceutically acceptable, salt of said compound, of said enantiomer of said compound, of said diastereomer of said compound, or of said tautomer of said compound.

14. A pharmaceutical composition comprising a compound according to claim 1 and a pharmaceutically acceptable carrier.

15. A method of treating prostate cancer in a subject comprising administering to the subject a therapeutically effective amount of a compound according to claim 1 such that the cancer is treated.

16. A method of treating a hormone responsive prostate cancer in a subject comprising administering to the subject a therapeutically effective amount of a compound according to claim 1 such that the prostate cancer is treated.

17. A method of treating a hormone refractory prostate cancer in a subject comprising administering to the subject a therapeutically effective amount of a compound according to claim 1 such that the prostate cancer is treated.

18. A method of treating a hormone refractory prostate cancer in a subject comprising administering to the subject a therapeutically effective amount of a compound according to claim 1 to inhibit the androgen receptor of the tumor cells of the prostate cancer such that the prostate cancer is treated.

19. A method of treating a hormone refractory prostate cancer according to claim 18 in a subject wherein the prostate cancer is characterized by having one or more mutations in the androgen receptors of the prostate cancer cells.

20. A method of treating a hormone refractory prostate cancer according to claim 19 in a subject wherein the prostate cancer is characterized by having one or more mutations in the ligand-binding domain of the androgen receptors of the prostate cancer cells.

21. A method according to claim 20 wherein the one or more mutations of the androgen receptor are selected from T877A, W741C, W741L, L701H, H874Y, and F876L, and combinations thereof.

22. A method according to claim 18 wherein the androgen receptor in the tumor cells is selectively inhibited compared to the androgen receptor in non-tumor cells.

23. A method for inhibiting the subcellular relocalization of an androgen receptor of a prostate cancer cell in a subject comprising administering to the subject a therapeutically effective amount of a compound according to claim 1 such that the prostate cancer is treated.

24. A method according to claim 23 wherein the subcellular relocalization of the androgen receptor is subcellular relocation from the cytoplasm to the nucleus.

25. A method for trapping an androgen receptor in the cytoplasm of a prostate cancer cell in a subject comprising administering to the subject a therapeutically effective amount of a compound according to claim 1 such that the prostate cancer is treated.

26. A method according to claim 23 wherein the prostate cancer cell is a hormone responsive prostate cancer cell.

27. A method according to claim 23 wherein the prostate cancer cell is a hormone refractory prostate cancer cell.

28. A method according to claim 23 wherein the androgen receptor is characterized as having one or more mutations.

29. A method according to claim 28 wherein the one or more mutations of the androgen receptor is in the ligand-binding domain of the androgen receptor.

30. A method according to claim 29 wherein the one or more mutations of the androgen receptor are selected from T877A, W741C, W741L, L701H, H874Y, and F876, and combinations thereof.

31. A method of treating prostate cancer in a subject comprising administering to the subject a therapeutically effective amount of a compound having the formula:

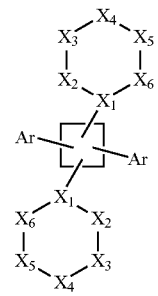

wherein in each ring system,

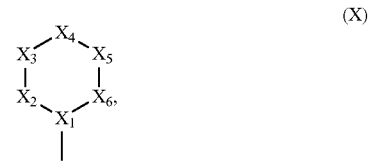

(X)

each $X_1$ is —C≡;
each of $X_2$, $X_3$, $X_4$, $X_5$, and $X_6$ is independently selected from —CH≡, —CR$^1$≡, —CR$^2$≡, —NH—, —NR$^1$—, —NR$^2$—, —N≡, and —CO—;
such that each ring system (X) contains 1 to 3 nitrogen atoms, each ring system (X) contains no more than 2-CO—, and each ring system (X) contains no more than one of each $R^1$ and each $R^2$;
each $R^1$ and $R^2$ is independently selected from (a) F, (b) Cl, (c) Br, (d) I, (e) —C$_1$-C$_8$ alkyl, (f) —C$_2$-C$_8$ alkenyl, (g) —C$_2$-C$_8$ alkynyl, (h) —C$_3$-C$_8$ cycloalkyl, (i) —C$_3$-C$_8$ cycloalkenyl, (j) —C$_8$ cycloalkynyl, (k) phenyl, (l) a 7 to 10-membered saturated, unsaturated, or aromatic fused bicyclic carbocyle, (m) a 3 to 10-membered saturated, unsaturated, or aromatic heterocycle or fused bicyclic heterocycle containing one or more heteroatoms selected from nitrogen, oxygen, sulfur, and combinations thereof, (n) —OR$^3$, (o) —NR$^3$R$^3$, (p) —CN, (q) —N$_3$, (r) —SR$^3$, (s) —SOR$^3$, (t) —SO$_2$R$^3$, (u) —COOR$^3$, (v) —COR$^3$, (w) —CONR$^3$R$^3$, (x) —NR$^3$COR$^3$—, (y) —NR$^3$CONR$^3$R$^3$, (z) —(C$_1$-C$_8$ alkyl)OR$^3$, (aa) —(C$_1$-C$_8$ alkyl)NR$^3$R$^3$, (bb) —(C$_1$-C$_8$ alkyl)SR$^3$, (cc) —(C$_1$-C$_8$ alkyl)SOR$^3$, (dd) —(C$_1$-C$_8$ alkyl)SO$_2$R$^3$, (ee) —(C$_1$-C$_8$ alkyl)COOR$^3$, (ff) —(C$_1$-C$_8$ alkyl)COR$^3$, (gg) —(C$_1$-C$_8$ alkyl)CONR$^3$R$^3$, (hh) —(C$_1$-C$_8$ alkyl)NR$^3$COR$^3$, and (ii) —(C$_1$-C$_8$ alkyl)NR$^3$CONR$^3$R$^3$,
wherein each of (e) through (j) immediately recited above is optionally substituted with one or more F, Cl, Br, I, —OH, —SH, —NH$_2$, —NH(C$_1$-C$_8$ alkyl), or —N(C$_1$-C$_8$ alkyl)$_2$ and
wherein each of (k) through (l) immediately recited above is optionally substituted with one or more $R^4$ or $R^5$;
each $R^3$ is independently selected from (a) H, (b) —C$_1$-C$_8$ alkyl, (c) —C$_2$-C$_8$ alkenyl, (d) —C$_2$-C$_8$ alkynyl, (e) —C$_3$-C$_8$ cycloalkyl, (f) —C$_3$-C$_8$ cycloalkenyl, (g) —C$_8$ cycloalkynyl, (h) phenyl, (i) naphthyl, (j) —C$_1$-C$_8$ alkyl(phenyl), and (k) —C$_1$-C$_8$ alkyl(naphthyl), wherein each of (b) through (k) immediately recited above is optionally substituted with one or more $R^5$;
each $R^4$ is independently selected from (a) F, (b) Cl, (c) Br, (d) I, (e) —C$_1$-C$_8$ alkyl, (f) —C$_2$-C$_8$ alkenyl, (g)

—$C_2$-$C_8$ alkynyl, (h) —$C_3$-$C_8$ cycloalkyl, (i) —$C_3$-$C_8$ cycloalkenyl, and (j) —$C_8$ cycloalkynyl, wherein each of (e) through (j) immediately recited above is optionally substituted with one or more $R^5$;

each $R^5$ is independently selected from (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$, each Ar is independently selected from (a) phenyl, (b) naphthyl, (c) a 5 or 6-membered heteroaromatic ring containing one or more heteroatoms selected from nitrogen, oxygen, sulfur, and combinations thereof, and (d) a 7 to 10-membered heteroaromatic ring or fused bicyclic heteroaromatic ring containing one or more heteroatoms selected from nitrogen, oxygen, sulfur, and combinations thereof, wherein each of (a) through (d) immediately recited above is optionally substituted with one or more (a) F, (b) Cl, (c) Br, (d) I, (e) —$C_1$-$C_8$ alkyl, (f) —$C_2$-$C_8$ alkenyl, (g) —$C_2$-$C_8$ alkynyl, (h) —$C_3$-$C_8$ cycloalkyl, (i) —$C_3$-$C_8$ cycloalkenyl, (j) —$C_8$ cycloalkynyl, (k) phenyl, (l) —$OR^6$, (m) —$NR^6R^6$, (n) —CN, (o) —$N_3$, -(p) —$SR^6$, (q) —$SOR^6$, (r) —$SO_2R^6$, (s) —$COOR^6$, (t) —$COR^6$, (u) —$CONR^6R^6$, (v) —$NR^6COR^6$—, and (w) —$NR^6CONR^6R^6$, wherein each of (e) through (k) immediately recited above is optionally substituted with one or more F, Cl, Br, I, —OH, —SH, —$NH_2$, —NH($C_1$-$C_8$ alkyl), and —N($C_1$-$C_8$ alkyl)$_2$;

each $R^6$ is independently selected from (a) H, (b) —$C_1$-$C_8$ alkyl, (c) —$C_2$-$C_8$ alkenyl, (d) —$C_2$-$C_8$ alkynyl, (e) —$C_3$-$C_8$ cycloalkyl, (f) —$C_3$-$C_8$ cycloalkenyl, (g) —$C_8$ cycloalkynyl, (h) phenyl, (i) naphthyl, (j) —$C_1$-$C_8$ alkyl(phenyl), and (k) —$C_1$-$C_8$ alkyl(naphthyl), wherein each of (b) through (i) immediately recited above is optionally substituted with one or more $R^7$; and each $R^7$ is independently selected from one or more (a) F, (b) Cl, (c) Br, (d) I, (e) —OH, (f) —$NH_2$, (g) —CN, (h) —SH, (i) —COOH, (j) —CHO, (k) —$CONH_2$, (l) —O(—$C_1$-$C_8$ alkyl), (m) —NH(—$C_1$-$C_8$ alkyl), (n) —N(—$C_1$-$C_8$ alkyl)$_2$, (o) —S(—$C_1$-$C_8$ alkyl), (p) —COO(—$C_1$-$C_8$ alkyl), (q) —CO(—$C_1$-$C_8$ alkyl), (r) —CONH(—$C_1$-$C_8$ alkyl), and (s) —CON(—$C_1$-$C_8$ alkyl)$_2$; and or an enantiomer, diastereomer, or tautomer of said compound, or a pharmaceutically acceptable, salt of said compound, of said enantiomer of said compound, of said diastereomer of said compound, or of said tautomer of said compound, such that the cancer is treated.

* * * * *